(12) United States Patent
Kym et al.

(10) Patent No.: US 6,593,480 B2
(45) Date of Patent: *Jul. 15, 2003

(54) GLUCOCORTICOID RECEPTOR ANTAGONISTS FOR TREATMENT OF DIABETES

(75) Inventors: Philip R. Kym, Grayslake, IL (US); Benjamin C. Lane, Libertyville, IL (US); John K. Pratt, Kenosha, WI (US); Tom Von Geldern, Richmond, IL (US); Martin Winn, Deerfield, IL (US); Jehrod Brenneman, Austin, TX (US); Jyoti R. Patel, Libertyville, IL (US); David L. Arendsen, Libertyville, IL (US); Irini Akritopoulou-Zanze, Lake Bluff, IL (US); Kimba L. Ashworth, Gurnee, IL (US); Kresna Hartandi, Gurnee, IL (US)

(73) Assignee: Abbott Laboratories, Abbott Park, IL (US)

(*) Notice: Subject to any disclaimer, the term of this patent is extended or adjusted under 35 U.S.C. 154(b) by 191 days.

This patent is subject to a terminal disclaimer.

(21) Appl. No.: 09/795,998

(22) Filed: Feb. 28, 2001

(65) Prior Publication Data

US 2001/0041802 A1 Nov. 15, 2001

Related U.S. Application Data

(63) Continuation-in-part of application No. 09/654,322, filed on Sep. 1, 2000, now Pat. No. 6,329,534.
(60) Provisional application No. 60/151,839, filed on Sep. 1, 1999.

(51) Int. Cl.$^7$ .................. C07D 311/80; C07D 409/00
(52) U.S. Cl. .................. 549/390; 549/60; 549/383
(58) Field of Search ................ 549/390, 60, 383

(56) References Cited

U.S. PATENT DOCUMENTS 5,929,058 A    7/1999   Deisher

FOREIGN PATENT DOCUMENTS

GB         2091721          8/1982
WO     WO 99/41256 A        8/1999
WO         0116128          3/2001

OTHER PUBLICATIONS

DeFronzo, Diabetes Review, 5(3), (1997) pp. 177–269.
De Feo, et al., Am. J. Physiol., 257 (1989) pp. E35–E42.
Rooney, et al., J. Clin. Endocrinol. Metab., 77 (1994).
Dinneen et al., J. Clin. Invest., 92 (1993) pp. 2283–2290.
Boyle, Diabetes Review, 1(3) (1993) pp. 302–308.
Naeser, Diabetologia, 9 (1973) pp. 376–379.
Solomon et al., Horm. Metab. Res., 9, (1977) pp. 152–156.
Exton et al., Recent Prog. Horm. Res., 26, (1970) pp. 411–457.
Kraus–Friedmann, Physiol. Rev., 64, (1984) pp. 170–259.
Beato, Cell, 56, (1989) pp. 335–344.
Yamamato, Annu. Rev. Genet., 19, (1989) pp. 209–215.
Hanson and Patel, *Adv. Enzymol.*, Meister, Ed. New York, John Wiley & Sons, Inc. (1994) pp. 203–281.
Argaud et al., Diabetes 45, (1996) pp. 1563–1571.
Friedman et al., J. Biol. Chem., 272 (50), (1997) pp. 31475–31481.

*Primary Examiner*—Amelia Owens
(74) *Attorney, Agent, or Firm*—Christopher P. Rogers

(57) ABSTRACT

Compounds of formula I

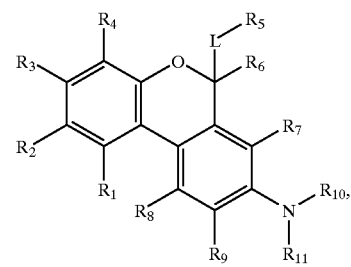

are useful for treating type II diabetes, obesity, hyperglycemia, inadequate glucose clearance, hyperinsulinemia, hypertriglyceridemia, and high-circulating glucocorticoid levels, preparations of the compounds, compositions containing the compounds, and methods of treatment using the compounds.

46 Claims, No Drawings

GLUCOCORTICOID RECEPTOR ANTAGONISTS FOR TREATMENT OF DIABETES

This application is a continuation-in-part application of U.S. application Ser. No. 09/654,322, filed Sep. 1, 2000, now U.S. Pat. No. 6,329,534 which claims benefit the of provisional U.S. application Ser. No. 60/151,839, filed Sep. 1, 1999.

TECHNICAL FIELD

The instant invention is directed to glucocorticoid receptor-selective antagonists which are useful for treating type II diabetes, obesity, hyperglycemia, inadequate glucose clearance, hyperinsulinemia, hypertriglyceridemia, and high-circulating glucocorticoid levels, preparations of the compounds, compositions containing the compounds, and methods of treatment using the compounds.

BACKGROUND OF THE INVENTION

Non insulin-dependent diabetes mellitus (type II diabetes), a debilitating disease characterized by abnormal elevation of blood glucose levels, is driven by three factors: increased hepatic glucose production, inadequate clearance of glucose via insulin mediated pathways, and decreased uptake of circulating glucose by tissues. (Diabetes Review 5(3), 177–269, (1997)). Administration of agents which decrease hepatic glucose production are a fundamental approach to controlling blood glucose levels (Am. J. Physiol. 257, E35–E42 (1989). J. Clin. Endocrinol. Metab. 77, 1180–1183 (1994) and J. Clin. Invest., 92, 2283–2290 (1993)).

Glucocorticoids have been shown to have major influences on glucose production.

Glucocorticoid excess aggravates established diabetes and glucocorticoid deficiency reduces blood glucose and improves glucose control in diabetic mice. (Diabetes Review, 1(3), 301–308, (1993). Diabetologia, 9, 376–379 (1973). Horm. Metab. Res., 9, 152–156 (1977)). The underlying mechanism responsible for these effects is believed to be glucocorticoid-induced upregulation of hepatic enzymes required for gluconeogenesis. (Recent Prog. Horm. Res., 26, 411–457 (1970). Physiol. Rev., 64, 170–259 (1984).

The glucocorticoids are lipid soluble hormones synthesized in the adrenal cortex. They readily pass through cell membranes, enter the cytoplasm of target tissues, and bind to glucocorticoid receptors in the cytoplasm by complexation with heat shock proteins. Upon binding of the hormone to its receptor, the receptor undergoes a conformational change which results in dissociation of heat shock proteins and translocation of the ligand-bound glucocorticoid receptor into the nucleus where it can either initiate or repress specific gene transcription. Transcriptional activation occurs when the ligand bound receptor complex homodimerizes, and the homodimeric receptor ligand complex binds to chromosomal DNA at sequence-specific sites in the promoter region of regulated genes. (Cell, 56, 335–344 (1989). Annu. Rev. Genet., 19, 209–215 (1989)). Among the genes which glucocorticoids up-regulate are those which play key roles in gluconeogenesis and glycogenolysis, particularly PEPCK and glucose-6-phosphatase. (*Advanced Enzymology.*, Meister, Ed. New York, John Wiley and Sons, Inc., 203–281 (1994). and Diabetes 45, 1563–1571(1996)).

Phosphoenolpyruvatecarboxy kinase (PEPCK) catalyzes the conversion of oxaloacetate to phosphoenolpyruvate and glucose-6-phosphatase catalyzes the conversion of glucose-6-phosphate into glucose, both of which are required for the synthesis of glucose from oxaloacetate in the liver. Recently, it has been shown that Aventis® (mifepristone), a potent glucocorticoid receptor (GR) antagonist, reduces mRNA levels of PEPCK and glucose-6-phosphate in the liver and causes a 50% reduction of plasma glucose levels in obese diabetic db/db transgenic mice. (J. Biol. Chem. 272(50), 31475–31481 (1997)). While steroid-based GR antagonists have been useful in demonstrating efficacy for in vivo glucose lowering effects, the utility of such agents is limited due to side effects resulting from potent cross-reactivity with other steroid receptors, in particular progesterone receptor (PR) and mineralocorticoid receptor (MR).

Because agents which function as glucocorticoid antagonists represent a novel approach to controlling type II diabetes, agents which antagonize the glucocorticoid receptor have been the subject of active current research for their clinical potential. Reference is made to U.S. Pat. No. 5,929, 058, which discloses a method for treating type II diabetes comprising administering a combination of nonselective steroidal agents exhibiting mineralcorticoid receptor agonist activity and glucocorticoid receptor antagonist activity.

Thus, it would be an important contribution to the art to provide non-steroidal, glucocorticoid-selective agents which antagonize the glucocorticoid receptor. These compounds would be particularly useful for treating type II diabetes and the symptoms thereof, such as hyperglycemia, inadequate glucose clearance, obesity, hyperinsulinemia, hypertriglyceridemia, and high circulating glucocorticoid levels.

SUMMARY OF THE INVENTION

In its principle embodiment, therefore, the instant invention is directed to compounds which are useful for treating type II diabetes, obesity, hyperglycemia, inadequate glucose clearance, hyperinsulinemia, hypertriglyceridemia, and high-circulating glucocorticoid levels, said compounds having formula I

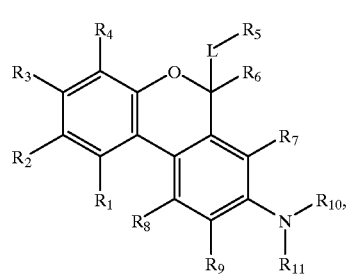

or a pharmaceutically acceptable salt or prodrug thereof, wherein $R^1$ is selected from the group consisting of (1) alkanoyl, cyano, halo, hydroxy;

(2) alkyl, alkenyl, alkynyl, alkoxy, alkanoyloxy;

wherein each group defining (2) can be optionally substituted with 1–4 substituents independently selected from alkoxy, alkoxycarbonyl, amino, carboxamido, cyano, halo, hydroxy, oxo, unsubstituted or substituted aryl, unsubstituted or substituted heteroaryl, and unsubstituted or substituted heterocyclyl;

wherein the substituted aryl, substituted heteroaryl, and substituted heterocyclyl groups are substituted with 1–5 substituents independently selected from alkyl, alkenyl, alkynyl, alkoxy, alkoxyalkyl, alkoxycarbonyl, alkoxycarbonylalkyl, amino, aminoalkyl, carboxamido, carboxamidoalkyl, carboxy, carboxyalkyl, cyano, cyanoalkyl, hydroxy, hydroxyalkyl, hydroxyalkoxy, halo, haloalkyl, perfluoroalkyl, and perfluoroalkoxy;

(3) cycloalkyl, aryl, heteroaryl, heterocyclyl;

wherein each group defining (3) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, carboxamido, carboxamidoalkyl, carboxy, carboxyalkyl, cyano, cyanoalkyl, hydroxy, hydroxyalkyl, hydroxyalkoxy, halo, haloalkyl, oxo, perfluoroalkyl, and perfluoroalkoxy;

(4) $CO_2R^{12}$, $OR^{12}$, $SR^{12}$, $S(O)R^{12}$, and $SO_2R^{12}$;

wherein $R^{12}$ is selected from the group consisting of alkyl, cycloalkyl, aryl, heteroaryl, and heterocyclyl;

wherein each group can be optionally substituted with 1–5 substituents independently selected from alkyl, alkenyl, alkoxyalkoxy, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;

$R_2$ is selected from hydrogen and $R_1$; or $R_1$ and $R_2$ together are $-X^1-Y^1-Z^1-$, wherein $X^1$ is selected from a covalent bond, O and $CH_2$; $Y^1$ is selected from $C(O)$, alkylene, and alkenylene; and $Z^1$ is selected from $CH_2$, $CH_2O$, $CH_2NR^{13}$, $NR^{13}$, and O;

wherein $R^{13}$ is selected from
 (1) hydrogen
 (2) alkyl,
 wherein the alkyl can be optionally substituted with 1–4 substituents independently selected from alkenyl, alkoxy, cycloalkyl, aryl, and halo, and
 (3) aryl;

$R^3$, $R^4$, $R^7$, $R^8$, and $R^9$ are independently selected from hydrogen and $R_1$;

L is selected from a covalent bond and alkylene;

$R^5$ is selected from
 (1) alkanoyl, alkoxy, alkenyloxy, alkynyloxy, alkoxycarbonyl, cyano;
 (2) aryl, arylalkyl, heteroaryl, and heterocyclyl,
 wherein each group defining (2) can be optionally substituted with 1–5 substituents independently selected from alkanoylamino, alkanoylaryloxy, alkyl, alkylsulfonamido, alkenyl, alkenyloxy, alkynyl, alkoxy, alkoxyalkoxy, alkoxyalkyl, alkoxyalkynyl, alkoxyaryl, alkoxycarbonyl, alkoxycarbonylalkyl, alkoxycarbonylalkenyloxy, amino, aminoalkyl, aminoaryl, aryl, arylalkyl, arylalkenyl, arylalkynyl, aryloxy, arylsulfonamido, carboxamido, carboxamidoalkyl, carboxy, carboxyalkyl, carboxyaryl, cyano, cyanoalkyl, heteroaryl, (heteroaryl)heteroarylsulfonamido, heterocyclyl, hydroxy, hydroxyalkyl, hydroxyalkoxy, hydroxyalkynyl, halo, haloalkyl, haloalkylsulfonamido, nitro, oxo, perfluoroalkyl, perfluoroalkoxy and trialkylsilylalkyl;
 (3) alkyl, alkenyl, alkynyl, cycloalkyl,
 wherein each group defining (3) can be optionally substituted with 1–4 substituents independently selected from alkoxy, alkenyloxy, alkoxycarbonyl, amino, aryl, carboxamido, carboxy, cyano, halo, hydroxy, and oxo;

$R^6$ is selected from hydrogen and alkyl; or

-L-$R^5$ and $R^6$ together are selected from

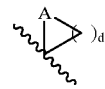

(1)

wherein d is 1–4 and A is selected from $CH_2$, O, S, $SO_2$, and $NR^{13}$ and

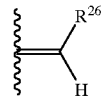

(2)

wherein the carbon—carbon double bond of (2) can be in the E or Z configuration and $R^{26}$ selected from
 (1) alkyl,
 wherein the alkyl can be optionally substituted with 1–4 substituents independently selected from alkenyl, alkynyl, alkoxy, alkoxycarbonyl, amino, aryl, carboxamido, carboxy, cyano, heteroaryl, heterocyclyl, hydroxy, and halo;
 (2) aryl, heteroaryl, heterocyclyl, cycloalkyl, and cycloalkenyl;
 wherein each group defining (2) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;

$R_{10}$ and $R_{11}$ are independently selected from
 (1) hydrogen,
 (2) alkyl,
 wherein the alkyl can be optionally substituted with 1–4 substituents independently selected from (a) alkenyl, (b) alkynyl, (c) alkoxy, (d) aryl, (e) cycloalkyl, (f) heteroaryl, (g) heterocyclyl, (h) alkoxycarbonyl, (i) carboxy, and (j) halo;
 wherein (a)–(c) can be optionally substituted with 1–4 substituents independently selected from aryl, alkoxy, cycloalkyl, heteroaryl, heterocyclyl, alkoxycarbonyl, carboxy, and halo; and
 wherein (d)–(g) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, heteroaryl, heterocyclyl, hydroxy, hydroxyalkyl, hydroxyalkoxy, halo, haloalkyl, nitro, perfluoroalkyl, and perfluoroalkoxy;
 (3) aryl, cycloalkyl, heteroaryl, heterocyclyl;
 wherein each group defining (3) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;

(4) —SO$_2$R$^{35}$ and —C(O)R$^{36}$;
wherein R$^{35}$ and R$^{36}$ are independently selected from
  (a) alkoxy, amino,
  (b) alkyl, alkenyl,
  wherein each group defining (b) can be optionally substituted with 1–4 substituents independently selected from (i) alkenyl, (ii) alkynyl, (iii) alkoxy, (iv) aryl, (v) cycloalkyl, (vi) hetcroaryl, (vii) heterocyclyl, (viii) alkoxycarbonyl, (ix) carboxy, and (x) halo;
  wherein (i)–(iii) can be optionally substituted with 1–4 substituents independently selected from aryl, alkoxy, cycloalkyl, heteroaryl, heterocyclyl, alkoxycarbonyl, carboxy, and halo; and
  wherein (iv)-(vii) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;
  (c) aryl, cycloalkyl, heteroaryl, heterocyclyl;
  wherein each group defining (c) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy.

In another embodiment, the present invention is directed to methods of selectively modulating the antagonism effects of the glucocorticoid receptor in a mammal comprising administering a therapeutically effective amount of a compound of formula I.

In yet another embodiment, the invention is directed to a method of treating diabetes, hyperglycemia, hyperinsulinemia, inadequate glucose clearance, obesity, hypertension, and high glucocorticoid levels, the method comprising administering one or more compounds of formula I.

In yet another embodiment, the invention is directed to pharmaceutical compositions containing compounds of formula I.

DETAILED DESCRIPTION OF THE INVENTION

The term "alkanoyl" refers to an alkyl group attached to the parent molecular group through a carbonyl group.

The term "alkanyloxy" refers to an alkyl group attached to the parent molecular group through an oxygen atom.

The term "alkenyl" refers to a monovalent straight or branched chain group of two to twelve carbons derived from a hydrocarbon having at least one carbon—carbon double bond. The alkenyl groups of this invention can be optionally substituted with 1–5 substituents selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle groups are substituted with at least one substituent selected from alkyl, alkoxy, carboxy, azido, carboxaldehyde, halo, hydroxy, perfluoroalkyl, and perfluoroalkoxy.

The term "alkenyloxy" refers to an alkenyl group attached to the parent molecular group through an oxygen atom, with the proviso that the double bond is not directly attached to the oxygen atom.

The term "alkoxy" refers to an alkyl group attached to the parent molecular group through an oxygen atom.

The term "alkoxyalkyl" refers to an alkoxy group attached to the parent molecular group through an alkylene group.

The term "alkoxyalkoxy," refers to an alkoxy group attached to the parent molecule through an alkoxy group.

The term "alkoxyalkynyl," refers to an alkoxy group attached to the parent molecule through an alkynyl group.

The term "alkoxyaryl" refers to an alkoxy group attached to the parent molecule through an aryl group.

The term "alkoxycarbonyl" refers to an ester group, for example, an alkoxy group attached to the parent molecular moiety through a carbonyl group.

The term "alkoxycarbonylalkyl" refers to an alkyl group to which is attached at least one alkoxycarbonyl group.

The term "alkoxycarbonylalkenyloxy" refers to an alkoxycarbonyl group attached to the parent molecule through an alkenyloxy group.

The term "alkyl" refers to a monovalent straight or branched chain group of one to twelve carbons derived from a saturated hydrocarbon. The alkyl groups of this invention can be optionally substituted with 1–5 substituents selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle groups substituting the alkyl groups of this invention are substituted with at least one substituent selected from alkyl, alkoxy, carboxy, azido, carboxaldehyde, halo, hydroxy, perfluoroalkyl, and perfluoroalkoxy.

The term "alkyl sulfonamido," refers to an alkyl group attached to the parent molecule through a sulfonamido group.

The term "alkylene" refers to a divalent straight or branched chain group of one to twelve carbons derived from an alkane.

The term "alkenylene" refers to a divalent straight or branched chain group of one to twelve carbons with at least one double bond.

The term "alkynyl" refers to a monovalent straight or branched chain hydrocarbon of two to twelve carbons with at least one carbon—carbon triple bond. The alkynyl groups of this invention can be optionally substituted with 1–5 substituents selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle groups substituting the alkyl groups of this invention are substituted with at least one substituent selected from alkyl, alkoxy, carboxy, azido, carboxaldehyde, halo, hydroxy, perfluoroalkyl, and perfluoroalkoxy.

The term "alkynyloxy" refers to an alkynyl group attached to the parent molecular group through an oxygen aton, with the proviso that the triple bond is not directly attached to the oxygen atom.

The term "alkanoylamino" refers to an alkanoyl group attached to the parent molecule through an amino group.

The term "alkanoylaryl" refers to an alkanoyl group attached to the parent molecule through an aryl group.

The term "alkanoylaryloxy" refers to an alkanoylary group attached to the parent molecule through an oxy group.

The term "alkanoyloxyalkyl," as used herein, refers to an alkyl group, as defined herein, to which is attached at least one alkanoyloxy substituent.

The term "alkanoyloxyalkenyl," as used herein, refers to an alkenyl group, as defined herein, to which is attached at least one alkanoyloxy substituent.

The term "amino" refers to —N($R^{20}$)($R^{21}$) wherein $R^{20}$ and $R^{21}$ are independently selected from the group consisting of hydrogen, unsubstituted or substituted alkyl, unsubstituted or substituted alkenyl, unsubstituted or substituted alkynyl, unsubstituted or substituted alkoxyalkyl, unsubstituted or substituted aryl, unsubstituted or substituted heteroryl, unsubstituted or substituted heterocyclyl, unsubstituted or substituted cycloalkyl, haloalkyl, alkoxyalkyl.

The term "aminoalkyl" refers to an alkyl group, as defind herein, to which is attached at least one amino group.

The term "aminoaryl" refers to an amino group attached to the parent molecule through an aryl group.

The term "aryl" refers to a mono- or bicyclic carbocyclic ring system having one or two aromatic rings. The aryl group can also be fused to a cyclohexane, cyclohexene, cyclopentane or cyclopentene ring. The aryl groups of this invention can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The substituted aryl, heteroaryl, and heterocycle groups substituting the aryl groups of this invention are substituted with at least one substituent selected from alkyl, alkoxy, carboxy, azido, carboxaldehyde, halo, hydroxy, perfluoroalkyl, and perfluoroalkoxy.

The term "arylalkyl" refers to an aryl group attached to the parent molecule through an alkyl group.

The term "arylalkenyl," refers to an aryl group attached to the parent molecule through an alkenyl group.

The term "arylalkynyl" refers to an aryl group attached to the parent molecule through an alkynyl group.

The term "aryloxy" refers to an aryl group attached to the parent molecule through an oxygen atom.

The term "arylsulfanamido," refers to an aryl group attached to the parent molecule through a sulfonamido group.

The term "carboxy" refers to —$CO_2H$.

The term "carboxyalkyl," as used herein, refers to an alkyl group, as defined herein, to which is attached at least one carboxy substituent.

The term "carboxyaryl," as used herein, refers to an aryl group, as defined herein, to which is attached at least one carboxy substituent The term "carboxamido" refers to an amino group, as defined herein, attached to the parent molecular group through a C(O) group.

The term "carboxamidoalkyl," as used herein, refers to an alkyl group, as defined herein, to which is attached at least one carboxamido substituent.

The term "cyano" refers to —CN.

The term "cyanoalkyl," as used herein, refers to an alkyl group, as defined herein, to which is attached at least one cyano substituent.

The term "cycloalkenyl" refers to a monovalent group derived from a cyclic or bicyclic hydrocarbon of three to twelve carbons that has at least one carbon—carbon double bond.

The term "cycloalkyl" refers to a monovalent group three to twelve carbons derived from a saturated cyclic or bicyclic hydrocarbon. The cycloalkyl groups of this invention can be optionally substituted with 1–5 substituents independently selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle substituting the cycloalkyl groups of this invention are substituted with 1–5 substituents independently selected from alkyl, alkoxy, carboxy, azido, carboxaldehyde, halo, hydroxy, perfluoroalkyl, and perfluoroalkoxy.

The term "halo" or "halogen" refers to F, Cl, Br, or I.

The term "haloalkyl" refers to an alkyl group substituted with one or more halogen atoms.

The term "haloalkylsulfonamido" refers to a haloalkyl group attached to the parent molecule through a sulfonamido group.

The term "haloalkoxy" refers to a haloalkyl group attached to the parent molecular group through an oxygen atom.

The term "heterocyclyl," as used herein, refers to cyclic, non-aromatic, four-, five-, six-, or seven-membered rings containing at least one atom selected from the group consisting of oxygen, nitrogen, and sulfur. The four-membered rings have zero double bonds, the five-membered rings have zero or one double bonds, and the six- and seven-membered rings have zero, one, or two double bonds. Heterocycle groups of the invention are exemplified by dihydropyridinyl, morpholinyl, piperazinyl, pyrrolidinyl, tetrahydropyridinyl, piperidinyl, thiomorpholinyl, 1,3-dioxolanyl, 1,4-dioxanyl, 1,3-dioxanyl, and the like. The heterocycle groups of this invention can be fused to an aryl group or a heteroaryl group. The heterocycle groups of the invention are connected to the parent molecular group through a substitutable carbon or nitrogen atom in the ring.

Heterocyclyls also include bridged bicyclic groups wherein a monocyclic heterocyclic group is bridged by an alkylene group such as

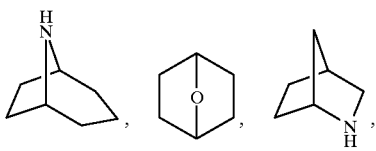

and the like.

The heterocycle groups of this invention can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxallehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The substituted aryl, heteroaryl, and heterocycle groups substituting the heterocycle groups of this invention are substituted with at least one substituent selected from alkyl, alkoxy, carboxy, azido, carboxaldehyde, halo, hydroxy, perfluoroalkyl, and perfluoroalkoxy.

The term "heteroaryl," as used herein, refers to cyclic, aromatic five- and six-membered groups, wherein at least one atom is selected from the group consisting of N, O, and S, and the remaining atoms are carbon. The five-membered rings have two double bonds, and the six-membered rings have three double bonds. The heteroaryl groups of the invention are connected to the parent molecular group through a substitutable carbon or nitrogen in the ring. Heteroaryls are exemplified by furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, triazinyl, and the like. The heteroaryl groups of this invention can be fused to an aryl group, a heterocycle, or another heteroaryl. The heteroaryl groups of this invention can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The substituted aryl, heteroaryl, and heterocycle substituting the heteroaryl groups of this invention are substituted with at least one substituent selected from alkyl, alkoxy, carboxy, azido, carboxaldehyde, halo, hydroxy, perfluoroalkyl, and perfluoroalkoxy.

The term "(heteroaryl)heteroarylsulfonamido" refers to a heteroarylsubstituted heteroaryl group attached to the parent molecule through a sulfonamido group.

The term "hydroxy" refers to —OH.

The term "hydroxyalkyl" refers to a hydroxy group attached to the parent molecule through an alkyl group.

The term "hydroxyalkoxy" refers to an alkoxy group to which ia attached at least one hydroxy group.

The term "hydroxyalkynyl" refers to a hydroxy group attached to the parent molecule through an alkynyl group.

The term "N-protected amino" refers to groups intended to protect an amino group against undesirable reactions during synthetic procedures. Commonly used N-protecting groups are disclosed in Greene, "Protective Groups In Organic Synthesis," (John Wiley & Sons, New York (1981)). Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "O-protected carboxy" refers to a carboxylic acid protecting ester or amide group typically employed to block or protect the carboxylic acid functionality while the reactions involving other functional sites of the compound are performed. Carboxy protecting groups are disclosed in Greene, "Protective Groups in Organic Synthesis" (1981). Additionally, a carboxy protecting group can be used as a prodrug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667.

The term "oxo" refers to (=O).

The term "sulfonamido," as used herein, refers to sulfonyl group appended to the parent molecular moiety through a amino group.

The term "sulfonyl" refers to an —SO$_2$-group.

The term "trialkylsilylalkyl" refers to a trialkyl silyl group attached to the parent molecule through an alkyl group.

The term "pharmaceutically acceptable prodrugs" represents those prodrugs of the compounds of the present invention which are, within the scope of sound medical judgement, suitable for use in contact with the tissues of humans and lower animals with undue toxicity, irritation allergic response, and the like, commensurate with a reasonable benefit/risk ratio, and effective for their intended use, as well as the zwitterionic forms, where possible, of the compounds of the invention.

The term "prodrug" represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt" represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66:1–19 (1977). The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention can exist as stereoisomers where asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Geometric isomers can also exist in the compounds of the present invention. The present invention contemplates the various geometric isomers and mixtures thereof resulting from the arrangement of substituents around a carbon—carbon double bond or arrangement of substituents around a ring. Substituents around a carbon—carbon double bond are designated as being in the Z or E configuration where the term "Z" represents substituents on the same side of the carbon—carbon double bond and the term "E" represents substituents on opposite sides of the carbon—carbon double bond. The arrangement of substituents around a ring are designated as cis or trans where the term "cis" represents substituents on the same side of the plane of the ring and the term "trans" represents substituents on opposite sides of the plane of the ring. Mixtures of compounds where the substitutients are disposed on both the same and opposite sides of plane of the ring are designated cis/trans.

The present invention also provides pharmaceutical compositions, which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Conversely, reduced particle size may maintain biological activity.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposorres or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposoines. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

The compounds of the invention can be prepared by employing reactions shown in the Schemes below. It will be readily apparent to one of ordinary skill in the art that the compounds can be synthesized by substitution of the appropriate reactants in these syntheses, and that the steps themselves can be conducted in varying order. For example, in the schemes below, $R^2$, $R^3$, $R^4$, $R^6$, $R^7$, and $R^8$, whenever convenient, are hydrogen for ease of illustration only. The chemistry employed in the schemes can be conducted when these groups are other than hydrogen. It will also be apparent that protection and deprotection steps can be performed to successfully complete the syntheses of the compounds. A thorough discussion of protecting groups is provided in *Protective Groups in Organic Synthesis,* 3rd edition, John Wiley & Sons, New York (1999).

Abbreviations that have been used in the descriptions of the scheme and the examples that follow are: DMF for N,N-dimethylformamide, DMSO for dimethylsulfoxide; TPAP for tetra-n-propylammonium perruthenate; and THF for tetrahydrofuran.

Scheme I

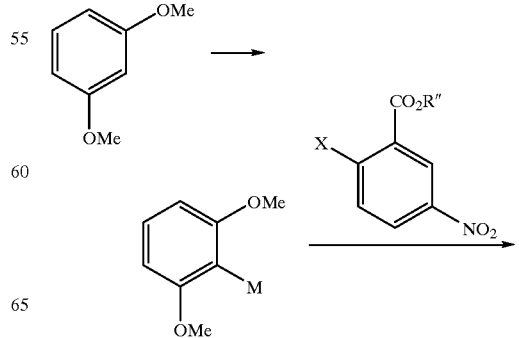

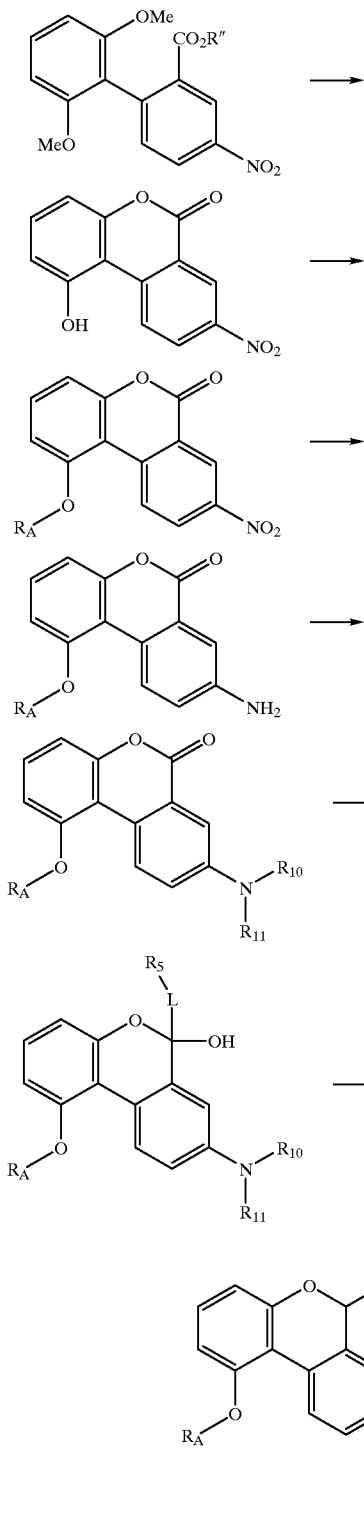

presence of a palladium (II) catalyst or the like) to provide a biaryl coupling product. Cleavage of the methyl ethers (for example using hydrogen bromide, boron tribromide, TMS-iodide, or the like) leads to lactonization to provide a phenolic product which may be reacted with an alkyl halide (for example methyl iodide or benzyl bromide or the like) in the presence of base to provide the corresponding ether. Reduction of the nitro group (for example, using hydrogen gas and a platinum, palladium, or nickel catalyst, or alternatively using a metal like zinc or iron or the like) provides an aniline which can be reacted with an electrophilic reagent (for example, bromine or n-bromosuccinimide) to derivatize the 7-position. This substituent may optionally be exchanged (for example, using a palladium catalyst and an organometallic reagent like tetramethyltin), after the aniline has been protected (for example as a t-butyl carbamate or the like). Functionalization of the C-6 position may be accomplished through the addition of an organometallic reagent (for example n-butyllithium or phenylmagnesium bromide or the like). the, resultant hemiacetal may be reacted in the presence of a Lewis acid (for example boron trialuoride etherate or trimethylsilyl triflate or the like) with a nucleophile (for example allyltrimethylsilane, tetramethyltin, anisole or the like), or alternatively with a reducing agent like triethylsilane or the like. Conversion to the target compound is accomplished through removal of the aniline protecting group (which may have occurred spontaneously in the previous step) and sequential reaction of the resultant aniline with one or more electrophilic reagents (for example, methyl iodide, propionyl chloride, methanesulfonyl chloride, or the like).

Scheme II

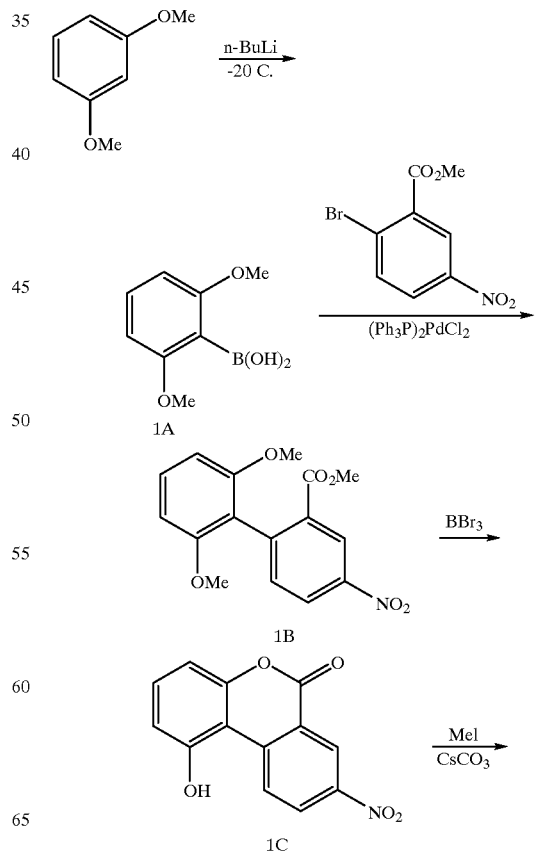

One method for the synthesis of compounds of this invention is described in Scheme I. In this route a derivatized resorcinol dimethyl ether is metallated at the 2-position using a strong base (for example n-butyllithium or s-butyllithium or the like) and transmetallated (for example to provide the organozincate or boronic acid derivative), and is then coupled with an aryl halide (for example in the

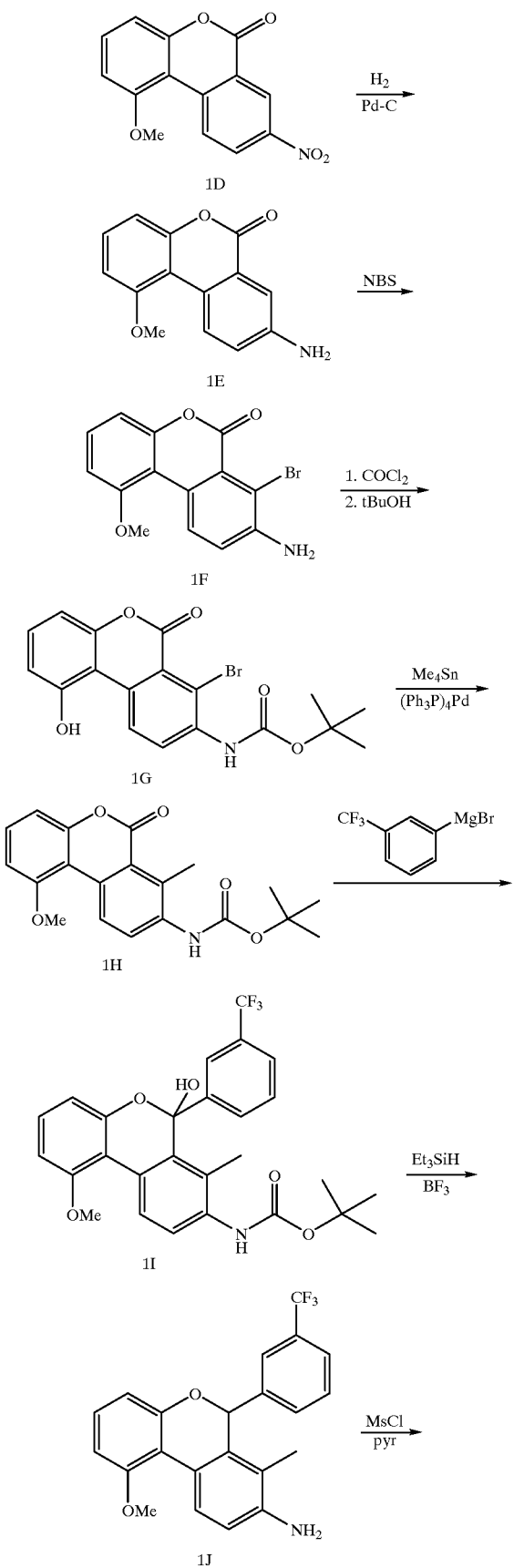

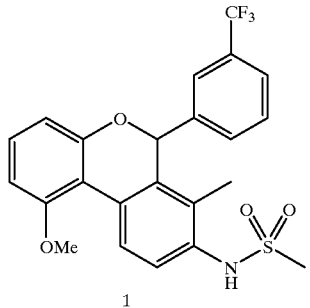

A specific implementation of this generic route is demonstrated in Scheme II. Resorcinol dimethyl ether is metallated with n-butyllithium at −20° C., treated with a trimethylborate and hydrolyzed upon workup with 2M HCl to provide boronic acid 1A. Treatment of 1A with methyl 5-nitro-2-bromobenzoate in the presence of dichloiobis(triphenylphosphine)palladium (II) provides the biaryl coupling product 1B. Demethylation of 1B with BBr$_3$ occurs with spontaneous lactonizationto provide hydroxylactone 1C, which is then treated methyl iodide and cesium carbonate to provide 1D. Conversion of 1D to amine 1E is accomplished using hydrogen gas and a palladium catalyst such as 10% palladium on carbon. Treatment of aniline 1E with N-bromosuccinimide results in regioselective bromination to form 1F, which is protected as its t-butyl carbamate 1G by treatment with triphosgene and t-butyl alcohol. Conversion of 1G to 1H may be accomplished using tetramethyltin in the presence of tetrakis(triphenylphosphine)palladium(0). Introduction of functionalization at the C-6 position is accomplished through addition of 3-trifluoromethylphenylmagnesium bromide to the C-6 carbonyl of 1H to provide 1I, followed by deoxygenation with BF$_3{}^-$OEt$_3$ and triethylsilane to provide the free aniline 1J. Final conversion of 1J to 1 may be accomplished by treatment of aniline 1J with methanesulfonyl chloride to provide sulfonamide 1.

Scheme III

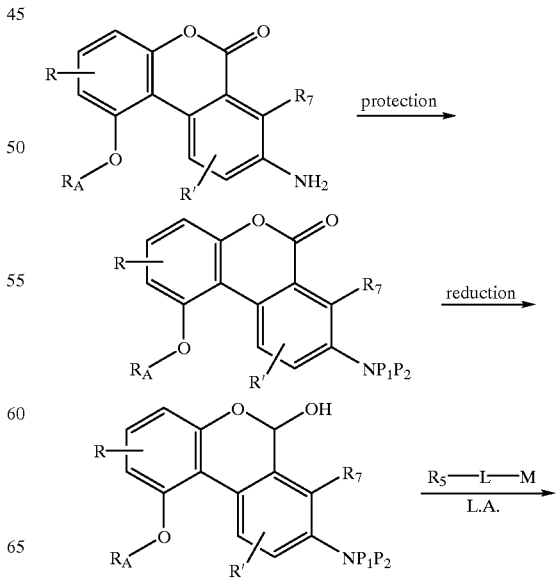

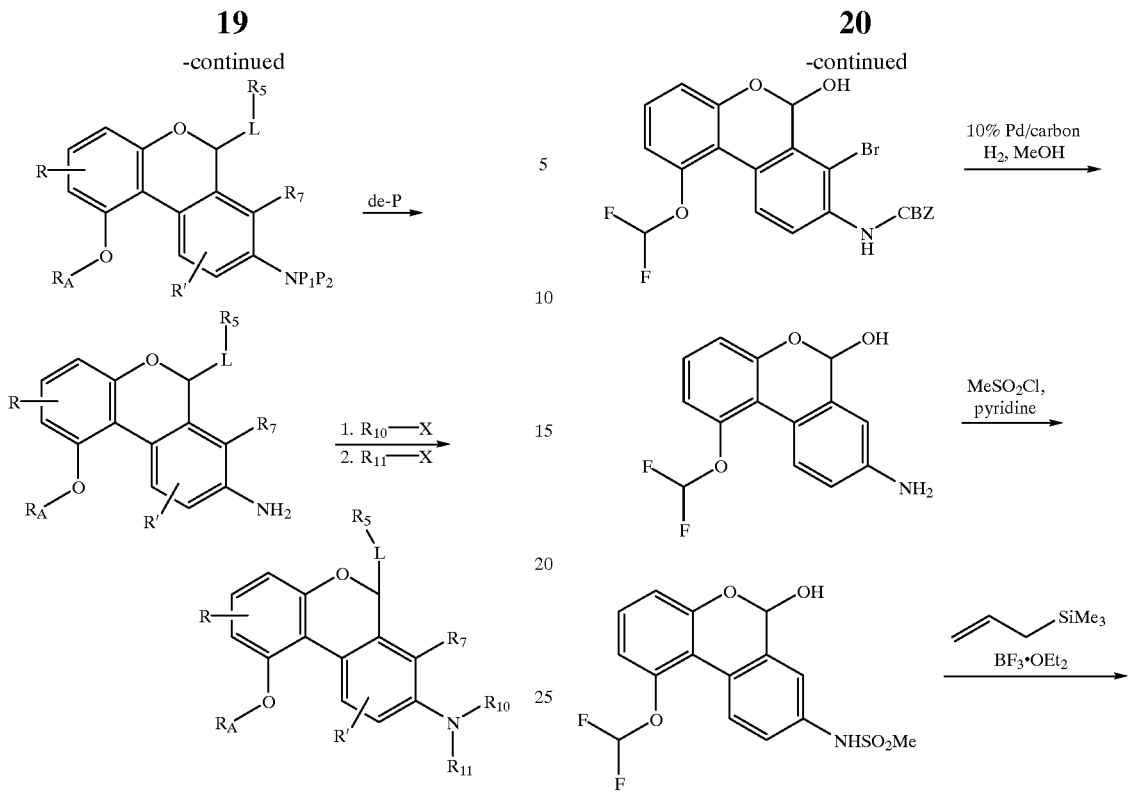

Scheme III demonstrates an alternative synthesis starting from lactone in which the order of the addition and reduction steps are reversed. After protection of the aniline group (for example as a benzyl or tert-butyl carbamate), reduction (for example using sodium borohydride, DIBAL, lithium aluminum hydride, or the like) provides a lactol. Addition of a nucleophile (for example allyltrimethylsilane, phenylmagnesium bromide, anisole, or the like) in the presence of a Lewis acidic catalyst (for example boron trifluoride etherate, zinc chloride, trimethylsilyl triflate, or the like) provides the corresponding cyclic ether, which may be deprotected using trifluoroacetic acid or hydrogenation over a palladium or platinum catalyst or the like) and reacted with a series of electrophilic reagents (for example methanesulfonyl chloride or acetyl chloride or benzyl bromide or the like) to provide the desired analog. Alternatively the nitrogen substituents may be replaced prior to the addition of the C-6 substituent.

Scheme IV

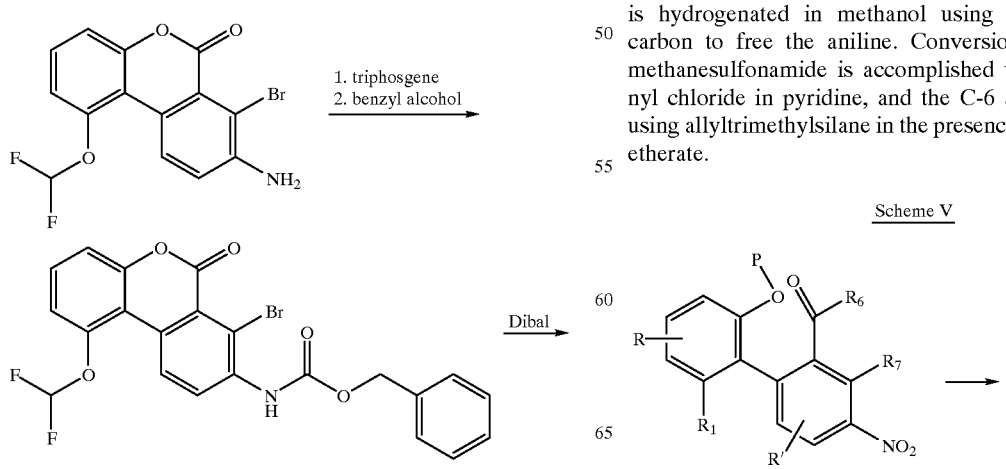

The generic synthesis described above is specifically exemplified in Scheme IV. An intermediate bromoaniline, prepared as described in Schemes I and II, is protected as the corresponding benzyl carbamate through the action of phosgene followed by addition of benzyl alcohol. DIBAL reduction of the lactone provides the corresponding lactol, which is hydrogenated in methanol using 10% palladium-on-carbon to free the aniline. Conversion of the aniline to methanesulfonamide is accomplished using methanesulfonyl chloride in pyridine, and the C-6 allyl group is added using allyltrimethylsilane in the presence of boron trifluoride etherate.

Scheme V

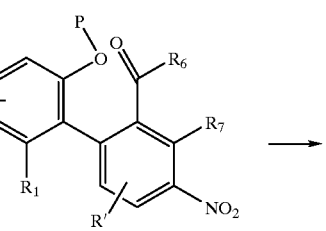

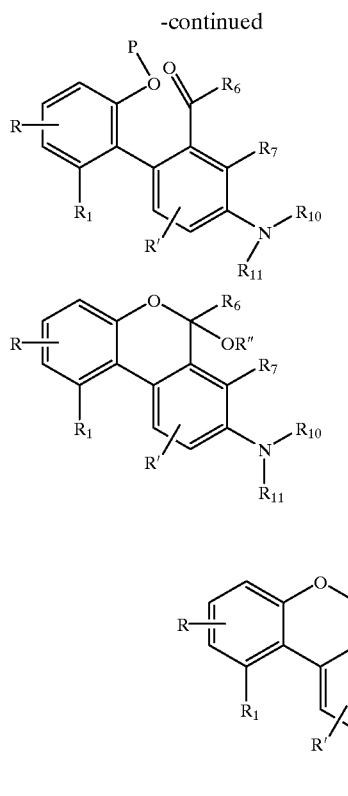

Alternatively (Scheme V) the addition of the nucleophile may occur after final modification of aniline nitrogen. Thus, removal of the phenolic protecting group results in cyclization to a lactol, which is reacted with a nucleophile under Lewis acidic conditions to provide product.

Scheme VI

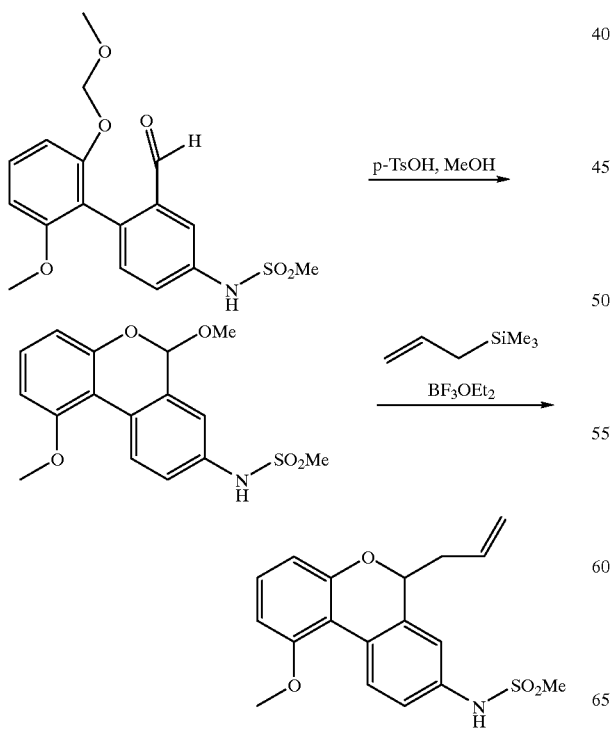

In a specific exemplification, the MOM-aldehyde shown in Scheme VI is deprotected with p-toluenesulfonic acid in methanol to provide a lactol methyl acetal. Upon treatment with allyltrimethylsilane in the presence of boron trifluoride etherate, this acetal is converted to the corresponding C6-allyl derivative.

Scheme VII

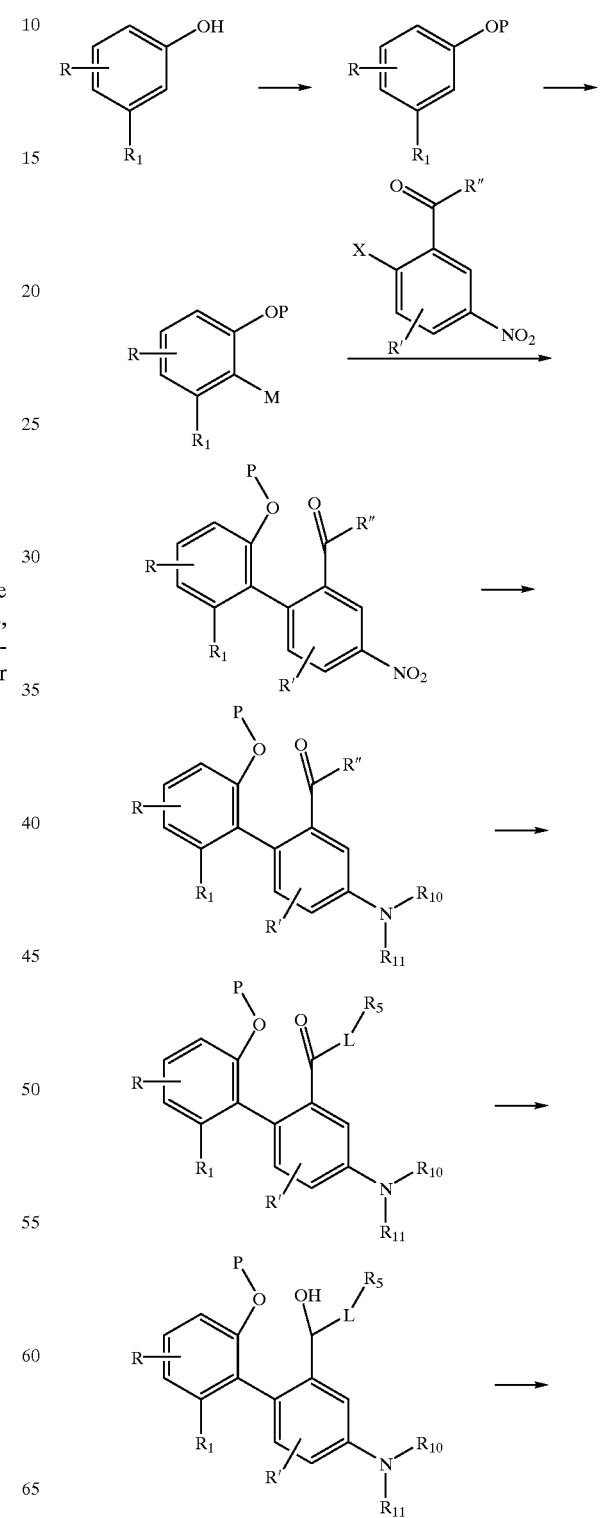

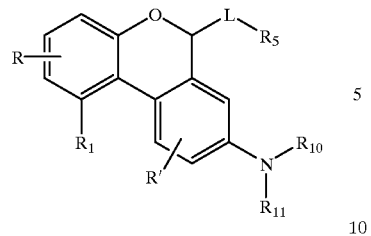

Yet another route to the compounds of the present invention is described generically in Scheme VII. A substituted phenol is protected (for example, as a methyl ether, trimethylsilyl ether, or methoxymethyl ether or the like), then is metallated and coupled with an aromatic halide as described in Scheme I. After reduction and derivatization of the nitro group as described previously, the B-ring carbonyl group is modified to provide an aldehyde or ketone (for example, through reduction using DIBAL and oxidation using TPAP arid N-methylmorpholine oxide to generate an aldehyde, or addition of an organometallic reagent like phenyllithium to generate a ketone). Addition of an organometallic reagent (for example, n-butyllithium, or 3-allyloxyphenylmagnesium bromide, or the like) produces an alcohol. After deprotection (for example, using HBr in acetic acid, or aqueous or alcoholic HCl, or trimethylsilyliodide, or the like) the resultant phenol is cyclized to produce the desired analog under acidic conditions (for example, upon treatment with p-toluenesulfonic acid in toluene, or boron trifluoride etherate, or trimethylsilyl triflate, or the like).

Scheme VIII

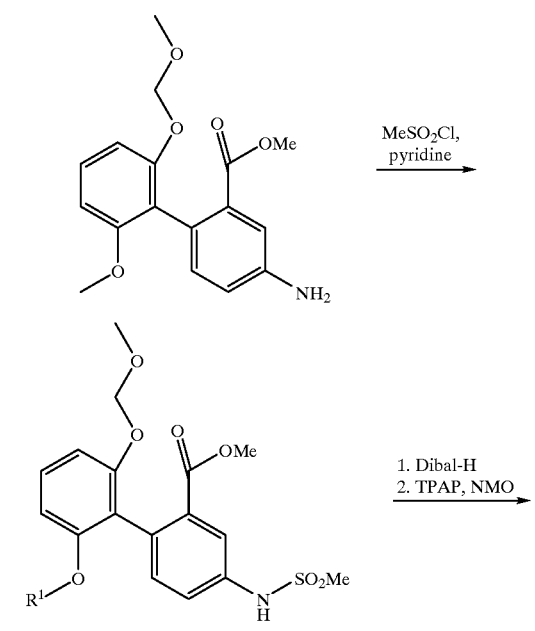

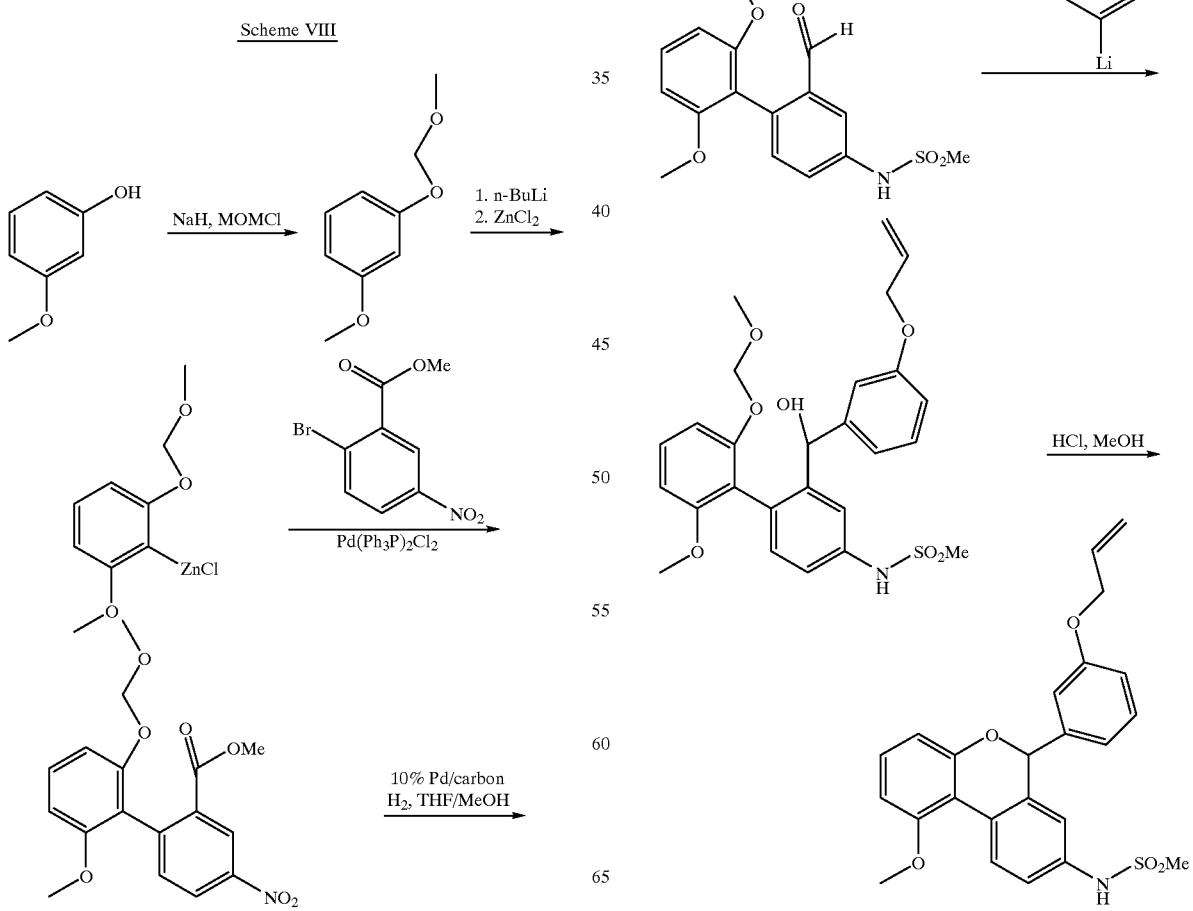

Scheme VIII demonstrates a specific synthesis according to Scheme VII. 3-Methoxyphenol is converted to its methoxyethyl ether through treatment with MOM-Cl in the presence of sodium or cesium carbonate. Metallation with n-butyllithium at low temperature, followed by transmetallation with zinc chloride and palladium-mediated coupling with methyl 2-bromo-4-nitrobenzoate, provides the biaryl derivative. The nitro group is reduced using hydrogen gas in the presence of a 10% palladium-on-carbon catalyst and sulfonylated using methanesulfonyl chloride in pyridine; the ester is reduced to an alcohol with DIBAL and oxidized back to the aldehyde using tetrapropyl ammonium perruthenate (TPAP) with N-methylmorpholine as cooxidant. Addition of 3-methoxyethoxyphenyllithium provides an alcohol which may be cyclized by treatment with HCl in methanol to provide the desired analog.

Scheme IX

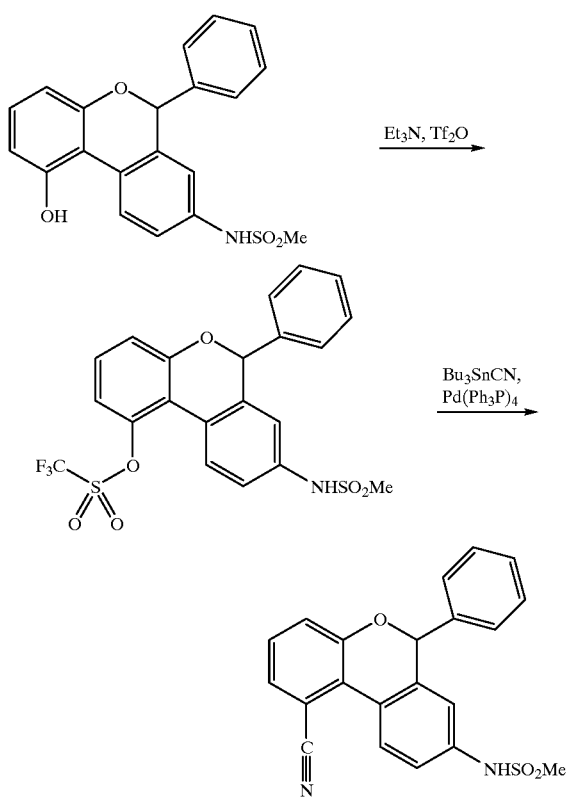

Compounds of the present invention may also be prepared through modification of other compounds of the present invention. Thus, as shown in Scheme IX, the phenol derivative may be reacted with trifluoromethansulfonic anhydride to produce a phenyl triflate, which may be coupled with a variety of nucleophiles under palladium catalysis. One example is tributyltin-cyanide, which produces the corresponding nitrile derivative.

The invention will now be described in connection with preferred embodiments of the Schemes, which are not intended to limit its scope. On the contrary, the invention covers all alternatives, modifications, and equivalents which are included within the scope of the claims. Thus, the following examples show an especially preferred practice of the invention, it being understood that the examples are for the purposes of illustration of certain preferred embodiments and are presented to provide what is believed to be the most useful and readily understood description of its procedures and conceptual aspects.

EXAMPLE 1

(1-methoxy-6-(3-trifluoromethyl)phenyl-7-methyl-6H-dibenzo(b,d)pyran-8-yl)methanesulfonamide

EXAMPLE 1A (2,6-dimethoxy)phenylboronic acid

A solution of 1,3-dimethoxybenzene (33.2 g, 240 mmol) in hexanes (20 mL) at −20° C. was treated sequentially with n-butyllithium (100 mL of a 2.4M solution in hexanes, 240 mmol) and N,N,N',N'-tetramethylethylenediamine (1.81 mL, 12 mmol), stirred for 1.5 hours, cooled to −78° C., treated with triisopropylborate (60.9 mL, 264 mmol) in diethyl ether (60 mL) over 1.5 hours with additional diethyl ether (150 mL) added to maintain stirring, stirred at 23° C. for 2 hours, poured into ice (150 mL) and 3M HCl (150 mL), and extracted with ethyl acetate. The extract was dried ($Na_2SO_4$), filtered, and concentrated, during which a white solid precipitated. The solid was collected by filtration and washed with hexanes to provide the desired compound, which used without further purification. MS (DCI/$NH_3$) m/z 200 $(M+NH_4)^+$.

EXAMPLE 1B methyl 5-nitro-2-(2,6-dimethoxyphenyl)-benzoate

A mixture of Example 1A, methyl 5-nitro-2-bromobenzoate (25.8 g, 99.2 mmol), (21.7 g, 119 mmol), cesium carbonate (97.1 g, 298 mmol), and dichlorobis(triphenylphosphine)palladium(II) (3.5 g, 5.0 mmol) in DMF (300 mL) was stirred for 24 hours at 80° C., cooled to 23° C., treated with water (600 mL), and extracted with ethyl acetate. The extract was dried ($Na_2SO_4$), filtered, and concentrated, during which a light yellow solid precipitated. The mixture was placed in a freezer (−20° C.) for 2 hours and filtered to provide the desired compound. MS (DCI/$NH_3$) m/z 318 $(M+H)^+$ and 335 $(M+NH_4)^+$.

EXAMPLE 1C 1-hydroxy-8-nitro-dibenzo(b,d)pyran-6-one

A solution of of Example 1B (11.1 g, 35.1 mmol) in dichloromethane (60 mL) at −78° C. was treated with boron tribromide (25.0 g, 99.8 mmol), warmed to 23° C. for 1 hour, recooled to −78° C., treated with methanol (100 mL), warmed to 0° C., and filtered. The resulting, solid was recrystallized from methanol to provide the desired compound. MS (DCI/$NH_3$) m/z 275 $(M+NH_4)^+$.

EXAMPLE 1D 1-methoxy-8-nitro-dibenzo(b,d)pyran-6-one

A mixture of Example 1C (10.7 g, 41.6 mmol) and cesium carbonate (20.0 g, 61.4 mmol) in DMF (130 mL) at 23° C. was treated with methyl iodide (22.8 g, 161 mmol), stirred for 4 hours, treated with water, and extracted with 1:1 ethyl acetate/hexane. The extract was concentrated, and the concentrate was filtered, washed with water (100 mL), and dried under vacuum to provide the desired compound. MS (DCI/$NH_3$) m/z 289 $(M+NH_4)^+$.

EXAMPLE 1E 1-methoxy-8-amino-dibenzo(b,d)pyran-6-one

A suspension of Example 1D (11.2 g, 41.3 mmol) in dioxane (400 mL) at 23° C. was treated with 10% palladium on carbon (580 mg), heated at 65° C. under hydrogen gas (balloon) for 60 hours, filtered through diatomaceous earth (Celite®) while hot, and concentrated, during which a precipitate formed. The precipitate was filtered and dried under vacuum to provide the desired compound. Concentration of the mother liquor to half of its original volume afforded a second crop of desired compound. MS (DCI/NH$_3$) m/z 242 (M+H)$^+$ and 259 (M+NH$_4$)$^+$.

EXAMPLE 1F 1-methoxy-7-bromo-8-amino-dibenzo(b,d)pyran-6-one

To a solution of Example 1E (3.0 g, 12.5 mmol) in dioxane (300 mL) and THF (100 mL) at 23° C. was slowly added pyridinium tribromide (4.0 g, 12.5 mmol) over 15 minutes. The mixture was stirred for 14 hours, treated with water (400 mL), and extracted with ethyl acetate. The extract was dried (Na$_2$SO$_4$), filtered, treated with charcoal (2 g), filtered through diatomaceous earth (Celite®) and concentrated to provide the desired compound. MS (DCI/NH$_3$) m/z 338 (M+NH)$^+$.

EXAMPLE 1G 1-methoxy-7-bromo-8-(tert-butylcarbamyl)-dibenzo(b,d)pyran-6-one

A suspension of Example 1F (1.8 g, 5.7 mmol) and triphosgene (0.74 g, 2.5 mmol) in THF (300 mL) was heated at reflux for 3 hours, concentrated, and placed under high vacuum for 1 hour. The concentrate was dissolved in THF (40 mL) and tert-butyl alcohol (250 mL), and the resulting solution was treated with triethylamine (0.58 g, 5.7 mmol), heated at 50° C. for 2 hours, and concentrated. The concentrate was purified by flash column chromatography on silica gel with 20% ethyl acetate/hexanes to provide the desired compound. MS (DCI/NH$_3$) m/z 437 (M+NH$_4$)$^+$.

EXAMPLE 1H 1-methoxy-7-methyl-8-(tert-butylcarbamyl)-dibenzo(b,d)pyran-6-one

A solution of Example 1G (1.0 g, 2.4 mmol) and (1,3-bis(diphenylphosphino)ferrocene)palladium (II) chloride-dichloromethane (220 mg, 0.27 mmol) in 1-methyl-2-pyrrolidinone (2 mL) was treated with isopropenyltrimethylstannane (0.98 g, 4.8 mmol), heated at 80° C. for 24 hours, cooled to room temperature, treated with saturated potassium fluoride, and extracted with ethyl acetate. The extract was washed with brine, dried (MgSO$_4$), filtered, and concentrated. The concentrate was purified by flash column chromatography on silica gel with 5–15% ethyl acetate/hexanes to provide the desired compound. MS (DCI/NH$_3$) m/z 373 (M+NH$_4$)$^+$.

EXAMPLE 1I (1-methoxy-6-hydroxy-6-(3-trifluoromethyl)phenyl-7-methyl-dibenzo(b,d)pyran-8-yl)tert-butyl carbamate A solution of Example 1H (0.29 g, 0.81 mmol) in THF (50 mL) at −30° C. was treated with a solution of 3-trifluoromethylphenylmagnesium bromide in diethyl ether (0.4M, 12 mL, 4.9 mmol), warmed to 0° C., stirred for 20 hours, treated with saturated NH$_4$Cl, warmed to 25° C., and extracted with ethyl acetate. The extract was dried (Na$_2$SO$_4$), filtered, and concentrated. The residue was purified by flash chromatography on silica gel with 20% ethyl acetate/hexanes to provide the desired compound.

EXAMPLE 1J (1-methoxy-6-(3-trifluoromethyl)phenyl-7-methyl-6H-dibenzo(b,d)pyran-8-yl)amine A solution of Example 1I (0.1 g, 0.20 mmol) in dichloromethane (30 mL) at 0° C. was treated with triethylsilane (0.23 g, 2.0 mmol) and BF$_3$OEt$_2$ (0.28 g, 2.0 mmol), warmed to room temperature, stirred for 16 hours, and treated with saturated NaHCO$_3$ to provide two layers. The laters were separated, and the organic layer was dried (Na$_2$SO$_4$), filtered, and concentrated. The concentrate was purified by flash chromatography on silica gel with 20% ethyl acetate/hexanes to provide the desired compound. MS (DCI/NH$_3$) m/z 386 (M+H)$^+$.

EXAMPLE 1K (1-methoxy-6-(3-trifluoromethyl)phenyl-7-methyl-6H-dibenzo(b,d)pyran-8-yl)methanesulfonamide A solution of Example 1J (0.025 g, 0.065 mmol) in dichloromethane (7 mL) at 0° C. was treated with methanesulfonyl chloride (6 µL, 0.075 mmol), warmed to room temperature, stirred for 14 hours, and treated with saturated NaHCO$_3$ to provide two layers. The organic layer was dried (Na$_2$SO$_4$), filtered, and concentrated. The residue was purified by flash chromatography on silica gel with 42% ethyl acetate/hexanes to provide the desired compound. mp 217–218° C.; MS (DCI/NH$_3$) m/z 464 (M+H)$^+$ and 481 (M+NH$_4$)$^+$; $^1$H NMR (300 MHz, DMSO-d$_6$) δ 9.25 (s, 1H), 8.3 (d, 1H), 7.61 (d, 1H), 7.55 (s, 1H), 7.50 (t, 1H), 7.41 (d, 1H), 7.28 (d, 1H), 7.12 (t, 1H), 6.7 (s, 1H), 6.69 (dd, 1H), 6.6 (dd, 1H), 3.85 (s, 3H), 3.02 (s, 3H), 2.2 (s, 3H).

EXAMPLE 2

1-methoxy-6-phenyl-7-bromo-6H-dibenzo(b,d)pyran-8-yl)methanesulfonamide

Example 1H and phenyl magnesium bromide were processed as described in Example 1I–K to provide the titled compound. MS (DCI/NH$_3$) m/z 477 (M+NH$_4$)$^+$; $^1$H NMR (300 MHz, DMSO-d$_6$) δ 9.51 (s, 1H), 8.43 (d, J=9 Hz, 1H), 7.57 (d, J=9 Hz, 1H), 7.27–7.12 (m, 6H), 6,70 (d, J=7 Hz, 1H), 6.62–6.59 (m, 2H), 3.87 (s, 3H), 3.12 (s, 3H).

EXAMPLE 3

(1-methoxy-6-(3-trifluoromethyl)phenyl-7-vinyl-6H-dibenzo(b,d)pyran-8-yl)methanesulfonamide Example 1G and tetravinyl tin were processed as described in Example 1H–K to provide the titled compound. MS (DCI/NH$_3$) m/z 493 (M+NH$_4$)$^+$; $^1$H NMR (300 MHz, DMSO-d$_6$) δ 9.12 (s, 1H), 7.37 (d, J=8 Hz, 1H), 7.59 (d, J=8 Hz, 1H), 7.52–7.45 (m, 3H), 7.30 (d, J=8 Hz, 1H), 7.11 (t, J=8 Hz, 1H), 6.86 (dd, J=18, 12 Hz, 1H), 6.68 (d, J=8 Hz, 1H), 6.57 (d, J=8 Hz, 1H), 6.55 (s, 1H), 5.51 (dd, J=12, 1 Hz, 1H), 5.03 (dd, J=18, 1 Hz, 1H), 3.86 (s, 3H), 3.03 (s, 3H).

EXAMPLE 4

8-Amino-7-bromo-1-difluoromethoxy-6-phenyl-6H-dibenzo[b,d]pyran

EXAMPLE 4A

8-Nitro-1-difluoromethoxy-6H-dibenzo[b,d]pyran-6-one

A solution of Example 1C (6.63 g, 25.8 mmol), K2CO3 (10.93 g) and CHClF$_2$ (22 g) in dimethylformamide (77 mL)

were heated in an autoclave at 85° C. for 20 minutes. The mixture was concentrated under reduced pressure, diluted with aqueous HCl (1M) and the resulting brown solid was filtered. The solid was recrystallized from $CHCl_3$ to provide the titled compound (5.195 g, 66%).

EXAMPLE 4B

8-Amino-1-difluoromethoxy-6H-dibenzo[b,d]pyran-6-one

The solution of Example 4A (6.56 g.) was suspended in. dioxane (250 mL) and hydrogenated over 10% Pd/C at 4 atmospheres $H_2$ at 50° for 3 hours. The solvent was removed under reduced pressure, diethylether was and the resulting solid filtered to provide the titled compound (5.55 g, 94%).

EXAMPLE 4C

8-Amino-7-bromo-1-difluoromethoxy-6H-dibenzo[b,d]pyran-6-one

Example 4B (4.026 g.) was brominated as described in example 1F to provide the titled compound (3.82 g, 74% yield).

EXAMPLE 4D

8-Amino-7-bromo-1-difluoromethoxy-6-hydroxy-6-phenyl-6H-dibenzo[b,d]pyran

Phenyllithium (31 ml of 1,8 M. in cyclohexane, 55.62 mmole) was added to Example 4C (2.50 g, 7.022 mmol) in THF (150 mL) at −78° C. The mixture was stirred 80 minutes at −78° C., acetic acid (12 mL) was added, the mixture was warmed to 25°, water (50 mL) was added and the mixture was extracted with ethyl acetate. The combined ethyl acetate was dried ($Na_2SO_4$), filtered and concentrated under reduced pressure to provide the titled compound (2.21 g).

EXAMPLE 4

8-Amino-7-bromo-1-difluoromethoxy-6-phenyl-6H-dibenzo[b,d]pyran

Example 4D (2.21 g.) was reduced with triethylsilane as described in example 1J to provide the titled compound (1.19 g, 56%). $^1$H NMR (300 MHz, $CDCl_3$) δ 4.31 (br s, 2H), 6.41 (t, J=75 Hz, 1H, $CHF_2$), 6.60 (s, 1H), 6.68 (dd, J=9 Hz, 1 Hz, 1H), 6.79 (dd, J=9 Hz, 1 Hz, 1H), 6.89 (d, J=9 Hz, 1H), 7.00 (t, J=9 Hz, 1H), 2.20–7.25 (m, 5H), 8.13 (d, J=9 Hz, 1H); MS (APCI) m/e 418, 420 (M+H).

EXAMPLE 5

N-(1-methoxy-6-phenyl-6H-dibenzo[b,d]pyran-8-yl)methanesulfonamide

EXAMPLE 5A

N-methoxy-N-methyl-2-bromo-5-nitrobenzamide

2-Bromo-5-nitrobenzoic acid (3.62 g., 14.71 mmole) and thionyl chloride (11 mL) in dichloroethane (30 mL) was refluxed for 90 min, concentrated under reduced pressure, more dichloroethane was added and again concentrated to remove the excess thionyl chloride. The residue was dissolved in dichloroethane (30 mL) and to this was added methoxymethylamine HCl. (2.87 g, 29.42 mmole) and pyridine (8 mL). The mixture was stirred 2 hours, concentrated under reduced pressure. Toluene was added and the solution re-concentrated to remove the excess pyridine. The residue was dissolved in chloroform, and then washed with aqueous HCl (1M), water, aqueous $KHCO_3$, dried ($Na_2SO_4$), filtered and concentrated under reduced pressure to provide the titled compound (3.63 g, 85%)

EXAMPLE 5B

N-methoxy-N-methyl-4-nitro-2'-methoxymethoxy-6'-methoxy-biphenyl-2-carboxamide

Butyllithium (8.28 ml. of 2.5M in hexane, 20.69 mmole) was added to a solution of 1-methoxy-3 methoxymethoxy benzene (3.62 g., 21.55 mmole, (T. Kaufman, R. Srivastava, R. Sindelar, J. Med. Chem. 1995, 38, 1437–1445) in. THF (15 mL) at −30° C. The solution was stirred at ambient temperature for 1 hour, cooled to at 0° C. and anhydrous zinc chloride beads (3.5 g, 25.67 mmole) added. The mixture was stirred for 2 hours at 25°. Then a solution of N-methoxy-N-methyl-2-bromo-5-nitrobenzamide (5.00 g, 17.24 mmole) dissolved in THF (20 mL) was added. Bis(triphenylphosphine) palladium dichloride (600 mg.) was added and the solution was stirred at 65° C. for 15 hours. After cooling, chloroform was added and the solution stirred with aqueous $KHCO_3$. The precipitated zinc salts were filtered, the water layer removed and the organic layer dried ($Na_2SO_4$), filtered concentrated under reduced pressure and the residuepurified on silica gel eluting with 8% ethyl acetate in $CH_2Cl_2$ to provide the titled compound (5.68 g, 88% yield).

EXAMPLE 5C

N-methoxy-N-methyl-4-amino-2'-methoxymethoxy-6'methoxy-biphenyl-2-carboxamide

A solution of Example 5B (5.67 g.) was dissolved in methanol (120 mL) and hydrogenated at 4 atm with 10% Pd/C (0.60 g) for 1 hour. The catalyst was removed by filtration and the solution concentrated to give the titled compound (5.44 g).

EXAMPLE 5D

4-Amino-2-benzoyl-2'-methoxymethoxy-6'-methoxy-biphenyl

A solution of Example 5C (5.44 g., 15.72 mmole) in THF (70 mL) and cooled to −5° C. was treated with of 1.8M phenyllithium in ether-cyclohexane (52.4 mL, 94.33 mmol). The mixture was stirred at −5° C. for 1 hour, cooled to −78° and a solution of aqueous $KHCO_3$ was added rapidly. The mixture was extracted with ether, which was combined, dried ($Na_2SO_4$), filtered, concentrated under reduced pressure and purified on silica gel eluting with 8% ethyl acetate in $CH_2Cl_2$ to provide the titled compound (4.84 g, 85% yield).

EXAMPLE 5E

4-Amino-2(alpha-hydroxybenzyl)-2'-methoxymethoxy-6'-methoxy-biphenyl

The compound of Example 5D (4.84, 13.31 mmol) in ethanol (45 mL) was heated at 65° C. with $NaBH_4$(2.03 g, 53.42 mmol). After 1 hour Chloroform and aqueous NaCl was added. The organic phase was separated, washed with aqueous $KHCO_3$, dried ($Na_2SO_4$), filtered and the solvent removed under reduced pressure to provide the titled compound (3.844 g, 80%).

EXAMPLE 5F

8-Amino-1-methoxy-6-phenyl-6H-dibenzo[b,d] pyran

The compound of Example 5E (3.449 g., 9.45 mmole) was dissolved in methanol (80 mL) containing 4N HCl in dioxane (80 mL)was stirred for 16 hours. The mixture was concentrated under reduced pressure, dissolved in chloroform washed with aqueous $KHCO_3$, dried ($Na_2SO_4$), filtered and reduced under pressure. The residue was dissolved in toluene (450 mL), toluenesulfonic acid $H_2O$ (7.18 g.) was added and the solution was heated at 85° C. for 30 minutes. The mixture was cooled, washed with aqueous $KHCO_3$, dried ($Na_2SO_4$), filtered and concentrated under reduced pressure. The residue was purified on silica eluting with $CH_2Cl_2$ to provide the titled compound (2.49 g, 87%).

EXAMPLE 5G

N-(1-methoxy-6-phenyl-6H-dibenzo[b,d]pyran-8-yl) methanesulfonamide

The solution of Example 5F (200 mg. 0.66 mmole), pyridine (300 mg) and methanesulfonyl chloride (227 mg., 2.00 mmole) in chloroform (3 mL) was stirred for 1 hour, washed with aqueous HCl (1M), dried ($Na_2SO_4$), filtered and concentrated under reduced pressure. Toluene was added and then concentrated. Heptane was added and concentrated under reduces pressure to provide the titled compound (199 mg. 80%). 1H NMR (300 MHz, $CDCl_3$) δ 2.95 (s, 3H), 3.94 (s, 3H), 6.00 (s, 1H), 6.30 (s, 1H), 6.61 (d, J=2 Hz, 1H), 6.62 (dd, J=10 Hz, 2 Hz, 1H), 6.69 (dd, J=9 Hz, 1 Hz, 1H), 7.15 (t, J=9 Hz, 1H), 7.25 (dd, J=9 Hz, 2 Hz, 1H), 7.32–7.39 (m, 5H), 8.45 (d, J=9 Hz, 1H); MS (APCI) m/e 382 (M+H), 399 (M+$NH_4$).

EXAMPLE 6

(1-methoxy-6-phenyl-6H-dibenzo(b,d)pyran-8-yl) benzenesulfonamide

A solution of Example 5F (50 mg. 0.16 mmole), pyridine (75 mg) and benzenesulfonyl chloride (86 mg., 0.5 mmole) in chloroform (1 mL) was stirred for 1 hour, washed with aqueous HCl (1M), dried ($Na_2SO_4$), filtered and concentrated under reduced pressure. The concentrate was purified by reverse-phase HPLC with $CH_3CN$/water to provide the titled product. MS (ESI(-)Q1MS) m/z 442 (M-H)$^-$; $^1$H NMR (300 MHz, DMSO-$d_6$) δ 10.38 (s, 1H), 8.22 (d, J=9 Hz, 1H), 7.70–7.50 (m, 5H), 7.36–7.29 (m, 3H), 7.16–7.06 (m, 4H), 6.76 (s, 1H), 6.69 (d, J=8 Hz, 1H), 6.62(d, J=8 Hz, 1H), 6.11 (s, 1H), 3.85 (s, 3H).

EXAMPLE 7

(1-methoxy-6-phenyl-6H-dibenzo(b,d)pyran-8-yl) ethanesulfonamide

Example 5F and ethylsulfonyl chloride were processed as described in Example 6 to provide the titled compound. MS (ESI(-)Q1MS) m/z 394 (M-H)$^-$; $^1$H NMR (300 MHz, DMSO-$d_6$) δ 9.88 (s, 1H), 8.33 (d, J=9 Hz, 1H), 7.35–7.22 (m, 6H), 7.14 (t, J=8 Hz, 1H), 6.90 (d, J=2 Hz, 1H), 6.73 (d, J=8 Hz, 1H), 6.63 (d, J=8 Hz, 1H), 6.21 (s, 1H), 3.88 (s, 3H), 3.10 (q, J=7 Hz, 2H), 1.17 (t, J=7 Hz, 3H).

EXAMPLE 8

(1-methoxy-6-phenyl-6H-dibenzo(b,d)pyran-8-yl) isopropanesulfonamide

Example 5F and isopropylsulfonyl chloride were processed as described in Example 6 to provide the titled compound. MS (ESI(-)Q1MS) m/z 408 (M-H)$^-$; $^1$H NMR (300 MHz, DMSO-$d_6$) δ 9.87 (br s, 1H), 8.32 (d, J=9 Hz, 1H), 7.37–7.22 (m, 6H), 7.15 (t, J=8 Hz, 1H), 6.90 (d, J=2 Hz, 1H), 6.73 (d, J=8 Hz, 1H), 6.64(d, J=8 Hz, 1H), 6.21 (s, 1H), 3.88 (s, 3H), 3.06 (m, 1H), 1.22 (d, J=7 Hz, 6H).

EXAMPLE 9

(1-methoxy-6-phenyl-6H-dibenzo(b,d)pyran-8-yl)- (2-thienyl)sulfonamide

Example 5F and 2-thiophenesulfonyl chloride were processed as described in Example 6 to provide the titled compound. MS (ESI(-)Q1MS) m/z 448 (M-H)$^-$; $^1$H NMR (300 MHz, DMSO-$d_6$) δ 10.5 (s, 1H), 8.29 (dd, J=9 Hz, 2 Hz, 1H), 7.92 (m, 1H), 7.47 (m, 1H), 7.37–7.30 (m, 3H), 7.19–7.10 (m, 5H), 6.82(s, 1H), 6.71 (d, J=8 Hz, 1H), 6.64(d, J=8 Hz, 1H), 6.18 (s, 1H), 3.87 (s, 3H).

EXAMPLE 10

(1-methoxy-6-phenyl-6H-dibenzo(b,d)pyran-8-yl)- (N,N-dimethyl)sulfonylurea

Example 5F and N,N-dimethylaminosulfonyl chloride were processed as described in Example 6 to provide the titled compound. MS (ESI(-)Q1MS) m/z 409 (M-H)$^-$; $^1$H NMR (300 MHz, DMSO-$d_6$) δ 9.96 (s, 1H), 8.30 (d, J=9 Hz, 1H), 7.37–7.25 (m, 5H), 7.19 (dd, J=8 Hz, 2 Hz, 1H), 7.14 (t, J=8 Hz, 1H), 6.82 (d, J=2 Hz, 1H), 6.73 (d, J=8 Hz, 1H), 6.63(d, J=8 Hz, 1H), 6.18 (s, 1H), 3.89 (s, 3H), 2.65 (s, 6H).

EXAMPLE 11

(1-methoxy-6-phenyl-6H-dibenzo(b,d)pyran-8-yl)- (2-phenyl-E-ethenyl) sulfonamide Example 5F and trans-β-styrenesulfonyl chloride were processed as described in Example 6 to provide the titled compound. MS (ESI(-)Q1MS) m/z 468 (M-H)$^-$; $^1$H NMR (300 MHz, DMSO-$d_6$) δ 10.20 (s, 1H), 8.30 (d, J=9 Hz, 1H), 7.69, (m, 2H), 7.48–7.39 (m, 4H), 7.29–7.10 (m, 8H), 6.90 (d, J=2 Hz, 1H), 6.71(d, J=8 Hz, 1H), 6.62 (d, J=8 Hz, 1H), 6.20 (s, 1H), 3.88 (s, 3H).

EXAMPLE 12

(1-methoxy-6-phenyl-6H-dibenzo(b,d)pyran-8-yl) acetamide

To Example 5F (30.3 mg, 0.1 mmole) in dichloromethane (2 mL) was added diisopropylethylamine on resin (40 mg, 0.2 mmoles) followed by acetyl chloride (11.8 mg, 0.15 mmoles). The reaction mixture was shaken at room temperature overnight. The resin was filtered off and washed with DCM (2×1 mL). Filtrates pooled and concentrated in vacuo. Obtained 25.6 mg (74%) of pure product. $^1$H-NMR (500 MHz, DMSO-$d_6$) δ 10.00 (s, 1H), 8.30 (d, J=8.8 Hz, 1H), 7.60 (dd, J=8.7, 2.2 Hz, 1H), 7.31 (m, 6H), 7.13 (t, J=8.3 Hz, 1H), 6.72 (d, J=7.8 Hz, 1H), 6.62 (dd, J=8.1, 0.9 Hz, 1H), 6.16 (s, 1H), 3.89 (s, 3 H), 2.02 (s, 3H); MS (ESI+) (M+H)$^+$ at m/e 346.

EXAMPLE 13

(1-methoxy-6-phenyl-6H-dibenzo(b,d)pyran-8-yl) propionamide

Example 5F and propionyl chloride were processed as described in Example 12 to provide the titled compound.

¹H-NMR (500 MHz, DMSO-d₆) δ 9.92 (s, 1H), 8.31 (d, J=8.8 Hz, 1H), 7.61 (dd, J=8.7, 2.2 Hz, 1H), 7.32 (m, 6H), 7.13 (t, J=8.1 Hz, 1H), 6.72 (d, J=8.4 Hz, 1H), 6.62 (dd, J=8.0, 1.0 Hz, 1H), 6.16 (s, 1H), 3.89 (s, 3H), 2.29 (dd, J=15.3, 7.5 Hz, 2H), 1.05 (t, J=7.4 Hz, 3H);. MS (ESI+) (M+H)⁺ at m/e 360.

EXAMPLE 14

1-methoxy-6-phenyl-6H-dibenzo(b,d)pyran-8-yl)-(2-methyl)propionamide

Example 5F and isobutyryl chloride were processed as described in Example 12 to provide the titled compound. ¹H-NMR (500 MHz, DMSO-d₆) δ 9.88 (s, 1H), 8.31 (d, J=8.7 Hz, 1H), 7.62 (dd, J=8.7, 2.2 Hz, 1H), 7.32 (m, 6H), 7.13 (t, J=8.1 Hz, 1H), 6.72 (d, J=7.5 Hz, 1H), 6.61 (dd, J=8.1, 1.0 Hz, 1H), 6.16 (s, 1H), 3.90 (s, 3H), 2.57 (m, 1H), 1.07 (dd, J=7.0, 1.7 Hz, 6H); MS (ESI+) (M+H)⁺ at m/e 374.

EXAMPLE 15

(1-methoxy-6-phenyl-6H-dibenzo(b,d)pyran-8-yl)benzamide

Example 5F and benzoyl chloride were processed as described in Example 12 to provide the titled compound. ¹H NMR (500 MHz, DMSO-d₆) δ 10.33 (s, 1H), 8.37 (d, J=8.7 Hz, 1H), 7.93 (d, J=7.2 Hz, 2H), 7.81 (dd, J=8.7, 2.5 Hz, 1H), 7.55 (m, 4H), 7.34 (m, 5H), 7.15 (t, J=8.3 Hz, 1H), 6.74 (d, J=8.4 Hz, 1H), 6.64 (dd, J=8.1, 0.9 Hz, 1H), 6.23 (s, 1H), 3.91 (s, 3H); MS (ESI(+)) m/z 408 (M+H)⁺.

EXAMPLE 16

(1-methoxy-6-phenyl-6H-dibenzo(b,d)pyran-8-yl)cyclopropanecarboxamide

Example 5F and cyclopropanecarbonyl chloride were processed as described in Example 12 to provide the titled compound. ¹H NMR (500 MHz, DMSO-d₆) δ 10.25 (s, 1H), 8.31 (d, J=8.8 Hz, 1H), 7.60 (dd, J=8.7, 2.5 Hz, 1H), 7.32 (m, 6H), 7.13 (t, J=8.3 Hz, 1H), 6.72 (d, J=8.4 Hz, 1H), 6.62 (dd, J=8.1, 0.9 Hz, 1H), 6.17 (s, 1H), 3.88 (s, 3H), 1.76 (m, 1H), 0.77 (m, 4H); MS (ESI(+)) m/z 372 (M+H)⁺.

EXAMPLE 17

(1-methoxy-6-phenyl-6H-dibenzo(b,d)pyran-8-yl)-(2-methoxy)acetamide

Example 5F and methoxyacetyl chloride were processed as described in Example 12 to provide the titled compound. 1H NMR (500 MHz, DMSO-d₆) δ 9.84 (s, 1H), 8.32 (d, J=8.8 Hz, 1H), 7.68 (dd, J=8.7, 2.2 Hz, 1H), 7.40 (d, J=2.2 Hz, 1H), 7.31 (m, 5H), 7.14 (t, J=8.1 Hz, 1H), 6.72 (d, J=8.4 Hz, 1H), 6.62 (dd, J=8.0, 0.8 Hz, 1H), 6.18 (s, 1H), 3.97 (s, 2H), 3.89 (s, 3H), 3.35 (s, 3H); MS (ESI(+)) m/z 376 (M+H)⁺.

EXAMPLE 18

1-methoxy-6-phenyl-6H-dibenzo(b,d)pyran-8-yl)-(2-fluoro)benzenesulfonamide

Example 5F and 2-fluorophenylsulfonyl chloride were processed as described in Example 6 to provide the titled compound. MS (ESI(−)Q1MS) m/z 460 (M−H)⁻; ¹H NMR (300 MHz, DMSO-d₆) δ 10.71 (s, 1H), 8.23 (dd, J=8 Hz, 1Hz, 1H), 7.72–7.67 (m, 2H), 7.45 (m, 5H), 7.18–7.06 (m, 4H), 6.77 (br s, 1H), 6.70 (d, J=8 Hz, 1H), 6.62 (d, J=8 Hz, 1H), 6.12 (s, 1H), 3.84 (s, 3H).

EXAMPLE 19

(1-methoxy-6-phenyl-6H-dibenzo(b,d)pyran-8-yl)ethylamine

Example 5F (30.3 mg, 0.1 mmole) in methanol (1 mL) was added to acetaldehyde (6.61 μL, 0.15 mmoles) followed by 4 A molecular sieves. The reaction was shaken at room temperature for an hour. Diisopropylethylamine (10 μL) was added to the reaction and continued shaking for another hour. The reaction was filtered off to remove the sieves and borohydride resin (80 mg, 0.2 mmoles) was added to the reaction and shaken at room temperature overnight. The resin was filtered off and washed with methanol (3×1 mL). Filterates pooled and concentrated in vacuo. The residue was purified by preparative HPLC to provide the titled compound. ¹H-NMR (500 MHz, DMSO-d₆) δ 8.16 (d, J=8.7 Hz, 1H), 7.30 (m, 5H), 7.02 (t, J=8.2 Hz, 1H), 6.66 (d, J=7.5 Hz, 2H), 6.57 (dd, J=7.9, 0.8 Hz, 1H), 6.29 (s, 1H), 6.07 (s, 1H), 5.75 (s, 1H), 3.87 (s, 3H), 3.03 (dd, J=14.2, 7.1 Hz, 2H), 1.13 (t, J=7.2 Hz, 3H); MS (ESI+) (M+H)⁺ at m/e 332.

EXAMPLE 20

(1-methoxy-6-phenyl-6H-dibenzo(b,d)pyran-8-yl)cyclopropylmethylamine

Example 5F and cyclopropanecarboxaldehyde were processed as described in Example 19 to provide the titled compound. ¹H NMR (500 MHz, DMSO-d₆) δ 8.16 (d, J=8.7 Hz, 1H), 7.18–7.41 (m, 5H), 7.02 (t, J=8.1 Hz, 1H), 6.67 (d, J=8.1 Hz, 2H), 6.58 (dd, J=7.9, 0.8 Hz, 1H), 6.32 (s, 1H), 6.08 (s, 1H), 5.76 (s, 1H), 3.87 (s, 3H), 2.91 (d, J=6.6 Hz, 2H), 1.01 (m, 1H), 0.45 (m, 2H), 0.2 (m, 2H); MS (ESI(+)) m/z 358 (M+H)⁺.

EXAMPLE 21

(1-methoxy-6-phenyl-6H-dibenzo(b,d)pyran-8-yl)benzylamine

Example 5F and benzaldehyde were processed as described in Example 19 to provide the titled compound. ¹H NMR (500 MHz, DMSO-d₆) δ 8.08 (d, J=8.7 Hz, 1H), 7.29 (m, 7H), 7.22 (m, 3H), 7.00 (t, J=8.3 Hz, 1H), 6.64 (d, J=7.8 Hz, 1H), 6.59 (dd, J=8.7, 2.5 Hz, 1H), 6.56 (dd, J=8.1, 1 Hz, 1H), 6.26 (d, J=2.5 Hz, 1H), 6.01 (s, 1H), 5.75 (s, 1H), 4.24 (s, 2H), 3.83 (s, 3H); MS (ESI(+)) m/z 394 (M+H)⁺.

EXAMPLE 22

(1-methoxy-6-phenyl-6H-dibenzo(b,d)pyran-8-yl)trifluoroacetamide

Example 5F (200 mg. 0.64 mmole) was dissolved in trifluoroacetic acid (1 mL) and stirred for 1 hour, diluted with EtOAc, washed with aqueous HCl (1M), dried (Na₂SO₄), filtered and concentrated under reduced pressure. The concentrate was purified by reverse-phase HPLC with CH₃CN/water to provide the desired product. MS (ESI(−)Q1MS) m/z 398 (M−H)⁻; ¹H NMR (300 MHz, DMSO-d₆) δ 11.33 (s, 1H), 8.41 (d, J=8 Hz, 1H), 7.75 (dd, J=8 Hz, 1 Hz, 1H), 7.38–7.29 (m, 6H), 7.20 (t, J=8 Hz, 1H), 6.75 (d, J=8 Hz, 1H), 6.66 (dd, J=8 Hz, 1 Hz, 1H), 6.23 (s, 1H), 3.90 (s, 3H).

EXAMPLE 23

6R-(1-methoxy-6-phenyl-6H-dibenzo(b,d)pyran-8-yl)methanesulfonamide

Example 5F was resolved by chiral HPLC chromatography using a Chiralcel OD column and eluting with a solvent mixture of 60:40 hexane:ethanol. The product which eluted at 8.3 minutes (20 mg) was collected and dissolved in chloroform (1 mL) containing pyridine (0.100 mL). The resulting solution was cooled to 0° C., treated with methanesulfonyl chloride (23 mg., 0.2 mmole), stirred 1 hour at 25° C., treated with dilute HCl, and extracted with diethyl ether. The extract was dried ($Na_2SO_4$) filtered from charcoal, and concentrated. The concentrate was azeotroped four times from toluene to remove any excess methanesulfonyl chloride and once from heptane to provide the titled compound (19 mg, 80%). TLC (95:5 dichloromethane/ethyl acetate) single spot: Rf=0.5; MS (APCI(+)) m/z 382 $(M+H)^+$ and 399 $(M+NH_4)^+$; $^1$H NMR (300 MHz, $CDCl_3$) δ 2.95 (s, 3H), 3.94 (s, 3H), 6.00 (s, 1H), 6.30 (s, 1H), 6.61 (d, J=2 Hz, 1H), 6.62 (dd, J=10 Hz, 2 Hz, 1H), 6.69 (dd, J=9 Hz, 1 Hz, 1H), 7.15 (t, J=9 Hz, 1H), 7.25 (dd, J=9 Hz, 2 Hz, 1H), 7.32–7.39 (m, 5H), 8.45 (d, J=9 Hz, 1H).

EXAMPLE 24

6S-(1-methoxy-6-phenyl-6H-dibenzo(b,d)pyran-8-yl)methanesulfonamide

The compound of example 5F was resolved by chiral HPLC chromatography using a Chiralcel OD column and eluting with a solvent mixture of 60:40 hexanes:ethanol. The peak that eluted at 21.9 minutes was collected and processed as described in Example 23 to provide the desired product. Anomalous dispersion from the heavy atom effect of sulfur through X-ray crystallography provided the assignment of absolute stereochemistry at the chiral center as "S". MS (APCI(+)) m/z 382 $(M+H)^+$ and 399 $(M+NH_4)^+$; $^1$H NMR (300 MHz, $CDCl_3$) δ 2.95 (s, 3H), 3.94 (s, 3H), 6.00 (s, 1H), 6.30 (s, 1H), 6.61 (d, J=2 Hz, 1H), 6.62 (dd, J=10 Hz, 2 Hz, 1H), 6.69 (dd, J=9 Hz, 1Hz, 1H), 7.15 (t, J=9 Hz, 1H), 7.25 (dd, J=9 Hz, 2 Hz, 1H), 7.32–7.39 (m, 5H), 8.45 (d, J=9 Hz, 1H).

EXAMPLE 25

N-(1-difluoromethoxy-6-phenyl-6H-dibenzo[b,d]pyran-8-yl)methanesulfonamide

EXAMPLE 25A

8-Amino-1-difluoromethoxy-6-phenyl-6H-dibenzo[b,d]pyran

A solution of Example 4 (1.19 g), triethylamine (2.8 mL) and 10% Pd/C (120 mg) in ethyl acetate (100 mL) was shaken under 1.5 atms. hydrogen for 15 minutes. The mixture was filtered and concentrated under reduced pressure. The residue was taken up in toluene (50 mL), washed with aqueous $KHCO_3$, dried ($Na_2SO_4$), filtered and concentrated. The resulting material was purified on silica eluting with 25% hexane −75% $CH_2Cl_2$ to provide the titled compound (0.763 g, 80%). $^1$H NMR (300 MHz, $CDCl_3$) δ 3.75 (br s, 2H), 5.95 (s, 1H), 6.14 (d, J=3 Hz, 1H), 6.50 (t, J=75 Hz, 1H, $CHF_2$) 6.71 (dd, J=9 Hz, 3 Hz, 1H), 6.77 (dd, J=9 Hz, 1Hz, 1H), 6.87 (dd, J=9 Hz, 1Hz, 1H), 7.05 (t, J=8 Hz, H), 7.30–7.40 (m, 5H), 8.12 (d, J=9 Hz, 1H). MS (APCI) m/e 340 (M+H).

EXAMPLE 25B

N-(1-difluoromethoxy-6-phenyl-6H-dibenzo[b,d]pyran-8-yl)methanesulfonamide

Example 25A (176 mg 0.519 mmole) and methanesulfonyl chloride was processed as described in Example 5G to provide the titled compound (161 mg, 74%). $^1$H NMR (300 MHz, $CDCl_3$) δ 3.00 (s, 3H), 6.04 (s, 1H), 6.39 (s, 1H), 6.55 (t, J=75, 1H, $CHF_2$) 6.68 (d, J=3 Hz, 1H), 6.81 (dd, J=9 Hz, 1 Hz, 1H), 6.91 (dd, J=8 Hz, 2 Hz, 1H), 7.17 (t, J=9 Hz, 1H), 7.27 (dd, J=9 Hz, 3 Hz, 1H), 7.30–7.40 (m, 5H), 8.31 (d, J=9 Hz, 1H). MS (APCI) m/e 418 (M+H), 435 $(M+NH_4+)$

EXAMPLE 26

N-(1-difluoromethoxy-6-phenyl-6H-dibenzo[b,d]pyran-8-yl)-thiophene-2-sulfonamide Example 5F (100 mg.) and 2-thiophenesulfonyl chloride was processed as described in Example 5G to provide the titled compound (79 mg, 55%). $^1$H NMR (300 MHz, DMSO-$d_6$) δ 6.23 (s, 1H), 6.82–6.92 (m, 3H), 7.11 (t, J=5 Hz, 1H), 7.15–7.72 (m, 3H), 7.25 (t, J=9 Hz, 1H), 7.30 (t, J=75 Hz, 1H), $CHF_2$), 7.31–7.41 (m, 3H), 7.46 (dd, J=5 Hz, 1 Hz, 1H), 7.94 (dd, J=5 Hz, 1 Hz, 1H), 8.10 (d, J=9 Hz, 1H), 10.62 (s, 1H). MS (APCI) m/e 486 (M+H), 503 $(M+NH_4+)$

EXAMPLE 27

(1-difluoromethoxy-6-propyl-6H-dibenzo(b,d)pyran-8-yl)-methanesulfonamide

EXAMPLE 27A 1-difluoromethoxy-8-nitro-6H-dibenzo(b,d)pyran-6-one

A mixture of Example 1C (6.63 g, 25.8 mmol) and powdered potassium carbonate (10.93 g, 79.2 mmol) in DMF (77 mL) in a stainless steel Parr reactor at −40° C. was treated with chlorodifluoromethane (22 g, 0.25 mol) through Tygon tubing until the supply cylinder had lost the desired weight. The reactor valves were closed, and the mixture was heated to 85° C. for 20 minutes, cooled to room temperature, and vented. The red solution was decanted from the potassium carbonate and concentrated. The concentrate was treated with water (200 mL) and 2M HCl (200 mL) and filtered to provide a solid. The solid dissolved in warm $CH_3CN$ (200 mL), treated with charcoal, filtered through diatomaceous earth (Celite®), and concentrated to provide a first crop of desired product. The concentrate was suspended in $CHCl_3$ and filtered. The filtrate was concentrated to provide a second crop of desired product. MS (ESI(−) Q1MS) m/z 306 (M—M)$^-$.

EXAMPLE 27B 8-amino-1-difluoromethoxy-6H-dibenzo(b,d)pyran-6-one

A Paar hydrogenation vessel was charged with Example 27A (3.39 g, 11.0 mmol), THF (100 mL), and 10% palladium on carbon (300 mg). The mixture was shaken under hydrogen gas (60 psi) for 6 hours, filtered through diatomaceous earth (Celite®), and concentrated provide the desired product. MS (ESI(−)Q1MS) m/z 276 (M−H)$^-$.

EXAMPLE 27C 8-amino-7-bromo-1-difluoromethoxy-6H-dibenzo(b,d)pyran-6-one

A solution of Example 27B (4.03 g, 14.54 mmol) in THF (200 mL) at room temperature was treated over 15 minutes with pyridinium tribromide (5.16 g, 15.26 mmol), stirred for 14 hours, and concentrated. The concentrate was treated with water (200 mL), stirred at room temperature for 15 minutes, and filtered. The resulting solid was washed with water (200 mL), suspended in hot $CH_3CN$, cooled to room temperature, and filtered to provide a first crop of desired product. The filtrate was treated with charcoal, filtered, and concentrated to provide a solid which was suspended in diethyl ether and filtered to provide a second crop of desired product. MS (ESI(−)Q1MS) m/z 355 (M−H)$^-$.

EXAMPLE 27D 8-benzyloxycarbonylamino-7-bromo-1-difluoromethoxy-6H-dibenzo(b,d)pyran-6-one A solution of Example 27C (1.13 g, 3.19 mmol) in THF (100 mL) was treated with triphosgene (0.95 g, 3.19 mmol), heated at reflux for 4 hours, treated with benzyl alcohol, (3.44 g. 31.9 mmol), heated at reflux for 16 hours, cooled to room temperature, and concentrated to a fraction of its original volume. The solution was cooled to 0° C. and filtered to provide the desired product. MS (ESI(−)Q1MS) m/z 488 (M−H)$^-$.

EXAMPLE 27E 8-benzyloxycarbonylamino-7-bromo-1-difluoromethoxy-6H-dibenzo(b,d)pyran-6-ol A solution of Example 27D (0.52 g, 1.08 mmol) in dichloromethane (100 mL) at −78° C. was treated with disobutylaluminum hydride in heptane (1.30 mL, 1.30 mmol), stirred for 30 minutes at −78° C., and treated with ethyl acetate (10 mL) and sodium potassium tartrate (50 mL) to provide two layers. The layers were separated, and the aqueous layer was extracted with ethyl acetate. The extract was dried ($Na_2SO_4$), filtered, and concentrated. The concentrate was purified by flash column chromatography on silica gel with 20–50% ethyl acetate/hexanes to provide the desired product. MS (ESI(−)Q1MS) m/z 490 (M−H)$^-$.

EXAMPLE 27F 8-amino-1-difluoromethoxy-6H-dibenzo(b,d)pyran-6-ol

A mixture of Example 27E (0.5 g, 1.04 mmol) and 10% palladium on carbon (50 mg) in methanol (50 mL) was shaken under hydrogen gas (balloon) for 6 hours, filtered through diatomaceous earth (Celite®), and concentrated to provide the desired product. MS (ESI(−)Q1MS) m/z 278 (M−H)$^-$.

EXAMPLE 27G 1-difluoromethoxy-6-hydroxy-(6H-dibenzo(b,d)pyran-8-yl)methanesulfonamide A solution of Example 27F (0.058 g, 0.208 mmol) in pyridine (2 mL) was treated with methanesulfonylchloride (0.024 g, 0.21 mmol), stirred at room temperature for 18 hours, and concentrated The concentrate was purified by flash column chromatography on silica gel with 20–50% ethyl acetate/hexanes) to provide the desired product. MS (ESI(−)Q1MS) m/z 356 (M−H)$^-$.

EXAMPLE 27H 1-difluoromethoxy-6-allyl-(6H-dibenzo(b,d)pyran-8-yl)methanesulfonamide A solution of Example 27G (0.14 g, 0.39 mmol) in dichloromethane (10 mL) at −78° C. was treated with allyltrimethylsilane (0.13 g, 1.16 mmol) and borontrifluoride etherate (0.156 g, 1.16 mmol), stirred for 1 hour, and treated with saturated sodium bicarbonate (10 mL) to provide two laters. The layers were separated, and the aqueous layer was extracted with ethyl acetate. The extract was dried ($Na_2SO_4$), filtered, and concentrated. The concentrate was purified by flash column chromatography on silica gel with 20–50% ethyl acetate/hexanes to provide the desired product. MS (ESI(−)Q1MS) m/z 380 (M−H)$^-$.

EXAMPLE 27I 1-difluoromethoxy-6-propyl-6H-dibenzo(b,d)pyran-8-yl)-methanesulfonamide A mixture of Example 27H (0.05 g, 0.131 mmol) and 10% palladium on carbon (5 mg) in methanol (50 mL) was shaken under hydrogen gas (balloon) for 6 hours, filtered through diatomaceous earth (Celite®), and concentrated to provide the desired product. MS (ESI(−)Q1MS) m/z 382 (M−H)$^-$; $^1$H NMR (300 MHz, DMSO-$d_6$) δ 9.98 (s, 1H), 8.09 (d, J=9 Hz, 1H), 7.31 (t, J=74 Hz, 1H), 7.27 (t, J=8 Hz, 1H), 7.20 (dd, J=8 Hz, 2 Hz, 1H), 7.12 (d, J=2 Hz, 1H), 6.92–6.86 (m, 2H), 5.15 (m, 1H), 3.07 (s, 3H), 1.80–1.38 (m, 7H).

EXAMPLE 28

(1-difluoromethoxy-6-(4-(N-methylamino)phenyl)-7-bromo-6H-dibenzo(b,d)pyran-8-yl)-amine A mixture of Example 30 (0.05 g, 0.10 mmol) and 10% palladium on carbon (5 mg) in THF (5 mL) was shaken under hydrogen gas (balloon) for 6 hours, filtered through diatomaceous earth (Celite®), and concentrated. The concentrate was purified by reverse-phase HPLC with $CH_3CN$/water to provide the desired product. MS (ESI(−)Q1MS) m/z 449 (M−H)$^-$; $^1$H NMR (300 MHz, DMSO-$d_6$) δ 7.97 (d, J=9 Hz, 1H), 7.22 (t, J=74 Hz, 1H), 7.05 (t, J=8 Hz, 1H), 6.90 (d, J=8 Hz, 1H), 6.85 (d, J=8 Hz, 2H), 6.76 (d, J=8 Hz, 1H), 6.70 (d, J=8 Hz, 1H), 6.35 (d, J=8 Hz, 2H), 6.32 (s, 1H), 5.72 (s, 2H), 5.20 (q, J=7 Hz, 1H), 2.58 (d, J=7 Hz, 3H).

EXAMPLE 29

(1-difluoromethoxy-6-(4-(N-propyl-N-methylamino)phenyl)-7-bromo-6H-dibenzo(b,d)pyran-8-yl)-amine A mixture of Example 30 (0.05 g, 0.10 mmol) and 10% palladium on carbon (5 mg) in THF (5 mL) was shaken under hydrogen gas (balloon) for 6 hours, filtered through diatomaceous earth (Celite®), and concentrated. The concentrate was purified by reverse-phase HPLC with $CH_3CN$/water to provide the desired product. MS (ESI(+)Q1MS) m/z 489 (M+H)$^+$; $^1$H NMR (300 MHz, DMSO-$d_6$) δ 7.97 (d, J=9 Hz, 1H), 7.23 (t, J=74 Hz, 1H), 7.06 (t, J=8 Hz, 1H), 6.92(d, J=8 Hz, 2H), 6.90 (d, J=8 Hz, 2H), 6.78–6.68 (m, 2H), 6.50 (d, J=8 Hz, 2H), 6.36 (s, 1H), 5.72 (s, 2H), 2.80 (s, 3H), 2.51 (m, 2H), 1.42 (m, 2H), 0.82 (t, J=7 Hz, 3H).

EXAMPLE 30

(1-difluoromethoxy-6-(4-(N-allyl-N-methylamino)phenyl)-6H-dibenzo(b,d)pyran-8-yl)-methanesulfonamide A solution of Example 27G (0.14 g, 0.39 mmol) in dichloromethane (10 mL) at −78° C. was treated with N-allyl-N-methylaniline (0.17 g, 1.16 mmol) and borontrifluoride etherate (0.156 g, 1.16 mmol), stirred for 1 hour, and treated with saturated sodium bicarbonate (10 mL) to provide two laters. The layers were separated, and the aqueous layer was extracted with ethyl acetate. The extract was dried ($Na_2SO_4$), filtered, and concentrated. The concentrate was purified by flash column chromatography on silica gel with 20–50% ethyl acetate/hexanes to provide the desired product. MS (ESI(+)Q1MS) m/z 487 (M+H)+; 1H NMR (300 MHz, DMSO-$d_6$) δ 9.95 (s, 1H), 8.18 (d, J=9 Hz, 1H), 7.32 (t, J=74 Hz, 1H), 7.28 (dd, J=8 Hz, 2 Hz, 1H), 7.21(t, J=8 Hz, 1H), 7.04(d, J=8 Hz, 2H), 6.91 (d, J=2 Hz, 1H), 6.83 (t, J=8 Hz, 1H), 6.63 (d, J=8 Hz, 2H), 6.15 (s, 1H), 5.84–5.73 (m, 1H), 5.12–5.05 (m, 2H), 3.80 (m, 2H), 3.02 (s, 3H), 2.88 (s, 3H).

EXAMPLE 31

(1-difluoromethoxy-6-allyl-6H-dibenzo(b,d)pyran-8-yl)-methanesulfonamide

A solution of Example 27G (0.14 g, 0.39 mmol) in dichloromethane (10 mL) at −78° C. was treated with allyltrimethylsilane (0.13 g, 1.16 mmol) and borontrifluoride etherate (0.156 g, 1.16 mmol), stirred for 1 hour, and treated with saturated sodium bicarbonate (10 mL) to provide two laters. The layers were separated, and the aqueous layer was extracted with ethyl acetate. The extract was dried ($Na_2SO_4$), filtered, and concentrated. The concentrate was purified by flash column chromatography on silica gel with 20–50% ethyl acetate/hexanes to provide the desired product. MS (ESI(-)Q1MS) m/z 380 (M–H)−; 1H NMR (300 MHz, DMSO-$d_6$) δ 9.99 (s, 1H), 8.10 (d, J=9 Hz, 1H), 7.31 (t, J=74 Hz, 1H), 7.27 (t, J=8 Hz, 1H), 7.20 (dd, J=8 Hz, 2 Hz, 1H), 7.14(d, J=2 Hz, 1H), 6.92–6.86 (m, 2H), 5.92–5.78 (m, 1H), 5.22 (dd, J=7 Hz, 7 Hz, 1H), 5.12–5.01 (m, 2H), 3.07 (s, 3H), 2.48–2.37 (m, 2H).

EXAMPLE 32

(1methoxy-6-(4-allyloxy)phenyl-6H-dibenzo(b,d)pyran-8-yl)-methanesulfonamide

EXAMPLE 32A methyl 5-nitro-2-(2-methoxy-6-methoxymethoxyphenyl)-benzoate

A solution of 1-methoxy-3-methoxymethoxy benzene (3.62 g., 21.55 mmole), prepared as described in *J. Med. Chem.* 1995, 38, 1437–1445, in THF (15 mL) at −30° C. was treated with n-butyllithium (8.28 ml. of 2.5M in hexane, 20.69 mmole), stirred for 1 hour at 25° C., cooled to 0° C., treated with anhydrous zinc chloride beads (3.5 g, 25.67 mmole), stirred for 2 hours at 25° C., treated with a solution of methyl-2-bromo-5-nitrobenzoate (5.0 g, 19.23 mmol) in THF (20 mL) and bis(triphenylphosphine)palladium dichloride (600 mg), stirred it 65° C. for 15 hours, cooled, and treated with chloroform and aqueous $KHCO_3$. The precipitated zinc salts were filtered, and the water layer was removed, and the organic layer dried over ($Na_2SO_4$), filtered, and concentrated. The concentrate was purified by flash column chromatography on silica gel with 8% ethyl acetate in dichloromethane to provide the desired product. MS (ESI(-)Q1MS) m/z 346 (M–H)−.

EXAMPLE 32B methyl 5-amino-2-(2-methoxy-6-methoxymethoxyphenyl)-benzoate

A solution of Example 32A (10.0 g) and 10% Pd/C (1.0 g) in methanol (200 mL) at room temperature was hydrogenated at 4 atm for 1 hour, filtered through diatomaceous earth (Celite®), and concentrated to provide the desired product. MS (ESI(-)QIMS) m/z 316 (M–H)−.

EXAMPLE 32C methyl 5-methanesulfonylamino-2-(2-methoxy-6-methoxymethoxyphenyl)-benzoate A solution of Example 32B (10 g, 34.8 mmol), in pyridine (50 mL) at room temperature was treated with methanesulfonyl chloride (2.7 mL, 34.8 mmol), stirred at room temperature for 16 hours, and concentrated. The concentrate was treated with ethyl acetate (100 mL), and the resulting solution was washed with 2N HCl, dried ($Na_2SO_4$), filtered, and concentrated. The concentrate was recrystallized from ethanol to provide the desired product. MS (ESI(-)Q1MS) m/z 394 (M–H)−.

EXAMPLE 32D (4-(2-methoxy-6-methoxymethoxyphenyl)-5-hydroxymethyl)phenyl-methanesulfonamide A solution of Example 32C (14.95 g, 37.84 mmol) in dichloromethane (200 mL) at 0° C. was treated with a solution of diisobutylaluminumhydride in heptane (114 mL, 114 mmol), stirred for 1 hour at 0° C., and treated with ethyl acetate (100 mL) and saturated sodium potassium tartrate (100 mL) to provide two layers. The layers were separated, and the aqueous layer was extracted with ethyl acetate. The extract was dried ($Na_2SO_4$), filtered, and concentrated to provide the desired product. MS (ESI(-)Q1MS) m/z 366 (M–H)−.

EXAMPLE 32E (4-(2-methoxy-6-methoxymethoxyphenyl)-5-formyl)phenyl-methanesulfonamide A suspension of Example 32D (11.74 g, 31.97 mmol) and oven-dried, powdered 4MS (10 g) in dichloromethane (200 mL) and $CH_3CN$ (75 mL) at 0° C. was treated with N-methylmorpholine-N-oxide (5.62 g, 47.96 mmol) and tetrapropylammoniumperruthenate (0.56 g, 1.60 mmol), stirred at room temperature for 1 hour, and concentrated. The concentrate was purified by flash column chromatography on silica gel with 50% ethyl acetate/hexanes to provide the desired product. MS (ESI(-)Q1MS) m/z 364 (M–H)−.

EXAMPLE 32F (4-(2-methoxy-6-methoxymethoxyphenyl)-5-(1-hydroxy-1-(4-allyloxyphenyl)methyl)phenyl-methanesulfonamide A solution of 4-allyloxyphenyllithium (24.3 mmol) was generated by treating 4-allyloxyphenyl bromide (6.45 g, 30.4 mmol) with n-butyllithium (9.72 mL of a 2.5M solution in hexanes, 24.3 mmol) at −78° C. for 30 minutes.

A solution of Example 32E (2.22 g, 6.08 mmol) in THF (100 mL) at −78° C. was treated via cannula over 30 minutes with the solution of 4-allyloxyphenyllithium, stirred for 2 hours, treated sequentially with methanol (10 mL), saturated $NaHCO_3$ (100 mL) and ethyl acetate (200 mL). The layers were separated, and the aqueous layer was extracted with ethyl acetate. The extract was dried ($Na_2SO_4$), filtered, and concentrated. The concentrate was purified by silica gel chromatography with 20–50% ethyl acetate/hexanes to provide the desired. MS (ESI(-)Q1MS) m/z 498 (M–H)−.

EXAMPLE 32G (1-methoxy-6-(4-allyloxy)phenyl-6H-dibenzo(b,d)pyran-8-yl)-methanesulfonamide A solution of of Example 32F (1.8 g, 3.6 mmol) in methanol (100 mL) at 0° C. was treated with a solution of 2M HCl in diethyl ether (90 mL, 180 mmol), warmed to room temperature, stirred for 24 hours, poured slowly onto a mixture of ice (100 g) and saturated NaHCO$_3$ (500 mL), and extracted with ethyl acetate. The extract was dried (Na$_2$SO$_4$), filtered, and concentrated. The concentrate was purified by flash column chromatography on silica gel with 20–50% ethyl acetate/hexanes to provide the desired product. MS (ESI(−)Q1MS) m/z 436 (M−H)$^-$; $^1$H NMR (300 MHz, DMSO-d$_6$) δ 9.83 (s, 1H), 8.34 (d, J=9 Hz, 1H), 7.23 (dd, J=8 Hz, 2 Hz, 1H), 7.18 (d, J=8 Hz, 2H), 7.13 (t, J=8 Hz, 1H), 6.91 (d, J=8 Hz, 2H), 6.86 (d, J=2 Hz, 1H), 6.72 (d, J=8 Hz, 1H), 6.59 (d, J=8 Hz, 1H), 6.14 (s, 1H), 6.09–5.95 (m, 1H), 5.41–5.21 (m, 2H), 4.52 (m, 2H), 3.89 (s, 3H), 3.00 (s, 3H).

EXAMPLE 33

(1-methoxy-6-(3-allyloxy)phenyl-6H-dibenzo(b,d)pyran-8-yl)-methanesulfonamide

A solution of 3-allyloxyphenyllithium (24.3 mmol) was generated by treating 4-allyloxyphenyl bromide (6.45 g, 30.4 mmol) with n-butyllithium (9.72 mL of a 2.5M solution in hexanes, 24.3 mmol) at −78° C. for 30 minutes.

Example 32E and 3-allyloxyphenyllithium were processed as described in Examples 32F and 32G to provide the titled compound. MS (ESI(−)Q1MS) m/z 436 (M−H)$^-$; $^1$H NMR (300 MHz, DMSO-d$_6$) δ 9.86 (s, 1H), 8.33 (d, J=9 Hz, 1H), 7.28–7.22 (m, 3H), 7.16 (d, J=8 Hz, 2H), 7.13 (t, J=8 Hz, 1H), 6.92 (d, J=8 Hz, 2H), 6.90–6.80 (m, 3H), 6.73 (d, J=8 Hz, 1H), 6.65 (d, J=8 Hz, 1H), 6.19 (s, 1H), 6.06–5.92 (m, 1H), 5.39–5.20 (m, 2H), 4.52–4.47 (m, 2H), 3.89 (s, 3H), 3.00 (s, 3H).

EXAMPLE 34

(1-methoxy-6-(3-hydroxy)phenyl-6H-dibenzo(b,d)pyran-8-yl)-methanesulfonamide

A solution of 3-methoxymethyloxyphenyllithium (25 mmol) was generated by treating 4-methoxymethyloxyphenyl bromide (6.48 g, 30 mmol) with n-butyllithium (9.8 mL of a 2.5M solution in hexanes, 25 mmol) at −78° C. for 30 minutes.

Example 32E and 3-methoxymethyloxyphenyllithium were processed as described in Examples 32F and 32G to provide the titled compound. MS (ESI(−)Q1MS) m/z 396 (M−H)$^-$; $^1$H NMR (300 MHz, DMSO-d$_6$) δ 9.86 (s, 1H), 9.41 (s, 1H), 8.32 (d, J=9 Hz, 1H), 7.24 (dd, J=9 Hz, 2 Hz, 1H), 7.17 (d, J=8 Hz, 1H), 7.13 (t, J=8 Hz, 1H), 6.91 (d, J=2 Hz, 2H), 6.75–6.60 (m, 4H), 6.12 (s, 1H), 3.89 (s, 3H), 3.01 (s, 3H).

EXAMPLE 35

(1-(2-thienyl)-6-phenyl-6H-dibenzo(b,d)pyran-8-yl)-methanesulfonamide

EXAMPLE 35A 1,3-bismethoxymethoxybenzene

To a stirred solution of dry NaH (28.8 g, 1.2 mol, 2.2 eq) in 1100 mL of dry DMF at 0° C., was added dropwise, a solution of resorcinol (60 g, 0.55 mol, 1 eq) in 150 mL of DMF. After stirring for 1 h, chloromethyl methyl ether (104 mL, 1.38 mmol, 2.5 eq) was added, and the resulting mixture was allowed to stir overnight at ambient temperature. The reactions was then quenched with 750 mL of saturated NH$_4$Cl, and extracted with EtOAc (2×500 mL). The organic layers where first rinsed with 10% NaOH (4×250 mL), then with brine (2×400 mL). The organic layer was dried over Na$_2$SO$_4$, filtered, and concentrated in vacuo to afford 107.86 g (0.54 mol, 99%) of the titled compound. MS (ESI(−)Q1MS) m/z 197 (M−H)$^-$;

EXAMPLE 35B methyl 5-nitro-2-(2-methoxymethoxy-6-methoxymethoxyphenyl)-benzoate To a stirred solution of 35A (45.65 g, 230.3 mmol, 1.25 eq) in 165 mL of dry THF at −30° C., was added a 2.5M solution of n-BuLi (88.44 mL, 221.1 mmol, 1.20 eq). Upon complete addition of the base, the reaction mixture was allowed to warm to ambient temperature and stir for 1 h. The mixture was then cooled to 0° C., and anhydrous beads of ZnCl$_2$ (37.66 g, 276.4 mmol, 1.50 eq) were added. The reaction was again warmed to ambient temperature, and allowed to stir for 2 h. To this mixture was added a solution of p-nitro-bromo-methylester (C$_8$H$_6$NO$_4$Br) (47.91 g, 184.2 mmol, 1.00 eq) in 130 mL of dry THF. Followed by addition of solid dichlorobis(triphenylphosphine)palladium(II) chloride (7.76 g, 11.1 mmol, 0.06 eq) at 0° C. The reaction vessel was adequately vented and heated at 65° C. overnight. The mixture was then cooled, and saturated NaHCO$_3$ was added, and the resulting ppt of Zn(OH)$_2$ was filtered off through Celite. The resulting mixture was extracted with CHCl$_3$ (2×300 mL) and EtOAc (1×300). The organics were rinsed with brine and dried over Na$_2$SO$_4$. Concentration of the solution in vacuo, followed by recrystallization from MeOH/hexanes (4:1) or EtOAc/hexanes (3:1) to afford the titled compound. MS (ESI, −Q1MS) m/e 377 (M−H).

EXAMPLE 35C methyl 5-amino-2-(2-methoxymethoxy-6-methoxymethoxyphenyl)-benzoate To a mechanically stirred solution of 35B (1.66 g, 4.44 mmol, 1.0 eq) in aqueous ethanol (1:4), were added iron powder (283 mg, 5.07 mmol, 1.2 eq) and NH$_4$Cl (28 mg, 0.53 mmol, 0.12 eq). The mixture was vented through a drying tube and heated at 95° C. for 6 h. Upon cooling, the reaction mixture was filtered through a course frit, and concentrated in vacuo. The residue was dissolved in EtOAc/THF and rinsed with NaHCO$_3$, then brine. The combined organics were dried over Na$_2$SO$_4$ and concentrated to afford a crude solid. The solid was purified by flash chromatography (2:1 hexane/EtOAc) to afford the titled compound. MS (DCI/NH$_3$, +Q1MS) m/e 365 (M+NH$_3$).

EXAMPLE 35D methyl 5-methanesulfonylamino-2-(2-methoxymethoxy-6-methoxymethoxyphenyl)-benzoate Mesyl chloride (1.39 mL, 18.0 mmol, 1.15 eq) was added dropwise to a solution of 35 C (5.44 g, 15.7 mmol, 1 eq) in 75 mL of dry pyridine at 0° C. The mixture was allowed to stir and warm to ambient temperature overnight. The resulting solution was concentrated in vacuo then dissolved in EtOAc. The organic layer was rinsed with 1M HCl (3×100 mL), then rinsed with brine (200 mL). The combined organics were dried over $Na_2SO_4$, filtered, and concentrated to afford the titled compound. MS (ESI, −Q1MS) m/e 424 (M−H).

EXAMPLE 35E (4-(2-methoxymethoxy-6-methoxymethoxyphenyl)-5-hydroxymethyl)phenyl-methanesulfonamide To a solution of 35D (6.46 g, 15.2 mmol, 1 eq) in 500 mL of dry $CH_2Cl_2$ at −78° C., was added dropwise, a 1.5M solution of DIBAL-H (51 mL, 75.9 mmol, 5 eq). The reaction was warmed to 0° C. and mixed for 2 h before cooling to −78° C. and quenching with EtOAc. The resulting solution was poured into an 1L solution of $EtOAc/Na^+K^+$ tartrate (1:1), and allowed to mix overnight. The layers were then separated, and the organics were rinsed with brine, and dried over $Na_2SO_4$. Filtration and concentration in vacuo provided a crude solid that was recrystallized from MeOH to afford the titled compound. MS ($DCI/NH_3$, +Q1MS) m/e 415 ($M+NH_3$).

EXAMPLE 35F (1-hydroxy-6-phenyl-6H-dibenzo(b,d)pyran-8-yl)-methanesulfonamide A mixture of 35E (4.17 g, 10.5 mmol), powdered molecular sieves, NMO (1.84 g, 15.7 mmol), and TPAP (295 mg, 0.84 mmol) in $CH_3CN$ (350 mL) was stirred at room temperature for 2 hours and concentrated. The concentrate was dissolved in ethyl acetate and filtered through a silica gel plug with 1:1 hexane/ethyl acetate. The filtrate was concentrated to provide the aldehyde (3.52 g, 8.90 mmol). Without additional purification, half of this material was dissolved in THF (150 mL), cooled to −78° C., treated over five minutes with 1.8M phenyllithium (7.94 mL, 14.29 mmol), stirred for 2 hours, treated with methanol (10 mL), warmed to room temperature, poured into saturated $NaHCO_3$ and extracted with ethyl acetate. The extract was washed with brine, dried ($Na_2SO_4$), filtered, and concentrated. The concentrate was purified by flash column chromatography on silica gel with 2:1 hexanes/ethyl acetate to provide a major product (2.057 g). A fraction of this material (104 mg, 0.219 mmol) was dissolved in 5 mL of methanol at room temperature, treated with 2M hydrogen chloride in diethyl ether (5.4 mL, 11 mmol), stirred for 20 hours, poured into cold saturated $NaHCO_3$ and extracted with ethyl acetate. The extract was washed with brine, dried ($Na_2SO_4$), filtered, and concentrated to provide the titled compound. MS (ESI, −Q1MS) m/e 366 (M−H).

EXAMPLE 35G 1-(trifluoromethanesulfonyloxy)-6-phenyl-6H-dibenzo(b,d)pyran-8-yl)-methanesulfonamide A solution of Example 35F (70 mg, 0.19 mmol) and triethylamine (80 μL, 0.57 mmol) in dichloromethane (6 mL) at −78° C. was treated with trifuloromethanesulfonic anhydride (48 μL, 0.29 mmol), stirred for 30 minutes, treated with saturated $NaHCO_3$ (2 mL) and extracted with ethyl acetate. The extract was washed with brine, dried ($Na_2SO_4$), filtered, and concentrated. The concentrate was purified by flash column chromatography on silica with 3:1 hexanes/ethyl acetate to provide the titled compound. MS ($DCI/NH_3$, +Q1MS) m/e 517 ($M+NH_3$).

EXAMPLE 35H (1-(2-thienyl)-6-phenyl-6H-dibenzo(b,d)pyran-8-yl)-methanesulfonamide A solution of of Example 35G (58 mg, 0.12 mmol) in of dry DMF (2 mL) was treated with 2-(tributylstannyl) thiophene (369 μL, 1.2 mmol) and tetrakis (triphenylphosphine) palladium (O) (13 mg, 0.012 mmol), heated at 120° C. for 14 hours, cooled to ambient temperature, poured into ethyl acetate (10 mL), washed with saturated KF, 1M HCl, and brine, dried ($Na_2SO_4$), filtered, and concentrated. The concentrate was purified by flash column chromatography on silica gel with 3:1 hexanes/ethyl acetate to provide the titled compound. MS (ESI(−)Q1MS) m/z 432 (M−H)−; $^1$H NMR (400 MHz, DMSO-$d_6$) δ 9.86 (br s, 1H), 7.63–7.61 (d, J=5.0 Hz, 1H), 7.42–7.35 (m, 4H), 7.25–7.21 (t, J=7.8 Hz, 1H), 7.14–7.12 (t, J=3.8 Hz, 1H), 7.06–6.99 (m, 2H), 6.90–6.86 (d, J=16.3 Hz, 2H), 6.27 (s, 1H), 2.97 (s, 3H).

EXAMPLE 36

(1-ethynyl-6-phenyl-6H-dibenzo(b,d)pyran-8-yl) methanesulfonamide

Example 35G and tributylethynylstannane were processed as described in Example 35H to provide the titled compound. MS (ESI(−)Q1MS) m/z 374 (M−H)−; $^1$H NMR (400 MHz, DMSO-$d_6$) δ 9.98 (br s, 1H), 8.73–8.71 (d, J=8.7 Hz, 1H), 7.39–7.27 (m, 6H), 7.22–7.17 (m, 2H), 7.08–7.05 (dd, J=4.0, 2.6 Hz, 1H), 6.90 (d, J=2.1 Hz, 1H), 6.27 (s, 1H), 4.50 (s, 1H), 3.01 (s, 3H).

EXAMPLE 37

(1-vinyl-6-phenyl-6H-dibenzo(b,d)pyran-8-yl) methanesulfonamide

Example 35G and tributylvinyl tin were processed as described in Example 35H to provide the titled compound. MS (ESI(−)Q1MS) m/z 376 (M−H)−; $^1$H NMR (400 MHz, DMSO-$d_6$) δ 9.93 (br s, 1H), 7.69–7.67 (d, J=9.0 Hz, 1H), 7.39–7.29 (m, 6H), 7.22–7.16 (m, 2H), 7.10–7.03 (dd, J=10.9, 6.6 Hz, 1H), 6.99–6.96 (dd, J=6.1, 1.4 Hz, 1H), 6.88 (d, J=2.4 Hz, 1H), 6.18 (s, 1H), 5.84–5.80 (dd, J=16.1, 0.9 Hz, 1H), 5.43–5.40 (dd, J=9.5, 1.4 Hz, 1H), 3.01 (s, 3H).

EXAMPLE 38

(1-acetyl-6-phenyl-6H-dibenzo(b,d)pyran-8-yl) methanesulfonamide

Example 35B and tributyl(1-ethoxyvinyl)tin were processed as described in Example 35H to afford the ethoxyvinyl chromene, which was hydrolyzed in situ with 2M HCl/THF (1:1) to provide the titled compound. MS (ESI(−) QIMS) m/z 392 (M−H)−; $^1$H NMR (400 MHz, DMSO-$d_6$) δ 9.98 (br s, 1H), 7.38–7.34 (m, 5H), 7.39–7.22 (m, 3H), 7.14–7.11 (m, 2H), 6.91 (d, J=1.9 Hz, 1H), 6.31 (s, 1H), 3.02 (s, 3H), 2.48 (s, 3H).

EXAMPLE 39

(1-(propyn-1-yl)-6-phenyl-6H-dibenzo(b,d)pyran-8-yl)methanesulfonamide

Example 35G and tributylpropynylstannane were processed as described in Example 35H to provide the titled compound. MS (ESI(−)Q1MS) m/z 388 (M−H)−; $^1$H NMR (400 MHz, DMSO-$d_6$) δ 9.98 (br s, 1H), 8.74–8.76 (d, J=8.7 Hz, 1H), 7.38–7.28 (m, 6H), 7.16–7.09 (m, 2H), 6.99–6.97 (dd, J=6.4, 1.2 Hz, 1H), 6.92 (d, J=1.9 Hz, 1H), 6.25 (s, 1H), 3.03 (s, 3H), 2.13 (s, 3H).

EXAMPLE 40

(1-(2-furanyl)-6-phenyl-6H-dibenzo(b,d)pyran-8-yl)methanesulfonamide

Example 35G and tributyl(stannyl)furan were processed as described in Example 35H to provide the titled compound. MS (ESI(-)Q1MS) m/z 416 (M–H)$^-$; $^1$H NMR (400 MHz, DMSO-$d_6$) δ 9.87 (br s, 1H), 7.71–7.70 (d, J=0.7 Hz, 1H), 7.40–7.34 (m, 5H), 7.30–7.26 (t, J=8.0, 1H), 7.12–7.10 (dd, J=6.4, 1.2 Hz, 1H), 7.07–7.05 (dd, J=6.9, 1.2 Hz, 1H), 7.01–6.99 (dd, J=6.4, 2.4 Hz, 1H), 6.85 (d, J=2.4 Hz, 1H), 6.71–6.70 (d, J=3.3 Hz, 1H), 6.66–6.64 (dd, J=1.4, 1.9 Hz, 1H), 6.53–6.61 (d, J=8.5 Hz, 1H), 6.26 (s, 1H), 2.99 (s, 3H).

EXAMPLE 41

(1-allyl-6-phenyl-6H-dibenzo(b,d)pyran-8-yl)methanesulfonamide

Example 35G and allyltributyltin were processed as described in Example 35H to provide the titled compound. MS (ESI(-)Q1MS) m/z 390 (M–H)$^-$; $^1$H NMR (300 MHz, DMSO-$d_6$) δ 9.91 (br s, 1H), 7.76–7.73 (d, J=8.8 Hz, 1H), 7.40–7.26 (m, 6H), 7.19–7.14 (t, J=7.8 Hz, 1H), 6.92–6.87 (m, 2H), 6.84–6.83 (d, J=2.0 Hz, 1H), 6.16–6.03 (m, 2H), 5.19–5.15 (dd, J=8.5, 1.7 Hz, 1H), 5.07–5.00 (dd, J=15.3, 2.0 Hz, 1H), 3.71–3.69 (br dd, J=4.4, 1Hz, 2H), 3.00 (s, 3H).

EXAMPLE 42

(1-carbomethoxy-6-phenyl-6H-dibenzo(b,d)pyran-8-yl)methanesulfonamide

To a solution of Example 35G (76 mg, 0.152 mmol, 1.0 eq) in 5 mL of 10:1 DMSO/MeOH, were added ethylenebisdiphenylphosphine (6 mg, 0.0152 mmol, 0.10 eq), NEt$_3$ (49 μL, 0.35 mmol, 2.3 eq), and palladium acetate (3.4 mg, 0.0152 mmol, 0.10 eq). The reaction, vessel was purged with N$_2$, then carbon monoxide was vigorously bubbled through the solution for 6 min before attaching a balloon containing CO(g) to the system and heating overnight at 60° C. Upon cooling, the mixture was poured into H$_2$O (25 mL) and extracted with EtOAc (4×25 mL). The combined organics were rinsed with brine (2×50 mL) and dried over Na$_2$SO$_4$. The resulting crude residue was chromatographed on SiO$_2$ with 3:1 hexane)EtOAc to afford the titled compound as white needles (19 mg, 0.046 mmol, 31%). MS (ESI(-)Q1MS) m/z 408 (M–H)$^-$; $^1$H NMR (300 MHz, DMSO-$d_6$) δ 9.96 (br s, 1H), 7.42–7.32 (m, 6H), 7.32–7.29 (m, 1H), 7.26–7.23 (m, 2H), 7.19–7.17 (dd, J=6.4, 1.7 Hz, 1H), 6.84 (d, J=0.5 Hz, 1H), 6.27 (s, 1H), 3.82 (s, 3H), 3.01 (s, 3H).

EXAMPLE 43

(1-cyano-6-phenyl-6H-dibenzo(b,d)pyran-8-yl)methanesulfonamide

Example 35G and tributyltin cyanide were processed as described in Example 35H to provide the titled compound. MS (ESI(-)Q1MS) m/z 375 (M–H)$^-$; $^1$H NMR (400 MHz, DMSO-$d_6$) δ 0.14 (br s, 1H), 8.34–8.32 (d, J=8.5 Hz, 1H), 7.55–7.53 (dd, J=4.5, 2.1 Hz, 1H), 7.40–7.34 (m, 6H), 7.31–7.29 (dd, J=5.9, 1.9 Hz, 2H), 6.96 (d, J=2.4 Hz, 1H), 6.40 (s, 1H), 3.06 (s, 3H).

EXAMPLE 44

(1-ethoxy-6-phenyl-6H-dibenzo(b,d)pyran-8-yl)methanesulfonamide

A solution of Example 35F (77 mg, 0.210 mmol) in THF (5 mL) at 0° C. was treated with bistrimethylsilylacetamide (52 μL, 0.210 mmol), stirred for 1 hour, and concentrated. The concentrate was dissolved in THF (5 mL), cooled to 0° C., treated with 1M potassium tert-butoxide (210 μL, 0.210 mmol), stirred for 1 hour, treated with ethyl iodide (17 μL, 0.210 mmol), stirred at room temperature for 72 hours, treated with 1M HCl (5 mL), stirred for 2 hours, poured into saturated NaHCO$_3$, and extracted with ethyl acetate. The extract was washed with brine, dried (Na$_2$SO$_4$), filtered, and concentrated. The concentrate was purified by reverse-phase HPLC with CH$_3$CN/water to provide the desired product as the fraction which eluted at 25 minutes. MS (ESI(-)Q1MS) m/z 394 (M–H)$^-$; $^1$H NMR (400 MHz, DMSO-$d_6$) δ 9.84 (br s, 1H), 8.43–8.41 (d, J=8.7 Hz, 1H), 7.37–7.23 (m, 6H), 7.14–7.10 (t, J=8.0 Hz, 1H), 6.89 (d, J=2.4 Hz, 1H), 6.71–6.69 (dd, J=7.6, 0.7 Hz, 1H), 6.63–6.60 (dd, J=7.3, 1.0 Hz, 1H), 6.20 (s, 1H), 4.16–4.09 (m, 2H), 3.00 (s, 3H), 1.46–1.42 (t, J=6.9, 3H).

EXAMPLE 45

(1-(2-propynyl)oxy-6-phenyl-6H-dibenzo(b,d)pyran-8-yl)methanesulfonamide

Example 35F and propargylbromide were processed as described in Example 44 to provide the titled compound. MS (ESI(-)Q1MS) m/z 404 (M–H)$^-$; $^1$H NMR (400 MHz, DMSO-$d_6$) δ 9.86 (br s, 1H), 8.37–8.35 (d, J=8.7 Hz, 1H), 7.37–7.23 (m, 6H), 7.17–7.13 (t, J=8.3 Hz, 1H), 6.89 (d, J=2.4 Hz, 1H), 6.80–6.78 (dd, J=7.6, 0.7 Hz, 1H), 6.68–6.65 (dd, J=7.3, 0.7 Hz, 1H), 6.22 (s, 1H), 4.93–4.92 (d, J=2.4 Hz, 2H), 3.00 (s, 3H).

EXAMPLE 46

(1-methoxy-6-(2-carboethoxyethyl)-6H-dibenzo(b,d)pyran-8-yl)-methanesulfonamide

EXAMPLE 46A (1,6-dimethoxy-6H-dibenzo(b,d)pyran-8-yl)methanesulfonamide

A solution of Example 32E (1.0 g, 2.7 mmol) in methanol (50 mL) at room temperature was treated with para-toluenesulfonic acid (1.04 g, 5.4 mmol), stirred for 3 hours at room temperature, and treated with saturated NaHCO$_3$ (50 mL) and ethyl acetate (50 mL) to provide two layers. The layers were separated, and the aqueous layer was extracted with ethyl acetate. The extract was dried (Na$_2$SO$_4$), filtered, and concentrated. The concentrate was purified by flash column chromatography on silica gel with 50% ethyl acetate/hexanes to provide the desired product (0.92 g, 99%) as a white foam. MS (ESI(-)Q1MS) m/z 334 (M–H)$^-$.

EXAMPLE 46B (1-methoxy-6-(2-carboethoxyethyl)-6H-dibenzo(b,d)pyran-8-yl)methanesulfonamide The reaction was performed on a Quest 210 parallel synthesis instrument. The reaction vessel was dried by heating for 30 minutes at 110° C. under a stream of argon.

A solution of the compound of Example 46A (33 mg, 0.1 mmol) in dichloromethane (10 mL) at −15° C. was treated dropwise with boron trifluoride etherate (38 μL, 0.3 mmol) and 3-ethoxy-3-oxopropylzinc bromide (660 μL, 0.33 mmol), warmed to −10° C. for 15 minutes and treated with saturated NaHCO$_3$ (4 mL) to provide two layers. The layers were separated, and the aqueous layer was extracted with dichloromethane. The extract was dried (Na$_2$SO$_4$), filtered, and concentrated. The concentrate was purified by high throughput HPLC (0.1% TFA/MeCN gradient) to provide the desired product. MS (ESI(−)Q1MS) m/z 404 (M−H)$^−$; $^1$H NMR (500 MHz, CD$_3$OD) δ 1.23 (t, 3H, J=7.2 Hz), 1.99 (m, 1H), 2.09 (m, 1H), 2.49 (m, 2H), 2.99 (s, 3H), 3.92 (s, 3H), 4.10 (q, 2H, J=7.2 Hz), 5.04 (dd, 1H, J=9.4, 4.7 Hz), 6.59 (dd, 1H, J=8.1, 1.2 Hz), 6.72 (dd, 1H, J=8.5, 1.0 Hz), 7.08 (d, 1H, J=2.5 Hz), 7.15 (t, 1H, J=8.3 Hz), 7.20 (dd, 1H, J=8.8, 2.5 Hz), 8.36 (d, 1H, J=8.8 Hz).

EXAMPLE 47

(1-methoxy-6-(4-cyanophenyl)-6H-dibenzo(b,d)pyran-8-yl)methanesulfonamide

Example 46A and 4-cyanophenylzinc bromide were processed as described in Example 46B to provide the titled compound. MS (ESI(−)Q1MS) m/z 405 (M−H)$^−$; $^1$H NMR (500 MHz, CD$_3$OD) δ 2.96 (s, 3H), 3.91 (s, 3H), 6.16 (s, 1H), 6.63 (dd, 1H, J=8.3, 1.2 Hz), 6.71 (dd, 1H, J=8.4, 0.9 Hz), 6.92 (d, 1H, J=2.5 Hz), 7.14 (t, 1H, J=8.3 Hz), 7.28 (dd, 1H, J=8.7, 2.5 Hz), 7.49 (d, 1H, J=8.1 Hz), 7.67 (d, 1H, J=8.4 Hz), 8.43 (d, 1H, J=8.7 Hz).

EXAMPLE 48

(1-methoxy-6-(6-cyanohexyl)-6H-dibenzo(b,d)pyran-8-yl)methanesulfonamide

Example 46A and 6-cyanohexylzinc bromide were processed as described in Example 46B to provide the titled compound. MS (ESI(−)Q1MS) m/z 413 (M−H)$^−$; $^1$H NMR (500 MHz, CD$_3$OD) δ 1.29–1.49 (m, 5H), 1.60 (m, 4H), 1.83 (m, 1H), 2.39 (t, 2H, J=7.0 Hz), 2.98 (s, 1H), 3.92 (s, 1H), 4.98 (dd, 1H, J=8.9, 4.8 Hz), 5.01 (dd, 1H, J=9.1, 4.1 Hz), 6.59 (d, 1H, J=8.1 Hz), 6.71 (d, 1H, J=8.4 Hz), 7.07 (d, 1H, J=2.2 Hz), 7.15 (t, 1H, J=8.1 Hz), 7.17 (dd, 1H, J=8.4, 2.5 Hz), 8.35 (d, 1H, J=8.5 Hz).

EXAMPLE 49

(1-methoxy-6-(3-cyanobenzyl)-6H-dibenzo(b,d)pyran-8-yl)methanesulfonamide

Example 46A and 3-cyanobenzylzinc bromide were processed as described in Example 46B to provide the titled compound. MS (ESI(−)Q1MS) m/z 419 (M−H)$^−$; $^1$H NMR (500 MHz, CD$_3$OD) δ 2.93 (s, 3H), 2.99 (dd, 1H, J=13.2, 5.9 Hz), 3.12 (dd, 1H, J=14.0, 8.7 Hz), 3.94 (s, 3H), 5.29 (dd, 1H, J=8.6, 5.4 Hz), 6.52 (dd, 1H, J=8.1, 1.3 Hz), 6.74 (d, 1H, J=9.3 Hz), 6.94 (d, 1H, J=2.5 Hz), 7.19 (m, 2H), 7.43 (m, 3H), 7.54 (m, 1H), 8.39 (d, 1H, J=8.7 Hz).

EXAMPLE 50

(1-methoxy-6-(3-cyanophenyl)-6H-dibenzo(b,d)pyran-8-yl)methanesulfonamide

Example 46A and 3-cyanophenylzinc iodide were processed as described in Example 46B to provide the titled compound. MS (ESI(−)Q1MS) m/z 405 (M−H)$^−$; $^1$H NMR (500 MHz, CD$_3$OD) δ 2.97 (s, 3H), 3.92 (s, 3H), 6.14 (s, 1H), 6.64 (dd, 1H, J=8.2, 1.0 Hz), 6.71 (dd, 1H, J=8.5, 1.0 Hz), 6.91 (d, 1H, J=2.5 Hz), 7.15 (t, 1H, J=8.3 Hz), 7.29 (dd, 1H, J=8.7, 2.5 Hz), 7.49 (t, 1H, J=8.0 Hz), 7.60 (m, 3H), 7.64 (m, 3H), 8.44 (d, 1H, J=8.7 Hz).

EXAMPLE 51

(1-methoxy-6-(3-carboethoxyphenyl)-6H-dibenzo(b,d)pyran-8-yl)methanesulfonamide

Example 46A and 3-(ethoxycarbonyl)phenylzinc bromide were processed as described in Example 46B to provide the titled compound. MS (ESI(−)Q1MS) m/z 452 (M−H)$^−$; $^1$H NMR (500 MHz, CD$_3$OD) δ 1.34 (t, 3H, J=7.0 Hz), 2.94 (s, 3H), 3.90 (s, 3H), 4.32 (q, 2H, J=7.1 Hz), 6.11 (s, 1H), 6.62 (d, 1H, J=8.2 Hz), 6.69 (d, 1H, J=8.4 Hz), 6.87 (d, 1H, J=2.5 Hz), 7.12 (t, 1H, J=8.3 Hz), 7.27 (dd, 1H, J=8.8, 2.2 Hz), 7.42 (m, 1H), 7.55 (d, 1H, J=7.5 Hz), 7.95 (m, 2H), 8.42 (d, 1H, J=8.5 Hz).

EXAMPLE 52

(1-methoxy-6-(4-carboethoxyphenyl)-6H-dibenzo(b,d)pyran-8-yl)methanesulfonamide

Example 46A and 3-(ethoxycarbonyl)phenylzinc iodide were processed as described in Example 46B to provide the titled compound. MS (ESI(−)Q1MS) m/z 452 (M−H)$^−$; $^1$H NMR (500 MHz, CD$_3$OD) δ 1.35 (t, 3H, J=6.9 Hz), 2.94 (s, 1H), 3.91 (s, 1H), 4.33 (q, 1H, J=7.0 Hz), 6.11 (s, 1H), 6.62 (dd, 1H, J=8.1, 1.0 Hz), 6.69 (d, 1H, J=8.4 Hz), 6.86 (t, 1H, J=2.6 Hz), 7.13 (t, 1H, J=8.3 Hz), 7.27 (dt, 1H, J=8.8, 2.2 Hz), 7.42 (m, 2H), 7.94 (m, 2H), 8.42 (d, 1H, J=8.7 Hz).

EXAMPLE 53

(1-methoxy-6-allyl-6H-dibenzo(b,d)pyran-8-yl)methanesulfonamide

Example 46A and allyltrimethylsilane were processed as described in Example 46B to provide the titled compound. MS (ESI(−)Q1MS) m/z 344 (M−H)$^−$; $^1$H NMR (300 MHz, DMSO-d$_6$) δ 9.86 (s, 1H), 8.28 (d, J=9 Hz, 1H), 7.19 (t, J=8 Hz, 1H), 7.16 (dd, J=8 Hz, 2 Hz, 1H), 7.09 (d, J=2 Hz, 1H), 6.75 (d, J=8 Hz, 1H), 6.59 (d, J=8 Hz, 1H), 5.92–5.78 (m, 1H), 5.15 (dd, J=7 Hz, 7 Hz, 1H), 5.10–5.01 (m, 2H), 3.80 (s, 3H), 3.02 (s, 3H), 2.57–2.32 (m, 2H).

EXAMPLE 54

(1-methoxy-6-(2-thienyl)-6H-dibenzo(b,d)pyran-8-yl)methanesulfonamide

Example 46A and 2-thienylzinc bromide were processed as described in Example 46B to provide the titled compound. MS (ESI(−)Q1MS) m/z 386 (M−H)$^−$; $^1$H NMR (500 MHz, CD$_3$OD) δ 2.96 (s, 3H), 3.92 (s, 3H), 6.35 (s, 1H), 6.58 (d, 1H, J=8.1 Hz), 6.70 (d, 1H, J=8.1 Hz), 6.82 (d, 1H, J=3.5 Hz), 6.87 (dd, 1H, J=4.9, 3.4 Hz), 7.06 (d, 1H, J=2.5 Hz), 7.11 (t, 1H, J=8.1 Hz), 7.26 (dd, 1H, J=8.6, 2.3 Hz), 7.30 (dd, 1H, J=5.0, 0.9 Hz), 8.42 (d, 1H, J=8.4 Hz).

EXAMPLE 55

(1-methoxy-6-cyclohexyl-6H-dibenzo(b,d)pyran-8-yl)methanesulfonamide

Example 46A and cyclohexylzinc bromide were processed as described in Example 46B to provide the titled compound. MS (ESI(−)Q1MS) m/z 386 (M−H)$^−$; $^1$H NMR (500 MHz, CD$_3$OD) δ 0.98–1.22 (m, 5H), 1.40 (m, 1H), 1.54–1.75 (m, 4H), 2.04 (m, 1H), 2.97 (s, 3H), 3.93 (s, 3H), 4.63 (d, 1H, J=9.0 Hz), 6.58 (d, 1H, J=8.1 Hz), 6.70 (d, 1H, J=8.1 Hz), 7.00 (d, 1H, J=2.2 Hz), 7.14 (t, 1H, J=8.3 Hz), 7.18 (dd, 1H, J=8.6, 2.4 Hz), 8.34 (d, 1H, J=8.7 Hz).

EXAMPLE 56

(1-methoxy-6-(4-ethoxybenzyl)-6H-dibenzo(b,d)pyran-8-yl)methanesulfonamide

Example 46A and 4-ethoxybenzylzinc chloride were processed as described in Example 46B to provide the titled compound. MS (ESI(–)Q1MS) m/z 438 (M–H)$^-$; $^1$H NMR (500 MHz, CD$_3$OD) δ 1.36 (t, 3H, J=7.0 Hz), 2.81 (dd, 1H, J=13.8, 6.6 Hz), 2.85 (s, 3H), 3.96 (s, 3H), 3.99 (q, 2H, J=7.0 Hz), 5.17 (dd, 1H, J=7.7, 7.0 Hz), 6.56 (d, 1H, J=8.1 Hz), 6.74 (d, 1H, J=8.4 Hz), 6.78 (d, 2H, J=8.7 Hz), 6.79 (d, 1H, J=3.1 Hz), 6.97 (d, 2H, J=8.7 Hz), 7.15 (dd, 1H, J=8.6, 2.4 Hz), 7.18 (t, 1H, J=8.1 Hz), 8.38 (d, 1H, J=8.7 Hz).

EXAMPLE 57

(1-methoxy-6-(4-chlorobutyl)-6H-dibenzo(b,d)pyran-8-yl)methanesulfonamide

Example 46A and 4-chlorobutylzinc bromide were processed as described in Example 46B to provide the titled compound. MS (ESI(–)Q1MS) m/z 394 (M–H)$^-$; $^1$H NMR (500 MHz, CD$_3$OD) δ 1.62 (m, 1H), 1.68 (m, 2H), 1.77 (m, 2H), 1.86 (m, 1H), 2.98 (s, 3H), 3.53 (t, 2H, J=6.5 Hz), 3.93 (s, 3H), 4.99 (dd, 1H, J=8.9, 4.3 Hz), 6.60 (d, 1H, J=9.0 Hz), 6.71 (d, 1H, J=8.4 Hz), 7.08 (d, 1H, J=2.2 Hz), 7.15 (t, 1H, J=8.1 Hz), 7.18 (dd, 1H, J=8.6, 2.3 Hz), 8.35 (d, 1H, J=8.5 Hz).

EXAMPLE 58

(1-methoxy-6-(5-chlorothien-2-yl)-6H-dibenzo(b,d)pyran-8-yl)methanesulfonamide

Example 46A and 5-chloro-2-thienylzinc bromide were processed as described in Example 46B to provide the titled compound. MS (ESI(–)Q1MS) m/z 420 (M–H)$^-$; $^1$H NMR (500 MHz, CD$_3$OD) δ 2.98 (s, 3H), 3.92 (s, 3H), 6.28 (s, 1H), 6.59 (dd, 1H, J=3.5, 1.0 Hz), 6.60 (dd, 1H, J=1.0, 0.9 Hz), 6.71 (dd, 1H, J=8.5, 1.0 Hz), 6.72 (d, 1H, J=3.7 Hz), 7.10 (d, 1H, J=2.2 Hz), 7.14 (t, 1H, J=8.3 Hz), 7.27 (dd, 1H, J=8.7, 2.3 Hz), 8.43 (d, 1H, J=8.7 Hz).

EXAMPLE 59

(1-methoxy-6-(3-methoxyphenyl)-6H-dibenzo(b,d)pyran-8-yl)methanesulfonamide

Example 46A and 3-methoxyphenylzinc iodide were processed as described in Example 46B to provide the titled compound. MS (ESI(–)Q1MS) m/z 410 (M–H)$^-$; $^1$H NMR (500 MHz, CD$_3$OD) δ 2.93 (s, 3H), 3.73 (s, 3H), 3.92 (s, 3H), 5.99 (s, 1H), 6.62 (dd, 1H, J=8.1, 0.9 Hz), 6.70 (dd, 1H, J=8.4, 0.9 Hz), 6.87 (m, 3H), 7.13 (t, 1H, J=8.1 Hz), 7.22 (t, 1H, J=8.3 Hz), 7.25 (dd, 1H, J=8.7, 2.5 Hz), 8.40 (d, 1H, J=8.7 Hz).

EXAMPLE 60

(1-methoxy-6-(3-chlorophenyl)-6H-dibenzo(b,d)pyran-8-yl)methanesulfonamide

Example 46A and 3-chlorophenylzinc iodide were processed as described in Example 46B to provide the titled compound. MS (ESI(–)Q1MS) m/z 414 (M–H)$^-$; $^1$H NMR (500 MHz, CD$_3$OD) δ 2.95 (s, 3H), 3.92 (s, 3H), 6.05 (s, 1H), 6.62 (dd, 1H, J=8.1, 0.9 Hz), 6.70 (d, 1H, J=8.4 Hz), 6.88 (d, 1H, J=2.5 Hz), 7.14 (t, 1H, J=8.3 Hz), 7.22 (m, 1H), 7.27 (m, 3H), 7.31 (m, 1H), 8.42 (d, 1H, J=8.7 Hz).

EXAMPLE 61

(1-methoxy-6-(4-chlorophenyl)-6H-dibenzo(b,d)pyran-8-yl)methanesulfonamide

Example 46A and 4-chlorophenylzinc iodide were processed as described in Example 46B to provide the titled compound. MS (ESI(–)Q1MS) m/z 414 (M–H)$^-$; $^1$H NMR (500 MHz, CD$_3$OD) δ 2.94 (s, 3H), 3.91 (s, 3H), 6.04 (s, 1H), 6.59 (dd, 1H, J=8.1, 0.9 Hz), 6.69 (d, 1H, J=8.4 Hz), 6.84 (d, 1H, J=2.2 Hz), 7.12 (t, 1H, J=8.3 Hz), 7.29 (m, 5H), 8.41 (d, 1H, J=8.7 Hz).

EXAMPLE 62

(1-methoxy-6-(5-bromothien-2-yl)-6H-dibenzo(b,d)pyran-8-yl)methanesulfonamide

Example 46A and 5-bromo-2-thienylzinc bromide were processed as described in Example 46B to provide the titled compound. MS (ESI(–)Q1MS) m/z 466 (M–H)$^-$; $^1$H NMR (500 MHz, CD$_3$OD) δ 2.98 (s, 3H), 3.93 (s, 3H), 6.30 (s, 1H), 6.58 (dd, 1H, J=3.9, 1.1 Hz), 6.59 (dd, 1H, J=8.0, 0.9 Hz), 6.72 (dd, 1H, J=8.5, 1.0 Hz), 6.85 (d, 1H, J=3.7 Hz), 7.10 (d, 1H, J=2.5 Hz), 7.14 (t, 1H, J=8.3 Hz), 7.28 (dd, 1H, J=8.7, 2.5 Hz), 8.43 (d, 1H, J=8.8 Hz).

EXAMPLE 63

(1-methoxy-6-(3,4-dichlorophenyl)-6H-dibenzo(b,d)pyran-8-yl)methanesulfonamide

Example 46A and 3,4-dichlorophenylzinc iodide were processed as described in Example 46B to provide the titled compound. MS (ESI(–)Q1MS) m/z 449 (M–H)$^-$; $^1$H NMR (500 MHz, CD$_3$OD) δ 2.97 (s, 3H), 3.91 (s, 3H), 6.07 (s, 1H), 6.64 (dd, 1H, J=8.2, 1.0 Hz), 6.70 (d, 1H, J=8.4 Hz), 6.93 (d, 1H, J=2.4 Hz), 7.15 (t, 1H, J=8.3 Hz), 7.22 (d, 2H, J=1.2 Hz), 7.30 (dd, 1H, J=8.7, 2.5 Hz), 7.33 (m, 1H), 8.43 (d, 1H, J=8.4 Hz).

EXAMPLE 64

(1-methoxy-6-(3-(2-methoxyethyl)aminocarbonyl)phenyl-6H-dibenzo(b,d)pyran-8-yl)methanesulfonamide

EXAMPLE 64A (1-methoxy-6-(3-carboxyphenyl)-6H-dibenzo(b,d)pyran-8-yl)methanesulfonamide A solution of Example 51 (0.34 g, 0.76 mmol) in THF (5 mL) and ethanol (5 mL) was treated with a solution of 10% LiOH (5 mL), stirred at room temperature for 20 hours, and poured into a mixture of ice, 1M HCl (50 mL) and ethyl acetate (50 mL). The layers were separated, and the aqueous layer was extracted with ethyl acetate. The extract was dried (Na$_2$SO$_4$), filtered, and concentrated to provide the desired product.(0.26 g, 80%) as a white solid MS (ESI(–)Q1MS) m/z 424 (M–H)$^-$.

EXAMPLE 64B (1-methoxy-6-(3-(2-methoxyethyl)aminocarbonyl)phenyl-6H-dibenzo(b,d)pyran-8-yl)methanesulfonamide A solution of Example 64A (0.26 g, 0.61 mmol), 2-(1H-benzotriazol-1-yl)-1,1,3,3-tetramethyluroniumtetrafluoroborate (0.29 g, 0.91 mmol), and methoxyethylamine (0.068 g, 0.91 mmol) in DMF (2 mL) was treated with diisopropylethylamine (0.24 g, 1.83 mmol), stirred at room temperature for 14 hours, and poured onto a mixture of ice, 1M HCl (50 mL), and ethyl acetate (50 mL). The layers were separated, and the aqueous layer was extracted with ethyl acetate. The extracts were dried ($Na_2SO_4$), filtered, and concentrated. The concentrate was purified by flash column chromatography on silica gel with 20–50% ethyl acetate/hexanes to provide the desired product (0.220 g, 72%) as a white solid. MS (ESI(-)Q1MS) m/z 481 (M-H)$^-$; $^1$H NMR (300 MHz, DMSO-$d_6$) δ 9.84 (s, 1H), 8.52 (t, J=5 Hz, 1H), 8.45 (d, J=9 Hz, 1H), 7.85–7.79 (m, 2H), 7.45–7.40 m, 2H), 7.26 (dd, J=9 Hz, 2 Hz, 1H), 7.16 (t, J=8 Hz, 1H), 6.85 (d, J=8 Hz, 2H), 6.75 (d, J=2 Hz, 1H), 6.65 (d, J=8 Hz, 1H), 6.25 (s, 1H), 3.89) (s, 3H), 3.45–3.35 (m, 4H), 3.25 (s, 3H), 3.00 (s, 3H), 2.70 (s, 3H).

EXAMPLE 65

(1-methoxy-2-hydroxy-6-phenyl-6H-dibenzo(b,d)pyran-8-yl)methanesulfonamide

Methoxyhydroquinone was processed according to example 35A–F to provide the titled compound. MS (ESI(-)) m/z 396 (M-H)$^-$; $^1$H NMR (300 MHz, CDCl$_3$) δ 2.99 (s, 3H), 3.72 (s, 3H), 5.95 (s, 1H), 6.45 (s, 1H), 6.62 (d, J=2 Hz, 1H), 6.72 (dd, J=10 Hz, 2 Hz, 1H), 6.85 (dd, J=9 Hz, 1 Hz, 1H), 7.15 (t, J=9 Hz, 1H), 7.25 (dd, J=9 Hz, 2 Hz, 1H), 7.40–7.70 (m, 4H), 8.35 (d, J=9 Hz, 1H).

EXAMPLE 66

(1,2-methylenedioxy-6-phenyl-6H-dibenzo(b,d)pyran-8-yl)methanesulfonamide 3,4-methylenedioxyphenol was processed according to example 32 to provide the titled compound. MS (ESI(-)) m/z 394 (M-H)$^-$; $^1$H NMR (300 MHz, CDCl$_3$) δ 2.95 (s, 3H), 6.18 (s, 2H), 6.30 (s, 1H), 6.51 (d, J=2 Hz, 2H), 6.68 (dd, J=10 Hz, 2 Hz, 2H), 7.24–7.29 (m, 4H), 7.31–7.39 (m, 2H), 8.45 (d, J=9 Hz, 1H).

EXAMPLE 67

(1-methoxy-3-methyl-6-phenyl-6H-dibenzo(b,d)pyran-8-yl)methanesulfonamide

5-Methyl-1,3-dimethoxybenzene was processed as described in Example 1, using phenylmagnesium bromide in Example 1I, to provide the titled compound. MS (APCI(+)) m/z 396 (M+H)$^+$ and 413 (M+NH$_4$)$^+$; $^1$H NMR (300 MHz, DMSO-$d_6$) δ 2.24 (s, 3H), 2.98 (s, 3H), 3.8, 6 (s, 3H), 6.19 (s, 1H), 6.45 (s, 1H), 6.56 (s, 1H), 6.89 (d, J=2 Hz, 1H), 7.2–7.4 (m, 6H), 8.30 (d, J=9 Hz, 1H), 9.80 (s, 1H).

EXAMPLE 68

(1-methoxy-4-methyl-6-phenyl-6H-dibenzo(b,d)pyran-8-yl)methanesulfonamide

4-Methyl-1,3-dimethoxybenzene was processed as described in Example 1, using phenylmagnesium bromide in Example 1I, to provide the titled compound. MS (APCI(+)) m/z 396 (M+H), 413 (M+NH$_4$); $^1$H NMR (300 MHz, DMSO-$d_6$) δ 2.13 (s, 3H), 3.01 (s, 3H), 3.83 (s, 3H), 6.27 (s, 1H), 6.62 (d, J=9 Hz, 1H), 6.95 (d, J=2 Hz, 1H), 7.01 (dd, J=9 Hz, 1 Hz, 1H), 7.2–7.4 (m, 6H), 8.33 (d, J=9 Hz, 1H), 9.85 (s, 1H).

EXAMPLE 69

(1-methoxy-6-(2-pyridyl)-6H-dibenzo(b,d)pyran-8-yl)methanesulfonamide

A solution of (4-(2-methoxy-6-methoxymethoxyphenyl)-5-(1-hydroxy-1-(2-pyridyl)methyl)phenyl methanesulfonamide (0.030 g, 0.075 mmol), prepared according to the procedures of Examples 32A–F, in THF (1 mL) was treated with tributylphoshine (0.045 g, 0.23 mmol) and 1,1'-(azodicarbonyl)dipiperidine (0.057 g, 0.23 mmol), stirred for 4 hours at room temperature, and treated with saturated NaCl (10 mL) and ethyl acetate (10 mL) to provide two layers. The layers were separated, and the aqueous layer was extracted with ethyl acetate. The extract was dried ($Na_2SO_4$), filtered, and concentrated. The concentrate was purified by reverse phase HPLC with 20–100% $CH_3CN$/water to provide the desired product. MS (ESI(-)Q1MS) m/z 381 (M-H)$^-$; $^1$H NMR (300 MHz, DMSO-$d_6$) δ 9.83 (s, 1H), 8.53 (m, 1H), 8.31 (d, J=8 Hz, 1H), 7.79 (dt, J=8 Hz, 2 Hz, 1H), 7.39 (d, J=8 Hz, 1H), 7.32 (m, 1H), 7.22 (m, 1H), 7.18 (d, J=8 Hz, 1H), 6.93 (d, J=2 Hz, 1H), 6.75 (d, J=8 Hz, 1H), 6.70 (d, J=8 Hz, 1H), 6.21 (s, 1H), 3.90 (s, 3H), 3.00 (s, 3H).

EXAMPLE 70

(1-methoxy-6-(3-pyridyl)-6H-dibenzo(b,d)pyran-8-yl)methanesulfonamide (4-(2-methoxy-6-methoxymethoxyphenyl)-5-(1-hydroxy-1-(3-pyridyl)methyl)phenyl methanesulfonamide, prepared according to the procedures of Examples 32A–F, was processed as described in Example 69 to provide the titled compound. MS (ESI(-)Q1MS) m/z 381 (M-H)$^-$; $^1$H NMR (300 MHz, DMSO-$d_6$) δ 9.89 (s, 1H), 8.57 (dd, J=8 Hz, 2 Hz, 1H), 8.53 (d, J=2 Hz, 1H), 8.37 (d, J=8 Hz, 1H), 7.72 (dt, J=8 Hz, 2 Hz, 1H), 7.47 (d, J=8 Hz, 1H), 7.45 (d, J=8 Hz, 1H), 7.28 (dd, J=8 Hz, 2 Hz, 1H), 7.17 (t, J=8 Hz, 1H), 6.93 (d, J=2 Hz, 1H), 6.75 (d, J=8 Hz, 1H), 6.67 (d, J=8 Hz, 1H), 6.38 (s, 1H), 3.90 (s, 3H), 3.01 (s, 3H).

EXAMPLE 71

(1-methoxy-6-(2-bromoprop-2-en-1-yl)-6H-dibenzo(b,d)pyran-8-yl)methanesulfonamide Example 46A and (2-bromoallyl)trimethylsilane were processed as described in Example 46B to provide the titled compound. MS (ESI(-)Q1MS) m/z 422 (M-H)$^-$; $^1$H NMR (499 MHz, CDCl$_3$) δ 8.44 (d, J=8.8 Hz, 1H), 7.19 (dd, J=5.3, 2.8 Hz, 1H), 7.17 (dd, J=4.8, 2.3 Hz, 1H), 7.07 (d, J=2.5 Hz, 1H), 6.66 (dd, J=8.3 Hz, 2H), 6.44 (s, 1H), 5.51 (d, J=1.8 Hz, 1H), 5.47 (m, 1H), 5.43 (dd, J=8.7, 5.4 Hz, 1H), 3.96 (s, 3H), 3.03 (s, 3H), 3.00 (ddd, J=14.3, 8.4, 0.6 Hz, 1H), 2.64 (ddd, J=14.7, 5.1, 0.8 Hz, 1H).

EXAMPLE 72

(1-methoxy-6-(2-(1-oxocyclohexyl))-6H-dibenzo(b,d)pyran-8-yl)methanesulfonamide

Example 46A and 1-(trimethylsiloxy)cyclohexene were processed as described in Example 46B to provide the titled compound. MS (ESI(-)Q1MS) m/z 400 (M-H)$^-$; 1:1 mixture of isomers: $^1$H NMR (499 MHz, CDCl$_3$) δ 8.42 (d, J=8.4 Hz, 1H), 8.36 (d, J=8.7 Hz, 1H), 7.29 (m, 1H), 7.17 (m, 4H), 6.99 (m, 1H), 6.62 (m, 4H), 6.48 (brs, 1H), 6.46 (brs, 1H), 5.61 (d, J=8.4 Hz, 1H), 5.44 (d, J=9.0 Hz, 1H), 3.96 (s, 3H), 3.95 (s, 3H), 3.04 (s, 3H), 3.03 (s, 3H), 2.88 (m, 2H), 2.52 (m, 1H), 2.32 (m, 2H), 2.20 (m, 1H), 2.00 (m, 2H), 1.66–1.91 (m, 4H), 1.62 (m, 2H), 1.48 (m, 4H).

EXAMPLE 73

(1-methoxy-6-(3-chloroprop-2-en-1-yl)-6H-dibenzo(b,d)pyran-8-yl)methanesulfonamide Example 46A and (3-chloroallyl)trimethysilane were processed as described in Example 46B to provide the titled compound. MS (ESI(-)Q1MS) m/z 378 (M–H)⁻; ¹H NMR (499 MHz, CDCl₃) δ 8.44 (d, J=8.4 Hz, 1H), 7.20 (m, 2H), 6.67 (dd, J=8.3, 0.8 Hz, 1H), 6.59 (dd, J=8.3, 1.2 Hz, 1H), 6.49 (s, 1H), 6.03 (m, 1H), 5.26 (d, J=10.3 Hz, 1H), 5.17 (d, J=16.9 Hz, 1H), 5.05 (d, J=9.0 Hz, 1H), 4.40 (dd, J=9.0, 8.5 Hz, 1H), 3.96 (s, 3H), 3.03 (s, 3H).

EXAMPLE 74

(1-methoxy-6-(inden-3-yl)-6H-dibenzo(b,d)pyran-8-yl)methanesulfonamide

Example 46A and [1H-inden-1-yltrimethylsilane] were processed as described in Example 46B to provide the titled compound. MS (ESI(-)Q1MS) m/z 418 (M–H)⁻; 2:1 mixture of isomers: ¹H NMR (499 MHz, CDCl₃) δ 8.51 (m, 1H), 8.46 (m, 2H), 7.81 (m, 2H), 7.32 (m, 9H), 7.21 (m, 6H), 7.01 (m, 1H), 6.96 (m, 2H), 6.88 (m, 1H), 6.80 (m, 5H), 6.72 (m, 6H), 6.36 (m, 3H), 5.98 (m, 2H), 5.30 (s, 1H), 4.91 (d, J=9.0 Hz, 2H), 4.86 (d, J=8.7 Hz, 1H), 3.99 (s, 9H), 3.95 (m, 1H), 2.99 (s, 3H), 2.93 (s, 6H).

EXAMPLE 75

(1-methoxy-6-(5-chloropent-1-yl)-6H-dibenzo(b,d)pyran-8-yl)methanesulfonamide

Example 46A and 5-chloropentylzinc bromide were processed as described in Example 46B to provide the titled compound. MS (ESI(-)Q1MS) m/z 408 (M–H)⁻; ¹H NMR (499 MHz, CDCl₃) δ 8.40 (d, J=8.8 Hz, 1H), 7.18 (t, J=8.1 Hz, 1H), 7.12 (dd, J=8.4, 2.5 Hz, 1H), 7.05 (d, J=2.5 Hz, 1H), 6.66 (t, J=8.6 Hz, 1H), 6.31 (s, 1H), 5.00 (dd, J=9.3, 4.7 Hz, 1H), 3.95 (s, 3H), 3.52 (t, J=6.7 Hz, 2H), 3.02 (s, 3H), 1.92 (m, 1H), 1.77 (m, 2H), 1.64 (m, 2H), 1.46 (m, 4H).

EXAMPLE 76

(1-methoxy-6-(4-methylphenyl)-6H-dibenzo(b,d)pyran-8-yl)methanesulfonamide

Example 46A and 4-methylphenylzinc iodide were processed as described in Example 46B to provide the titled compound. MS (ESI(-)Q1MS) m/z 394 (M–H)⁻; ¹H NMR (499 MHz, CDCl₃) δ 8.45 (d, J=8.7 Hz, 1H), 7.24 (m, 3H), 7.15 (m, 3H), 6.64 (m, 3H), 6.23 (s, 1H), 5.97 (s, 1H), 3.95 (s, 3H), 2.97 (s, 3H), 2.35 (s, 3H).

EXAMPLE 77

(1-methoxy-6-(3-fluorophenyl)-6H-dibenzo(b,d)pyran-8-yl)methanesulfonamide

Example 46A and 3-fluorophenylzinc iodide were processed as described in Example 46B to provide the titled compound. MS (ESI(-)Q1MS) m/z 398 (M–H)⁻; ¹H NMR (499 MHz, CDCl₃) δ 8.47 (d, J=8.8 Hz, 1H), 7.32 (m, 1H), 7.24 (m, 1H), 7.17 (t, J=8.3 Hz, 1H), 7.12 (m, 1H), 7.04 (m, 2H), 6.72 (m, 1H), 6.70 (dd, J=8.1, 1.0 Hz, 1H), 6.64 (dd, J=8.4, 0.9 Hz, 1H), 6.29 (s, 1H), 6.01 (s, 1H), 3.94 (s, 3H), 2.99 (s, 3H).

EXAMPLE 78

N-[1-(allyloxy)-6-phenyl-6H-benzo[c]chromen-8-yl]methanesulfonamide

Example 35F and allylbromide were processed as described in Example 44 to provide the titled compound. ¹H NMR (300 MHz, DMSO-d₆) δ 9.84 (s, 1H), 8.39 (d, J=8 Hz, 1H), 7.37–7.22 (m, 6H), 7.13 (t, J=8 Hz, 1H), 6.89 (J=2 Hz, 1H), 6.73 (d, J=8 Hz, 1H), 6.63 (d, J=8 Hz, 1H), 6.21 (s, 1H), 6.19–6.11 (m, 1H), 5.45 (d, J=16 Hz, 1H), 5.32 (d, J=11 Hz, 1H), 4.68 (d, J=5 Hz, 2H), 3.00 (s, 3H); MS (ESI,-Q1MS) m/e 406 (M–H).

EXAMPLE 79 ethyl 6-{1-methoxy-8-[(methylsulfonyl)amino]-6H-benzo[c]chromen-6-yl}hexanoate

Example 46A and 6-ethoxy-6-oxohexylzinc bromide were processed as described in Example 46B to provide the titled compound. ¹H NMR (300 MHz, DMSO-d₆) δ 9.92 (s, 1 H), 8.39 (d, J=8 Hz, 1H), 7.31–7.21 (m, 31H), 6.82 (J=8 Hz, 1H), 6.64 (d, J=8 Hz, 1H), 6.07 (s, 1H), 3.93 (s, 3H), 3.82–3.74 (m, 2H), 3.04 (s, 3H), 1.52–1.47 (m, 2H), 1.30–1.11 (m, 8H), 1.06 (t, J=7H, 3H); MS (ESI,-Q1MS) m/e 446 (M–H).

EXAMPLE 80

N-(6-{3-[allyl(methyl)amino]phenyl}-1-methoxy-6H-benzo[c]chromen-8-yl)methanesulfonamide

EXAMPLE 80A

3-Bromo-N-methyl-N-allylaniline

A solution of formic acid (24.3 g, 98%, 528 mmol) in Ac₂O (43.94 g, 430 mmol) was heated to 55° C. for 2 hours, cooled to room temperature. The mixture was diluted with toluene (25 mL) followed by the addition of of 3-bromoaniline (28 g, 163 mmol) in toluene (40 mL). The solution was stirred cold for 30 minutes after which the solvents were removed under vacuo and the residue crystallized from hexane to give N-(3-bromophenyl)formamide (32.79 g). The material was added in portions to 1M. BH3 in THF (450 mL) at 0° C., heated to refluxing for 3 hours and cooled to ambient temperature. The solvents were removed under reduced pressure, the residue was treated with aqueous hydrochloric acid (1M, 200 mL) for for ½ hour, the pH was adjusted to 12 with the addition of sodium hydroxide (1M). The solution was extracted with diethyl ether (3×75 mL), the combined ether layers dried (MgSO₄, filtered and concentrated under reduced pressure to give the titled compound (29.48).

EXAMPLE 80B

N-allyl-3-bromo-N-methylaniline 80A (16.25 g, 88.3 mmol) and allyl bromide (12.8 g, 105 mmol) were combined and heated to 95° C. for 1 hour, cooled to ambient temperature, diluted with water The pH was adjusted to 12 with the addition of NaOH (1M), the solution extracted with diethyl ether, the combined ether layers were dried (MgSO₄), filtered and concentrated under reduced pressure. The residue was purified on silica gel using 2% ethyl acetate in hexane to provide the titled compound (17.69 g).

EXAMPLE 80C

N-[2-[{3-[allyl(methyl)amino]phenyl}(hydroxy)methyl]-2'-methoxy-6'-(methoxymethoxy)[1,1'-biphenyl]-4-yl]methanesulfonamide To a solution of BuLi (18.9 mL, 2.5 M, 47.2 mmol) in THF (30 mL) at −78° C. was added dropwise) 80B (11.61 g, 51.6 mmol) in THF (15 mL). The mixture was stirred cold for ½ hour, and to this was added dropwise a solution of 3.415 (9.356 mM) Ex 32E in THF (18 mL). The mixture was stirred cold for 1 hour after which a solution of aqueous $KHCO_3$ (6.2 g in 50 mL water) was added and the mixture extracted with ethyl acetate (3×50 mL). The combined organic was dried ($Na_2SO_4$), filtered and concentrated under reduced pressure to give an oil. The oil was purified on silica using 25% ethyl acetate in hexane to provide the titled compound (4.30 g).

EXAMPLE 80D

N-(6-{3-[allyl(methyl)amino]phenyl}-1-methoxy-6H-benzo[c]chromen-8-yl)methanesulfonamide A solution of Ex 80C (5.66 g., 11.05 mmol) in methanol (100 mL) and 4N HCl in dioxane (100 mL) was stirred at ambient temperature for 14 hours, concentrated under filtered, dried ($Na_2SO_4$), filtered and concentrated under reduced pressure. The residue was dissolved in toluene (400 mL) containing TosOH $H_2O$ (8.40 g, 44.21 mM) and heated to 85° C. for 30 min, cooled to ambient temperature, diluted with THF (75 mL) containing aqueous $KHCO_3$ (6 g 60 mL water), stirred for ½ hour. The organic layer was separated, dried ($Na_2SO_4$), filtered and concentrated under reduced pressure to provide an oil which was purified on silica with 5% ethyl acetate in dichloromethane to provide the titled compound (4.15 g, 84% yield). NMR ($CDCl_3$, 300 MHz) δ 2.91 (s, 3H), 2.96 (s, 3H), 3.85–3.91 (m, 2H), 3.94 (s, 3H), 5.07–5.16 (m, 2H), 5.72–5.86 (M, 1H), 5.90 (s, 1H), 6.31 (s, 1H), 6.60–6.72 (m, 5H), 6.75 (br.s, 1H), 7.14 (t, J=8 Hz, 1H), 7.20 (t, J=7 Hz, 1H), 7.27 (dd, J=2 Hz, 9 Hz, 1H), 8.42 (d, J=9 Hz, 1H).

EXAMPLE 81

N-{1-methoxy-6-[3-(methylamino)phenyl]-6H-benzo[c]chromen-8-yl}methanesulfonamide A solution of 80D (4.13 g, 9.17 mmol) and $(Ph_3P)_3RhCl$ (1.24 g, 1.34 mmol) in 20% aqueous $CH_3CN$ (200 mL) was heated to azeotrope with the addition of fresh solvents for 5 hours: The solvents were removed under reduced pressure and the residue was purified on silica gel with 5% ethyl acetate in dichloromethane to provide the titled compound (3.20 g, 85%). Tet. Lett. 22 (16), 1483–1486, 1981). NMR ($CDCl_3$, 300 MHz) δ 2.80 (s, 3H), 2.96 (s, 3H), 3.93 (s, 3H), 5.89 (s, 1H), 6.88 (s, 1H), 6.55–6.73 (m, 6H), 7.13 (t, J=8 Hz, 1H), 7.18 (t, J=8 Hz, 1H), 7.27 (dd, J=2 Hz, 9 Hz, 1H), 8.42 (d, J=9 Hz, 1H).

EXAMPLE 82

N-[6-(3-bromophenyl)-1-methoxy-6H-benzo[c]chromen-8-yl]methanesulfonamide

Example 46A and 3-bromophenylzinc iodide were processed as described in Example 46B to provide the titled compound. $^1$H NMR (300 MHz, $CDCL_3$) δ 8.46 (d, J=8.5 Hz, 1 H), 7.51 (t, J=1.5 Hz, 1H), 7.46 (dt, J=7.5, 1.7 Hz, 1H), 7.25 (m, 2H), 7.16 (t, J=8.1 Hz, 2H), 6.66 (m, 3H), 6.31 (s, 1H), 5.97 (s, 1H), 3.94 (s, 3H), 3.00 (s, 3H); MS (ESI, –Q1MS) m/e 460.

EXAMPLE 83

N-(1-methoxy-6-{3-[methyl(methylsulfonyl)amino]phenyl}-6H-benzo[c]chromen-8-yl)methanesulfonamide A solution of Example 81 (0.093 g, 0.23 mmol), pyridine (0.12 g, 1.5 mmol) and $MeSO_2Cl$ (0.08 g, 0.70 mmol) in $CHCl_3$ (1 mL) was stirred for 1 hour, diluted with $CHCl_3$ (25 mL), extracted with aqueous HCl (3×25 mL, 1M), dried ($Na_2SO_4$), filtered, and concentrated under reduced pressure to provide the titled compound (0.10 g, 92%). 1H NMR ($CDCl_3$ 300 MHz) δ 2.79 (s, 3H), 2.99 (s, 3H), 3.80 (s, 3H), 3.94 (s, 3H), 6.01 (s, 1H), 6.45 (s, 1H), 6.64 (dd, 9 Hz, 1Hz)1H), 6.70 (dd, J=8 Hz, 2 Hz, 1H), 6.73 (d, J=3 Hz, 1H), 7.15 (t, J=9 Hz, 1H), 7.72 (dd, J=8 Hz, 3 Hz, 1H), 7.28–7.42 (m, 4H), 8.44 (d, J=9 HZ, 1H).

EXAMPLE 84

N-(1-methoxy-6-pentyl-6H-benzo[c]chromen-8-yl)methanesulfonamide

Example 46A and bromo(pentyl)zinc were processed as described in Example 46B to provide the titled compound. $^1$H NMR (500 MHz, CD3OD) δ 8.35 (d, J=8.4 Hz, 1H), 7.17 (dd, J=8.6, 2.3 Hz, 1H), 7.15 (t, J=8.3 Hz, 1H), 7.06 (d, J=2.5 Hz, 1H), 6.71 (dd, J=8.3, 0.8 Hz, 1H), 6.59 (dd, J=8.1, 1.2 Hz, 1H), 4.96 (dd, J=8.9, 4.8 Hz, 1H), 3.93 (s, 3 H), 2.97 (s, 3H), 1.83 (m, 1H), 1.62 (m, 1H), 1.54 (m, 1H), 1.45 (m, 1H), 1.30 (m, 4H), 0.88 (m, 3H); MS (ESI –Q1MS) m/e 374 (M–H).

EXAMPLE 85

N-[6-(3,5-difluorobenzyl)-1-methoxy-6H-benzo[c]chromen-8-yl]methanesulfonamide

Example 46A and bromo(3,5-difluorobenzyl)zinc were processed as described in Example 46B to provide the titled compound. $^1$H NMR (500 MHz, CD3OD) δ 8.40 (d, J=8.7 Hz, 1H), 7.20 (m, 2H), 6.95 (d, J=2.2 Hz, 1H), 6.75 (m, 4H), 6.54 (dd, J=8.1, 0.9 Hz, 1H), 5.28 (dd, J=8.7, 5.3 Hz, 1H), 3.96 (s, 3H), 3.09 (dd, J=13.9, 8.9 Hz, 1H), 2.94 (dd, J=7.9, 5.4 Hz, 1H), 2.92 (s, 3H); MS (ESI –Q1MS) m/e 430 (M–H).

EXAMPLE 86

N-[1-methoxy-6-(3-methylphenyl)-6H-benzo[c]chromen-8-yl]methanesulfonamide

Example 46A and bromo(3-methylphenyl)zinc were proccesed as described in Example 46B to provide the titled compound. $^1$H NMR (500 MHz, CD3OD) δ 8.40 (d, J=8.7 Hz, 1H), 7.25 (dd, J=8.7, 2.5 Hz, 1H), 7.20 (t, J=7.6 Hz, 1H), 7.12 (m, 4H), 6.79 (d, J=2.5 Hz, 1H), 6.70 (d, J=7.8 Hz, 1H), 6.60 (dd, J=8.1, 1.2 Hz, 1H), 5.97 (s, 1H), 3.93 (s, 3H), 2.92 (s, 3H), 2.29 (s, 3H); MS (ESI –Q1MS) m/e 394 (M–H).

EXAMPLE 87

N-[6-(3,5-dimethylphenyl)-1-methoxy-6H-benzo[c]chromen-8-yl]methanesulfonamide

Example 46A and bromo(3,5-dimethyl-phenyl)zinc were proccesed as described in Example 46B to provide the titled compound. $^1$H NMR (500 MHz, CD3OD) δ 8.39 (d, J=8.7 Hz, 1H), 7.25 (dd, J=8.6, 2.3 Hz, 1H), 7.13 (t, J=8.3 Hz, 1H), 6.95 (br.s, 1H), 6.94 (br.s, 2H), 6.77 (d, J=2.2 Hz, 1H), 6.71 (dd, J=8.4, 0.91 Hz, 1H), 6.60 (dd, J=8.1, 0.9 Hz, 1H), 5.92 (s, 1H), 3.93 (s, 3H), 2.92 (s, 3H), 2.25 (s, 6H); MS (ESI –Q1MS) m/e 408 (M–H).

EXAMPLE 88

N-[1-methoxy-6-(4-phenoxyphenyl)-6H-benzo[c]chromen-8-yl]methanesulfonamide

Example 46A and 3-phenoxyphenyl boronic acid were proccesed as described in Example 46B to provide the titled compound. ¹H NMR (500 MHz, CD3OD) δ 8.41 (d, J=8.7 Hz, 1H), 7.46 (d, J=9.0 Hz, 1H), 7.34 (m, 3H), 7.24 (dd, J=8.6, 2.3 Hz, 1H), 7.14 (t, J=8.3 Hz, 1H), 6.99 (m, 2H), 6.93 (d, J=8.7 Hz, 2H), 6.90 (d, J=9.0 Hz, 1H), 6.84 (d, J=2.5 Hz, 1H), 6.72 (dd, J=8.4, 0.9 Hz, 1H), 6.60 (dd, J=8.1, 0.9 Hz, 1H), 6.02 (s, 1H), 3.94 (s, 3H), 2.94 (s, 3H); MS (ESI +Q1MS) m/e 474 (M+H).

EXAMPLE 89

N-{1-methoxy-6-[(E)-2-phenylethenyl]-6H-benzo[c]chromen-8-yl}methanesulfonamide

Example 46A and (E)-2-phenylethenyl boronic acid were proccesed as described in Example 46B to provide the titled compound. ¹H NMR (500 MHz, CD3OD) δ 8.39 (d, J=8.4 Hz, 1H), 7.36 (m, 2H), 7.27 (m, 3H), 7.22 (m, 1H), 7.16 (t, J=8.3 Hz, 1H), 7.13 (d, J=2.5 Hz, 1H), 6.73 (dd, J=8.4, 0.9 Hz, 1H), 6.65 (m, 1H), 6.62 (m, 1H), 6.43 (dd, J=15.9, 6.9 Hz, 1H), 5.61 (d, J=6.9 Hz, 1H), 3.94 (s, 3H), 2.97 (s, 3H); MS (ESI -Q1MS) m/e 406 (M-H).

EXAMPLE 90

N-(6-cyano-1-methoxy-6H-benzo[c]chromen-8-yl)methanesulfonamide

Example 46A and trimethylsilanecarbonitrile were proccesed as described in Example 46B to provide the titled compound. ¹H NMR (500 MHz, CD3OD) δ 8.44 (d, J=9.0 Hz, 1 H), 7.34 (m, 2H), 7.28 (t, J=8.3 Hz, 1H), 6.89 (dd, J=8.4, 0.9 Hz, 1H), 6.75 (dd, J=8.3, 1.1 Hz, 1H), 6.27 (s, 1H), 3.99 (s, 3H), 3.03 (s, 3H); MS (ESI -Q1MS) m/e 329 (M-H).

EXAMPLE 91

N-{1-methoxy-6-[3-(phenylethynyl)phenyl]-6H-benzo[c]chromen-8-yl}methanesulfonamide Example 82 and phenylacetylene were processed as described in Example 93 to provide the titled material. ¹H NMR (500 MHz, CDCL₃) δ 8.46 (d, J=8.7 Hz, 1H), 7.51 (m, 4H), 7.34 (m, 5H), 7.28 (dd, J=8.7, 2.5 Hz, 1H), 7.17 (t, J=8.1 Hz, 1H), 6.70 (dd, J=8.1, 0.9 Hz, 1H), 6.65 (m, 2H), 6.27 (s, 1H), 5.99 (s, 1H), 3.95 (s, 3H), 2.99 (s, 3H); MS (ESI, -Q1MS) m/e 480 (M-H).

EXAMPLE 92

N-{1-methoxy-6-[5-(3-methoxy-1-propynyl)-2-thienyl]-6H-benzo[c]chromen-8-yl}methanesulfonamide Example 62 and methylpropargylether were processed as described in Example 93 to provide the titled compound. ¹H NMR (500 MHz, CDCL₃) δ 8.47 (d, J=8.7 Hz, 1H), 7.22 (dd, J=8.7, 2.5 Hz, 1H), 7.15 (t, J=8.3 Hz, 1H), 7.01 (d, J=2.5 Hz, 1H), 6.98 (d, J=3.7 Hz, 1H), 6.69 (dd, J=3.7, 0.9 Hz, 1H), 6.67 (dd, J=8.3, 1.1 Hz, 1H), 6.63 (dd, J=8.4, 0.9 Hz, 1H), 6.34 (s, 1H), 6.26 (s, 1H), 4.27 (s, 2H), 3.93 (s, 3H), 3.39 (s, 3H), 3.03 (s, 3H); MS (ESI, -Q1MS) m/e 454 (M-H).

EXAMPLE 93

N-{1-methoxy-6-[5-(phenylethynyl)-2-thienyl]-6H-benzo[c]chromen-8-yl}methanesulfonamide To a solution of Example 62 (47 mg, 0.10 mmol), Pd(PPh₃)₂Cl₂ (≈5 mg, 0.007 mmol) and CuI 1:0.005 g) in CH₃CN/TEA (1 mL, 5:1 mixture) under an atmosphere of argon was added phenylacetylene (15 mg, 0.15 mmol). The mixture was heated to 85° C. on a shaker for 2 hours, cooled to ambient temperature and concentrated under reduced pressure. The residue was diluted with DMSO/MeOH (1:1, 1 mL) and purified by preparative HPLC using aqueous 0.1% TFA and CH₃CN to provide the titled compound. (16.2 mg, 33%). ¹H NMR (500 MHz, CDCL₃) δ 8.48 (d, J=8.7 Hz, 1H), 7.45 (m, 2H), 7.31 (m, 3H), 7.23 (dd, J=8.7, 2.5 Hz, 1 H), 7.16 (t, J=8.1 Hz, 1H), 7.04 (m, 2H), 6.73 (dd, J=3.7, 0.9 Hz, 1H), 6.69 (dd, J=8.1, 0.9 Hz, 1H), 6.64 (dd, J=8.3, 0.8 Hz, 1H), 6.39 (s, 1H), 6.29 (s, 1H), 3.94 (s, 3H), 3.04 (s, 3H); MS (ESI, -Q1MS) m/e 486 (M-H).

EXAMPLE 94 ethyl (2E)-4-(3-{1-methoxy-8-[(methylsulfonyl)amino]-6H-benzo[c]chromen-6-yl}phenoxy)-2-butenoate

EXAMPLE 94A

N-{1-methoxy-6-[3-(2-oxoethoxy)phenyl]-6H-benzo[c]chromen-8-yl}methanesulfonamide A solution of Example 33 (1 g, 2.28 mmol), sodium periodate (0.74 g, 3.43 mmol) and osmiumtetroxide (0.5 mL of 2.5% solution in toluene)in diethylether (5 mL) and water (5 mL) was stirred for 48 hours and then diluted with EtOAc (25 mL) and aqueous NaCl (25 mL). The layers were separated and the organic layer was dried (Na₂SO₄), filtered and concentrated under reduced pressure. The residue was purified on silica with 50% Ethyl acetate in hexanes to provide the titled compound. MS (ESI, -Q1MS) m/e 438 (M-H).

EXAMPLE 94B ethyl (2E)-4-(3-{1-methoxy-8-[(methylsulfonyl)amino]-6H-benzo[c]chromen-6-yl}phenoxy)-2-butenoate A solution of Example 94A (0.040 g, 0.089 mmol), triethylphosphono-acetate (0.030 g., 0.130 mmol) and cesium carbonate (0.109 g, 0.336 mmol) in toluene (1 mL) was stirred at 80° C. for 16 hours and then diluted with EtOAc (10 mL) and brine (25 mL). The layers were separated and the organic layer was dried (Na₂SO₄), filtered and concentrated under reduced pressure. The residue was purified by HPLC using aqueous 0.1% TFA and CH₃CN to provide the titled compound (¹H NMR (300 MHz, DMSO-d₆) δ 9.85 (s, 1H), 8.33 (d, J=9.1 Hz, 1H), 7.26–7.22 (m, 2H), 7.13 (t, J=8 Hz, 1H), 6.92–6.80 (m, 4H), 6.73 (d, J=8 Hz, 1H), 6.65 (d, J=9 Hz, 1H), 6.19 (s, 1H), 6.08–6.02 (m, 2H), 4.75–4.73 (m, 2H), 4.13 (q, J=7 Hz, 2H), 3.88 (s, 3H), 3.00 (s, 3H), 1.22 (t, J=7 Hz, 3H); MS (ESI, -Q1MS) m/e 508 (M-H).

EXAMPLE 95

N-{1-methoxy-6-[3-(4-methoxybutoxy)phenyl]-6H-benzo[c]chromen-8-yl}methanesulfonamide A solution of Example 94A (0.05 g, 0.114 mmol), methoxyethylphosphonium bromide (0.068 g, 0.171 mmol) and aqueous sodium hydroxide (1 mL, 6.0M) in THF (1 mL) was stirred for 16 hours, and then diluted with EtOAc (10 mL) and brine (25 mL). The layers were separated and the organic layer was dried (Na₂SO₄), filtered and concentrated under reduced pressure. The residue and 10% Pd on carbon (0.005 g) in anhydrous THF (2 mL) were shaken under hydrogen gas (balloon) for 6 hours. The mixture was filtered through diatomaceous earth (Celite®), washing the filtrant with dry TUF (2×20 mL). The combined organics were concentrated under reduced pressure and purified by HPLC using 0.1% TFA and MeCN to provide the titled compound (1H NMR (300 MHz, DMSO-d$_6$) δ 9.84 (s, 1H), 8.33 (d, J=9 Hz, 1H), 7.26–7.22 (m, 2H), 7.15 (t, J=8 Hz, 1H), 6.92–6.80 (m, 4H), 6.73 (d, J=8 Hz, 1H), 6.65 (d, J=9 Hz, 1H), 6.18 (s, 1H), 3.89 (t, J=6 Hz, 2H), 3.88 (s, 3H), 3.46–3.43 (m, 2H), 3.21 (s, 3H), 3.00 (s, 3H), 1.71–1.57 (m, 4H); MS (ESI, −Q1MS) m/e 508 (M−H).

EXAMPLE 96

N-{6-(5-bromo-2-thienyl)-1-(difluoromethoxy)-6H-benzo[c]chromen-8-yl}methanesulfonamide

EXAMPLE 96A benzyl 7-bromo-1-(difluoromethoxy)-6-methoxy-6H-benzo[c]chromen-8-ylcarbamate A solution of Example 27E (4.1 g, 8.3 mmol) and toluenesulfonic acid (1 g, 5.2 mmol) in methanol (100 mL) was stirred for 1 hour, and reduced in volume under reduced pressure. The solid was then collected by filtration to provide the titled compound. MS(ESI(−)Q1MS) m/z 504 and 506 (M−H)⁻.

EXAMPLE 96B 1-(difluoromethoxy)-6-methoxy-6H-benzo[c]chromen-8-amine

A mixture of Example 96A (82 mg, 0.16mmol) and 10% palladium on carbon (8 mg) in methanol (10 ml) and THF (10 ml) was stirred under hydrogen gas for 1.5 hour, filtered through diatomaceous earth (Celite®), and concentrated to provide the desired product. MS (ESI(+)Q1MS) m/z 294 (M+H)⁺.

EXAMPLE 96C

N-[1-(difluoromethoxy)-6-methoxy-6H-benzo[c]chromen-8-yl]methanesulfonamide

To a solution of Example 96B (3.9 g, 13 mmol) in pyridine (40ml) at 0° C. was added methylsulfonylchloride (1.5 g, 13 mmol). The mixture was stirred for 15 hour, concentrated under reduced pressure. The residue was dissolved in 10% HCl solution (50 mL) and extracted with ethyl acetate (3×30 mL). The combined extract were dried (MgSO$_4$), filtered and concentrated under reduced pressure. The residue was recrystallized from ethyl acetate in hexanes to provide the titled compound. MS (ESI(−)Q1MS) m/z 370 (M−H)⁻.

EXAMPLE 96D

N-[6-(5-bromo-2-thienyl)-1-(difluoromethoxy)-6H-benzo[c]chromen-8-yl]methanesulfonamide A solution of Example 96C (50 mg, 0.13 mmol) in dichloromethane (20 ml) at −20° C. was treated with borontrifluoridediethyletherate (184 mg, 1.3 mmol) dropwise, stirred for 5 minutes, treated with 5-bromo-2-thienylzincbromide (7.8 ml of 0.5M solution in THF, 3.9 mmol) dropwise over 2 minutes, stirred for 15 minutes, treated with saturated NaHCO$_3$ solution (15ml), extracted with dichloromethane. The extract was concentrated and the concentrate was purified by flash column chromatography on silica gel with dichloromethane to provide the desired product. MS (ESI(−)Q1MS) m/z 500 and 502 (M−H)⁻; ¹H NMR (400 MHz, CD$_3$OD) δ 8.29 (d, J=9 Hz, 1H), 7.32 (dd, J=9 Hz, 2 Hz, 1H), 7.21(t, J=9 Hz, 1H), 7.16 (d, J=2 Hz, 1H), 6.88 (t, J=74 Hz, 1H), 6.84–6.89 (m, 3H), 6.59 (dd, J=4 Hz, 1Hz, 1H), 6.39 (s, 1H), 3.01 (s, 3H).

EXAMPLE 97

N-[1-methoxy-6-(3-thienyl)-6H-benzo[c]chromen-8-yl]methanesulfonamide

Example 46A and 3-thienylboronic acid were processed as described in Example 46B to provide the titled compound. ¹H NMR (500 MHz, CD3OD) δ 8.40 (d, J=8.7 Hz, 1H), 7.33 (dd, J=5.1, 3.0 Hz, 1H), 7.25 (dd, J=8.7, 2.5 Hz, 1H), 7.12 (t, J=8.3 Hz, 1H), 7.10 (m, 1H), 7.04 (dd, J=5.0, 1.2 Hz, 1H), 6.97 (d, J=2.5 Hz, 1H), 6.70 (dd, J=8.4, 0.9 Hz, 1 H), 6.59 (dd, J=8.1, 0.9 Hz, 1H), 6.13 (s, 1H), 3.92 (s, 31H), 2.95 (s, 31H); MS (ESI −Q1MS) m/e 386 (M−H).

EXAMPLE 98

N-{6-[(1E)-1-heptenyl]-1-methoxy-6H-benzo[c]chromen-8-yl}methanesulfonamide

Example 46A and (1-E)-1-heptenylboronic acid were processed as described in Example 46B to provide the titled compound. ¹H NMR (500 MHz, CD3OD) δ 8.34 (d, J=8.7 Hz, 1H), 7.20 (dd, J=8.7, 2.5 Hz, 1H), 7.14 (t, J=8.3 Hz, 1H), 7.08 (d, J=2.2 Hz, 1 H), 6.71 (dd, J=8.4, 0.9 Hz, 1H), 6.59 (dd, J=8.1, 0.9 Hz, 1H), 5.67 (m, 2H), 5.38 (d, J=5.6 Hz, 1H), 3.93 (s, 3H), 2.97 (s, 3H), 2.04 (m, 2H), 1.14–1.39 (m, 6H), 0.86 (t, J=7.3 Hz, 3H); MS (ESI −Q1MS) m/e 400 (M−H).

EXAMPLE 99

N-(1-methoxy-6-{3-[(E)-2-phenylethenyl]phenyl}-6H-benzo[c]chromen-8-yl)methanesulfonamide A solution of Example 82 (0.046 g, 0.1 mmol) in EtOH/DME/toluene (1 mL, 2:1:1) was added to phenylvinylboronic acid (0.015 g, 0.1 mmol). A solution of Pd(PPh$_3$)$_4$ (0.006 g, 0.005 mmol) in DME (0.5 mL) and aqueous Na$_2$CO$_3$ (20 mg in 0.3 mL H$_2$O, 0.2 mmol) were added. The reaction mixture was heated to 90° C. on a shaker for 15 min then concentrated, diluted with DMSO/MeOH (1:1, 1 mL) and purified by HPLC with 0.1% TFA, water, and CH$_3$CN to provide the titled compound (8 mg, 17%). ¹H NMR (500 MHz, CDCL$_3$) δ 8.46 (d, J=8.4 Hz, 1H), 7.50 (m, 4H), 7.36 (dd, J=15.3, 7.8 Hz, 3H), 7.26 (m, 3H), 7.17 (t, J=8.1 Hz, 1H), 7.09 (s, 2H), 6.72 (d, J=9.0 Hz, 1H), 6.65 (m, 2H), 6.24 (s, 1H), 6.01 (s, 1 H), 3.95 (s, 3H), 2.97 (s, 3H); MS (CI, +Q1MS) m/e 483.

EXAMPLE 100

N-[1-methoxy-6-(5-phenyl-2-thienyl)-6H-benzo[c]chromen-8-yl]methanesulfonamide

Example 62 and phenylboronic acid were processed as described in Example 99 to provide the titled compound. ¹H NMR (500 MHz, CDCL$_3$) δ 8.48 (d, J=8.7 Hz, 1H), 7.50 (d, J=7.2 Hz, 2H), 7.33 (m, 2H), 7.23 (m, 2H), 7.15 (t, J=8.3 Hz, 1H), 7.08 (d, J=3.7 Hz, 1H), 7.02 (d, J=2.5 Hz, 1H), 6.81 (d, J=3.4 Hz, 1H), 6.70 (d, J=7.2 Hz, 1H), 6.64 (d, J=8.1 Hz, 1H), 6.38 (s, 1H), 6.31 (s, 1H), 3.94 (s, 3H), 3.02 (s, 3H); MS (ESI, −Q1MS) m/e 462 (M−H).

EXAMPLE 101

N-(1-methoxy-6-{5-[(E)-2-phenylethenyl]-2-thienyl}-6H-benzo[c]chromen-8-yl)methanesulfonamide Example 62 and phenylvinylboronic acid were processed as described in Example 99 to provide the titled compound. $^1$H NMR (500 MHz, CDCL$_3$) δ 8.48 (d, J=8.7 Hz, 1H), 7.40 (m, 2H), 7.31 (m, 2H), 7.23 (m, 2H), 7.16 (t, J=8.3 Hz, 1H), 7.09 (d, J=16.2 Hz, 1H), 7.01 (d, J=2.5 Hz, 1H), 6.83 (m, 1H), 6.82 (d, J=16.8 Hz, 1H), 6.73 (dd, J=3.7, 0.9 Hz, 1H), 6.70 (dd, J=8.1, 0.9 Hz, 1H), 6.64 (dd, J=8.4, 0.9 Hz, 1H), 6.37 (s, 1H), 6.28 (s, 1H), 3.94 (s, 3H), 3.03 (s, 3H); MS (ESI, −Q1MS) m/e 488 (M−H).

EXAMPLE 102

N-{6-[5-(5-hydroxy-1-pentynyl)-2-thienyl]-1-methoxy-6H-benzo[c]chromen-8-yl}methanesulfonamide Example 62 and 4-pentyn-1-ol were processed as described in Example 93 to provide the titled compound. $^1$H NMR (500 MHz, CDCL$_3$) δ 8.46 (d, J=8.7 Hz, 1H), 7.22 (dd, J=8.7, 2.5 Hz, 1H), 7.14 (t, J=8.3 Hz, 1H), 7.00 (d, J=2.5 Hz, 1H), 6.87 (d, J=3.4 Hz, 1H), 6.67 (m, 2H), 6.63 (d, J=8.4 Hz, 1H), 6.42 (s, 1H), 6.24 (s, 1H), 3.93 (s, 3H), 3.76 (t, J=6.2 Hz, 2H), 3.02 (s, 3H), 2.51 (t, J=6.9 Hz, 2H), 1.81 (m, 2H); MS (ESI, −Q1MS) m/e 468 (M−H).

EXAMPLE 103

N-[6-(3-bromophenyl)-1-(difluoromethoxy)-6H-benzo[c]chromen-8-yl]methanesulfonamide Example 96C and 3bromophenylzinc iodide were processed as described in Example 96D to provide the titled compound. $^1$H NMR (400 MHz, DMSO-d$_6$) δ 9.99 (s, 1H), 8.18 (d, J=9 Hz, 1H), 7.47–7.56 (m, 2H), 7.14–7.35 (m, 5H), 6.89–6.95 (m, 3H), 6.34 (s, 1H), 3.04 (s, 3H). MS (ESI(−) Q1MS) m/z 494 and 496 (M−H).

EXAMPLE 104

N-[1-(hydroxymethyl)-6-phenyl-6H-benzo[c]chromen-8-yl]methanesulfonamide

To a solution of Example 42 (0.125 g, 0.30 mmol) in dichloromethane (15 mL) at 0° C. was added diisobutylaluminum hydride (1.0 mL of 1.5M, 1.5 mmol). The reaction was stirred for 2 hours cold, then diluted with ethyl acetate/aqueous sodium potassium tartrate (1:1 40 mL). The mixture was stirred for 16 hours, the layers separated and the aqueous layer extracted with ethyl acetate (2×30 mL). The combined organic layers were washed with aqueous NaCl, dried (MgSO$_4$), filtered and concentrated under reduced pressure. The residue was purified on silica using 20% ethyl acetate hexanes to provide the titled compound. $^1$H NMR (300 MHz, CDCl$_3$) δ 1.25 (t, 2H), 2.99 (s, 3H), 3.72 (s, 3H), 5.95 (s, 1H), 6.45 (s, 1H), 6.62 (d, J=2 Hz, 1H), 6.72 (dd, J=10 Hz, 2 Hz, 1H), 6.85 (dd, J=9 Hz, 1 Hz, 1H), 7.15 (t, J=9 Hz, 1H), 7.25 (dd, J=9 Hz, 2 Hz, 1H), 7.40–7.70 (m, 4H), 8.35 (d, J=9 Hz, 1H); MS (ESI−) m/e 380 (M−H).

EXAMPLE 105

N-[2-(allyloxy)-1-methoxy-6-phenyl-6H-benzo[c]chromen-8-yl]methanesulfonamide

A solution of Example 65 (0.1 g, 0.3 mmol) and N,O-bis(trimethylsilyl)acetamide (0.062 mL, 0.3 mmol) in tetrahydrofuran (10 mL) at 0° C. were stirred for 1 hour then concentrated under reduced pressure. The residue was dissolved in tetrahydrofuran cooled to 0° C., lithium diisopropyl amide (0.2 mL of 1.5M, 0.3 mmol) was added with stirring, 1 hour later allyl bromide was added. The reaction was stirred for 16 hours, followed by the slow addition of aqueous HCl (5 mL of 1M). The reaction was diluted with aqueous NaHCO$_3$, extracted with ethyl acetate (2×20 mL). The combined organic layers were dried (MgSO$_4$), filtered, concentrated under reduce pressure and purified on silica using 20% ethyl acetate hexanes to provide the titled compound. $^1$H NMR (300 MHz, CDCl$_3$) δ 1.25 (t, 2H), 2.99 (s, 3H), 3.72 (s, 3H), 5.10 (m, 2H), 5.50 (s, 1H), 5.95 (s, 1H), 6.45 (s, 1H), 6.62 (d, J=2 Hz, 1H), 6.72 (dd, J=10 Hz, 2 Hz, 1H), 6.85 (dd, J=9 Hz, 1Hz, 1H), 7.15 (t, J=9 Hz, 1H), 7.25 (dd, J=9 Hz, 2 Hz, 1H), 7.40–7.70 (m, 4H), 8.35 (d, J=9 Hz, 1H); MS (ESI−) m/e 436 (M−H).

EXAMPLE 106

N-{1-methoxy-2-[(2-methoxyethoxy)methoxy]-6-phenyl-6H-benzo[c]chromen-8-yl}methanesulfonamide Example 65 and methoxyethoxymethoxymethyl chloride were processed as described in Example 105 to provide the titled compound. $^1$H NMR (300 MHz, CDCl$_3$) δ 2.99 (s, 3H), 3.25 (m, 2H), 3.65 (m, 2H), 3.72 (s, 3H), 3.85 (s, 3H), 5.95(s, 1H), 6.45 (s, 1H), 6.62 (d, J=2 Hz, 1H), 6.72 (dd, J=10 Hz, 2 Hz, 1H), 6.85 (dd, J=9 Hz, 1 Hz, 1H), 7.15 (t, J=9 Hz, 1H), 7.25 (dd, J=9 Hz, 2 Hz, 1H), 7.40–7.70 (m, 4H), 8.35 (d, J=9 Hz, 1H); MS (ESI−) m/e 484 (M−H).

EXAMPLE 107

N-[1-(difluoromethoxy)-6-(3-fluorophenyl)-6H-benzo[c]chromen-8-yl]methanesulfonamide Example 96C and 3-fluorophenylzinc iodide were processed as described in Example 96D to provide the titled compound. $^1$H NMR (400 MHz, DMSO-d$_6$) δ 10.00 (s, 1H), 8.19 (d, J=9 Hz, 1H), 6.90–7.51 (m, 10H), 6.35 (s, 1H), 3.32 (s, 3H); MS (ESI(−)Q1MS) m/z 434 (M−H).

EXAMPLE 108

N-[1-(difluoromethoxy)-6-(3-methoxyphenyl)-6H-benzo[c]chromen-8-yl]methanesulfonamide Example 96C and 3-methoxyphenylzinc iodide were processed as described in Example 96d to provide the titled compound. MS (ESI(−)Q1MS) m/z 446 (M−H)$^-$; $^1$H NMR (400 MHz, CD$_2$Cl$_2$) δ 8.29 (d, J=9 Hz, 1H), 7.24–7.28 (m, 2H), 7.19 (t, J=9 Hz, 1H), 6.41–6.92 (m, 7H), 6.05 (s, 1H), 3.75 (s, 3H), 2.99 (s, 3H).

EXAMPLE 109

N-[6-(4-bromophenyl)-1-(difluoromethoxy)-6H-benzo[c]chromen-8-yl]methanesulfonamide Example 96C and 4-bromophenylzinc iodide were processed as described in Example 96D to provide the titled compound. MS (ESI(−)Q1MS) m/z 494 and 496 (M−H)$^-$; $^1$H NMR (300 MHz, DMSO-d$_6$) δ 9.99 (s, 1H), 8.17 (d, J=9 Hz, 1H), 7.56 (d, J=8 Hz, 2H), 7.07–7.32 (m, 5H), 6.88–6.93 (m, 3H), 6.31 (s, 1H), 3.04 (s, 3H).

EXAMPLE 110

N-(3-{1-methoxy-8-[(methylsulfonyl)amino]-6H-benzo[c]chromen-6-yl}phenyl)-N-methylacetamide A solution of Example 81 (0.078 g, 0.19 mmol) and acetic anhydride (0.1 g, 0.88 mmol) in dimethoxyethane (0.5 mL)

was stirred for 2 hours, slowly added to aqueous KHCO$_3$ and extracted with ethyl acetate (3×30 mL). The combined ethyl acetate was dried (MgSO4), filtered and concentrated under reduced pressure to provide the titled compound (0.075 g, 87%). M.p.165–168°. NMR (CDCl$_3$ 300 MHz) δ 1.75 (s, 3H), 2.98 (s, 3H), 3.22 (s, 3H), 3.92 (s, 3H), 6.05 (s, 1H), 6.61 (dd, J=8 Hz, 1 Hz, 1H), 6.63 (s, 1H), 6.66 (dd, J=1 Hz, 9 Hz, 1H), 6.86 (s, 1H), 7.14 (t, J=8 Hz, 1H), 7.10–7.22 (m, 3H), 7.70 (dt, J=1Hz, 8 Hz, 1H), 7.39 (t, J=8 Hz, 1H), 8.44 (d, J=9 Hz, 1H).

EXAMPLE 111

N-{1-nethoxy-6-[3-(4-pentenyl)phenyl]-6H-benzo[c]chromen-8-yl}methanesulfonamide A solution of Example 82 (0.046 g, 0.1 mmol) and Pd(PPh$_3$)$_2$Cl$_2$ (0.007 g, 0.01 mmol) in THF (1.5 mL) was flushed with argon before the addition of 4-pentenylzinc bromide (0.7 mL of 0.5M soln in THF, 0.35 mmol). The vessel was heated at 65° C. for 16 hours, cooled to ambient temperature, diluted with aqueous NaHCO$_3$ (1.5 mL) and extracted with CHCl$_3$ (2×1.5 mL). The combined organic solution was dried (MgSO4), filtered and concentrated under reduced pressure. The residue was diluted with DMSO/MeOH (1:1, 1 mL) and purified by HPLC with aqueous 0.1% TFA and CH$_3$CN to provide the titled compound (0.011 g, 24%). $^1$H NMR (500 MHz, CD$_3$OD) δ 8.40 (d, J=8.7 Hz, 1H), 7.23 (m, 2H), 7.12 (m, 4H), 6.83 (br.s, 1H), 6.83 (m, 1H), 6.70 (d, J=8.1 Hz, 1H), 6.60 (d, J=8.1 Hz, 1H), 4.94 (m, 2H), 4.94 (m, 1H), 3.93 (s, 3H), 2.92 (s, 3H), 2.58 (m, 21H), 1.99 (m, 21H), 1.64 (m, 1H), 1.58 (m, 1H); MS (ESI, –Q1MS) m/e 448 (M–H).

EXAMPLE 112

N-{6-[3-(3-cyanopropyl)phenyl]-1-methoxy-6H-benzo[c]chromen-8-yl}methanesulfonamide Example 82 and 3-cyanopropylzinc iodide were processed as described in Example 111 to provide the titled compound. $^1$H NMR (500 MHz, CD$_3$OD) δ 8.40 (d, J=8.4 Hz, 1H), 7.25 (m, 2H), 7.15 (m, 4H), 6.85 (d, J=2.5 Hz, 1H), 6.70 (d, J=8.4 Hz, 1H), 6.61 (d, J=9.0 Hz, 1H), 6.02 (s, 1H), 3.93 (s, 3H), 2.93 (s, 3H), 2.71 (t, J=7.3 Hz, 2H), 2.29 (t, J=7.2 Hz, 2H), 1.88 (m, 2H); MS (ESI, –Q1MS) m/e 447 (M–H).

EXAMPLE 113

N-{6-[3-(4-cyanobutyl)phenyl]-1-methoxy-6H-benzo[c]chromen-8-yl}methanesulfonamide Example 82 and 4-cyanobutylzinc iodide were processed as described in Example 111 to provide the titled compound. $^1$H NMR (500 MHz, CD$_3$OD) δ 8.40 (d, J=8.4 Hz, 1H), 7.24 (m, 2H), 7.15 (m, 4H), 6.83 (d, J=2.2 Hz, 1H), 6.71 (d, J=8.4 Hz, 1H), 6.61 (d, J=8.1 Hz, 1H), 6.01 (s, 1H), 3.93 (s, 3H), 2.93 (s, 3H), 2.63 (t, J=7.5 Hz, 2H), 2.39 (t, J=7.0 Hz, 2H), 1.70 (m, 2H), 1.56 (m, 2H); MS (ESI, –Q1MS) m/e 461 (M–H).

EXAMPLE 114 ethyl 3-{1-(difluoromethoxy)-8-[(methylsulfonyl)amino]-6H-benzo[c]chromen-6-yl}benzoate Example 96C and [3-(ethoxycarbonyl)phenyl]zinc bromide were processed as described in Example 96D to provide the titled compound. $^1$H NMR(500 MHz, DMSO-d$_6$) δ 9.97 (s, 1H), 8.18 (d, J=9 Hz, 1H), 7.89–7.95 (m, 2H), 7.15–7.59 (m, 5H), 6.89–6.95 (m, 3H), 6.41 (s, 1H), 4.28 (q, J=7 Hz, 2H), 3.03 (s, 3H), 1.29 (t, J=7 Hz, 3H). MS (ESI(–)Q1MS) m/z 488 (M–H).

EXAMPLE 115 ethyl 4-(3-{1-(difluoromethoxy)-8-[(methylsulfonyl)amino]-6H-benzo[c]chromen-6-yl}phenyl)butanoate Example 96C and [3-(4-ethoxy-4-oxobutyl)phenyl]zinc bromide were processed as described in Example 96D to provide the titled compound. $^1$H NMR(400 MHz, CDCl$_3$) δ 8.28 (d, J=9 Hz, 1H), 7.14–7.33 (m, 5H), 7.02 (s, 1H), 6.91 (d, J=8 Hz, 1H), 6.82 (d, J=8 Hz, 1H), 6.61 (d, J=2 Hz, 1H), 6.56 (t, J=73 Hz, 1H), 5.97 (s, 1H), 4.06 (1, J=7 Hz, 2H), 2.97 (s, 3H), 2.66 (t, J=7 Hz, 2H), 2.28 (t, J=7 Hz, 2H), 1.95 (m, J=7 Hz, 2H), 1.23 (t, J=7 Hz, 3H); MS (ESI(–)Q1MS m/z 530 (M–H).

EXAMPLE 116

N-[6-[3-(allyloxy)phenyl]-1-(difluoromethoxy)-6H-benzo[c]chromen-8-yl]methanesulfonamide Example 96C and [3-(allyloxy)phenyl](bromo)zinc bromide were processed as described in Example 96D to provide the titled compound. $^1$H NMR (300 MHz, DMSO-d$_6$) δ 9.98 (s, 1H), 8.17 (d, J=9 Hz, 1H), 7.33 (t, J=74 Hz, 1H), 7.31–7.17 (m, 4H), 6.94–6.82 (m, 6H), 6.23 (s, 1H), 6.06–5.92 (m, 1H), 5.38–5.19 (m, 2H), 4.51–4.49 (m, 2H), 3.03 (s, 3 H; MS (ESI, –Q1MS) m/e 472 (M–H).

EXAMPLE 117

N-{1-(difluoromethoxy)-6-[3-(3-methoxypropyl)phenyl]-6H-benzo[c]chromen-8-yl}methanesulfonamide A solution of allylmethylether (0.015 g, 0.2 mmol) and 9-BBN (0.4 mL of 0.5M solution in THF, 0.2 mmol) was shaken for 3 hours at 65° C, cooled down to 23° C., treated with solution of Example 103 (0.05 g, 0.10 mmol), [1,1'-Bis(diphenylphosphino)-ferrocene]dichloropalladium(II), complex with dichloromethane (0.004 g, 0.005 mmol), and sodium methoxide (0.016 g, 0.3 mmol) in THF (1 mL), shaken at 65° C. for 15 hours, cooled down to 23° C., treated with water (50 mL), and extracted with ethyl acetate(3×50 mL). The combined extracts were dried (MgSO$_4$), filtered and concentrated under reduced pressure. The concentrate was purified by HPLC with aqueous 0.1% TFA and CH$_3$CN to provide the titled compound. $^1$H NMR (300 MHz, DMSO-d$_6$) δ 9.98 (s, 1H), 8.15 (d, J=9 Hz, 1H), 7.07–7.56 (m, 7H), 6.87–6.92 (m, 3H), 6.25 (s, 1H), 3.24 (t, J=6 Hz, 2H), 3.14 (s, 3H), 3.01 (s, 3H), 2.56 (t, J=7 Hz, 2H), 1.72 (m, J=7 Hz, 2H); MS (ESI(–)Q1MS m/z 488 (M–H).

EXAMPLE 118 ethyl 3-(3-{1-(difluoromethoxy)-8-[(methylsulfonyl)amino]-6H-benzo[c]chromen-6-yl}phenyl)propanoate A solution of Example 103 (0.05 g, 0.10 mmol), tetrakis(triphenylphosphine) palladium(O) (0.01, 0.01 mmol), and 3-ethoxy-3-oxopropylzincbromide (0.6 ml of 0.5M solution in THF) in THF (2 mL) was shaken in a sealed tube at 80° C. for 15 hours, treated with water (2 mL), and extracted with ethyl acetate. The extract was the concentrated and the residue was purified by high throughput HPLC with aqueous 0.1% TFA and CH$_3$CN to provide the titled compound. $^1$H NMR (300 MHz, DMSO-d$_6$) δ 9.98 (s, 1H), 8.17 (d, J=9 Hz, 1H), 6.52–7.74 (m, 10H), 6.31 (s, 1H), 4.18 (q, J=7 Hz, 2H), 3.02 (s, 3H), 1.25 (t, J=7 Hz, 3H); MS (ESI(–)Q1MS m/z 516 (M–H).

EXAMPLE 119 ethel 6-(3-{1-(difluoromethoxy)-8-[(methylsulfonyl) amino]-6H-benzo[c]chromen-6-yl}phenyl)hexanoate Example 103 and bromo(5-ethoxy-5-oxopentyl)zinc were processed as described in Example 118 to provide the titled compound. $^1$H NMR (300 MHz, DMSO-d$_6$) δ 9.97 (s, 1H), 8.15 (d, J=8 Hz, 1H), 6.87–7.60 (m, 10H), 6.24 (s, 1H), 4.03 (q, J=7 Hz, 2H), 3.01(s, 3H), 2.24 (t, J=7 Hz, 2H), 1.22–1.53 (m, 6H), 1.15 (t, J=7 Hz, 3H); MS (ESI(–)Q1MS m/z 558 (M–H).

EXAMPLE 120

N-{1-(difluoromethoxy)-6-[3-(3-ethoxypropyl) phenyl]-6H-benzo[c]chromen-8-yl}methanesulfonamide Example 103 and Allyl ethyl ether were processed as described in example 117 to provide the title compound. $^1$H NMR (300 MHz, DMSO-d$_6$) δ 9.97 (s, 1H), 8.15 (d, J=9 Hz, 1H), 7.07–7.56 (m, 7H), 6.87–6.92 (m, 3H), 6.25(s, 1H), 3.35 (q, J=7 Hz, 2H), 3.27 (t, J=6 Hz, 2H), 3.01 (s, 3H), 2.57 (t, J=8 Hz, 2H), 1.71 (m, J=7 Hz, 2H), 1.08 (t, J=7 Hz, 3H); MS (ESI(–)Q1MS m/z 502 (M–H).

EXAMPLE 121

4-(3-{1-(difluoromethoxy)-8-[(methylsulfonyl) amino]-6H-benzo[c]chromen-6-yl}phenyl)butanoic acid A solution of Example 115 (110 mg, 0.21 mmol) and aqueous LiOH (1 ml of 10% solution) in methanol (1 ml) was stirred for 3 hours, neutralized with 1M HCl, and extracted with ethyl acetate. The extract was dried (MgSO$_4$) and concentrated. The concentrate was purified by high throughput HPLC with aqueous 0.1% TFA and CH$_3$CN to provide the titled compound. $^1$H NMR (300 MHz, DMSO-d$_6$) δ 8.15 (d, J=9 Hz, 1H) 6.87–7.56 (m, 10H), 6.24 (s, 1H), 3.00 (s, 1H), 2.55 (t, J=7 Hz, 2H), 2.17 (t, J=7 Hz, 2H), 1.73 (m, J=7 Hz, 2H); MS (ESI(–)Q1MS m/z 502 (M–H).

EXAMPLE 122

3'-{1-methoxy-8-[(methylsulfonyl)amino]-6H-benzo [c]chromen-6-yl}[1,1'-biphenyl]-4-carboxylic acid Example 82 and 4-carboxyphenylboronic acid were processed as described in Example 99 to provide the titled compound. $^1$H NMR (500 MHz, CD3OD) δ 8.43 (d, J=8.7 Hz, 1H), 8.06 (d, J=8.4 Hz, 2H), 7.65 (m, 2H), 7.64 (d, J=8.4 Hz, 2H), 7.61 (d, J=7.8 Hz, 1H), 7.43 (t, J=7.6 Hz, 1H), 7.35 (d, J=7.8 Hz, 1H), 7.27 (dd, J=8.7, 2.5 Hz, 1H), 7.15 (t, J=8.3 Hz, 1H), 6.72 (d, J=8.4 Hz, 1H), 6.66 (d, J=8.1 Hz, 1 ), 6.14 (s, 1H), 3.93 (s, 3H), 2.93 (s, 3H); MS (ESI –Q1MS) m/e 500 (M–H).

EXAMPLE 123

N-[1-methoxy-6-(4'-methyl[1,1'-biphenyl]-3-yl)-6H-benzo[c]chromen-8-yl]methanesulfonamide Example 82 and 4-methylphenyllboronic acid were processed as described in Example 99 to provide the titled compound. $^1$H NMR (500 MHz, CD3OD) δ 8.42 (d, J=8.7 Hz, 1H), 7.55 (s, 1H), 7.52 (d, J=7.8 Hz, 1H), 7.41 (d, J=8.1 Hz, 2H), 7.37 (t, J=7.6 Hz, 1H), 7.27 (m, 2H), 7.21 (d, J=8.1 Hz, 2H), 7.14 (t, J=8.3 Hz, 1H), 6.90 (d, J=2.5 Hz, 1H), 6.71 (d, J=8.4 Hz, 1H), 6.65 (d, J=8.1 Hz, 1H), 6.10 (s, 1H), 3.93 (s, 3H), 2.92 (s, 3H), 2.35 (s, 3H); MS (ESI –Q1MS) m/e 470 (M–H).

EXAMPLE 124

N-[1-methoxy-6-(3'-methoxyl[1,1'-biphenyl]-3-yl)-6H-benzo[c]chromen-8-yl]methanesulfonamide Example 82 and 3-methoxyphenylboronic acid were processed as described in Example 99 to provide the titled compound. $^1$H NMR (500 MHz, CD3OD) δ 8.43 (d, J=8.7 Hz, 1H), 7.55 (m, 1H), 7.52 (d, J=7.8 Hz, 1H), 7.38 (t, J=7.6 Hz, 1H), 7.29 (m, 3H), 7.14 (t, J=8.3 Hz, 1H), 7.09 (d, J=7.8 Hz, 1H), 7.03 (m, 1H), 6.93 (d, J=2.2 Hz, 1H), 6.88 (dd, J=8.4, 2.5 Hz, 1H), 6.71 (d, J=8.1 Hz, 1H), 6.65 (d, J=8.1 Hz, 1H), 6.12 (s, 1 H), 3.92 (s, 3H), 3.81 (s, 3H), 2.92 (s, 3H); MS (ESI –Q1MS) m/e 486 (M–H).

EXAMPLE 125

N-[1-methoxy-6-(4'-methoxy[1,1'-biphenyl]-3-yl)-6H-benzo[c]chromen-8-yl]methanesulfonamide Example 82 and 4-methoxyphenylboronic acid were processed as described in Example 99 to provide the titled compound. $^1$H NMR (500 MHz, CD3OD) δ 8.42 (d, J=8.7 Hz, 1H), 7.52 (s, 1H), 7.49 (d, J=7.8 Hz, 1H), 7.45 (d, J=8.7 Hz, 2H), 7.35 (t, J=7.6 Hz, 1H), 7.27 (dd, J=8.7, 2.5 Hz, 1H), 7.23 (d, J=7.8 Hz, 1H), 7.14 (t, J=8.3 Hz, 1H), 6.94 (d, J=8.7 Hz, 2H), 6.89 (d, J=2.5 Hz, 1H), 6.70 (d, J=8.1 Hz, 1H), 6.64 (d, J=8.1 Hz, 1H), 6.08 (s, 1H), 3.92 (s, 3H), 3.80 (s, 3H), 2.92 (s, 3H); MS (ESI –Q1MS) m/e 486 (M–H).

EXAMPLE 126

N-[6-(4'-chloro[1,1'-biphenyl]-3-yl)-1-methoxy-6H-benzo[c]chromen-8-yl]methanesulfonamide Example 82 and 4-chlorophenylboronic acid were processed as described in Example 99 to provide the titled compound. $^1$H NMR (500 MHz, CD3OD) δ 8.42 (d, J=8.7 Hz, 1 H), 7.58 (m, 1H), 7.53 (m, 3H), 7.41 (m, 3H), 7.31 (d, J=7.8 Hz, 1H), 7.26 (dd, J=8.6, 2.3 Hz, 1H), 7.15 (t, J=8.3 Hz, 1H), 6.90 (d, J=2.5 Hz, 1H), 6.72 (d, J=8.4 Hz, 1H), 6.65 (dd, J=8.1, 1.2 Hz, 1H), 6.12 (s, 1H), 3.93 (s, 3H), 2.93 (s, 3H); MS (ESI –Q1MS) m/e 490 (M–H).

EXAMPLE 127

N-[6-(3',4'-dichloro[1,1'-biphenyl]-3-yl)-1-methoxy-6H-benzo[c]chromen-8-yl]methanesulfonamide Example 82 and 3,4-dichlorophenylboronic acid were processed as described in Example 99 to provide the titled compound. $^1$H NMR (500 MHz, CD3OD) δ 8.42 (d, J=8.7 Hz, 1H), 7.65 (d, J=2.2 Hz, 1H), 7.55 (m, 1H), 7.53 (m, 1H), 7.51 (m, 1H), 7.44 (dd, J=8.3, 2.0 Hz, 1H), 7.41 (t, J=7.8 Hz, 1H), 7.34 (d, J=7.8 Hz, 1H), 7.26 (dd, J=8.7, 2.5 Hz, 1H), 7.14 (t, J=8.3 Hz, 1H), 6.92 (d, J=2.2 Hz, 1H), 6.71 (d, J=8.1 Hz, 1H), 6.64 (dd, J=8.1, 0.9 Hz, 1H), 6.12 (s, 1H), 3.92 (s, 3H), 2.93 (s, 3H); MS (ESI –Q1MS) m/e 524 (M–H).

EXAMPLE 128

N-[6-(4'-hydroxy[1,1'-biphenyl]-3-yl)-1-methoxy-6H-benzo[c]chromen-8-yl]methanesulfonamide Example 82 and 4-hydroxyphenylboronic acid were processed as described in Example 99 to provide the titled compound. ¹H NMR (500 MHz, CD3OD) δ 8.42 (d, J=8.7 Hz, 1H), 7.51 (s, 1H), 7.48 (d, J=7.5 Hz, 1H), 7.37 (d, J=8.7 Hz, 2H), 7.36 (m, 1H), 7.27 (dd, J=8.6, 2.3 Hz, 1H), 7.22 (d, J=7.8 Hz, 1H), 7.15 (t, J=8.3 Hz, 1H), 6.89 (d, J=2.5 Hz, 1H), 6.82 (d, J=8.7 Hz, 2H), 6.72 (d, J=8.4 Hz, 1H), 6.65 (d, J=8.1 Hz, 1H), 6.09 (s, 1H), 4.52 (br.s, 1H), 3.93 (s, 3H), 2.92 (s, 3H); MS (ESI −Q1MS) m/e 472 (M−H).

EXAMPLE 129

N(3-{1-methoxy-8-[(methylsulfonyl)amino]-6H-benzo[c]chromen-6-yl}phenyl)-N-methylbenzenesulfonamide A solution of Example 81 (0.02 g, 0.049 mmol) in pyridine (1 mL) was added to benzenesulfonyl chloride (9 mg, 0.05 mmol) and stirred at room temperature overnight. The solvent was removed and the crude product was purified by HPLC with 0.1% TFA, water and CH₃CN to provide the titled compound (3 mg, 3%). ¹H NMR (500 MHz, CD3OD) δ 8.40 (d, J=8.7 Hz, 1H), 7.60 (m, 1H), 7.42 (m, 4H), 7.29 (m, 2H), 7.23 (dd, J=8.7, 2.5 Hz, 1H), 7.13 (t, J.=8.3 Hz, 1H), 7.03 (m, 1H), 6.96 (s, 1H), 6.87 (d, J=2.2 Hz, 1H), 6.70 (d, J=8.1 Hz, 1H), 6.58 (d, J=7.8 Hz, 1H), 6.00 (s, 1H), 3.93 (s, 3H), 3.08 (s, 3H), 2.94 (s, 3 H); MS (ESI −Q1MS) m/e 549 (M−H).

EXAMPLE 130

3-chloro-N-(3-{1-methoxy-8-[(methylsulfonyl)amino]-6H-benzo[c]chromen-6-yl}phenyl)-N-methyl-1-propanesulfonamide Example 81 and 3-chloropropylsulfonyl chloride were processed as described in Example 129 to provide the titled compound. ¹H NMR (500 MHz, CD3OD) δ 8.41 (d, J=8.7 Hz, 1H), 7.39 (m, 1H), 7.36 (m, 2H), 7.28 (m, 1H), 7.23 (dd, J=8.7, 2.5 Hz, 1H), 7.14 (t, J=8.3 Hz, 1H), 6.92 (d, J=2.2 Hz, 1H), 6.71 (d, J=8.4 Hz, 1H), 6.64 (dd, J=8.1, 0.9 Hz, 1H), 6.09 (s, 1H), 3.92 (s, 3H), 3.61 (t, J=6.4 Hz, 2H), 3.27 (s, 3H), 3.14 (m, 2H), 2.95 (s, 3H), 2.12 (m, 2H); MS (ESI −Q1MS) m/e 549 (M−H).

EXAMPLE 131

N-(3-{1-methoxy-8-[(methylsulfonyl)amino]-6H-benzo[c]chromen-6-yl}phenyl)-N-methylethanesulfonamide Example 81 and ethanesulfonyl chloride were processed as described in Example 129 to provide the titled compound. ¹H NMR (500 MHz, CD3OD) δ 8.41 (d, J=8.7 Hz, 1H), 7.38 (m, 1H), 7.35 (m, 2H), 7.25 (m, 2H), 7.13 (t, J=8.3 Hz, 1H), 6.91 (d, J=2.5 Hz, 1 H), 6.70 (d, J=8.1 Hz, 1H), 6.63 (dd, J=8.1, 0.9 Hz, 1H), 6.08 (s, 1H), 3.92 (s, 3H), 3.26 (s, 3H), 2.98 (q, J=7.4 Hz, 2H), 2.94 (s, 3H), 1.23 (t, J=7.5 Hz, 3H); MS (ESI −Q1MS) m/e 501 (M−H).

EXAMPLE 132

N-(3-{1-methoxy-8-[(methylsulfonyl)amino]-6H-benzo[c]chromen-6-yl}phenyl)-N-methyl-1-propanesulfonamide Example 81 and propanesulfonyl chloride were processed as described in Example 129 to provide the titled compound. ¹H NMR (500 MHz, CD3OD) δ 8.41 (d, J=8.7 Hz, 1 H), 7.38 (m, 1H), 7.35 (m, 2H), 7.25 (m, 2H), 7.13 (t, J=8.3 Hz, 1H), 6.91 (d, J=2.5 Hz, 1H), 6.70 (d, J=8.4 Hz, 1H), 6.63 (dd, J=8.1, 0.9 Hz, 1H), 6.09 (s, 1H), 3.92 (s, 3H), 3.25 (s, 3H), 2.95 (s, 3H), 2.93 (m, 2H), 1.71 (m, 2H), 0.98 (t, J=7.5 Hz, 3H); MS (ESI −Q1MS) m/e 515 (M−H).

EXAMPLE 133

N-{6-[4'-(dimethylamino)[1,1'-biphenyl]-3-yl]-1-methoxy-6H-benzo[c]chromen-8-yl}methanesulfonamide Example 82 and 4-dimethylaminophenylboronic acid were processed as described in Example 99 to provide the titled compound. ¹H NMR (500 MHz, CD3OD) δ 8.42 (d, J=8.7 Hz, 1H), 7.61 (d, J=8.4 Hz, 2H), 7.57 (s, 1H), 7.55 (d, J=7.8 Hz, 1H), 7.40 (t, J=7.6 Hz, 1H), 7.28 (m, 4H), 7.15 (t, J=8.3 Hz, 1H), 6.92 (d, J=2.2 Hz, 1H), 6.72 (d, J=8.4 Hz, 1H), 6.65 (d, J=8.1 Hz, 1H), 6.11 (s, 1H), 3.93 (s, 3H), 3.15 (s, 6H), 2.93 (s, 3H); MS (ESI −Q1MS) m/e 499 (M−H).

EXAMPLE 134

N-(1-(difluoromethoxy)-6-{3-[3-(trimethylsilyl)propyl]phenyl}-6H-benzo[c]chromen-8-yl)methanesulfonamide Example 103 and allyltrimethylsilane were processed as described in example 117 to provide the titled compound. ¹H NMR (300 MHz, DMSO-d₆) δ 10.02 (s, 1H), 8.22 (d, J=8 Hz, 1H), 7.10–7.61 (m, 7H), 6.92–6.98 (m, 3H), 6.32 (s, 1H), 3.07 (s, 3H), 2.60 (t, J=7 Hz, 2H), 1.50–1.60 (m, 2H), 0.47–0.52 (m, 2H); MS (ESI(−)Q1MS m/z 530 (M−H).

EXAMPLE 135 ethyl 5-(3-{1-(difluoromethoxy)-8-[(methylsulfonyl)amino]-6H-benzo[c]chromen-6-yl}phenyl)-2-methylpentanoate Example 103 and ethyl 2-methyl-4-pentenoate were processed as described in example 117 to provide the titled compound. ¹H NMR (300 MHz, DMSO-d₆) δ 9.97 (s, 1H), 8.15 (d, J=8 Hz, 1H), 7.05–7.56 (m, 7H), 6.86–6.91(m, 3H), 6.25 (s, 1H), 4.03 (q, J=7 Hz, 2H), 3.01 (s, 3H), 2.33–2.42 (m, 1H), 1.24–1.56 (m, 4H), 1.14 (t, J=7 Hz, 3H), 1.02 (d, J=7 Hz, 3H); MS (ESI(−)Q1MS m/z 558 (M−H).

EXAMPLE 136

N-{1-(difluoromethoxy)-6-[3-(4-phenylbutyl)phenyl]-6H-benzo[c]chromen-8-yl}methanesulfonamide Example 103 and 4-phenyl-1-butene were processed as described in example 117 to provide the titled compound. ¹H NMR (300 MHz, DMSO-d₆) δ 9.97 (s, 1H), 8.15 (d, J=9 Hz, 1H), 7.04–7.56 (m, 12H), 6.86–6.90(m, 3H), 6.25 (s, 1H), 3.00 (s, 3H), 2.52–2.58 (m, 4H), 1.47–1.515 (m, 4H); MS (ESI(−)Q1MS m/z 548 (M−H).

EXAMPLE 137

N-[6-[3-(6-cyanohexyl)phenyl]-1-(difluoromethoxy)-6H-benzo[c]chromen-8-yl]methanesulfonamide Example 103 and ethyl 6-heptenenitrile were processed as described in example 117 to provide the titled compound. ¹H NMR (300 MHz, DMSO-d₆) δ 9.97 (s, 1H), 8.16 (d, J=9 Hz, 1H), 7.05–7.56 (m, 7H), 6.87–6.91 (m, 3H), 6.25 (s, 1H), 3.02 (s, 3H), 2.53 (t, J=8 Hz, 2H), 2.45 (t, J=7 Hz, 2H), 1.46–1.55 (m, 4H), 1.20–1.39 (m, 4H); MS (ESI(−)Q1MS m/z 525 (M−H).

EXAMPLE 138

N-{1-methoxy-6-[5-(3-methoxypropyl)-2-thienyl]-6H-benzo[c]chromen-8-yl}methanesulfonamide A solution of Example 92 (0.05 g, 0.11 mmol) was treated with 10% Pd/C (0.011 g) in MeOH (2 mL) under an atmosphere of hydrogen (50 psi) for 1.5 hour, followed by 10% Pd/C (0.012 g) under an atmosphere of hydrogen 50 psi for 3 hours. The mixture was filtered and concentrated under reduced pressure to afford the titled compound (38 mg, 0.08 mmol, 75%). $^1$H NMR (500 MHz, CD$_3$OD) δ 8.41 (d, J=8.7 Hz, 1H), 7.25 (dd, J=8.7, 2.5 Hz, 1 H), 7.11 (t, J=8.3 Hz, 1H), 7.05 (d, J=2.2 Hz, 1H), 6.69 (dd, J=8.4, 0.9 Hz, 1H), 6.61 (dd, J=3.4, 0.9 Hz, 1H), 6.57 (m, 2H), 6.25 (s, 1H), 3.92 (s, 3H), 3.35 (t, J=6.2 Hz, 2H), 3.28 (s, 3H), 2.96 (s, 3H), 2.77 (t, J=7.5 Hz, 2H), 1.81 (m, 2H); MS (ESI, –Q1MS) m/e 460 (M–H).

EXAMPLE 139

N-[1-methoxy-6-(3-phenoxyphenyl)-6H-benzo[c]chromen-8-yl]methanesulfonamide

A solution of Example 34 (0.05 g, 0.126 mmol), phenylboronic acid (0.031 g, 0.252 mmol), copper(II) acetate (0.046 g, 0.252 mmol), triethylamine (0.064 g, 0.63 mmol) and crushed 4 Å molecular sieves in dichloromethane (20 mL) was stirred at ambient temperature for 48 hours, diluted with EtOAc (5 mL), filtered through a Alltech silica cartridge (1 g), and concentrated under reduced pressure. The residue was purified by high throughput HPLC with aqueous 0.1% TFA and CH$_3$CN to provide the titled compound (. $^1$H NMR (300 MHz, DMSO-d$_6$) δ 9.87 (s, 1H), 8.31 (d, J=8 Hz, 1H), 7.39–7.33 (m, 3H), 7.22 (dd, J=8 Hz, 2 Hz, 1H), 7.19–7.13 (m, 2H), 7.01 (d, J=8 Hz, 1H), 6.96–6.90 (m, 5H), 6.74 (d, J=8 Hz, 1 H), 6.59 (d, J=8 Hz, 1H), 6.21 (s, 1H), 3.88 (s, 3H), 2.98 (s, 3H); MS (ESI, –Q1MS) m/e 472 (M–H).

EXAMPLE 140

N-{6-[3-(4-acetylphenoxy)phenyl]-1-methoxy-6H-benzo[c]chromen-8-yl}methanesulfonamide Example 34 and 4-acetylphenyl boronic acid were processed as described in Example 139 to provide the titled compound. $^1$H NMR (300 MHz, DMSO-d$_6$) δ 9.86 (s, 1H), 8.32 (d, J=8 Hz, 1H), 7.74 (d, J=8 Hz, 1H), 7.52 (t, J=8 Hz, 1H), 7.47 (t, J=5 Hz, 1H), 7.38 (t, J=8 Hz, 1H), 7.25–7.21 (m, 2H), 7.12 (t, J=8 Hz, 1H), 7.05 (d, J=8 Hz, 1H), 6.99 (d, J=8 Hz, 1H), 6.95–6.90 (m, 2H), 6.73 (d, J=8 Hz, 1H), 6.59 (d, J=8 Hz, 1H), 6.24 (s, 1H), 3.88 (s, 3H), 2.98 (s, 3H), 2.57 (s, 3H); MS (ESI, –Q1MS) m/e 514 (M–H).

EXAMPLE 141

N-{1-(difluoromethoxy)-6-[3-(6-methoxyhexyl)phenyl]-6H-benzo[c]chromen-8-yl}methanesulfonamide Example 103 and 6-methoxy-1-hexene were processed as described in example 117 to provide the titled compound. $^1$H NMR (300 MHz, DMSO-d$_6$) δ 9.97 (s, 1H), 8.15 (d, J=9 Hz, 1H), 7.05–7.56 (m, 7H), 6.86–6.91 (m, 3H), 6.25 (s, 1H), 3.26 (t, J=7 Hz, 2H), 3.19 (s, 3H), 3.01(s, 3H), 1.40–1.55 (m, 6H), 1.21–1.31 (m, 2H), 1.17 (t, J=7 Hz, 2H); MS (ESI(–)Q1MS m/z 530 (M–H).

EXAMPLE 142

N-(1-methoxy-6-{3-[4-oxo-4-(1-piperidinyl)butyl]phenyl}-6H-benzo[c]chromen-8-yl)methanesulfonamide A solution of Example 151 (90 mg) and TBTU [O-(1H-benzotriazol-1-yl)-N,N,N',N'-tetramethyl uronium tetrafluoroborate] (125 mg) in CH$_3$CN (0.9 mL) was stirred for 1 minute then piperidine (80 mg) was added and the mixture was stirred for 2.5 hours. Toluene was added and the mixture was washed with aqueous KHCO$_3$, H$_2$O, and aqueous HCl (1M). The solution was dried (Na$_2$SO$_4$), filtered and the solvent removed under reduced pressure to provide the titled compound (86 mg). $^1$NMR (CDCl$_3$) 300 MHz) δ 1.48–1.68 (m, 6H), 1.95 (quintet, J=7 Hz, 2H), 2.25 (t, J=7 Hz, 2H), 2.70 (t, J=7 Hz, 2H), 2.93 (s, 3H), 3.33–3.55 (broad m, 4H), 3.95 (s, 3H), 5.89 (s, 1H), 6.55 (d, J=3 Hz, 1H), 6.66 (d, J=9 Hz, 1H), 6.70 (dd, J=2 Hz, J=8 Hz, 1H), 7.15 (t, J=8 Hz, 1H), 7.16 )d, J=7 Hz, 1H), 7.26–7.35 (m, 3H), 7.49)dd, J=9 Hz, 1H), 7.72 (s, 1H), 8.40 (d, J=9 Hz).

EXAMPLE 143

N-[6-(4'-chloro[1,1'-biphenyl]-3-yl)-1-(difluoromethoxy)-6H-benzo[c]chromen-8-yl]methanesulfonamide A solution of Example 103 (0.05 g, 0.1mmol), 4-chlorophenylboronic (0.015 g, 0.1 mmol), tetrakis (triphenylphosphine) palladium(O) (0.00006 g, 0.00005 mmol), and sodiumcarbonate (0.021 g, 0.2 mmol) in ethylene glycol dimethyl ether (0.75 mL), toluene (0.1 mL), ethanol (0.35 mL) and H$_2$O (0.3 mL) was shaken at 90° C. for 20 minutes, and concentrated under reduced pressure. The residue was purified by HPLC with aqueous 0.1% TFA and CH$_3$CN to provide the titled compound. $^1$H NMR (300 MHz, DMSO-d$_6$) δ 9.98 (s, 1H), 8.18 (d, J=9 Hz, 1H), 7.09–7.66 (m, 1H), 6.89–6.97 (m, 3H), 6.38 (s, 1H), 3.03(s, 3H); MS (ESI(–)Q1MS m/z 526 (M–H).

EXAMPLE 144

N-[1-(difluoromethoxy)-6-(4'-fluoro[1,1'-biphenyl]-3-yl)-6H-benzo[c]chromen-8-yl]methanesulfonamide Example 103 and 4-fluorophenylboronic acid were processed as in Example 143 to provide the titled compound. $^1$H NMR (300 MHz, DMSO-d$_6$) δ 9.98 (s, 1H), 8.18 (d, J=9 Hz, 1H), 7.58–7.65 (m, 4H), 7.45 (t, J=8 Hz, 1H), 6.89–7.33 (m, 9H), 6.37 (s, 1H), 3.03 (s, 3H); MS (ESI(–)Q1MS m/z 510 (M–H).

EXAMPLE 145

N-[1-(difluoromethoxy)-6-(4'-methoxy[1,1'-biphenyl]-3-yl)-6H-benzo[c]chromen-8-yl]methanesulfonamide Example 103 and 4-methoxyphenylboronic acid were processed as in Example 143 to provide the titled compound. $^1$H NMR (300 MHz, DMSO-d$_6$) δ 9.96 (s, 1H), 8.17 (d, J=9 Hz, 1H), 7.47–7.58 (m, 4H), 7.41 (t, J=8 Hz, 1H), 7.17–7.32 (m, 4H), 6.88–7.02 (in, 5H), 6.35 (s, 1H), 3.79 (s, 3H), 3.01 (s, 3H); MS (ESI(–)Q1MS m/z 522 (M–H).

EXAMPLE 146

N-[6-(2'-chloro[1,1'-biphenyl]-3-yl)-1-(difluoromethoxy)-6H-benzo[c]chromen-8-yl]methanesulfonamide Example 103 and 2-chlorophenylboronic acid were processed as in Example 143 to provide the titled compound. $^1$H NMR (300 MHz, DMSO-d$_6$) δ 10.00 (s, 1H), 8.17 (d, J=9 Hz, 1H), 7.08–7.57 (m, 10H), 6.87–7.01 (m, 4H), 6.39 (s, 1H), 3.02 (s, 3H); MS (ESI(–)Q1MS m/z 526 (M–H).

EXAMPLE 147

N-[1-(difluoromethoxy)-6-(4'-methyl[1,1'-biphenyl]-3-yl)-6H-benzo[c]chromen-8-yl]methanesulfonamide Example 103 and 4-methylphenylboronic acid were processed as in Example 143 to provide the titled compound. $^1$H NMR (300 MHz, DMSO-d$_6$) δ 9.98 (s, 1H), 8.18 (d, J=9 Hz, 1H), 7.57–7.61 (m, 2H), 7.09–7.48 (m, 7H), 6.88–6.99 (m, 3H), 6.37 (s, 1H), 3.03 (s, 3H), 2.3:3 (s, 3H); MS (ESI(–) Q1MS m/z 506 (M–H).

EXAMPLE 148

4-methoxy-N-(3-{1-methoxy-8-[(methylsulfonyl)amino]-6H-benzo[c]chromen-6-yl}phenyl)-N-methylbenzenesulfonamide Example 81 and 4-methoxyphenylsulfonyl chloride were processed as described in Example 129 to provide the titled compound. $^1$H NMR (500 MHz, CD3OD) δ 8.41 (d, J=8.7 Hz, 1H), 7.34 (d, J=9.0 Hz, 21H), 7.28 (m, 21H), 7.23 (dd, J=8.4, 2.5 Hz, 1H), 7.13 (t, J=8.3 Hz, 1H), 7.05 (m, 1H), 7.01 (m, 1H), 6.93 (d, J=9.0 Hz, 2H), 6.85 (d, J=2.5 Hz, 1H), 6.71 (dd, J=8.4, 0.9 Hz, 1H), 6.59 (dd, J=8.1, 0.9 Hz, 1H), 5.99 (s, 1H), 3.93 (s, 3H), 3.84 (s, 3H), 3.06 (s, 3H), 2.93 (s, 3H); MS (ESI –Q1MS) m/e 579 (M–H).

EXAMPLE 149

5-(3-isoxazolyl)-N-(3-{1-methoxy-8-[(methylsulfonyl)amino]-6H-benzo[c]chromen-6-yl}phenyl)-N-methyl-2-thiophenesulfonamide Example 81 and 5-(3-isoxazolyl)-2-thiophenesulfonyl chloride were processed as described in Example 129 to provide the titled compound. $^1$H NMR (500 MHz, CD3OD) δ 8.48 (d, J=1.9 Hz, 1H), 8.35 (d, J=8.7 Hz, 1H), 7.51 (d, J=4.1 Hz, 1H), 7.33 (d, J=5.0 Hz, 2H), 7.18 (d, J=4.1 Hz, 1H), 7.16 (m, 2H), 7.10 (t, J=8.3 Hz, 1H), 7.04 (m, 1H), 6.89 (d, J=2.2 Hz, 1H), 6.79 (d, J=1.9 Hz, 1H), 6.68 (dd, J=8.3, 0.8 Hz, 1H), 6.54 (dd, J=8.1, 0.9 Hz, 1H), 6.03 (s, 1H), 3.92 (s, 3H), 3.18 (s, 3H), 2.94 (s, 3H); MS (ESI –Q1MS) m/e 622 (M–H).

EXAMPLE 150 ethyl 4-(3-{1-methoxy-8-[(methylsulfonyl)amino]-6H-benzo[c]chromen-6-yl}phenyl)butanoate Example 82 and chloro-(4-carboxyethoylbutanoyl) zinc were processed as described in Example 111 to provide the titled compound. $^1$NMR (CDCl$_3$ 300 MHz) δ 1.22 (t, J=7 Hz, 3H), 1.95 (quintet, J=7 Hz, 2H), 2.29 (t, J=7 Hz, 2H), 2.68 (t, J=7 Hz, 2H), 2.95 (s, 3H), 3.94 (s, 3H), 4.05 (q, J=7 Hz, 2H), 5.91 (s, 1H), 6.51 (d, J=3 Hz, 1H), 6.65 (d, J=9 Hz, 1H), 6.70 (dd, J=2 Hz, 8 Hz, 1H), 6.73 (s, 1H), 7.15 (t, J=8 Hz, 1H), 7.15–7.24 (m, 3H), 7.30 (t, J=7 Hz, 1H), 7.32 (d, J=9 Hz, 1H), 8.43 (d, J=9 Hz, 1H).

EXAMPLE 151

4-(3-{1-methoxy-8-[(methylsulfonyl)amino]-6H-benzo[c]chromen-6-yl}phenyl)butanoic acid A solution of Example 150 (0.78 g, 1.6 mmol) and NaOH (0.67 g, 16.7 mmol) in MeOH-H$_2$O (3 mL, 1:1) was stirred for 6 hours, diluted with aqueous HCl (50 mL, 1M) and extracted with ethyl acetate (3×35 mL). The combined ethyl acetate was dried (MgSO$_4$), filtered and concentrated under reduced pressure to provide the titled compound (0.76 g, 99%) of the title compound. $^1$NMR (CDCl$_3$ 300 MHz) δ 1.95 (quintet, J=7 Hz, 2H), 2.31 (t, J=7 Hz, 2H), 2.68 (t, J=7 Hz, 2H), 2.95 (s, 3H), 3.94 (s, 3H), 5.93 (s, 1H), 6.55 (d, J=3 Hz, 1H), 6.65 (d, J=9 Hz, 1H), 6.69 (dd, J=2 Hz, 8 Hz, 1H), 6.89 (s, 1H), 7.15 (t, J=8 Hz, 1H), 7.15–7.24 (m, 3H), 7.25–7.32 (m, 4H), 8.42 (d, J=9 Hz, 1H).

EXAMPLE 152

4-bromo-N-(3-{1-methoxy-8-[(methylsulfonyl)amino]-6H-benzo[c]chromen-6-yl}phenyl)-N-methylbenzenesulfonamide Example 81 and 4-bromophenylsulfonyl chloride were processed as described in Example 110 to provide the titled compound. $^1$NMR (CDCl$_3$ 300 MHz) δ 2.98 (s, 3H), 3.12 (s, 3H), 3.94 (s, 3H), 5.96 (s, 1H), 6.46 (s, 1H), 6, 65 (t, J=8 Hz, 1H), 6.78 (d, J=3 Hz, 1H), 6.96–7.04 (m, 1H), 7.14–7.21 (m, 3H), 7.79–7.84 (m, 2H), 7.84 (d, J=9 Hz, 2H), 7.55 (d, J=9 Hz, 2H), 8.44 (d, J=8 Hz, 1H).

EXAMPLE 153

N-{6-[4-(4-bromophenoxy)phenyl]-1-methoxy-6H-benzo[c]chromen-8-N-{6-[4-(4-bromophenoxy)phenyl]-1-methoxy-6H-dibenzo[c]chromen-8-yl}methanesulfonamide Example 32E and 4-(4-bromophenoxy)phenyllithium were processed as described in Example 32 to provide the titled compound. $^1$NMR (CDCl$_3$ 300 MHz) δ 2.98 (s, 3H), 3.12 (s, 3H), 3.94 (s, 3H), 5.96 (s, 1H), 6.46 (s, 1H), 6, 65 (t, J=8 Hz, 1H), 6.78 (d, J=3 Hz, 1H), 6.96–7.04 (m, 1H), 7.14–7.21 (m, 3H), 7.79–7.84 (m, 2H), 7.84 (d, J=9 Hz, 2H), 7.55 (d, J=9 Hz, 2H), 8.44 (d, J=8 Hz, 1H).

EXAMPLE 154

N-(4-bromo-1-methoxy-6-phenyl-6H-benzo[c]chromen-8-yl)methanesulfonamide

A solution of Example 5 (0.48 g. 1.26 mmol) and N-bromosuccinimide (0.234 g, 1.31 mmol) in CH$_3$CN (3 mL) was stirred for 1 hour. The mixture was diluted with chloroform, washed with aqueous KHCO$_3$, dried (Na$_2$SO$_4$) filtered and concentrated under reduced pressure. The residue was purified on silica using 40% ethyl acetate hexanes to provide the title compound (0.54 g). m.p. 122–123° NMR (CDCl$_3$ 300 MHz) δ 3.02 (s, 3H), 3.90 (s, 3H), 6.2D (s, 1H), 6.46 (s, 1H), 6.51 (d, J 9 Hz, 1H), 6.86 (d, J=3 Hz, 1H), 7.22–7.36 (m, 7H), 8.43 (d, J=9 Hz, 1H).

It will be evident to one skilled in the art that the invention is not limited to the forgoing examples, and that it can be embodied in other specific forms without departing from the essential attributes thereof. Thus, it is desired that the examples be considered as illustrative and not restrictive, reference being made to the claims, and that all changes which come within the meaning and range of equivalency of the claims be embraced therein. For example, the following compounds can be prepared according to the procedures described above:

(1-methoxy-6-allyl-6H-dibenzo(b,d)pyran-8-yl)methanesulfonamide, (1-methoxy-6-phenyl-6H-dibenzo(b,d)pyran-8-yl)methanesulfonamide, (1-methoxy-6-(3-chlorophenyl)-6H-dibenzo(b,d)pyran-8-yl)methanesulfonamide, (1-methoxy-6-(3-fluorophenyl)-6H-dibenzo(b,d)pyran-8-yl)methanesulfonamide,
(1-methoxy-6-(3-methoxyphenyl)-6H-dibenzo(b,d)pyran-8-yl)methanesulfonamide,
(1-methoxy-6-(3,4-dimethoxy)phenyl-6H-dibenzo(b,d)pyran-8-yl)methanesulfonamide,
(1-methoxy-6-(5-bromothien-2-yl)-6H-dibenzo(b,d)pyran-8-yl)methanesulfonamide,
(1-difluoromethoxy-6-allyl-6H-dibenzo(b,d)pyran-8-yl)methanesulfonamide,
(1-difluoromethoxy-6-phenyl-6H-dibenzo(b,d)pyran-8-yl)methanesulfonamide,
(1-difluoromethoxy-6-(3-chlorophenyl)-6H-dibenzo(b,d)pyran-8-yl)methanesulfonamide,
(1-difluoromethoxy-6-(3-fluorophenyl)-6H-dibenzo(b,d)pyran-8-yl)methanesulfonamide,
(1-difluoromethoxy-6-(3-methoxyphenyl)-6H-dibenzo(b,d)pyran-8-yl)methanesulfonamide,
(1-difluoromethoxy-6-(3,4-dimethoxy)phenyl-6H-dibenzo(b,d)pyran-8-yl)methanesulfonamide,
(1-difluoromethoxy-6-(5-bromothien-2-yl)-6H-dibenzo(b,d)pyran-8-yl)methanesulfonamide,
(1-trifluoromethyl-6-allyl-6H-dibenzo(b,d)pyran-8-yl)methanesulfonamide,
(1-trifluoromethyl-6-phenyl-6H-dibenzo(b,d)pyran-8-yl)methanesulfonamide,
(1-trifluoromethyl-6-(3-chlorophenyl)-6H-dibenzo(b,d)pyran-8-yl)methanesulfonamide,
(1-trifluoromethyl-6-(3-fluorophenyl)-6H-dibenzo(b,d)pyran-8-yl)methanesulfonamide,
(1-trifluoromethyl-6-(3-methoxyphenyl)-6H-dibenzo(b,d)pyran-8-yl)methanesulfonamide,
(1-trifluoromethyl-6-(3,4-dimethoxy)phenyl-6H-dibenzo(b,d)pyran-8-yl)methanesulfonamide,
(1-trifluoromethyl-6-(5-bromothien-2-yl)-6H-dibenzo(b,d)pyran-8-yl)methanesulfonamide,
(1-trifluoromethoxy-6-allyl-6H-dibenzo(b,d)pyran-8-yl)methanesulfonamide,
(1-trifluoromethoxy-6-phenyl-6H-dibenzo(b,d)pyran-8-yl)methanesulfonamide,
(1-trifluoromethoxy-6-(3-chlorophenyl)-6H-dibenzo(b,d)pyran-8-yl)methanesulfonamide,
(1-trifluoromethoxy-6-(3-fluorophenyl)-6H-dibenzo(b,d)pyran-8-yl)methanesulfonamide,
(1-trifluoromethoxy-6-(3-methoxyphenyl)-6H-dibenzo(b,d)pyran-8-yl)methanesulfonamide,
(1-trifluoromethoxy-6-(3,4-dimethoxy)phenyl-6H-dibenzo(b,d)pyran-8-yl)methanesulfonamide,
(1-trifluoromethoxy-6-(5-bromothien-2-yl)-6H-dibenzo(b,d)pyran-8-yl)methanesulfonamide,
(1-methylthio-6-allyl-6H-dibenzo(b,d)pyran-8-yl)methanesulfonamide,
(1-methylthio-6-phenyl-6H-dibenzo(b,d)pyran-8-yl)methanesulfonamide,
(1-methylthio-6-(3-chlorophenyl)-6H-dibenzo(b,d)pyran-8-yl)methanesulfonamide,
(1-methylthio-6-(3-fluorophenyl)-6H-dibenzo(b,d)pyran-8-yl)methanesulfonamide,
(1-methylthio-6-(3-methoxyphenyl)-6H-dibenzo(b,d)pyran-8-yl)methanesulfonamide,
(1-methylthio-6-(3,4-dimethoxy)phenyl-6H-dibenzo(b,d)pyran-8-yl)methanesulfonamide,
(1-methylthio-6-(5-bromothien-2-yl)-6H-dibenzo(b,d)pyran-8-yl)methanesulfonamide,
(1-ethylthio-6-allyl-6H-dibenzo(b,d)pyran-8-yl)methanesulfonamide,
(1-ethylthio-6-phenyl-6H-dibenzo(b,d)pyran-8-yl)methanesulfonamide,
(1-ethylthio-6-(3-chlorophenyl)-6H-dibenzo(b,d)pyran-8-yl)methanesulfonamide,
(1-ethylthio-6-(3-fluorophenyl)-6H-dibenzo(b,d)pyran-8-yl)methanesulfonamide,
(1-ethylthio-6-(3-methoxyphenyl)-6H-dibenzo(b,d)pyran-8-yl)methanesulfonamide,
(1-ethylthio-6-(3,4-dimethoxy)phenyl-6H-dibenzo(b,d)pyran-8-yl)methanesulfonamide,
(1-ethylthio-6-(5-bromothien-2-yl)-6H-dibenzo(b,d)pyran-8-yl)methanesulfonamide,
(1-trifluoromethylthio-6-allyl-6H-dibenzo(b,d)pyran-8-yl)methanesulfonamide,
(1-trifluoromethylthio-6-phenyl-6H-dibenzo(b,d)pyran-8-yl)methanesulfonamide,
(1-trifluoromethylthio-6-(3-chlorophenyl)-6H-dibenzo(b,d)pyran-8-yl)methanesulfonamide,
(1-trifluoromethylthio-6-(3-fluorophenyl)-6H-dibenzo(b,d)pyran-8-yl)methanesulfonamide,
(1-trifluoromethylthio-6-(3-methoxyphenyl)-6H-dibenzo(b,d)pyran-8-yl)methanesulfonamide,
(1-trifluoromethylthio-6-(3,4-dimethoxy)phenyl-6H-dibenzo(b,d)pyran-8-yl)methanesulfonamide,
(1-trifluoromethylthio-6-(5-bromothien-2-yl)-6H-dibenzo(b,d)pyran-8-yl)methanesulfonamide,
(1-ethoxy-6-allyl-6H-dibenzo(b,d)pyran-8-yl)methanesulfonamide,
(1-ethoxy-6-phenyl-6H-dibenzo(b,d)pyran-8-yl)methanesulfonamide,
(1-ethoxy-6-(3-chlorophenyl)-6H-dibenzo(b,d)pyran-8-yl)methanesulfonamide,
(1-ethoxy-6-(3-fluorophenyl)-6H-dibenzo(b,d)pyran-8-yl)methanesulfonamide,
(1-ethoxy-6-(3-methoxyphenyl)-6H-dibenzo(b,d)pyran-8-yl)methanesulfonamide,
(1-ethoxy-6-(3,4-dimethoxy)phenyl-6H-dibenzo(b,d)pyran-8-yl)methanesulfonamide,
(1-ethoxy-6-(5-bromothien-2-yl)-6H-dibenzo(b,d)pyran-8-yl)methanesulfonamide,
(1-methanesulfinyl-6-allyl-6H-dibenzo(b,d)pyran-8-yl)methanesulfonamide,
(1-methanesulfinyl-6-phenyl-6H-dibenzo(b,d)pyran-8-yl)methanesulfonamide,
(1-methanesulfinyl-6-(3-chlorophenyl)-6H-dibenzo(b,d)pyran-8-yl)methanesulfonamide,
(1-methanesulfinyl-6-(3-fluorophenyl)-6H-dibenzo(b,d)pyran-8-yl)methanesulfonamide,
(1-methanesulfinyl-6-(3-methoxyphenyl)-6H-dibenzo(b,d)pyran-8-yl)methanesulfonamide,
(1-methanesulfinyl-6-(3,4-dimethoxy)phenyl-6H-dibenzo(b,d)pyran-8-yl)methanesulfonamide,
(1-methanesulfinyl-6-(5-bromothien-2-yl)-6H-dibenzo(b,d)pyran-8-yl)methanesulfonamide,
(1-ethanesulfinyl-6-allyl-6H-dibenzo(b,d)pyran-8-yl)methanesulfonamide,
(1-ethanesulfinyl-6-phenyl-6H-dibenzo(b,d)pyran-8-yl)methanesulfonamide, (1-ethanesulfinyl-6-(3-chlorophenyl)-6H-dibenzo(b,d)pyran-8-yl)methanesulfonamide,
(1-ethanesulfinyl-6-(3-fluorophenyl)-6H-dibenzo(b,d)pyran-8-yl)methanesulfonamide,
(1-ethanesulfinyl-6-(3-methoxyphenyl)-6H-dibenzo(b,d)pyran-8-yl)methanesulfonamide,
(1-ethanesulfinyl-6-(3,4-dimethoxy)phenyl-6H-dibenzo(b,d)pyran-8-yl)methanesulfonamide,
(1-ethanesulfinyl-6-(5-bromothien-2-yl)-6H-dibenzo(b,d)pyran-8-yl)methanesulfonamide,
(1-methanesulfonyl-6-allyl-6H-dibenzo(b,d)pyran-8-yl)methanesulfonamide,
(1-methanesulfonyl-6-phenyl-6H-dibenzo(b,d)pyran-8-yl)methanesulfonamide,
(1-methanesulfonyl-6-(3-chlorophenyl)-6H-dibenzo(b,d)pyran-8-yl)methanesulfonamide,
(1-methanesulfonyl-6-(3-fluorophenyl)-6H-dibenzo(b,d)pyran-8-yl)methanesulfonamide,
(1-methanesulfonyl-6-(3-methoxyphenyl)-6H-dibenzo(b,d)pyran-8-yl)methanesulfonamide,
(1-methanesulfonyl-6-(3,4-dimethoxy)phenyl-6H-dibenzo(b,d)pyran-8-yl)methanesulfonamide,
(1-methanesulfonyl-6-(5-bromothien-2-yl)-6H-dibenzo(b,d)pyran-8-yl)methanesulfonamide,
(1-ethanesulfonyl-6-allyl-6H-dibenzo(b,d)pyran-8-yl)methanesulfonamide,
(1-ethanesulfonyl-6-phenyl-6H-dibenzo(b,d)pyran-8-yl)methanesulfonamide,
(1-ethanesulfonyl-6-(3-chlorophenyl)-6H-dibenzo(b,d)pyran-8-yl)methanesulfonamide,
(1-ethanesulfonyl-6-(3-fluorophenyl)-6H-dibenzo(b,d)pyran-8-yl)methanesulfonamide,
(1-ethanesulfonyl-6-(3-methoxyphenyl)-6H-dibenzo(b,d)pyran-8-yl)methanesulfonamide,
(1-ethanesulfonyl-6-(3,4-dimethoxy)phenyl-6H-dibenzo(b,d)pyran-8-yl)methanesulfonamide,
(1-ethanesulfonyl-6-(5-bromothien-2-yl)-6H-dibenzo(b,d)pyran-8-yl)methanesulfonamide,
(1-bromo-6-allyl-6H-dibenzo(b,d)pyran-8-yl)methanesulfonamide,
(1-bromo-6-phenyl-6H-dibenzo(b,d)pyran-8-yl)methanesulfonamide,
(1-bromo-6-(3-chlorophenyl)-6H-dibenzo(b,d)pyran-8-yl)methanesulfonamide,
(1-bromo-6-(3-fluorophenyl)-6H-dibenzo(b,d)pyran-8-yl)methanesulfonamide,
(1-bromo-6-(3-methoxyphenyl)-6H-dibenzo(b,d)pyran-8-yl)methanesulfonamide,
(1-bromo-6-(3,4-dimethoxy)phenyl-6H-dibenzo(b,d)pyran-8-yl)methanesulfonamide,
(1-bromo-6-(5-bromothien-2-yl)-6H-dibenzo(b,d)pyran-8-yl)methanesulfonamide,
(1-dimethylamino-6-allyl-6H-dibenzo(b,d)pyran-8-yl)methanesulfonamide,
(1-dimethylamino-6-phenyl-6H-dibenzo(b,d)pyran-8-yl)methanesulfonamide,
(1-dimethylamino-6-(3-chlorophenyl)-6H-dibenzo(b,d)pyran-8-yl)methanesulfonamide,
(1-dimethylamino-6-(3-fluorophenyl)-6H-dibenzo(b,d)pyran-8-yl)methanesulfonamide,
(1-dimethylamino-6-(3-methoxyphenyl)-6H-dibenzo(b,d)pyran-8-yl)methanesulfonamide,
(1-dimethylamino-6-(3,4-dimethoxy)phenyl-6H-dibenzo(b,d)pyran-8-yl)methanesulfonamide,
(1-dimethylamino-6-(5-bromothien-2-yl)-6H-dibenzo(b,d)pyran-8-yl)methanesulfonamide,
(1-diethylamino-6-allyl-6H-dibenzo(b,d)pyran-8-yl)methanesulfonamide,
(1-diethylamino-6-phenyl-6H-dibenzo(b,d)pyran-8-yl)methanesulfonamide,
(1-diethylamino-6-(3-chlorophenyl)-6H-dibenzo(bed)pyran-8-yl)methanesulfonamide,
(1-diethylamino-6-(3-fluorophenyl)-6H-dibenzo(b,d)pyran-8-yl)methanesulfonamide,
(1-diethylamino-6-(3-methoxyphenyl)-6H-dibenzo(b,d)pyran-8-yl)methanesulfonamide,
(1-diethylamino-6-(3,4-dimethoxy)phenyl-6H-dibenzo(b,d)pyran-8-yl)methanesulfonamide,
(1-diethylamino-6-(5-bromothien-2-yl)-6H-dibenzo(b,d)pyran-8-yl)methanesulfonamide,
(1-(N-methyl-N-ethylamino)-6-allyl-6H-dibenzo(b,d)pyran-8-yl)methanesulfonamide,
(1-(N-methyl-N-ethylamino)-6-phenyl-6H-dibenzo(b,d)pyran-8-yl)methanesulfonamide,
(1-(N-methyl-N-ethylamino)-6-(3-chlorophenyl)-6H-dibenzo(b,d)pyran-8-yl)methanesulfonamide,
(1-(N-methyl-N-ethylamino)-6-(3-fluorophenyl)-6H-dibenzo(b,d)pyran-8-yl)methanesulfonamide,
(1-(N-methyl-N-ethylamino)-6-(3-methoxyphenyl)-6H-dibenzo(b,d)pyran-8-yl)methanesulfonamide,
(1-(N-methyl-N-ethylamino)-6-(3,4-dimethoxy)phenyl-6H-dibenzo(b,d)pyran-8-yl)methanesulfonamide,
(1-(N-methyl-N-ethylamino)-6-(5-bromothien-2-yl)-6H-dibenzo(b,d)pyran-8-yl)methanesulfonamide,
(1-(2-thienyl)-6-allyl-6H-dibenzo(b,d)pyran-8-yl)methanesulfonamide,
(1-(2-thienyl)-6-phenyl-6H-dibenzo(b,d)pyran-8-yl)methanesulfonamide,
(1-(2-thienyl)-6-(3-chlorophenyl)-6H-dibenzo(b,d)pyran-8-yl)methanesulfonamide,
(1-(2-thienyl)-6-(3-fluorophenyl)-6H-dibenzo(b,d)pyran-8-yl)methanesulfonamide,
(1-(2-thienyl)-6-(3-methoxphenyl)-6H-dibenzo(b,d)pyran-8-yl)methanesulfonamide,
(1-(2-thienyl)-6-(3,4-dimethoxy)phenyl-6H-dibenzo(b,d)pyran-8-yl)methanesulfonamide,
(1-(2-thienyl)-6-(5-bromothien-2-yl)-6H-dibenzo(b,d)pyran-8-yl)methanesulfonamide,
(1-(2-furanyl)-6-allyl-6H-dibenzo(b,d)pyran-8-yl)methanesulfonamide,
(1-(2-furanyl)-6-phenyl-6H-dibenzo(b,d)pyran-8-yl)methanesulfonamide,
(1-(2-furanyl)-6-(3-chlorophenyl)-6H-dibenzo(b,d)pyran-8-yl)methanesulfonamide,
(1-(2-furanyl)-6-(3-fluorophenyl)-6H-dibenzo(b,d)pyran-8-yl)methanesulfonamide,
(1-(2-furanyl)-6-(3-methoxyphenyl)-6H-dibenzo(b,d)pyran-8-yl)methanesulfonamide,
(1-(2-furanyl)-6-(3,4-dimethoxy)phenyl-6H-dibenzo(b,d)pyran-8-yl)methanesulfonamide,
(1-(2-furanyl)-6-(5-bromothien-2-yl)-6H-dibenzo(b,d)pyran-8-yl)methanesulfonamide,
(1-ethynyl-6-allyl-6H-dibenzo(b,d)pyran-8-yl)methanesulfonamide, (1-ethynyl-6-phenyl-6H-dibenzo(b,d)pyran-8-yl) methanesulfonamide,
(1-ethynyl-6-(3-chlorophenyl)-6H-dibenzo(b,d)pyran-8-yl)methanesulfonamide,
(1-ethynyl-6-(3-fluorophenyl)-6H-dibenzo(b,d)pyran-8-yl)methanesulfonamide,
(1-ethynyl-6-(3-methoxyphenyl)-6H-dibenzo(b,d)pyran-8-yl)methanesulfonamide,
(1-ethynyl-6-(3,4-dimethoxy)phenyl-6H-dibenzo(b,d)pyran-8-yl)methanesulfonamide,
(1-ethynyl-6-(5-bromothien-2-yl)-6H-dibenzo(b,d)pyran-8-yl)methanesulfonamide,
(1-propyn-1-yl-6-allyl-6H-dibenzo(b,d)pyran-8-yl) methanesulfonamide,
(1-propyn-1-yl-6-phenyl-6H-dibenzo(b,d)pyran-8-yl) methanesulfonamide,
(1-propyn-1-yl-6-(3-chlorophenyl)-6H-dibenzo(b,d)pyran-8-yl)methanesulfonamide,
(1-propyn-1-yl-6-(3-fluorophenyl)-6H-dibenzo(b,d)pyran-8-yl)methanesulfonamide,
(1-propyn-1-yl-6-(3-methoxyphenyl)-6H-dibenzo(b,d)pyran-8-yl)methanesulfonamide,
(1-propyn-1-yl-6-(3,4-dimethoxy)phenyl-6H-dibenzo(b,d)pyran-8-yl)methanesulfonamide,
(1-propyn-1-yl-6-(5-bromothien-2-yl)-6H-dibenzo(b,d)pyran-8-yl)methanesulfonamide,
(1-vinyl-6-allyl-6H-dibenzo(b,d)pyran-8-yl) methanesulfonamide,
(1-vinyl-6-phenyl-6H-dibenzo(b,d)pyran-8-yl) methanesulfonamide,
(1-vinyl-6-(3-chlorophenyl)-6H-dibenzo(b,d)pyran-8-yl) methanesulfonamide,
(1-vinyl-6-(3-fluorophenyl)-6H-dibenzo(b,d)pyran-8-yl) methanesulfonamide,
(1-vinyl-6-(3-methoxyphenyl)-6H-dibenzo(b,d)pyran-8-yl)methanesulfonamide,
(1-vinyl-6-(3,4-dimethoxy)phenyl-6H-dibenzo(b,d)pyran-8-yl)methanesulfonamide,
(1-vinyl-6-(5-bromothien-2-yl)-6H-dibenzo(b,d)pyran-8-yl)methanesulfonamide,
(1-(propyn-2-yl)oxy-6-allyl-6H-dibenzo(b,d)pyran-8-yl) methanesulfonamide,
(1-(propyn-2-yl)oxy-6-phenyl-6H-dibenzo(b,d)pyran-8-yl)methanesulfonamide,
(1-(propyn-2-yl)oxy-6-(3-chlorophenyl)-6H-dibenzo(b,d)pyran-8-yl)methanesulfonamide,
(1-(propyn-2-yl)oxy-6-(3-fluorophenyl)-6H-dibenzo(b,d)pyran-8-yl)methanesulfonamide,
(1-(propyn-2-yl)oxy-6-(3-methoxyphenyl)-6H-dibenzo(b,d)pyran-8-yl)methanesulfonamide,
(1-(propyn-2-yl)oxy-6-(3,4-dimethoxy)phenyl-6H-dibenzo(b,d)pyran-8-yl)methanesulfonamide,
(1-(propyn-2-yl)oxy-6-(5-bromothien-2-yl)-6H-dibenzo(b,d)pyran-8-yl)methanesulfonamide,
(1-cyano-6-allyl-6H-dibenzo(b,d)pyran-8-yl) methanesulfonamide,
(1-cyano-6-phenyl-6H-dibenzo(b,d)pyran-8-yl) methanesulfonamide,
(1-cyano-6-(3-chlorophenyl)-6H-dibenzo(b,d)pyran-8-yl)methanesulfonamide,
(1-cyano-6-(3-fluorophenyl)-6H-dibenzo(b,d)pyran-8-yl) methanesulfonamide,
(1-cyano-6-(3-methoxyphenyl)-6H-dibenzo(b,d)pyran-8-yl)methanesulfonamide,
(1-cyano-6-(3,4-dimethoxy)phenyl-6H-dibenzo(b,d)pyran-8-yl)methanesulfonamide,
(1-cyano-6-(5-bromothien-2-yl)-6H-dibenzo(b,d)pyran-8-yl)methanesulfonamide,
(1-hydroxymethyl-6-allyl-6H-dibenzo(b,d)pyran-8-yl) methanesulfonamide,
(1-hydroxymethyl-6-phenyl-6H-dibenzo(b,d)pyran-8-yl) methanesulfonamide,
(1-hydroxymethyl-6-(3-chlorophenyl)-6H-dibenzo(b,d)pyran-8-yl)methanesulfonamide,
(1-hydroxymethyl-6-(3-fluorophenyl)-6H-dibenzo(b,d)pyran-8-yl)methanesulfonamide,
(1-hydroxymethyl-6-(3-methoxyphenyl)-6H-dibenzo(b,d)pyran-8-yl)methanesulfonamide,
(1-hydroxymethyl-6-(3,4-dimethoxy)phenyl-6H-dibenzo(b,d)pyran-8-yl)methanesulfonamide,
(1-hydroxymethyl-6-(5-bromothien-2-yl)-6H-dibenzo(b,d)pyran-8-yl)methanesulfonamide,
(1-formyl-6-allyl-6H-dibenzo(b,d)pyran-8-yl) methanesulfonamide,
(1-formyl-6-phenyl-6H-dibenzo(b,d)pyran-8-yl) methanesulfonamide,
(1-formyl-6-(3-chlorophenyl)-6H-dibenzo (b,d)pyran-8-yl)methanesulfonamide,
(1-formyl-6-(3-fluorophenyl)-6H-dibenzo(b,d)pyran-8-yl)methanesulfonamide,
(1-formyl-6-(3-methoxyphenyl)-6H-dibenzo(b,d)pyran-8-yl)methanesulfonamide,
(1-formyl-6-(3-dimethoxyphenyl)-6H-dibenzo(b,d)pyran-8-yl)methanesulfonamide,
(1-formaldoximino-6-allyl-6H-dibenzo(b,d)pyran-8-yl) methanesulfonamide,
(1-formaldoximino-6phenyl-6H-dibenzo(b,d)pyran-8-yl) methanesulfonamide,
(1-formaldoximino-6-(3-chlorophenyl)-6H-dibenzo(b,d)pyran-8-yl)methanesulfonamide,
(1-formaldoximino-6-(3-fluorophenyl)-6H-dibenzo(b,d)pyran-8-yl)methanesulfonamide,
(1-formaldoximino-6-(3-methoxyphenyl)-6H-dibenzo(b,d)pyran-8-yl)methanesulfonamide,
(1-formaldoximino-6-(3,4-dimethoxy)phenyl-6H-dibenzo(b,d)pyran-8-yl)methanesulfonamide,
(1-formaldoximino-6-(5-bromothien-2-yl)-6H-dibenzo(b,d)pyran-8-yl)methanesulfonamide,
(1-methoxymethyl-6-allyl-6H-dibenzo(b,d)pyran-8-yl) methanesulfonamide,
(1-methoxymethyl-6-phenyl-6H-dibenzo(b,d)pyran-8-yl) methanesulfonamide,
(1-methoxymethyl-6-(3-chlorophenyl)-6H-dibenzo(b,d)pyran-8-yl)methanesulfonamide,
(1-methoxymethyl-6-(3-fluorophenyl)-6H-dibenzo(b,d)pyran-8-yl)methanesulfonamide,
(1-methoxymethyl-6-(3-methoxyphenyl)-6H-dibenzo(b,d)pyran-8-yl)methanesulfonamide,
(1-methoxymethyl-6-(3,4-dimethoxy)phenyl-6H-dibenzo(b,d)pyran-8-yl)methanesulfonamide,
(1-methoxymethyl-6-(5-bromothien-2-yl)-6H-dibenzo(b,d)pyran-8-yl)methanesulfonamide,
(1-chloro-6-allyl-6H-dibenzo(b,d)pyran-8-yl) methanesulfonamide, (1-chloro-6-phenyl-6H-dibenzo(b,d)pyran-8-yl)methanesulfonamide,
(1-chloro-6-(3-chlorophenyl)-6H-dibenzo(b,d)pyran-8-yl)methanesulfonamide,
(1-chloro-6-(3-fluorophenyl)-6H-dibenzo(b,d)pyran-8-yl)methanesulfonamide,
(1-chloro-6-(3-methoxyphenyl)-6H-dibenzo(b,d)pyran-8-yl)methanesulfonamide,
(1-chloro-6-(3,4-dimethoxy)phenyl-6H-dibenzo(b,d)pyran-8-yl)methanesulfonamide,
(1-chloro-6-(5-bromothien-2-yl)-6H-dibenzo(b,d)pyran-8-yl)methanesulfonamide,
(1-ethyl-6-ally-6H-dibenzo(b,d)pyran-8-yl)methanesulfonamide,
(1-ethyl-6-phenyl-6H-dibenzo(b,d)pyran-8-yl)methanesulfonamide,
(1-ethyl-6-(3-chlorophenyl)-6H-dibenzo(b,d)pyran-8-yl)methanesulfonamide,
(1-ethyl-6-(3-fluorophenyl)-6H-dibenzo(b,d)pyran-8-yl)methanesulfonamide,
(1-ethyl-6-(3-methoxyphenyl)-6H-dibenzo(b,d)pyran-8-yl)methanesulfonamide,
(1-ethyl-6-(3,4-dimethoxy)phenyl-6H-dibenzo(b,d)pyran-8-yl)methanesulfonamide,
(1-ethyl-6-(5-bromothien-2-yl)-6H-dibenzo(b,d)pyran-8-yl)methanesulfonamide,
(1-methoxy-2-hydroxy-6-allyl-6H-dibenzo(b,d)pyran-8-yl)methanesulfonamide,
(1-methoxy-2-hydroxy-6phenyl-6H-dibenzo(b,d)pyran-8-yl)methanesulfonamide,
(1-methoxy-2-hydroxy-6-(3-chlorophenyl)-6H-dibenzo(b,d)pyran-8-yl)methanesulfonamide,
(1-methoxy-2-hydroxy-6-(3-fluorophenyl)-6H-dibenzo(b,d)pyran-8-yl)methanesulfonamide,
(1-methoxy-2-hydroxy-6-(3-methoxyphenyl)-6H-dibenzo(b,d)pyran-8-yl)methanesulfonamide,
(1-methoxy-2-hydroxy-6-(3,4-dimethoxy)phenyl-6H-dibenzo(b,d)pyran-8-yl)methanesulfonamide,
(1-methoxy-2-hydroxy-6-(5-bromothien-2-yl)-6H-dibenzo(b,d)pyran-8-yl)methanesulfonamide,
(1-methoxy-2-chloro-6-allyl-6H-dibenzo(b,d)pyran-8-yl)methanesulfonamide,
(1-methoxy-2-chloro-6-phenyl-6H-dibenzo(b,d)pyran-8-yl)methanesulfonamide,
(1-methoxy-2-chloro-6-(3-chlorophenyl)-6H-dibenzo(b,d)pyran-8-yl)methanesulfonamide,
(1-methoxy-2-chloro-6-(3-fluorophenyl)-6H-dibenzo(b,d)pyran-8-yl)methanesulfonamide,
(1-methoxy-2-chloro-6-(3-methoxyphenyl)-6H-dibenzo(b,d)pyran-8-yl)methanesulfonamide,
(1-methoxy-2-chloro-6-(3,4-dimethoxy)phenyl-6H-dibenzo(b,d)pyran-8-yl)methanesulfonamide,
(1-methoxy-2-chloro-6-(5-bromothien-2-yl)-6H-dibenzo(b,d)pyran-8-yl)methanesulfonamide,
(1-methoxy-2-bromo-6-allyl-6H-dibenzo(b,d)pyran-8-yl)methanesulfonamide,
(1-methoxy-2-bromo-6-phenyl-6H-dibenzo(b,d)pyran-8-yl)methanesulfonamide,
(1-methoxy-2-bromo-6-(3-chlorophenyl)-6H-dibenzo(b,d)pyran-8-yl)methanesulfonamide,
(1-methoxy-2-bromo-6-(3-fluorophenyl)-6H-dibenzo(b,d)pyran-8-yl)methanesulfonamide,
(1-methoxy-2-bromo-6-(3-methoxyphenyl)-6H-dibenzo(b,d)pyran-8-yl)methanesulfonamide,
(1-methoxy-2-bromo-6-(3,4-dimethoxy)phenyl-6H-dibenzo(b,d)pyran-8-yl)methanesulfonamide,
(1-methoxy-2-bromo-6-(5-bromothien-2-yl)-6H-dibenzo(b,d)pyran-8-yl)methanesulfonamide,
(1-methoxy-2-fluoro-6-allyl-6H-dibenzo(b,d)pyran-8-yl)methanesulfonamide,
(1-methoxy-2-fluoro-6-phenyl-6H-dibenzo(b,d)pyran-8-yl)methanesulfonamide,
(1-methoxy-2-fluoro-6-(3-chlorophenyl)-6H-dibenzo(b,d)pyran-8-yl)methanesulfonamide,
(1-methoxy-2-fluoro-6-(3-fluorophenyl)-6H-dibenzo(b,d)pyran-8-yl)methanesulfonamide,
(1-methoxy-2-fluoro-6-(3-methoxyphenyl)-6H-dibenzo(b,d)pyran-8-yl)methanesulfonamide,
(1-methoxy-2-fluoro-6-(3,4-dimethoxy)phenyl-6H-dibenzo(b,d)pyran-8-yl)methanesulfonamide,
(1-methoxy-2-fluoro-6-(5-bromothien-2-yl)-6H-dibenzo(b,d)pyran-8-yl)methanesulfonamide,
(1-methoxy-2-methyl-6-allyl-6H-dibenzo(b,d)pyran-8-yl)methanesulfonamide,
(1-methoxy-2-methyl-6-phenyl-6H-dibenzo(b,d)pyran-8-yl)methanesulfonamide,
(1-methoxy-2-methyl-6-(3-chlorophenyl)-6H-dibenzo(b,d)pyran-8-yl)methanesulfonamide,
(1-methoxy-2-methyl-6-(3-fluorophenyl)-6H-dibenzo(b,d)pyran-8-yl)methanesulfonamide,
(1-methoxy-2-methyl-6-(3-methoxyphenyl)-6H-dibenzo(b,d)pyran-8-yl)methanesulfonamide,
(1-methoxy-2-methyl-6-(3,4-dimethoxy)phenyl-6H-dibenzo(b,d)pyran-8-yl)methanesulfonamide,
(1-methoxy-2-methyl-6-(5-bromothien-2-yl)-6H-dibenzo(b,d)pyran-8-yl)methanesulfonamide,
(1-methoxy-2-allyloxy-6-allyl-6H-dibenzo(b,d)pyran-8-yl)methanesulfonamide,
(1-methoxy-2-allyloxy-6-phenyl-6H-dibenzo(b,d)pyran-8-yl)methanesulfonamide,
(1-methoxy-2-allyloxy-6-(3-chlorophenyl)-6H-dibenzo(b,d)pyran-8-yl)methanesulfonamide,
(1-methoxy-2-allyloxy-6-(3-fluorophenyl)-6H-dibenzo(b,d)pyran-8-yl)methanesulfonamide,
(1-methoxy-2-allyloxy-6-(3-methoxyphenyl)-6H-dibenzo(b,d)pyran-8-yl)methanesulfonamide,
(1-methoxy-2-allyloxy-6-(3,4-dimethoxy)phenyl-6H-dibenzo(b,d)pyran-8-yl)methanesulfonamide,
(1-methoxy-2-allyloxy-6-(5-bromothien-2-yl)-6H-dibenzo(b,d)pyran-8-yl)methanesulfonamide,
(1-methoxy-2-(2-allyloxy)ethoxy-6-allyl-6H-dibenzo(b,d)pyran-8-yl)methanesulfonamide,
(1-methoxy-2-(2-allyloxy)ethoxy-6-phenyl-6H-dibenzo(b,d)pyran-8-yl)methanesulfonamide,
(1-methoxy-2-(2-allyloxy)ethoxy-6-(3-chlorophenyl)-6H-dibenzo(b,d)pyran-8-yl)methanesulfonamide,
(1-methoxy-2-(2-allyloxy)ethoxy-6-(3-fluorophenyl)-6H-dibenzo(b,d)pyran-8-yl)methanesulfonamide,
(1-methoxy-2-(2-allyloxy)ethoxy-6-(3-methoxyphenyl)-6H-dibenzo(b,d)pyran-8-yl)methanesulfonamide,
(1-methoxy-2-(2-allyloxy)ethoxy-6-(3,4-dimethoxy)phenyl-6H-dibenzo(b,d)pyran-8-yl)methanesulfonamide,
(1-methoxy-2-(2-allyloxy)ethoxy-6-(5-bromothien-2-yl)-6H-dibenzo(b,d)pyran-8-yl)methanesulfonamide, (1-methoxy-2-(2-(2-methoxyethoxy)ethoxy)-6-allyl-6H-dibenzo(b,d)pyran-8-yl)methanesulfonamide,
(1-methoxy-2-(2-(2-methoxyethoxy)ethoxy)-6-phenyl-6H-dibenzo(b,d)pyran-8-yl)methanesulfonamide,
(1-methoxy-2-(2-(2-methoxyethoxy)ethoxy)-6-(3-chlorophenyl)-6H-dibenzo(b,d)pyran-8-yl)methanesulfonamide,
(1-methoxy-2-(2-(2-methoxyethoxy)ethoxy)-6-(3-fluorophenyl)-6H-dibenzo(b,d)pyran-8-yl)methanesulfonamide,
(1-methoxy-2-(2-(2-methoxyethoxy)ethoxy)-6-(3-methoxyphenyl)-6H-dibenzo(b,d)pyran-8-yl)methanesulfonamide,
(1-methoxy-2-(2-(2-methoxyethoxy)ethoxy)-6-(3,4-dimethoxy)phenyl-6H-dibenzo(b,d)pyran-8-yl)methanesulfonamide,
(1-methoxy-2-(2-(2-methoxyethoxy)ethoxy)-6-(5-bromothien-2-yl)-6H-dibenzo(b,d)pyran-8-yl)methanesulfonamide,
(1-difluoromethoxy-2-hydroxy-6-allyl-6H-dibenzo(b,d)pyran-8-yl)methanesulfonamide,
(1-difluoromethoxy-2-hydroxy-6-phenyl-6H-dibenzo(b,d)pyran-8-yl)methanesulfonamide,
(1-difluoromethoxy-2-hydroxy-6-(3-chlorophenyl)-6H-dibenzo(b,d)pyran-8-yl)methanesulfonamide,
(1-difluoromethoxy-2-hydroxy-6-(3-fluorophenyl)-6H-dibenzo(b,d)pyran-8-yl)methanesulfonamide,
(1-difluoromethoxy-2-hydroxy-6-(3-methoxyphenyl)-6H-dibenzo(b,d)pyran-8-yl)methanesulfonamide,
(1-difluoromethoxy-2-hydroxy-6-(3,4-dimethoxy)phenyl-6H-dibenzo(b,d)pyran-8-yl)methanesulfonamide,
(1-difluoromethoxy-2-hydroxy-6-(5-bromothien-2-yl)-6H-dibenzo(b,d)pyran-8-yl)methanesulfonamide,
(1-difluoromethoxy-2-chloro-6-allyl-6H-dibenzo(b,d)pyran-8-yl)methanesulfonamide,
(1-difluoromethoxy-2-chloro-6-phenyl-6H-dibenzo(b,d)pyran-8-yl)methanesulfonamide,
(1-difluoromethoxy-2-chloro-6-(3-chlorophenyl)-6H-dibenzo(b,d)pyran-8-yl)methanesulfonamide,
(1-difluoromethoxy-2-chloro-6-(3-fluorophenyl)-6H-dibenzo(b,d)pyran-8-yl)methanesulfonamide,
(1-difluoromethoxy-2-chloro-6-(3-methoxyphenyl)-6H-dibenzo(b,d)pyran-8-yl)methanesulfonamide,
(1-difluoromethoxy-2-chloro-6-(3,4-dimethoxyphenyl)-6H-dibenzo(b,d)pyran-8-yl)methanesulfonamide,
(1-difluoromethoxy-2-chloro-6-(5-bromothien-2-yl)-6H-dibenzo(b,d)pyran-8-yl)methanesulfonamide,
(1-difluoromethoxy-2-bromo-6-allyl-6H-dibenzo(b,d)pyran-8-yl)methanesulfonamide,
(1-difluoromethoxy-2-bromo-6-phenyl-6H-dibenzo(b,d)pyran-8-yl)methanesulfonamide,
(1-difluoromethoxy-2-bromo-6-(3-chlorophenyl)-6H-dibenzo(b,d)pyran-8-yl)methanesulfonamide,
(1-difluoromethoxy-2-bromo-6-(3-fluorophenyl)-6H-dibenzo(b,d)pyran-8-yl)methanesulfonamide,
(1-difluoromethoxy-2-bromo-6-(3-methoxyphenyl)-6H-dibenzo(b,d)pyran-8-yl)methanesulfonamide,
(1-difluoromethoxy-2-bromo-6-(3,4-dimethoxy)phenyl-6H-dibenzo(b,d)pyran-8-yl)methanesulfonamide,
(1-difluoromethoxy-2-bromo-6-(5-bromothien-2-yl)-6H-dibenzo(b,d)pyran-8-yl)methanesulfonamide,
(1-difluoromethoxy-2-fluoro-6-allyl-6H-dibenzo(b,d)pyran-8-yl)methanesulfonamide,
(1-difluoromethoxy-2-fluoro-6-phenyl-6H-dibenzo(b,d)pyran-8-yl)methanesulfonamide,
(1-difluoromethoxy-2-fluoro-6-(3-fluorophenyl)-6H-dibenzo(b,d)pyran-8-yl)methanesulfonamide,
(1-difluoromethoxy-2-fluoro-6-(3-methoxyphenyl)-6H-dibenzo(b,d)pyran-8-yl)methanesulfonamide,
(1-difluoromethoxy-2-fluoro-6-(3,4-dimethoxy)phenyl-6H-dibenzo(b,d)pyran-8-yl)methanesulfonamide,
(1-difluoromethoxy-2-fluoro-6-(5-bromothien-2-yl)-6H-dibenzo(b,d)pyran-8-yl)methanesulfonamide,
(1-difluoromethoxy-2-methyl-6-allyl-6H-dibenzo(b,d)pyran-8-yl)methanesulfonamide,
(1-difluoromethoxy-2-methyl-6-phenyl-6H-dibenzo(b,d)pyran-8-yl)methanesulfonamide,
(1-difluoromethoxy-2-methyl-6-(3chlorophenyl)-6H-dibenzo(b,d)pyran-8-yl)methanesulfonamide,
(1-difluoromethoxy-2-methyl-6-(3-fluorophenyl)-6H-dibenzo(b,d)pyran-8-yl)methanesulfonamide,
(1-difluoromethoxy-2-methyl-6-(3-methoxyphenyl)-6H-dibenzo(b,d)pyran-8-yl)methanesulfonamide,
(1-difluoromethoxy-2-methyl-6-(3,4-dimethoxy)phenyl-6H-dibenzo(b,d)pyran-8-yl)methanesulfonamide,
(1-difluoromethoxy-2-methyl-6-(5-bromothien-2-yl)-6H-dibenzo(b,d)pyran-8-yl)methanesulfonamide,
(1-difluoromethoxy-2-allyloxy-6-allyl-6H-dibenzo(b,d)pyran-8-yl)methanesulfonamide,
(1-difluoromethoxy-2-allyloxy-6-phenyl-6H-dibenzo(b,d)pyran-8-yl)methanesulfonamide,
(1-difluoromethoxy-2-allyloxy-6-(3chlorophenyl)-6H-dibenzo(b,d)pyran-8-yl)methanesulfonamide,
(1-difluoromethoxy-2-allyloxy-6-(3-fluorophenyl)-6H-dibenzo(b,d)pyran-8-yl)methanesulfonamide,
(1-difluoromethoxy-2-allyloxy-6-(3-methoxyphenyl)-6H-dibenzo(bud)pyran-8-yl)methanesulfonamide,
(1-difluoromethoxy-2-allyloxy-6-(3,4-dimethoxy)phenyl-6H-dibenzo(b,d)pyran-8-yl)methanesulfonamide,
(1-difluoromethoxy-2-allyloxy-6-(5-bromothien-2-yl)-6H-dibenzo(b,d)pyran-8-yl)methanesulfonamide,
(1-difluoromethoxy-2-(2-allyloxy)ethoxy-6-allyl-6H-dibenzo(b,d)pyran-8-yl)methanesulfonamide,
(1-difluoromethoxy-2-(2-allyloxy)ethoxy-6-phenyl-6H-dibenzo(b,d)pyran-8-yl)methanesulfonamide,
(1-difluoromethoxy-2-(2-allyloxy)ethoxy-6-(3-chlorophenyl)-6H-dibenzo(b,d)pyran-8-yl)methanesulfonamide,
(1-difluoromethoxy-2-(2-allyloxy)ethoxy-6-(3-fluorophenyl)-6H-dibenzo(b,d)pyran-8-yl)methanesulfonamide,
(1-difluoromethoxy-2-(2-allyloxy)ethoxy-6-(3-methoxyphenyl)-6H-dibenzo(b,d)pyran-8-yl)methanesulfonamide,
(1-difluoromethoxy-2-(2-allyloxy)ethoxy-6-(3,4-dimethoxy)phenyl-6H-dibenzo(b,d)pyran-8-yl)methanesulfonamide,
(1-difluoromethoxy-2-(2-allyloxy)ethoxy-6-(5-bromothien-2-yl)-6H-dibenzo)(b,d)pyran-8-yl)methanesulfonamide,
(1-difluoromethoxy-2-(2-(2-methoxyethoxy)ethoxy)-6-allyl-6H-dibenzo(b,d)pyran-8-yl)methanesulfonamide, (1-difluoromethoxy-2-(2-(2-methoxyethoxy)ethoxy)-6-phenyl-6H-dibenzo(b,d)pyran-8-yl)methanesulfonamide,
(1-difluoromethoxy-2-(2-(2-methoxyethoxy)ethoxy)-6-(3-chlorophenyl)-6H-dibenzo(b,d)pyran-8-yl)methanesulfonamide,
(1-difluoromethoxy-2-(2-(2-methoxyethoxy)ethoxy)-6-(3-fluorophenyl)-6H-dibenzo(b,d)pyran-8-yl)methanesulfonamide,
(1-difluoromethoxy-2-(2-(2-methoxyethoxy)ethoxy)-6-(3-methoxyphenyl)-6H-dibenzo(b,d)pyran-8-yl)methanesulfonamide,
(1-difluoromethoxy-2-(2-(2-methoxyethoxy)ethoxy)-6-(3,4-dimethoxy)phenyl-6H-dibenzo(b,d)pyran-8-yl)methanesulfonamide,
(1-difluoromethoxy-2-(2-(2-methoxyethoxy)ethoxy)-6-(5-bromothien-2-yl)-6H-dibenzo(b,d)pyran-8-yl)methanesulfonamide,
(1-methoxy-3-bromo-6-allyl-6H-dibenzo(b,d)pyran-8-yl)methanesulfonamide,
(1-methoxy-3-bromo-6-phenyl-6H-dibenzo(b,d)pyran-8-yl)methanesulfonamide,
(1-methoxy-3-bromo-6-(3-chlorophenyl)-6H-dibenzo(b,d)pyran-8-yl)methanesulfonamide,
(1-methoxy-3-bromo-6-(3-fluorophenyl)-6H-dibenzo(b,d)pyran-8-yl)methanesulfonamide,
(1-methoxy-3-bromo-6-(3-methoxyphenyl)-6H-dibenzo(b,d)pyran-8-yl)methanesulfonamide,
(1-methoxy-3-bromo-6-(3,4-dimethoxy)phenyl-6H-dibenzo(b,d)pyran-8-yl)methanesulfonamide,
(1-methoxy-3-bromo-6-(5-bromothien-2-yl)-6H-dibenzo(b,d)pyran-8-yl)methanesulfonamide,
(1-methoxy-3-chloro-6-allyl-6H-dibenzo(b,d)pyran-8-yl)methanesulfonamide,
(1-methoxy-3-chloro-6-phenyl-6H-dibenzo(b,d)pyran-8-yl)methanesulfonamide,
(1-methoxy-3-chloro-6-(3-chlorophenyl)-6H-dibenzo(b,d)pyran-8-yl)methanesulfonamide,
(1-methoxy-3-chloro-6-(3-fluorophenyl)-6H-dibenzo(b,d)pyran-8-yl)methanesulfonamide,
(1-methoxy-3-chloro-6-(3-methoxyphenyl)-6H-dibenzo(b,d)pyran-8-yl)methanesulfonamide,
(1-methoxy-3-chloro-6-(3,4-dimethoxy)phenyl-6H-dibenzo(b,d)pyran-8-yl)methanesulfonamide,
(1-methoxy-3-chloro-6-(5-bromothien-2-yl)-6H-dibenzo(b,d)pyran-8-yl)methanesulfonamide,
(1-methoxy-3-fluoro-6-allyl-6H-dibenzo(b,d)pyran-8-yl)methanesulfonamide,
(1-methoxy-3-fluoro-6-phenyl-6H-dibenzo(b,d)pyran-8-yl)methanesulfonamide,
(1-methoxy-3-fluoro-6-(3-chlorophenyl)-6H-dibenzo(b,d)pyran-8-yl)methanesulfonamide,
(1-methoxy-3-fluoro-6-(3-fluorophenyl)-6H-dibenzo(b,d)pyran-8-yl)methanesulfonamide,
(1-methoxy-3-fluoro-6-(3-methoxyphenyl)-6H-dibenzo(b,d)pyran-8-yl)methanesulfonamide,
(1-methoxy-3-fluoro-6-(3,4-dimethoxy)phenyl-6H-dibenzo(b,d)pyran-8-yl)methanesulfonamide,
(1-methoxy-3-fluoro-6-(5-bromothien-2-yl)-6H-dibenzo(b,d)pyran-8-yl)methanesulfonamide,
(1-methoxy-3-methyl-6-allyl-6H-dibenzo(b,d)pyran-8-yl)methanesulfonamide,
(1-methoxy-3-methyl-6-phenyl-6H-dibenzo(b,d)pyran-8-yl)methanesulfonamide,
(1-methoxy-3-methyl-6-(3-chlorophenyl)-6H-dibenzo(b,d)pyran-8-yl)methanesulfonamide,
(1-methoxy-3-methyl-6-(3-fluorophenyl)-6H-dibenzo(b,d)pyran-8-yl)methanesulfonamide,
(1-methoxy-3-methyl-6-(3-methoxyphenyl)-6H-dibenzo(b,d)pyran-8-yl)methanesulfonamide,
(1-methoxy-3-methyl-6-(3,4-dimethoxy)phenyl-6H-dibenzo(b,d)pyran-8-yl)methanesulfonamide,
(1-methoxy-3-methyl-6-(5-bromothien-2-yl)-6H-dibenzo(b,d)pyran-8-yl)methanesulfonamide,
(1-difluoromethoxy-3-bromo-6-allyl-6H-dibenzo(b,d)pyran-8-yl)methanesulfonamide,
(1-difluoromethoxy-3-bromo-6-phenyl-6H-dibenzo(b,d)pyran-8-yl)methanesulfonamide,
(1-difluoromethoxy-3-bromo-6-(3-chlorophenyl)-6H-dibenzo(b,d)pyran-8-yl)methanesulfonamide,
(1-difluoromethoxy-3-bromo-6-(3-fluorophenyl)-6H-dibenzo(b,d)pyran-8-yl)methanesulfonamide,
(1-difluoromethoxy-3-bromo-6-(3-methoxyphenyl)-6H-dibenzo(b,d)pyran-8-yl)methanesulfonamide,
(1-difluoromethoxy-3-bromo-6-(3,4-dimethoxy)phenyl-6H-dibenzo(b,d)pyran-8-yl)methanesulfonamide,
(1-difluoromethoxy-3-bromo-6-(5-bromothien-2-yl)-6H-dibenzo(b,d)pyran-8-yl)methanesulfonamide,
(1-difluoromethoxy-3-chloro-6-allyl-6H-dibenzo(b,d)pyran-8-yl)methanesulfonamide,
(1-difluoromethoxy-3-chloro-6-phenyl-6H-dibenzo(b,d)pyran-8-yl)methanesulfonamide,
(1-difluoromethoxy-3-chloro-6-(3-chlorophenyl)-6H-dibenzo(b,d)pyran-8-yl)methanesulfonamide,
(1-difluoromethoxy-3-chloro-6-(3-fluorophenyl)-6H-dibenzo(b,d)pyran-8-yl)methanesulfonamide,
(1-difluoromethoxy-3-chloro-6-(3-methoxyphenyl)-6H-dibenzo(b,d)pyran-8-yl)methanesulfonamide,
(1-difluoromethoxy-3-chloro-6-(3,4-dimethoxy)phenyl-6H-dibenzo(b,d)pyran-8-yl)methanesulfonamide,
(1-difluoromethoxy-3-chloro-6-(5-bromothien-2-yl)-6H-dibenzo(b,d)pyran-8-yl)methanesulfonamide,
(1-difluoromethoxy-3-fluoro-6-allyl-6H-dibenzo(b,d)pyran-8-yl)methanesulfonamide,
(1-difluoromethoxy-3-fluoro-6-phenyl-6H-dibenzo(b,d)pyran-8-yl)methanesulfonamide,
(1-difluoromethoxy-3-fluoro-6-(3-chlorophenyl)-6H-dibenzo(b,d)pyran-8-yl)methanesulfonamide,
(1-difluoromethoxy-3-fluoro-6-(3-fluorophenyl)-6H-dibenzo(b,d)pyran-8-yl)methanesulfonamide,
(1-difluoromethoxy-3-fluoro-6-(3-methoxyphenyl)-6H-dibenzo(b,d)pyran-8-yl)methanesulfonamide,
(1-difluoromethoxy-3-fluoro-6-(3,4-dimethoxy)phenyl-6H-dibenzo(b,d)pyran-8-yl)methanesulfonamide,
(1-difluoromethoxy-3-fluoro-6-(5-bromothien-2-yl)-6H-dibenzo(b,d)pyran-8-yl)methanesulfonamide,
(1-difluoromethoxy-3-methyl-6-allyl-6H-dibenzo(b,d)pyran-8-yl)methanesulfonamide,
(1-difluoromethoxy-3-methyl-6-phenyl-6H-dibenzo(b,d)pyran-8-yl)methanesulfonamide,
(1-difluoromethoxy-3-methyl-6-(3-chlorophenyl)-6H-dibenzo(bud)pyran-8-yl)methanesulfonamide,
(1-difluoromethoxy-3-methyl-6-(3-fluorophenyl)-6H-dibenzo(b,d)pyran-8-yl)methanesulfonamide, (1-difluoromethoxy-3-methyl-6-(3-methoxyphenyl)-6H-dibenzo(b,d)pyran-8-yl)methanesulfonamide,
(1-difluoromethoxy-3-methyl-6-(3,4-dimethoxy)phenyl-6H-dibenzo(b,d)pyran-8-yl)methanesulfonamide,
(1-difluoromethoxy-3-methyl-6-(5-bromothien-2-yl)-6H-dibenzo(b,d)pyran-8-yl)methanesulfonamide,
(1-methoxy-3-bromo-6-allyl-6H-dibenzo(b,d)pyran-8-yl)methanesulfonamide,
(1-methoxy-3-bromo-6-phenyl-6H-dibenzo(b,d)pyran-8-yl)methanesulfonamide,
(1-methoxy-3-bromo-6-(3-chlorophenyl)-6H-dibenzo(b,d)pyran-8-yl)methanesulfonamide,
(1-methoxy-3-bromo-6-(3-fluorophenyl)-6H-dibenzo(b,d)pyran-8-yl)methanesulfonamide,
(1-methoxy-3-bromo-6-(3-methoxyphenyl)-6H-dibenzo(b,d)pyran-8-yl)methanesulfonamide,
(1-methoxy-3-bromo-6-(3,4-dimethoxy)phenyl-6H-dibenzo(b,d)pyran-8-yl)methanesulfonamide,
(1-methoxy-3-bromo-6-(5-bromothien-2yl)-6H-dibenzo(b,d)pyran-8-yl)methanesulfonamide,
(1-methoxy-3-chloro-6-allyl-6H-dibenzo(b,d)pyran-8-yl)methanesulfonamide,
(1-methoxy-3-chloro-6-phenyl-6H-dibenzo(b,d)pyran-8-yl)methanesulfonamide,
(1-methoxy-3-chloro-6-(3-chlorophenyl)-6H-dibenzo(b,d)pyran-8-yl)methanesulfonamide,
(1-methoxy-3-chloro-6-(3-fluorophenyl)-6H-dibenzo(b,d)pyran-8-yl)methanesulfonamide,
(1-methoxy-3-chloro-6-(3-methoxyphenyl)-6H-dibenzo(b,d)pyran-8-yl)methanesulfonamide,
(1-methoxy-3-chloro-6-(3,4-dimethoxy)phenyl-6H-dibenzo(b,d)pyran-8-yl)methanesulfonamide,
(1-methoxy-3-chloro-6-(5-bromothien-2-yl)-6H-dibenzo(b,d)pyran-8-yl)methanesulfonamide,
(1-methoxy-3-fluoro-6-allyl-6H-dibenzo(b,d)pyran-8-yl)methanesulfonamide,
(1-methoxy-3-fluoro-6-phenyl-6H-dibenzo(b,d)pyran-8-yl)methanesulfonamide,
(1-methoxy-3-fluoro-6-(3-chlorophenyl)-6H-dibenzo(b,d)pyran-8-yl)methanesulfonamide,
(1-methoxy-3-fluoro-6-(3-fluorophenyl)-6H-dibenzo(b,d)pyran-8-yl)methanesulfonamide,
(1-methoxy-3-fluoro-6-(3-methoxyphenyl)-6H-dibenzo(b,d)pyran-8-yl)methanesulfonamide,
(1-methoxy-3-fluoro-6-(3,4-dimethoxy)phenyl-6H-dibenzo(b,d)pyran-8-yl)methanesulfonamide,
(1-methoxy-3-fluoro-6-(5-bromothien-2-yl)-6H-dibenzo(b,d)pyran-8-yl)methanesulfonamide,
(1-methoxy-3-methyl-6-allyl-6H-dibenzo(b,d)pyran-8-yl)methanesulfonamide,
(1-methoxy-3-methyl-6-phenyl-6H-dibenzo(b,d)pyran-8-yl)methanesulfonamide,
(1-methoxy-3-methyl-6-(3-chlorophenyl)-6H-dibenzo(b,d)pyran-8-yl)methanesulfonamide,
(1-methoxy-3-methyl-6-(3-fluorophenyl)-6H-dibenzo(b,d)pyran-8-yl)methanesulfonamide,
(1-methoxy-3-methyl-6-(3-methoxyphenyl)-6H-dibenzo(b,d)pyran-8-yl)methanesulfonamide,
(1-methoxy-3-methyl-6-(3,4-dimethoxy)phenyl-6H-dibenzo(b,d)pyran-8-yl)methanesulfonamide,
(1-methoxy-3-methyl-6-(5-bromothien-2-yl)-6H-dibenzo(b,d)pyran-8-yl)methanesulfonamide,
(1-difluoromethoxy-3-bromo-6-allyl-6H-dibenzo(b,d)pyran-8-yl)methanesulfonamide,
(1-difluoromethoxy-3-bromo-6-phenyl-6H-dibenzo(b,d)pyran-8-yl)methanesulfonamide,
(1-difluoromethoxy-3-bromo-6-(3-chlorophenyl)-6H-dibenzo(b,d)pyran-8-yl)methanesulfonamide,
(1-difluoromethoxy-3-bromo-6-(3-fluorophenyl)-6H-dibenzo(b,d)pyran-8-yl)methanesulfonamide,
(1-difluoromethoxy-3-bromo-6-(3-methoxyphenyl)-6H-dibenzo(b,d)pyran-8-yl)methanesulfonamide,
(1-difluoromethoxy-3-bromo-6-(3,4-dimethoxy)phenyl-6H-dibenzo(b,d)pyran-8-yl)methanesulfonamide,
(1-difluoromethoxy-3-bromo-6-(5-bromothien-2-yl)-6H-dibenzo(b,d)pyran-8-yl)methanesulfonamide,
(1-difluoromethoxy-3-chloro-6-allyl-6H-dibenzo(b,d)pyran-8-yl)methanesulfonamide,
(1-difluoromethoxy-3-chloro-6-phenyl-6H-dibenzo(b,d)pyran-8-yl)methanesulfonamide,
(1-difluoromethoxy-3-chloro-6-(3-chlorophenyl)-6H-dibenzo(b,d)pyran-8-yl)methanesulfonamide,
(1-difluoromethoxy-3-chloro-6-(3-fluorophenyl)-6H-dibenzo(b,d)pyran-8-yl)methanesulfonamide,
(1-difluoromethoxy-3-chloro-6-(3-methoxyphenyl)-6H-dibenzo(b,d)pyran-8-yl)methanesulfonamide,
(1-difluoromethoxy-3-chloro-6-(3,4-dimethoxy)phenyl-6H-dibenzo(b,d)pyran-8-yl)methanesulfonamide,
(1-difluoromethoxy-3-chloro-6-(5-bromothien-2-yl)-6H-dibenzo(b,d)pyran-8-yl)methanesulfonamide,
(1-difluoromethoxy-3-fluoro-6-allyl-6H-dibenzo(b,d)pyran-8-yl)methanesulfonamide,
(1-difluoromethoxy-3-fluoro-6-phenyl-6H-dibenzo(b,d)pyran-8-yl)methanesulfonamide,
(1-difluoromethoxy-3-fluoro-6-(3-chlorophenyl)-6H-dibenzo(b,d)pyran-8-yl)methanesulfonamide,
(1-difluoromethoxy-3-fluoro-6-(3-fluorophenyl)-6H-dibenzo(b,d)pyran-8-yl)methanesulfonamide,
(1-difluoromethoxy-3-fluoro-6-(3-methoxyphenyl)-6H-dibenzo(b,d)pyran-8-yl)methanesulfonamide,
(1-difluoromethoxy-3-fluoro-6-(3,4-dimethoxy)phenyl-6H-dibenzo(b,d)pyran-8-yl)methanesulfonamide,
(1-difluoromethoxy-3-fluoro-6-(5-bromothien-2-yl)-6H-dibenzo(b,d)pyran-8-yl)methanesulfonamide,
(1-difluoromethoxy-3-methyl-6-allyl-6H-dibenzo(b,d)pyran-8-yl)methanesulfonamide,
(1-difluoromethoxy-3-methyl-6-phenyl-6H-dibenzo(b,d)pyran-8-yl)methanesulfonamide,
(1-difluoromethoxy-3-methyl-6-(3-chlorophenyl)-6H-dibenzo(b,d)pyran-8-yl)methanesulfonamide,
(1-difluoromethoxy-3-methyl-6-(3-fluorophenyl)-6H-dibenzo(b,d)pyran-8-yl)methanesulfonamide,
(1-difluoromethoxy-3-methyl-6-(3-methoxyphenyl)-6H-dibenzo(b,d)pyran-8-yl)methanesulfonamide,
(1-difluoromethoxy-3-methyl-6-(3,4-dimethoxy)phenyl-6H-dibenzo(b,d)pyran-8-yl)methanesulfonamide,
(1-difluoromethoxy-3-methyl-6-(5-bromothien-2-yl)-6H-dibenzo(b,d)pyran-8-yl)methanesulfonamide,
(1-methoxy-6-cyclohexyl-6H-dibenzo(b,d)pyran-8-yl)methanesulfonamide,
(1-methoxy-6-propyl-6H-dibenzo(b,d)pyran-8-yl)methanesulfonamide,
(1-methoxy-6-(4-chlorobutyl)-6H-dibenzo(b,d)pyran-8-yl)methanesulfonamide, (1-methoxy-6-(6-cyanohexyl)-6H-dibenzo(b,d)pyran-8-yl)methanesulfonamide, (1-methoxy-6-(4-methoxy-2-buten-1-yl)-6H-dibenzo(b,d)pyran-8-yl)methanesulfonamide, (1-methoxy-6-(4-hydroxy-2-buten-1-yl)-6H-dibenzo(b,d)pyran-8-yl)methanesulfonamide, (1-methoxy-6-(4-(but-3-en-1-yloxy)-2-buten-1-yl)-6H-dibenzo(b,d)pyran-8-yl)methanesulfonamide, (1-methoxy-6-(4-(3-methoxypropoxy)-2-buten-1-yl)-6H-dibenzo(b,d)pyran-8-yl)methanesulfonamide, (1-methoxy-6-(4-allyloxybenzyl)-6H-dibenzo(b,d)pyran-8-yl)methanesulfonamide, (1-methoxy-6-(2-carboxyethyl)-6H-dibenzo(b,d)pyran-8-yl)methanesulfonamide, (1-methoxy-6-(3-carboxypropyl)-6H-dibenzo(b,d)pyran-8-yl)methanesulfonamide, (1-methoxy-6-(4-carboxybutyl)-6H-dibenzo(b,d)pyran-8-yl)methanesulfonamide, (1-methoxy-6-(5-carboxypentyl)-6H-dibenzo(b,d)pyran-8-yl)methanesulfonamide, (1-methoxy-6-(2-carbomethoxyethyl)-6H-dibenzo(b,d)pyran-8-yl)methanesulfonamide, (1-methoxy-6-(3-carbomethoxypropyl)-6H-dibenzo(b,d)pyran-8-yl)methanesulfonamide, (1-methoxy-6-(4-carbomethoxybutyl)-6H-dibenzo(b,d)pyran-8-yl)methanesulfonamide, (1-methoxy-6-(5-carbomethoxypentyl)-6H-dibenzo(b,d)pyran-8-yl)methanesulfonamide, (1-methoxy-6-(2-carboethoxyethyl)-6H-dibenzo(b,d)pyran-8-yl)methanesulfonamide, (1-methoxy-6-(3-carboethoxypropyl)-6H-dibenzo(b,d)pyran-8-yl)methanesulfonamide, (1-methoxy-6-(4-carboethoxybutyl)-6H-dibenzo(b,d)pyran-8-yl)methanesulfonamide, (1-methoxy-6-(5-carboethoxypentyl)-6H-dibenzo(b,d)pyran-8-yl)methanesulfonamide, (1-methoxy-6-(2,2-dimethyl-2-carboxyethyl)-6H-dibenzo(b,d)pyran-8-yl)methanesulfonamide, (1-methoxy-6-(3,3-dimethyl-3-carboxypropyl)-6H-dibenzo(b,d)pyran-8-yl)methanesulfonamide, (1-methoxy-6-(4,4-dimethyl-4-carboxybutyl)-6H-dibenzo(b,d)pyran-8-yl)methanesulfonamide, (1-methoxy-6-(5,5-dimethyl-5-carboxypentyl)-6H-dibenzo(b,d)pyran-8-yl)methanesulfonamide, (1-methoxy-6-(2,2-dimethyl-2-carbomethoxyethyl)-6H-dibenzo(b,d)pyran-8-yl)methanesulfonamide, (1-methoxy-6-(3,3-dimethyl-3-carbomethoxypropyl)-6H-dibenzo(b,d)pyran-8-yl)methanesulfonamide, (1-methoxy-6-(4,4-dimethyl-4-carbomethoxybutyl)-6H-dibenzo(b,d)pyran-8-yl)methanesulfonamide, (1-methoxy-6-(5,5-dimethyl-5-carbomethoxypentyl)-6H-dibenzo(b,d)pyran-8-yl)methanesulfonamide, (1-methoxy-6-(2,2-dimethyl-2-carboethoxyethyl)-6H-dibenzo(b,d)pyran-8-yl)methanesulfonamide, (1-methoxy-6-(3,3-dimethyl-3-carboethoxypropyl)-6H-dibenzo(b,d)pyran-8-yl)methanesulfonamide, (1-methoxy-6-(4,4-dimethyl-4-carboethoxybutyl)-6H-dibenzo(b,d)pyran-8-yl)methanesulfonamide, (1-methoxy-6-(5,5-dimethyl-5-carboethoxypentyl)-6H-dibenzo(b,d)pyran-8-yl)methanesulfonamide, (1-methoxy-6-(5-carboethoxypentyl)-6H-dibenzo(b,d)pyran-8-yl)methanesulfonamide, (1-methoxy-6-(6-hydroxyhexyl)-6H-dibenzo(b,d)pyran-8-yl)methanesulfonamide, (1-methoxy-6-(6-oxohexyl)-6H-dibenzo(b,d)pyran-8-yl)methanesulfonamide, (1-methoxy-6-(8-methoxyhexyl)-6H-dibenzo(b,d)pyran-8-yl)methanesulfonamide, (1-methoxy-6-(8-methoxyoctyl)-6H-dibenzo(b,d)pyran-8-yl)methanesulfonamide, (1-methoxy-6-(5-(N-(2-methoxyethyl)aminocarbonyl)pentyl)-6H-dibenzo(b,d)pyran-8-yl)methanesulfonamide, (1-methoxy-6-(5-(N-methyl-N-(2-methoxyethyl)aminocarbonyl)pentyl)-6H-dibenzo(b,d)pyran-8-yl)methanesulfonamide, (1-methoxy-6-(3-(2-carboxyethyl)phenyl)-6H-dibenzo(b,d)pyran-8-yl)methanesulfonamide, (1-methoxy-6-(3-(3-carboxypropyl)phenyl)-6H-dibenzo(b,d)pyran-8-yl)methanesulfonamide, (1-methoxy-6-(3-(4-carboxybutyl)phenyl)-6H-dibenzo(b,d)pyran-8-yl)methanesulfonamide, (1-methoxy-6-(3-(5-carboxypentyl)phenyl)-6H-dibenzo(b,d)pyran-8-yl)methanesulfonamide, (1-methoxy-6-(3-(2-carbomethoxyethyl)phenyl)-6H-dibenzo(b,d)pyran-8-yl)methanesulfonamide, (1-methoxy-6-(3-(3-carbomethoxypropyl)phenyl)-6H-dibenzo(b,d)pyran-8-yl)methanesulfonamide, (1-methoxy-6-(3-(4-carbomethoxybutyl)phenyl)-6H-dibenzo(b,d)pyran-8-yl)methanesulfonamide, (1-methoxy-6-(3-(5-carbomethoxypentyl)phenyl)-6H-dibenzo(b,d)pyran-8-yl)methanesulfonamide, (1-methoxy-6-(3-(2-carboethoxyethyl)phenyl)-6H-dibenzo(b,d)pyran-8-yl)methanesulfonamide, (1-methoxy-6-(3-(3-carboethoxypropyl)phenyl)-6H-dibenzo(b,d)pyran-8-yl)methanesulfonamide, (1-methoxy-6-(3-(4-carboethoxybutyl)phenyl)-6H-dibenzo(b,d)pyran-8-yl)methanesulfonamide, (1-methoxy-6-(3-(5-carboethoxypentyl)phenyl)-6H-dibenzo(b,d)pyran-8-yl)methanesulfonamide, (1-methoxy-6-(3-(2,2-dimethyl-2-carboxyethyl)phenyl)-6H-dibenzo(b,d)pyran-8-yl)methanesulfonamide, (1-methoxy-6-(3-(3,3-dimethyl-3-carboxypropyl)phenyl)-6H-dibenzo(b,d)pyran-8-yl)methanesulfonamide, (1-methoxy-6-(3-(4,4-dimethyl-4-carboxybutyl)phenyl)-6H-dibenzo(b,d)pyran-8-yl)methanesulfonamide, (1-methoxy-6-(3-(5,5-dimethyl-5-carboxypentyl)phenyl)-6H-dibenzo(b,d)pyran-8-yl)methanesulfonamide, (1-methoxy-6-(3-(2,2-dimethyl-2-carbomethoxyethyl)phenyl)-6H-dibenzo(b,d)pyran-8-yl)methanesulfonamide, (1-methoxy-6-(3-(3,3-dimethyl-3-carbomethoxypropylphenyl)-6H-dibenzo(b,d)pyran-8-yl)methanesulfonamide, (1-methoxy-6-(3-(4,4-dimethyl-4-carbomethoxybutyl)phenyl)-6H-dibenzo(b,d)pyran-8-yl)methanesulfonamide, (1-methoxy-6-(3-(5,5-dimethyl-5-carbomethoxypentyl)phenyl)-6H-dibenzo(b,d)pyran-8-yl)methanesulfonamide, (1-methoxy-6-(3-(2,2-dimethyl-2-carboethoxyethyl)phenyl)-6H-dibenzo(b,d)pyran-8-yl)methanesulfonamide, (1-methoxy-6-(3-(3,3-dimethyl-3-carboethoxypropyl)phenyl)-6H-dibenzo(b,d)pyran-8-yl)methanesulfonamide, (1-methoxy-6-(3-(4,4-dimethyl-4-carboethoxybutyl)phenyl)-6H-dibenzo(b,d)pyran-8-yl)methanesulfonamide, (1-methoxy-6-(3-(5,5-dimethyl-5-carboethoxypentyl)phenyl)-6H-dibenzo(b,d)pyran-8-yl)methanesulfonamide, (1-methoxy-6-(4-(2-carboxyethyl)phenyl)-6H-dibenzo(b,d)pyran-8-yl)methanesulfonamide, (1-methoxy-6-(4-(3-carboxypropyl)phenyl)-6H-dibenzo(b,d)pyran-8-yl)methanesulfonamide, (1-methoxy-6-(4-(4-carboxybutyl)phenyl)-6H-dibenzo(b,d)pyran-8-yl)methanesulfonamide, (1-methoxy-6-(4-(5-carboxypentyl)phenyl)-6H-dibenzo(b,d)pyran-8-yl)methanesulfonamide, (1-methoxy-6-(4-(2-carbomethoxyethyl)phenyl)-6H-dibenzo(b,d)pyran-8-yl)methanesulfonamide, (1-methoxy-6-(4-(3-carbomethoxypropyl)phenyl)-6H-dibenzo(b,d)pyran-8-yl)methanesulfonamide, (1-methoxy-6-(4-(4-carbomethoxybutyl)phenyl)-6H-dibenzo(b,d)pyran-8-yl)methanesulfonamide, (1-methoxy-6-(4-(5-carbomethoxypentyl)phenyl)-6H-dibenzo(b,d)pyran-8-yl)methanesulfonamide, (1-methoxy-6-(4-(2-carboethoxyethyl)phenyl)-6H-dibenzo(b,d)pyran-8-yl)methanesulfonamide, (1-methoxy-6-(4-(3-carboethoxypropyl)phenyl)-6H-dibenzo(b,d)pyran-8-yl)methanesulfonamide, (1-methoxy-6-(4-(4-carboethoxybutyl)phenyl)-6H-dibenzo(b,d)pyran-8-yl)methanesulfonamide, (1-methoxy-6-(4-(5-carboethoxypentyl)phenyl)-6H-dibenzo(b,d)pyran-8-yl)methanesulfonamide, (1-methoxy-6-(4-(2,2-dimethyl-2-carboxyethyl)phenyl)-6H-dibenzo(b,d)pyran-8-yl)methanesulfonamide, (1-methoxy-6-(4-(3,3-dimethyl-3-carboxypropyl)phenyl)-6H-dibenzo(b,d)pyran-8-yl)methanesulfonamide, (1-methoxy-6-(4-(4,4-dimethyl-4-carboxybutyl)phenyl)-6H-dibenzo(bud)pyran-8-yl)methanesulfonamide, (1-methoxy-6-(4-(5,5-dimethyl-5-carboxypentyl)phenyl)-6H-dibenzo(b,d)pyran-8-yl)methanesulfonamide, (1-methoxy-6-(4-(2,2-dimethyl-2-carbomethoxyethyl)phenyl)-6H-dibenzo(b,d)pyran-8-yl)methanesulfonamide, (1-methoxy-6-(4-(3,3-dimethyl-3-carbomethoxypropylphenyl)-6H-dibenzo(b,d)pyran-8-yl)methanesulfonamide, (1-methoxy-6-(4-(4,4-dimethyl-4-carbomethoxybutyl)phenyl)-6H-dibenzo(b,d)pyran-8-yl)methanesulfonamide, (1-methoxy-6-(4-(5,5-dimethyl-5-carbomethoxypentyl)phenyl)-6H-dibenzo(b,d)pyran-8-yl)methanesulfonamide, (1-methoxy-6-(4-(2,2-dimethyl-2-carboethoxyethyl)phenyl)-6H-dibenzo(b,d)pyran-8-yl)methanesulfonamide, (1-methoxy-6-(4-(3,3-dimethyl-3-carboethoxypropyl)phenyl)-6H-dibenzo(b,d)pyran-8-yl)methanesulfonamide, (1-methoxy-6-(4-(4,4-dimethyl-4-carboethoxybutyl)phenyl)-6H-dibenzo(b,d)pyran-8-yl)methanesulfonamide, (1-methoxy-6-(4-(5,5-dimethyl-5-carboethoxypentyl)phenyl)-6H-dibenzo(b,d)pyran-8-yl)methanesulfonamide, (1-methoxy-6-(3-(N-methyl-N-(N,N-dimethylaminocarbonyl)methylamino)phenyl)-6H-dibenzo(b,d)pyran-8-yl)methanesulfonamide, (1-methoxy-6-(3-(N-methyl-N-(N,N-diethylaminocarbonyl)methylamino)phenyl)-6H-dibenzo(b,d)pyran-8-yl)methanesulfonamide, (1-methoxy-6-(3-(2-(N-methyl-N-(N,N-dimethylaminocarbonyl)ethyl)amino)phenyl)-6H-dibenzo(b,d)pyran-8-yl)methanesulfonamide, (1-methoxy-6-(3-(2-(N-methyl-N-(N,N-diethylaminocarbonyl)ethyl)amino)phenyl)-6H-dibenzo(b,d)pyran-8-yl)methanesulfonamide, (1-methoxy-6-(3-(3-(N-methyl-N-(N,N-dimethylaminocarbonyl)propyl)amino)phenyl)-6H-dibenzo(b,d)pyran-8-yl)methanesulfonamide, (1-methoxy-6-(3-(3-(N-methyl-N-(N,N-diethylaminocarbonyl)propyl)amino)phenyl)-6H-dibenzo(b,d)pyran-8-yl)methanesulfonamide, (1-methoxy-6-(3-(N-methyl-N-acetyl)aminophenyl)-6H-dibenzo(b,d)pyran-8-yl)methanesulfonamide, (1-methoxy-6-(3-(N-methyl-N-propionyl)aminophenyl)-6H-dibenzo(b,d)pyran-8-yl)methanesulfonamide, (1-methoxy-6-(3-(N-methyl-N-methanesulfonyl)aminophenyl)-6H-dibenzo(b,d)pyran-8-yl)methanesulfonamide, (1-methoxy-6-(3-(N-methyl-N-ethanesulfonyl)aminophenyl)-6H-dibenzo(b,d)pyran-8-yl)methanesulfonamide, (1-methoxy-6-(4-chlorophenyl)-6H-dibenzo(b,d)pyran-8-yl)methanesulfonamide, (1-methoxy-6-(4-fluorophenyl)-6H-dibenzo(b,d)pyran-8-yl)methanesulfonamide, (1-methoxy-6-(4-methoxyphenyl)-6H-dibenzo(b,d)pyran-8-yl)methanesulfonamide, (1-methoxy-6-(3-hydroxyphenyl)-6H-dibenzo(b,d)pyran-8-yl)methanesulfonamide, (1-methoxy-6-(3-trifluoromethylphenyl)-6H-dibenzo(b,d)pyran-8-yl)methanesulfonamide, (1-methoxy-6-(3-methylphenyl)-6H-dibenzo(b,d)pyran-8-yl)methanesulfonamide, (1-methoxy-6-(3-bromophenyl)-6H-dibenzo(b,d)pyran-8-yl)methanesulfonamide, (1-methoxy-6-(4-bromophenyl)-6H-dibenzo(b,d)pyran-8-yl)methanesulfonamide, (1-methoxy-6-(3-cyanophenyl)-6H-dibenzo(b,d)pyran-8-yl)methanesulfonamide, (1-methoxy-6-(4-cyanophenyl)-6H-dibenzo(b,d)pyran-8-yl)methanesulfonamide, (1-methoxy-6-(3-carbomethoxyphenyl)-6H-dibenzo(b,d)pyran-8-yl)methanesulfonamide, (1-methoxy-6-(4-carbomethoxyphenyl)-6H-dibenzo(b,d)pyran-8-yl)methanesulfonamide, (1-methoxy-6-(3-carboethoxyphenyl)-6H-dibenzo(b,d)pyran-8-yl)methanesulfonamide, (1-methoxy-6-(4-carboethoxyphenyl)-6H-dibenzo(b,d)pyran-8-yl)methanesulfonamide, (1-methoxy-6-(3-ethoxyphenyl)-6H-dibenzo(b,d)pyran-8-yl)methanesulfonamide, (1-methoxy-6-(4-ethoxyphenyl)-6H-dibenzo(b,d)pyran-8-yl)methanesulfonamide, (1-methoxy-6-(3-allyloxyphenyl)-6H-dibenzo(b,d)pyran-8-yl)methanesulfonamide,
(1-methoxy-6-(4-allyloxyphenyl)-6H-dibenzo(b,d)pyran-8-yl)methanesulfonamide,
(1-methoxy-6-(3-allylphenyl)-6H-dibenzo(b,d)pyran-8-yl)methanesulfonamide,
(1-methoxy-6-(4-allylphenyl)-6H-dibenzo(b,d)pyran-8-yl)methanesulfonamide,
(1-methoxy-6-(thien-2-yl)-6H-dibenzo(b,d)pyran-8-yl)methanesulfonamide,
(1-methoxy-6-(5-chlorothien-2-yl)-6H-dibenzo(b,d)pyran-8-yl)methanesulfonamide,
(1-methoxy-6-(5-(3-methoxypropen-1-yl)thien-2-yl)-6H-dibenzo(b,d)pyran-8-yl)methanesulfonamide,
(1-methoxy-6-(5-(3-methoxypropyl)thien-2-yl)-6H-dibenzo(b,d)pyran-8-yl)methanesulfonamide,
(1-methoxy-6-(furan-2-yl)-6H-dibenzo(b,d)pyran-8-yl)methanesulfonamide,
(1-methoxy-6-(pyridin-2-yl)-6H-dibenzo(b,d)pyran-8-yl)methanesulfonamide,
(1-methoxy-6-(pyridin-3-yl)-6H-dibenzo(b,d)pyran-8-yl)methanesulfonamide,
(1-methoxy-6-(pyridin-4-yl)-6H-dibenzo(b,d)pyran-8-yl)methanesulfonamide,
(1-methoxy-6-(5-bromopyridin-3-yl)-6H-dibenzo(b,d)pyran-8-yl)methanesulfonamide,
(1-methoxy-6-(5-(N-methyl-N-(2-methoxyethyl)amino)pyridin-3-yl)-6H-dibenzo(b,d)pyran-8-yl)methanesulfonamide,
(1-methoxy-6-(5-(3-methoxypropen-1-yl)pyridin-3-yl)-6H-dibenzo(b,d)pyran-8-yl)methanesulfonamide,
(1-methoxy-6-(4-(N-methylamino)phenyl)-6H-dibenzo(b,d)pyran-8-yl)methanesulfonamide,
(1-methoxy-6-(4-(N-allyl-N-methylamino)phenyl)-6H-dibenzo(b,d)pyran-8-yl)methanesulfonamide,
(1-methoxy-6-(4-(N-propyl-N-methylamino)phenyl)-6H-dibenzo(b,d)pyran-8-yl)methanesulfonamide,
(1-methoxy-6-(3-(N-methanesulfonylamino)phenyl)-6H-dibenzo(b,d)pyran-8-yl)methanesulfonamide,
(1-methoxy-6-(3-(N-methyl-N-propanesulfonylamino)phenyl)-6H-dibenzo(b,d)pyran-8-yl)methanesulfonamide,
(1-methoxy-6-(3-(4-methoxybutoxy)phenyl)-6H-dibenzo(b,d)pyran-8-yl)methanesulfonamide,
(1-methoxy-6-(3-(4-methoxybut-2-en-1-yloxy)phenyl)-6H-dibenzo(b,d)pyran-8-yl)methanesulfonamide,
(1-methoxy-6-(3-(4-hydroxybut-2-en-1-yloxy)phenyl)-6H-dibenzo(b,d)pyran-8-yl)methanesulfonamide,
(1-methoxy-6-(3-(3-carboethoxyprop-2-en-1-yloxy)phenyl)-6H-dibenzo(b,d)pyran-8-yl)methanesulfonamide,
(1-methoxy-6-(3-(2-(2-methoxyethoxy)ethoxy)phenyl)-6H-dibenzo(b,d)pyran-8-yl)methanesulfonamide,
(1-methoxy-6-(3-((N-methyl-N-(2-methoxyethyl)amino)carbonyl)phenyl)-6H-dibenzo(b,d)pyran-8-yl)methanesulfonamide,
(1-methoxy-6-(3-(methylthiomethoxy)phenyl)-6H-dibenzo(b,d)pyran-8-yl)methanesulfonamide,
(1-methoxy-6-(3-(2-hydroxyethyl)phenyl)-6H-dibenzo(b,d)pyran-8-yl)methanesulfonamide,
(1-methoxy-6-(3-(2-methoxyethyl)phenyl)-6H-dibenzo(b,d)pyran-8-yl)methanesulfonamide,
(1-methoxy-6-(3-(2-(but-3-en-1-yloxy)ethyl)phenyl)-6H-dibenzo(b,d)pyran-8-yl)methanesulfonamide,
(1-methoxy-6-(3-(2-(N,N-dimethylaminocarbonyloxy)ethyl)phenyl)-6H-dibenzo(b,d)pyran-8-yl)methanesulfonamide,
(1-methoxy-6-(3-(N,N-dimethylaminocarbonyloxy)phenyl)-6H-dibenzo(b,d)pyran-8-yl)methanesulfonamide,
(1-methoxy-6-(3-(3-bromoprop-2-en-1-yloxy)phenyl)-6H-dibenzo(b,d)pyran-8-yl)methanesulfonamide,
(1-methoxy-6-(3-fluoro-5-methoxyphenyl)-6H-dibenzo(b,d)pyran-8-yl)methanesulfonamide,
(1-methoxy-6-(3-fluoro-5-hydroxyphenyl)-6H-dibenzo(b,d)pyran-8-yl)methanesulfonamide,
(1-methoxy-6-(3-fluoro-5-allyloxyphenyl)-6H-dibenzo(b,d)pyran-8-yl)methanesulfonamide,
(1-methoxy-6-(3-fluoro-5-(2-methoxyethoxy)phenyl)-6H-dibenzo(b,d)pyran-8-yl)methanesulfonamide,
(1-methoxy-6-(3-fluoro-5-(2-(2-methoxyethoxy)ethoxy)phenyl)-6H-dibenzo(b,d)pyran-8-yl)methanesulfonamide,
(1-methoxy-6-(3-fluoro-5-(2-allyloxyethoxy)phenyl)-6H-dibenzo(b,d)pyran-8-yl)methanesulfonamide,
(1-difluoromethoxy-6-cyclohexyl-6H-dibenzo(b,d)pyran-8-yl)methanesulfonamide,
(1-difluoromethoxy-6-propyl-6H-dibenzo(b,d)pyran-8-yl)methanesulfonamide,
(1-difluoromethoxy-6-(4-chlorobutyl)-6H-dibenzo(b,d)pyran-8-yl)methanesulfonamide,
(1-difluoromethoxy-6-(6-cyanohexyl)-6H-dibenzo(b,d)pyran-8-yl)methanesulfonamide,
(1-difluoromethoxy-6-(4-methoxy-2-buten-1-yl)-6H-dibenzo(b,d)pyran-8-yl)methanesulfonamide,
(1-difluoromethoxy-6-(4-hydroxy-2-buten-1-yl)-6H-dibenzo(b,d)pyran-8-yl)methanesulfonamide,
(1-difluoromethoxy-6-(4-(but-3-en-1-yloxy)-2-buten-1-yl)-6H-dibenzo(b,d)pyran-8-yl)methanesulfonamide,
(1-difluoromethoxy-6-(4-(3-methoxypropoxy)-2-buten-1-yl)-6H-dibenzo(b,d)pyran-8-yl)methanesulfonamide,
(1-difluoromethoxy-6-(4-allyloxybenzyl)-6H-dibenzo(b,d)pyran-8-yl)methanesulfonamide,
(1-difluoromethoxy-6-(2-carboxyethyl)-6H-dibenzo(b,d)pyran-8-yl)methanesulfonamide,
(1-difluoromethoxy-6-(3-carboxypropyl)-6H-dibenzo(b,d)pyran-8-yl)methanesulfonamide,
(1-difluoromethoxy-6-(4-carboxybutyl)-6H-dibenzo(b,d)pyran-8-yl)methanesulfonamide,
(1-difluoromethoxy-6-(5-carboxypentyl)-6H-dibenzo(b,d)pyran-8-yl)methanesulfonamide,
(1-difluoromethoxy-6-(2-carbomethoxyethyl)-6H-dibenzo(b,d)pyran-8-yl)methanesulfonamide,
(1-difluoromethoxy-6-(3-carbomethoxypropyl)-6H-dibenzo(b,d)pyran-8-yl)methanesulfonamide,
(1-difluoromethoxy-6-(4-carbomethoxybutyl)-6H-dibenzo(b,d)pyran-8-yl)methanesulfonamide,
(1-difluoromethoxy-6-(5-carbomethoxypentyl)-6H-dibenzo(b,d)pyran-8-yl)methanesulfonamide,
(1-difluoromethoxy-6-(2-carboethoxyethyl)-6H-dibenzo(b,d)pyran-8-yl)methanesulfonamide,
(1-difluoromethoxy-6-(3-carboethoxypropyl)-6H-dibenzo(b,d)pyran-8-yl)methanesulfonamide, (1-difluoromethoxy-6-(4-carboethoxybutyl)-6H-dibenzo(b,d)pyran-8-yl)methanesulfonamide,
(1-difluoromethoxy-6-(5-carboethoxypentyl)-6H-dibenzo(b,d)pyran-8-yl)methanesulfonamide,
(1-difluoromethoxy-6-(2,2-dimethyl-2-carboxyethyl)-6H-dibenzo(b,d)pyran-8-yl)methanesulfonamide,
(1-difluoromethoxy-6-(3,3-dimethyl-3-carboxypropyl)-6H-dibenzo(b,d)pyran-8-yl)methanesulfonamide,
(1-difluoromethoxy-6-(4,4-dimethyl-4-carboxybutyl)-6H-dibenzo(b,d)pyran-8-yl)methanesulfonamide,
(1-difluoromethoxy-6-(5,5-dimethyl-5-carboxypentyl)-6H-dibenzo(b,d)pyran-8-yl)methanesulfonamide,
(1-difluoromethoxy-6-(2,2-dimethyl-2-carbomethoxyethyl)-6H-dibenzo(b,d)pyran-8-yl)methanesulfonamide,
(1-difluoromethoxy-6-(3,3-dimethyl-3-carbomethoxypropyl)-6H-dibenzo(b,d)pyran-8-yl)methanesulfonamide,
(1-difluoromethoxy-6-(4,4-dimethyl-4-carbomethoxybutyl)-6H-dibenzo(b,d)pyran-8-yl)methanesulfonamide,
(1-difluoromethoxy-6-(5,5-dimethyl-5-carbomethoxypentyl)-6H-dibenzo(b,d)pyran-8-yl)methanesulfonamide,
(1-difluoromethoxy-6-(2,2-dimethyl-2-carboethoxyethyl)-6H-dibenzo(b,d)pyran-8-yl)methanesulfonamide,
(1-difluoromethoxy-6-(3,3-dimethyl-3-carboethoxypropyl)-6H-dibenzo(b,d)pyran-8-yl)methanesulfonamide,
(1-difluoromethoxy-6-(4,4-dimethyl-4-carboethoxybutyl)-6H-dibenzo(b,d)pyran-8-yl)methanesulfonamide,
(1-difluoromethoxy-6-(5,5-dimethyl-5-carboethoxypentyl)-6H-dibenzo(b,d)pyran-8-yl)methanesulfonamide,
(1-difluoromethoxy-6-(5-carboethoxypentyl)-6H-dibenzo(b,d)pyran-8-yl)methanesulfonamide,
(1-difluoromethoxy-6-(6-hydroxyhexyl)-6H-dibenzo(b,d)pyran-8-yl)methanesulfonamide,
(1-difluoromethoxy-6-(6-oxohexyl)-6H-dibenzo(b,d)pyran-8-yl)methanesulfonamide,
(1-difluoromethoxy-6-(6-methoxyhexyl)-6H-dibenzo(b,d)pyran-8-yl)methanesulfonamide,
(1-difluoromethoxy-6-(8-methoxyoctyl)-6H-dibenzo(b,d)pyran-8-yl)methanesulfonamide,
(1-difluoromethoxy-6-(5-(N-(2-methoxyethyl)aminocarbonyl)pentyl)-6H-dibenzo(b,d)pyran-8-yl)methanesulfonamide,
(1-difluoromethoxy-6-(5-(N-methyl-N-(2-methoxyethyl)aminocarbonyl)pentyl)-6H-dibenzo(b,d)pyran-8-yl)methanesulfonamide,
(1-difluoromethoxy-6-(3-(2-carboxyethyl)phenyl)-6H-dibenzo(b,d)pyran-8-yl)methanesulfonamide,
(1-difluoromethoxy-6-(3-(3-carboxypropyl)phenyl)-6H-dibenzo(b,d)pyran-8-yl)methanesulfonamide,
(1-difluoromethoxy-6-(3-(4-carboxybutyl)phenyl)-6H-dibenzo(b,d)pyran-8-yl)methanesulfonamide,
(1-difluoromethoxy-6-(3-(5-carboxypentyl)phenyl)-6H-dibenzo(b,d)pyran-8-yl)methanesulfonamide,
(1-difluoromethoxy-6-(3-(2-carbomethoxyethyl)phenyl)-6H-dibenzo(b,d)pyran-8-yl)methanesulfonamide,
(1-difluoromethoxy-6-(3-(3-carbomethoxypropyl)phenyl)-6H-dibenzo(b,d)pyran-8-yl)methanesulfonamide,
(1-difluoromethoxy-6-3-(4-carbomethoxybutyl)phenyl)-6H-dibenzo(b,d)pyran-8-yl)methanesulfonamide,
(1-difluoromethoxy-6-(3-(5-carbomethoxypentyl)phenyl)-6H-dibenzo(b,d)pyran-8-yl)methanesulfonamide,
(1-difluoromethoxy-6-(3-(2-carboethoxyethyl)phenyl)-6H-dibenzo(b,d)pyran-8-yl)methanesulfonamide,
(1-difluoromethoxy-6-(3-(3-carboethoxypropyl)phenyl)-6H-dibenzo(b,d)pyran-8-yl)methanesulfonamide,
(1-difluoromethoxy-6-(3-(4-carboethoxybutyl)phenyl)-6H-dibenzo(b,d)pyran-8-yl)methanesulfonamide,
(1-difluoromethoxy-6-(3-(5-carboethoxypentyl)phenyl)-6H-dibenzo(b,d)pyran-8-yl)methanesulfonamide,
(1-difluoromethoxy-6-(3-(2,2-dimethyl-2-carboxyethyl)phenyl)-6H-dibenzo(b,d)pyran-8-yl)methanesulfonamide,
(11-difluoromethoxy-6-(3-(3,3-dimethyl-3-carboxypropyl)phenyl)-6H-dibenzo(b,d)pyran-8-yl)methanesulfonamide,
(1-difluoromethoxy-6-(3-(4,4-dimethyl-4-carboxybutyl)phenyl)-6H-dibenzo(b,d)pyran-8-yl)methanesulfonamide,
(1-difluoromethoxy-6-(3-(5,5-dimethyl-5-carboxypentyl)phenyl)-6H-dibenzo(b,d)pyran-8-yl)methanesulfonamide,
(1-difluoromethoxy-6-(3-(2,2-dimethyl-2-carbomethoxyethyl)phenyl)-6H-dibenzo(b,d)pyran-8-yl)methanesulfonamide,
(1-difluoromethoxy-6-(3-(3,3-dimethyl-3-carbomethoxypropylphenyl)-6H-dibenzo(b,d)pyran-8-yl)methanesulfonamide,
(1-difluoromethoxy-6-(3-(4,4-dimethyl-4-carbomethoxybutyl)phenyl)-6H-dibenzo(b,d)pyran-8-yl)methanesulfonamide,
(1-difluoromethoxy-6-(3-(5,5-dimethyl-5-carbomethoxypentyl)phenyl)-6H-dibenzo(b,d)pyran-8-yl)methanesulfonamide,
(1-difluoromethoxy-6-(3-(2,2-dimethyl-2-carboethoxyethyl)phenyl)-6H-dibenzo(b,d)pyran-8-yl)methanesulfonamide,
(1-difluoromethoxy-6-(3-(3,3-dimethyl-3-carboethoxypropyl)phenyl)-6H-dibenzo(b,d)pyran-8-yl)methanesulfonamide,
(1-difluoromethoxy-6-(3-(4,4-dimethyl-4-carboethoxybutyl)phenyl)-6H-dibenzo(b,d)pyran-8-yl)methanesulfonamide,
(1-difluoromethoxy-6-(3-(5,5-dimethyl-5-carboethoxypentyl)phenyl)-6H-dibenzo(b,d)pyran-8-yl)methanesulfonamide,
(1-difluoromethoxy-6-(4-(2-carboxyethyl)phenyl)-6H-dibenzo(b,d)pyran-8-yl)methanesulfonamide,
(1-difluoromethoxy-6-(4-(3-carboxypropyl)phenyl)-6H-dibenzo(b,d)pyran-8-yl)methanesulfonamide,
(1-difluoromethoxy-6-(4-(4-carboxybutyl)phenyl)-6H-dibenzo(b,d)pyran-8-yl)methanesulfonamide,
(1-difluoromethoxy-6-(4-(5-carboxypentyl)phenyl)-6H-dibenzo(b,d)pyran-8-yl)methanesulfonamide,
(1-difluoromethoxy-6-(4-(2-carbomethoxyethyl)phenyl)-6H-dibenzo(b,d)pyran-8-yl)methanesulfonamide,
(1-difluoromethoxy-6-(4-(3-carbomethoxypropyl)phenyl)-6H-dibenzo(b,d)pyran-8-yl)methanesulfonamide, (1-difluoromethoxy-6-(4-(4-carbomethoxybutyl)phenyl)-6H-dibenzo(b,d)pyran-8-yl)methanesulfonamide,
(1-difluoromethoxy-6-(4-(5-carbomethoxypentyl)phenyl)6H-dibenzo(b,d)pyran-8-yl)methanesulfonamide,
(1-difluoromethoxy-6-(4-(2-carboethoxyethyl)phenyl)-6H-dibenzo(b,d)pyran-8-yl)methanesulfonamide,
(1-difluoromethoxy-6-(4-(3-carboethoxypropyl)phenyl)-6H-dibenzo(b,d)pyran-8-yl)methanesulfonamide,
(1-difluoromethoxy-6-(4-(4-carboethoxybutyl)phenyl)-6H-dibenzo(b,d)pyran-8-yl)methanesulfonamide,
(1-difluoromethoxy-6-(4-(5-carboethoxypentyl)phenyl)-6H-dibenzo(b,d)pyran-8-yl)methanesulfonamide,
(1-difluoromethoxy-6-(4-(2,2-dimethyl-2-carboxyethyl)phenyl)-6H-dibenzo(b,d)pyran-8-yl)methanesulfonamide,
(1-difluoromethoxy-6-(4-(3,3-dimethyl-3-carboxypropyl)phenyl)-6H-dibenzo(b,d)pyran-8-yl)methanesulfonamide,
(1-difluoromethoxy-6-(4-(4,4-dimethyl-4-carboxybutyl)phenyl)-6H-dibenzo(b,d)pyran-8-yl)methanesulfonamide,
(1-difluoromethoxy-6-(4-(5,5-dimethyl-5-carboxypentyl)phenyl)-6H-dibenzo(b,d)pyran-8-yl)methanesulfonamide,
(1-difluoromethoxy-6-(4-(2,2-dimethyl-2-carbomethoxyethyl)phenyl)-6H-dibenzo(b,d)pyran-8-yl)methanesulfonamide,
(1-difluoromethoxy-6-(4-(3,3-dimethyl-3-carbomethoxypropylphenyl)-6H-dibenzo(b,d)pyran-8-yl)methanesulfonamide,
(1-difluoromethoxy-6-(4-(4,4-dimethyl-4-carbomethoxybutyl)phenyl)-6H-dibenzo(b,d)pyran-8-yl)methanesulfonamide,
(1-difluoromethoxy-6-(4-(5,5-dimethyl-5-carbomethoxypentyl)phenyl)-6H-dibenzo(b,d)pyran-8-yl)methanesulfonamide,
(1-difluoromethoxy-6-(4-(2,2-dimethyl-2-carboethoxyethyl)phenyl)-6H-dibenzo(b,d)pyran-8-yl)methanesulfonamide,
(1-difluoromethoxy-6-(4-(3,3-dimethyl-3-carboethoxypropyl)phenyl)-6H-dibenzo(b,d)pyran-8-yl)methanesulfonamide,
(1-difluoromethoxy-6-(4-(4,4-dimethyl-4-carboethoxybutyl)phenyl)-6H-dibenzo(b,d)pyran-8-yl)methanesulfonamide,
(1-difluoromethoxy-6-(4-(5,5-dimethyl-5-carboethoxypentyl)phenyl)-6H-dibenzo(b,d)pyran-8-yl)methanesulfonamide,
(1-difluoromethoxy-6-(3-(N-methyl-N-(N,N-dimethylaminocarbonyl)methylamino)phenyl)-6H-dibenzo(b,d)pyran-8-yl)methanesulfonamide,
(1-difluoromethoxy-6-(3-(N-methyl-N-(N,N-diethylaminocarbonyl)methylamino)phenyl)-6H-dibenzo(b,d)pyran-8-yl)methanesulfonamide,
(1-difluoromethoxy-6-(3-(2-(N-methyl-N-(N,N-dimethylaminocarbonyl)ethyl)amino)phenyl)-6H-dibenzo(b,d)pyran-8-yl)methanesulfonamide,
(1-difluoromethoxy-6-(3-(2-(N-methyl-N-(N,N-diethylaminocarbonyl)ethyl)amino)phenyl)-6H-dibenzo(b,d)pyran-8-yl)methanesulfonamide,
(1-difluoromethoxy-6-(3-(3-(N-methyl-N-(N,N-dimethylaminocarbonyl)propyl)amino)phenyl)-6H-dibenzo(b,d)pyran-8-yl)methanesulfonamide,
(1-difluoromethoxy-6-(3-(3-(N-methyl-N-(N,N-diethylaminocarbonyl)propyl)amino)phenyl)-6H-dibenzo(b,d)pyran-8-yl)methanesulfonamide,
(1-difluoromethoxy-6-(3-(N-methyl-N-acetyl)aminophenyl)-6H-dibenzo(b,d)pyran-8-yl)methanesulfonamide,
(1-difluoromethoxy-6-(3-(N-methyl-N-propionyl)aminophenyl)-6H-dibenzo(b,d)pyran-8-yl)methanesulfonamide,
(1-difluoromethoxy-6-(3-(N-methyl-N-methanesulfonyl)aminophenyl)-6H-dibenzo(b,d)pyran-8-yl)methanesulfonamide,
(1-difluoromethoxy-6-(3-(N-methyl-N-ethanesulfonyl)aminophenyl)-6H-dibenzo(b,d)pyran-8-yl)methanesulfonamide,
(1-difluoromethoxy-6-(4-chlorophenyl)-6H-dibenzo(b,d)pyran-8-yl)methanesulfonamide,
(1-difluoromethoxy-6-(4-fluorophenyl)-6H-dibenzo(b,d)pyran-8-yl)methanesulfonamide,
(1-difluoromethoxy-6-(4-methoxyphenyl)-6H-dibenzo(b,d)pyran-8-yl)methanesulfonamide,
(1-difluoromethoxy-6-(3-hydroxyphenyl)-6H-dibenzo(b,d)pyran-8-yl)methanesulfonamide,
(1-difluoromethoxy-6-(3-trifluoromethylphenyl)-6H-dibenzo(b,d)pyran-8-yl)methanesulfonamide,
(1-difluoromethoxy-6-(3-methylphenyl)-6H-dibenzo(b,d)pyran-8-yl)methanesulfonamide,
(1-difluoromethoxy-6-(3-bromophenyl)-6H-dibenzo(b,d)pyran-8-yl)methanesulfonamide,
(1-difluoromethoxy-6-(4-bromophenyl)-6H-dibenzo(b,d)pyran-8-yl)methanesulfonamide,
(1-difluoromethoxy-6-(3-cyanophenyl)-6H-dibenzo(b,d)pyran-8-yl)methanesulfonamide,
(1-difluoromethoxy-6-(4-cyanophenyl)-6H-dibenzo(b,d)pyran-8-yl)methanesulfonamide,
(1-difluoromethoxy-6-(3-carbomethoxyphenyl)-6H-dibenzo(b,d)pyran-8-yl)methanesulfonamide,
(1-difluoromethoxy-6-(4-carbomethoxyphenyl)-6H-dibenzo(b,d)pyran-8-yl)methanesulfonamide,
(1-difluoromethoxy-6-(3-carboethoxyphenyl)-6H-dibenzo(b,d)pyran-8-yl)methanesulfonamide,
(1-difluoromethoxy-6-(4-carboethoxyphenyl)-6H-dibenzo(b,d)pyran-8-yl)methanesulfonamide,
(1-difluoromethoxy-6-(3-ethoxyphenyl)-6H-dibenzo(b,d)pyran-8-yl)methanesulfonamide,
(1-difluoromethoxy-6-(4-ethoxyphenyl)-6H-dibenzo(b,d)pyran-8-yl)methanesulfonamide,
(1-difluoromethoxy-6-(3-allyloxyphenyl)-6H-dibenzo(b,d)pyran-8-yl)methanesulfonamide,
(1-difluoromethoxy-6-(4-allyloxyphenyl)-6H-dibenzo(b,d)pyran-8-yl)methanesulfonamide,
(1-difluoromethoxy-6-(3-allylphenyl)-6H-dibenzo(b,d)pyran-8-yl)methanesulfonamide,
(1-difluoromethoxy-6-(4-allylphenyl)-6H-dibenzo(b,d)pyran-8-yl)methanesulfonamide,
(1-difluoromethoxy-6-(thien-2-yl)-6H-dibenzo(b,d)pyran-8-yl)methanesulfonamide,
(1-difluoromethoxy-6-(5-chlorothien-2-yl)-6H-dibenzo(b,d)pyran-8-yl)methanesulfonamide,
(1-difluoromethoxy-6-(5-(3-methoxypropen-1-yl)thien-2-yl)-6H-dibenzo(b,d)pyran-8-yl)methanesulfonamide, (1-difluoromethoxy-6-(5-(3-methoxypropyl)thien-2-yl)-6H-dibenzo(b,d)pyran-8-yl)methanesulfonamide, (1-difluoromethoxy-6-(furan-2-yl)-6H-dibenzo(b,d)pyran-8-yl)methanesulfonamide, (1-difluoromethoxy-6-(pyridin-2-yl)-6H-dibenzo(b,d)pyran-8-yl)methanesulfonamide, (1-difluoromethoxy-6-(pyridin-3-yl)-6H-dibenzo(b,d)pyran-8-yl)methanesulfonamide, (1-difluoromethoxy-6-(pyridin-4-yl)-6H-dibenzo(b,d)pyran-8-yl)methanesulfonamide, (1-difluoromethoxy-6-(5-bromopyridin-3-yl)-6H-dibenzo(b,d)pyran-8-yl)methanesulfonamide, (1-difluoromethoxy-6-(5-(N-methyl-N-(2-methoxyethyl)amino)pyridin-3-yl)-6H-dibenzo(b,d)pyran-8-yl)methanesulfonamide, (1-difluoromethoxy-6-(5-(3-methoxypropen-1-yl)pyridin-3-yl)-6H-dibenzo(b,d)pyran-8-yl)methanesulfonamide, (1-difluoromethoxy-6-(4-(N-methylamino)phenyl)-6H-dibenzo(b,d)pyran-8-yl)methanesulfonamide, (1-difluoromethoxy-6-(4-(N-allyl-N-methylamino)phenyl)-6H-dibenzo(b,d)pyran-8-yl)methanesulfonamide, (1-difluoromethoxy-6-(4-(N-propyl-N-methylamino)phenyl)-6H-dibenzo(b,d)pyran-8-yl)methanesulfonamide, (1-difluoromethoxy-6-(3-(N-methanesulfonylamino)phenyl)-6H-dibenzo(b,d)pyran-8-yl)methanesulfonamide, (1-difluoromethoxy-6-(3-(N-methyl-N-propanesulfonylamino)phenyl)-6H-dibenzo(b,d)pyran-8-yl)methanesulfonamide, (1-difluoromethoxy-6-(3-(4-methoxybutoxy)phenyl)-6H-dibenzo(b,d)pyran-8-yl)methanesulfonamide, (1-difluoromethoxy-6-(3-(4-methoxybut-2-en-1-yloxy)phenyl)-6H-dibenzo(b,d)pyran-8-yl)methanesulfonamide, (1-difluoromethoxy-6-(3-(4-hydroxybut-2-en-1-yloxy)phenyl)-6H-dibenzo(b,d)pyran-8-yl)methanesulfonamide, (1-difluoromethoxy-6-(3-(3-carboethoxyprop-2-en-1-yloxy)phenyl)-6H-dibenzo(b,d)pyran-8-yl)methanesulfonamide, (1-difluoromethoxy-6-(3-(2-(2-methoxyethoxy)ethoxy)phenyl)-6H-dibenzo(b,d)pyran-8-yl)methanesulfonamide, (1-difluoromethoxy-6-(3-((N-methyl-N-(2-methoxyethyl)amino)carbonyl)phenyl)-6H-dibenzo(b,d)pyran-8-yl)methanesulfonamide, (1-difluoromethoxy-6-(3-(methylthiomethoxy)phenyl)-6H-dibenzo(b,d)pyran-8-yl)methanesulfonamide, (1-difluoromethoxy-6-(3-(2-hydroxyethyl)phenyl)-6H-dibenzo(b,d)pyran-8-yl)methanesulfonamide, (1-difluoromethoxy-6-(3-(2-methoxyethyl)phenyl)-6H-dibenzo(b,d)pyran-8-yl)methanesulfonamide, (1-difluoromethoxy-6-(3-(2-(but-3-en-1-yloxy)ethyl)phenyl)-6H-dibenzo(b,d)pyran-8-yl)methanesulfonamide, (1-difluoromethoxy-6-(3-(2-(N,N-dimethylaminocarbonyloxy)ethyl)phenyl)-6H-dibenzo(b,d)pyran-8-yl)methanesulfonamide, (1-difluoromethoxy-6-(3-(N,N-dimethylaminocarbonyloxy)phenyl)-6H-dibenzo(b,d)pyran-8-yl)methanesulfonamide, (1-difluoromethoxy-6-(3-(3-bromoprop-2-en-1-yloxy)phenyl)-6H-dibenzo(b,d)pyran-8-yl)methanesulfonamide, (1-difluoromethoxy-6-(3-fluoro-5-methoxyphenyl)-6H-dibenzo(b,d)pyran-8-yl)methanesulfonamide, (1-difluoromethoxy-6-(3-fluoro-5-hydroxyphenyl)-6H-dibenzo(b,d)pyran-8-yl)methanesulfonamide, (1-difluoromethoxy-6-(3-fluoro-5-allyloxyphenyl)-6H-dibenzo(b,d)pyran-8-yl)methanesulfonamide, (1-difluoromethoxy-6-(3-fluoro-5-(2-methoxyethoxy)phenyl)-6H-dibenzo(b,d)pyran-8-yl)methanesulfonamide, (1-difluoromethoxy-6-(3-fluoro-5-(2-(2-methoxyethoxy)ethoxy)phenyl)-6H-dibenzo(b,d)pyran-8-yl)methanesulfonamide, (1-difluoromethoxy-6-(3-fluoro-5-(2-allyloxyethoxy)phenyl)-6H-dibenzo(b,d)pyran-8-yl)methanesulfonamide, (1-methoxy-6-allyl-7-bromo-6H-dibenzo(b,d)pyran-8-yl)methanesulfonamide, (1-methoxy-6-allyl-7-methyl-6H-dibenzo(b,d)pyran-8-yl)methanesulfonamide, (1-methoxy-6-phenyl-7-bromo-6H-dibenzo(b,d)pyran-8-yl)methanesulfonamide, (1-methoxy-6-phenyl-7-methyl-6H-dibenzo(b,d)pyran-8-yl)methanesulfonamide, (1-methoxy-6-(3-chlorophenyl)-7-bromo-6H-dibenzo(b,d)pyran-8-yl)methanesulfonamide, (1-methoxy-6-(3-chlorophenyl)-7-methyl-6H-dibenzo(b,d)pyran-8-yl)methanesulfonamide, (1-methoxy-6-(3-fluorophenyl)-7-bromo-6H-dibenzo(b,d)pyran-8-yl)methanesulfonamide, (1-methoxy-6-(3-fluorophenyl)-7-methyl-6H-dibenzo(b,d)pyran-8-yl)methanesulfonamide, (1-methoxy-6-(3-methoxyphenyl)-7-bromo-6H-dibenzo(b,d)pyran-8-yl)methanesulfonamide, (1-methoxy-6-(3-methoxyphenyl)-7-methyl-6H-dibenzo(b,d)pyran-8-yl)methanesulfonamide, (1-methoxy-6-(3,4-dimethoxy)phenyl-7-bromo-6H-dibenzo(b,d)pyran-8-yl)methanesulfonamide, (1-methoxy-6-(3,4-dimethoxy)phenyl-7-methyl-6H-dibenzo(b,d)pyran-8-yl)methanesulfonamide, (1-methoxy-6-(5-bromothien-2-yl)-7-bromo-6H-dibenzo(b,d)pyran-8-yl)methanesulfonamide, (1-methoxy-6-(5-bromothien-2-yl)-7-methyl-6H-dibenzo(b,d)pyran-8-yl)methanesulfonamide, (1-difluoromethoxy-6-allyl-7-bromo-6H-dibenzo(b,d)pyran-8-yl)methanesulfonamide, (1-difluoromethoxy-6-allyl-7-methyl-6H-dibenzo(b,d)pyran-8-yl)methanesulfonamide, (1-difluoromethoxy-6-phenyl-7-bromo-6H-dibenzo(b,d)pyran-8-yl)methanesulfonamide, (1-difluoromethoxy-6-phenyl-7-methyl-6H-dibenzo(b,d)pyran-8-yl)methanesulfonamide, (1-difluoromethoxy-6-(3-chlorophenyl)-7-bromo-6H-dibenzo(b,d)pyran-8-yl)methanesulfonamide, (1-difluoromethoxy-6-(3-chlorophenyl)-7-methyl-6H-dibenzo(b,d)pyran-8-yl)methanesulfonamide, (1-difluoromethoxy-6-(3-fluorophenyl)-7-bromo-6H-dibenzo(b,d)pyran-8-yl)methanesulfonamide, (1-difluoromethoxy-6-(3-fluorophenyl)-7-methyl-6H-dibenzo(b,d)pyran-8-yl)methanesulfonamide, (1-difluoromethoxy-6-(3-methoxyphenyl)-7-bromo-6H-dibenzo(b,d)pyran-8-yl)methanesulfonamide, (1-difluoromethoxy-6-(3-methoxyphenyl)-7-methyl-6H-dibenzo(b,d)pyran-8-yl)methanesulfonamide, (1-difluoromethoxy-6-(3,4-dimethoxy)phenyl-7-bromo-6H-dibenzo(b,d)pyran-8-yl)methanesulfonamide, (1-difluoromethoxy-6-(3,4-dimethoxy)phenyl-7-methyl-6H-dibenzo(b,d)pyran-8-yl)methanesulfonamide, (1-difluoromethoxy-6-(5-bromothien-2-yl)-7-bromo-6H-dibenzo(b,d)pyran-8-yl)methanesulfonamide, (1-difluoromethoxy-6-(5-bromothien-2-yl)-7-methyl-6H-dibenzo(b,d)pyran-8-yl)methanesulfonamide, (1-methoxy-6-allyl-8-methyl-6H-dibenzo(b,d)pyran-8-yl)methanesulfonamide, (1-methoxy-6-phenyl-8-methyl-6H-dibenzo(b,d)pyran-8-yl)methanesulfonamide, (1-methoxy-6-(3-chlorophenyl)-8-methyl-6H-dibenzo(b,d)pyran-8-yl)methanesulfonamide, (1-methoxy-6-(3-fluorophenyl)-8-methyl-6H-dibenzo(b,d)pyran-8-yl)methanesulfonamide, (1-methoxy-6-(3-methoxyphenyl)-8-methyl-6H-dibenzo(b,d)pyran-8-yl)methanesulfonamide, (1-methoxy-6-(3,4-dimethoxy)phenyl-8-methyl-6H-dibenzo(b,d)pyran-8-yl)methanesulfonamide, (1-methoxy-6-(5-bromothien-2-yl)-8-methyl-6H-dibenzo(b,d)pyran-8-yl)methanesulfonamide, (1-difluoromethoxy-6-allyl-8-methyl-6H-dibenzo(b,d)pyran-8-yl)methanesulfonamide, (1-difluoromethoxy-6-phenyl-8-methyl-6H-dibenzo(b,d)pyran-8-yl)methanesulfonamide, (1-difluoromethoxy-6-(3-chlorophenyl)-8-methyl-6H-dibenzo(b,d)pyran-8-yl)methanesulfonamide, (1-difluoromethoxy-6-(3-fluorophenyl)-8-methyl-6H-dibenzo(b,d)pyran-8-yl)methanesulfonamide, (1-difluoromethoxy-6-(3-methoxyphenyl)-8-methyl-6H-dibenzo(b,d)pyran-8-yl)methanesulfonamide, (1-difluoromethoxy-6-(3,4-dimethoxy)phenyl-8-methyl-6H-dibenzo(b,d)pyran-8-yl)methanesulfonamide, (1-difluoromethoxy-6-(5-bromothien-2-yl)-8-methyl-6H-dibenzo(b,d)pyran-8-yl)methanesulfonamide, (1-methoxy-6-allyl-9-allyl-6H-dibenzo(b,d)pyran-8-yl)methanesulfonamide, (1-methoxy-6-phenyl-9-allyl-6H-dibenzo(b,d)pyran-8-yl)methanesulfonamide, (1-methoxy-6-(3-chlorophenyl)-9-allyl-6H-dibenzo(b,d)pyran-8-yl)methanesulfonamide, (1-methoxy-6-(3-fluorophenyl)-9-allyl-6H-dibenzo(b,d)pyran-8-yl)methanesulfonamide, (1-methoxy-6-(3-methoxyphenyl)-9-allyl-6H-dibenzo(b,d)pyran-8-yl)methanesulfonamide, (1-methoxy-6-(3,4-dimethoxy)phenyl-9-allyl-6H-dibenzo(b,d)pyran-8-yl)methanesulfonamide, (1-methoxy-6-(5-bromothien-2-yl)-9-allyl-6H-dibenzo(b,d)pyran-8-yl)methanesulfonamide, (1-difluoromethoxy-6-allyl-9-allyl-6H-dibenzo(b,d)pyran-8-yl)methanesulfonamide, (1-difluoromethoxy-6-phenyl-9-allyl-6H-dibenzo(b,d)pyran-8-yl)methanesulfonamide, (1-difluoromethoxy-6-(3-chlorophenyl)-9-allyl-6H-dibenzo(b,d)pyran-8-yl)methanesulfonamide, (1-difluoromethoxy-6-(3-fluorophenyl)-9-allyl-6H-dibenzo(b,d)pyran-8-yl)methanesulfonamide, (1-difluoromethoxy-6-(3-methoxyphenyl)-9-allyl-6H-dibenzo(b,d)pyran-8-yl)methanesulfonamide, (1-difluoromethoxy-6-(3,4-dimethoxy)phenyl-9-allyl-6H-dibenzo(b,d)pyran-8-yl)methanesulfonamide, (1-difluoromethoxy-6-(5-bromothien-2-yl)-9-allyl-6H-dibenzo(b,d)pyran-8-yl)methanesulfonamide, (1-methoxy-6-allyl-6H-dibenzo(b,d)pyran-8-yl)acetamide, (1-methoxy-6-allyl-6H-dibenzo(b,d)pyran-8-yl)propionamide, (1-methoxy-6-allyl-6H-dibenzo(b,d)pyran-8-yl)-(2-methyl)propionamide, (1-methoxy-6-allyl-6H-dibenzo(b,d)pyran-8-yl)benzamide, (1-methoxy-6-allyl-6H-dibenzo(b,d)pyran-8-yl)cyclopropanamide, (1-methoxy-6-allyl-6H-dibenzo(b,d)pyran-8-yl)-(2-methoxy)acetamide, (1-methoxy-6-allyl-6H-dibenzo(b,d)pyran-8-yl)trifluoroacetamide, (1-methoxy-6-allyl-6H-dibenzo(b,d)pyran-8-yl)-N,N-dimethylurea, (1-methoxy-6-allyl-6H-dibenzo(b,d)pyran-8-yl)-N,N-dimethylthiourea, (1-methoxy-6-allyl-6H-dibenzo(b,d)pyran-8-yl)-N,N-dimethylsulfonylurea, (1-methoxy-6-allyl-6H-dibenzo(b,d)pyran-8-yl)-N,N-diethylsulfonylurea, (1-methoxy-6-allyl-6H-dibenzo(b,d)pyran-8-yl)-N-methyl-N-ethylsulfonylurea, (1-methoxy-6-allyl-6H-dibenzo(b,d)pyran-8-yl)aniline, (1-methoxy-6-allyl-6H-dibenzo(b,d)pyran-8-yl)-N-ethylaniline, (1-methoxy-6-allyl-6H-dibenzo(b,d)pyran-8-yl)-N-methylaniline, (1-methoxy-6-allyl-6H-dibenzo(b,d)pyran-8-yl)-N-(cyclopropylmethyl)aniline, (1-methoxy-6-allyl-6H-dibenzo(b,d)pyran-8-yl)-N-benzylaniline, (1-methoxy-6-allyl-6H-dibenzo(b,d)pyran-8-yl)benzenesulfonamide, (1-methoxy-6-allyl-6H-dibenzo(b,d)pyran-8-yl)ethanesulfonamide, (1-methoxy-6-allyl-6H-dibenzo(b,d)pyran-8-yl)isopropanesulfonamide, (1-methoxy-6-allyl-6H-dibenzo(b,d)pyran-8-yl)-(2-fluorobenzene)sulfonamide, (1-methoxy-6-allyl-6H-dibenzo(b,d)pyran-8-yl)-thiophene-2-sulfonamide, (1-methoxy-6-phenyl-6H-dibenzo(b,d)pyran-8-yl)acetamide, (1-methoxy-6-phenyl-6H-dibenzo(b,d)pyran-8-yl)propionamide, (1-methoxy-6-phenyl-6H-dibenzo(b,d)pyran-8-yl)-(2-methyl)propionamide, (1-methoxy-6-phenyl-6H-dibenzo(b,d)pyran-8-yl)benzamnide, (1-methoxy-6-phenyl-6H-dibenzo(b,d)pyran-8-yl)cyclopropanamide, (1-methoxy-6-phenyl-6H-dibenzo(b,d)pyran-8-yl)-(2-methoxy)acetamide, (1-methoxy-6-phenyl-6H-dibenzo(b,d)pyran-8-yl)
    trifluoroacetamide,
(1-methoxy-6-phenyl-6H-dibenzo(b,d)pyran-8-yl)-N,N-
    dimethylurea,
(1-methoxy-6-phenyl-6H-dibenzo(b,d)pyran-8-yl)-N,N-
    dimethylthiourea,
(1-methoxy-6-phenyl-6H-dibenzo(b,d)pyran-8-yl)-N,N-
    dimethylsulfonylurea,
(1-methoxy-6-phenyl-6H-dibenzo(b,d)pyran-8-yl)-N,N-
    diethylsulfonylurea,
(1-methoxy-6-phenyl-6H-dibenzo(b,d)pyran-8-yl)-N-
    methyl-N-ethylsulfonylurea,
(1-methoxy-6-phenyl-6H-dibenzo(b,d)pyran-8-yl)
    aniline,
(1-methoxy-6-phenyl-6H-dibenzo(b,d)pyran-8-yl)-N-
    methylaniline,
(1-methoxy-6-phenyl-6H-dibenzo(b,d)pyran-8-yl)-N-
    (cyclopropylmethyl)aniline,
(1-methoxy-6-phenyl-6H-dibenzo(b,d)pyran-8-yl)-N-
    benzylaniline,
(1-methoxy-6-phenyl-6H-dibenzo(b,d)pyran-8-yl)
    benzenesulfonamide,
(1-methoxy-6-phenyl-6H-dibenzo(b,d)pyran-8-yl)
    ethanesulfonamide,
(1-methoxy-6-phenyl-6H-dibenzo(b,d)pyran-8-yl)
    isopropanesulfonamide,
(1-methoxy-6-phenyl-6H-dibenzo(b,d)pyran-8-yl)-(2-
    fluorobenzene)sulfonamide,
(1-methoxy-6-phenyl-6H-dibenzo(b,d)pyran-8-yl)-
    thiophene-2-sulfonamide,
(1-methoxy-6-(3-chlorophenyl)-6H-dibenzo(b,d)pyran-
    8-yl)acetamide,
(1-methoxy-6-(3-chlorophenyl)-6H-dibenzo(b,d)pyran-
    8-yl)propionamide,
(1-methoxy-6-(3-chlorophenyl)-6H-dibenzo(b,d)pyran-
    8-yl)-(2-methyl)propionamide,
(1-methoxy-6-(3-chlorophenyl)-6H-dibenzo(b,d)pyran-
    8-yl)benzamide,
(1-methoxy-6-(3-chlorophenyl)-6H-dibenzo(b,d)pyran-
    8-yl)cyclopropanamide,
(1-1-methoxy-6-(3-chlorophenyl)-6H-dibenzo(b,d)
    pyran-8-yl)-(2-methoxy)acetamide,
(1-methoxy-6-(3-chlorophenyl)-6H-dibenzo(b,d)pyran-
    8-yl)trifluoroacetamide,
(1-methoxy-6-(3-chlorophenyl)-6H-dibenzo(b,d)pyran-
    8-yl)-N,N-dimethylurea,
(1-methoxy-6-(3-chlorophenyl)-6H-dibenzo(b,d)pyran-
    8-yl)-N,N-dimethylthiourea,
(1-methoxy-6-(3-chlorophenyl)-6H-dibenzo(b,d)pyran-
    8-yl)-N,N-dimethylsulfonylurea,
(1-methoxy-6-(3-chlorophenyl)-6H-dibenzo(b,d)pyran-
    8-yl)-N,N-diethylsulfonylurea,
(1-methoxy-6-(3-chlorophenyl)-6H-dibenzo(b,d)pyran-
    8-yl)-N-methyl-N-ethylsulfonylurea,
(1-methoxy-6-(3-chlorophenyl)-6H-dibenzo(b,d)pyran-
    8-yl)aniline,
(1-methoxy-6-(3-chlorophenyl)-6H-dibenzo(b,d)pyran-
    8-yl)-N-ethylaniline,
(1-methoxy-6-(3-chlorophenyl)-6H-dibenzo(b,d)pyran-
    8-yl)-N-methylaniline,
(1-methoxy-6-(3-chlorophenyl)-6H-dibenzo(b,d)pyran-
    8-yl)-N-(cyclopropylmethyl)aniline,
(1-methoxy-6-(3-chlorophenyl)-6H-dibenzo(b,d)pyran-
    8-yl)-N-benzylaniline,
(1-methoxy-6-(3-chlorophenyl)-6H-dibenzo(b,d)pyran-
    8-yl)benzenesulfonamide,
(1-methoxy-6-(3-chlorophenyl)-6H-dibenzo(b,d)pyran-
    8-yl)ethanesulfonamide,
(1-methoxy-6-(3-chlorophenyl)-6H-dibenzo(b,d)pyran-
    8-yl)isopropanesulfonamide,
(1-methoxy-6-(3-chlorophenyl)-6H-dibenzo(b,d)pyran-
    8-yl)-(2-fluorobenzene)sulfonamide,
(1-methoxy-6-(3-chlorophenyl)-6H-dibenzo(b,d)pyran-
    8-yl)-thiophene-2-sulfonamide,
(1-methoxy-6-(3-fluorophenyl)-6H-dibenzo(b,d)pyran-8-
    yl)acetamide,
(1-methoxy-6-(3-fluorophenyl)-6H-dibenzo(b,d)pyran-8-
    yl)propionamide,
(1-methoxy-6-(3-fluorophenyl)-6H-dibenzo(b,d)pyran-8-
    yl)-(2-methyl)propionamide,
(1-methoxy-6-(3-fluorophenyl)-6H-dibenzo(b,d)pyran-8-
    yl)benzamide,
(1-methoxy-6-(3-fluorophenyl)-6H-dibenzo(b,d)pyran-8-
    yl)cyclopropanamide,
(1-methoxy-6-(3-fluorophenyl)-6H-dibenzo(b,d)pyran-8-
    yl)-(2-methoxy)acetamide,
(1-methoxy-6-(3-fluorophenyl)-6H-dibenzo(b,d)pyran-8-
    yl)trifluoroacetamide,
(1-methoxy-6-(3-fluorophenyl)-6H-dibenzo(b,d)pyran-8-
    yl)-N,N-dimethylurea,
(1-methoxy-6-(3-fluorophenyl)-6H-dibenzo(b,d)pyran-8-
    yl)-N,N-dimethylthiourea,
(1-methoxy-6-(3-fluorophenyl)-6H-dibenzo(b,d)pyran-8-
    yl)-N,N-dimethylsulfonylurea,
(1-methoxy-6-(3-fluorophenyl)-6H-dibenzo(b,d)pyran-8-
    yl)-N,N-diethylsulfonylurea,
(1-methoxy-6-(3-fluorophenyl)-6H-dibenzo(b,d)pyran-8-
    yl)-N-methyl-N-ethylsulfonylurea,
(1-methoxy-6-(3-fluorophenyl)-6H-dibenzo(b,d)pyran-8-
    yl)aniline,
(1-methoxy-6-(3-fluorophenyl)-6H-dibenzo(b,d)pyran-8-
    yl)-N-ethylaniline,
(1-methoxy-6-(3-fluorophenyl)-6H-dibenzo(b,d)pyran-8-
    yl)-N-methylaniline,
(1-methoxy-6-(3-fluorophenyl)-6H-dibenzo(b,d)pyran-8-
    yl)-N-(cyclopropylmethyl)aniline,
(1-methoxy-6-(3-fluorophenyl)-6H-dibenzo(b,d)pyran-9-
    yl)-N-benzylaniline,
(1-methoxy-6-(3-fluorophenyl)-6H-dibenzo(b,d)pyran-8-
    yl)benzenesulfonamide,
(1-methoxy-6-(3-fluorophenyl)-6H-dibenzo(b,d)pyran-8-
    yl)ethanesulfonamide,
(1-methoxy-6-(3-fluorophenyl)-6H-dibenzo(b,d)pyran-8-
    yl)isopropanesulfonamide,
(1-methoxy-6-(3-fluorophenyl)-6H-dibenzo(b,d)pyran-8-
    yl)-(2-fluorobenzene)sulfonamide,
(1-methoxy-6-(3-fluorophenyl)-6H-dibenzo(b,d)pyran-8-
    yl)-thiophene-2-sulfonamide,
(1-methoxy-6-(3-methoxyphenyl)-6H-dibenzo(b,d)
    pyran-8-yl)acetamide,
(1-methoxy-6-(3-methoxyphenyl)-6H-dibenzo(b,d)
    pyran-8-yl)propionamide,
(1-methoxy-6-(3-methoxyphenyl)-6H-dibenzo(b,d)
    pyran-8-yl)-(2-methyl)propionamide, (1-methoxy-6-(3-methoxyphenyl)-6H-dibenzo(b,d)pyran-8-yl)benzamide,
(1-methoxy-6-(3-methoxyphenyl)-6H-dibenzo(b,d)pyran8-cyclopropanamide,
(1-methoxy-6-(3-methoxyphenyl)-6H-dibenzo(b,d)pyran-8-yl)-(2-methoxy)acetamide,
(1-methoxy-6-(3-methoxyphenyl)-6H-dibenzo(b,d)pyran-8-yl)trifluoroacetamide,
(1-methoxy-6-(3-methoxyphenyl)-6H-dibenzo(b,d)pyran-8-yl)-N,N-dimethylurea,
(1-methoxy-6-(3-methoxyphenyl)-6H-dibenzo(b,d)pyran-8-yl)-N,N-dimethylthiourea,
(1-methoxy-6-(3-methoxyphenyl)-6H-dibenzo(b,d)pyran-8-yl)-N,N-dimethylsulfonylurea,
(1-methoxy-6-(3-methoxyphenyl)-6H-dibenzo(b,d)pyran-8-yl)-N,N-diethylsulfonylurea,
(1-methoxy-6-(3-methoxyphenyl)-6H-dibenzo(b,d)pyran-8-yl)-N-methyl-N-ethylsulfonylurea,
(1-methoxy-6-(3-methoxyphenyl)-6H-dibenzo(b,d)pyran-8-yl)aniline,
(1-methoxy-6-(3-methoxyphenyl)-6H-dibenzo(b,d)pyran-8-yl)-N-ethylaniline,
(1-methoxy-6-(3-methoxyphenyl)-6H-dibenzo(b,d)pyran-8-yl)-N-methylaniline,
(1-methoxy-6-(3-methoxyphenyl)-6H-dibenzo(b,d)pyran-8-yl)-N-(cyclopropylmethyl)aniline,
(1-methoxy-6-(3-methoxyphenyl)-6H-dibenzo(b,d)pyran-8-yl)-N-benzylaniline,
(1-methoxy-6-(3-methoxyphenyl)-6H-dibenzo(b,d)pyran-8-yl)benzenesulfonamide,
(1-methoxy-6-(3-methoxyphenyl)-6H-dibenzo(b,d)pyran-8-yl)ethanesulfonamide,
(1-methoxy-6-(3-methoxyphenyl)-6H-dibenzo(b,d)pyran-8-yl)isopropanesulfonamide,
(1-methoxy-6-(3-methoxyphenyl)-6H-dibenzo(b,d)pyran-8-yl)-(2-fluorobenzene)sulfonamide,
(1-methoxy-6-(3-methoxyphenyl)-6H-dibenzo(b,d)pyran-8-yl)-thiophene-2-sulfonamide,
(1-methoxy-6-(3,4-dimethoxy)phenyl-6H-dibenzo(b,d)pyran-8-yl)acetamide,
(1-methoxy-6-(3,4-dimethoxy)phenyl-6H-dibenzo(b,d)pyran-8-yl)propionamide,
(1-methoxy-6-(3,4-dimethoxy)phenyl-6H-dibenzo(b,d)pyran-8-yl)-(2-methyl)propionamide,
(1-methoxy-6-(3,4-dimethoxy)phenyl-6H-dibenzo(b,d)pyran-8-yl)benzamide,
(1-methoxy-6-(3,4-dimethoxy)phenyl-6H-dibenzo(b,d)pyran-8-yl)cyclopropanamide,
(1-methoxy-6-(3,4-dimethoxy)phenyl-6H-dibenzo(b,d)pyran-8-yl)-(2-methoxy)acetamide,
(1-methoxy-6-(3,4-dimethoxy)phenyl-6H-dibenzo(b,d)pyran-8-yl)trifluoroacetamide,
(1-methoxy-6-(3,4-dimethoxy)phenyl-6H-dibenzo(b,d)pyran-8-yl)-N,N-dimethylurea,
(1-methoxy-6-(3,4-dimethoxy)phenyl-6H-dibenzo(b,d)pyran-8-yl)-N,N-dimethylthiourea,
(1-methoxy-6-(3,4-dimethoxy)phenyl-6H-dibenzo(b,d)pyran-8-yl)-N,N-dimethylsulfonylurea,
(1-methoxy-6-(3,4-dimethoxy)phenyl-6H-dibenzo(b,d)pyran-8-yl)-N,N-diethylsulfonylurea,
(1-methoxy-6-(3,4-dimethoxy)phenyl-6H-dibenzo(b,d)pyran-8-yl)-N-methyl-N-ethylsulfonylurea,
(1-methoxy-6-(3,4-dimethoxy)phenyl-6H-dibenzo(b,d)pyran-8-yl)aniline,
(1-methoxy-6-(3,4-dimethoxy)phenyl-6H-dibenzo(b,d)pyran-8-yl)-N-ethylaniline,
(1-methoxy-6-(3,4-dimethoxy)phenyl-6H-dibenzo(b,d)pyran-8-yl)-N-methylaniline,
(1-methoxy-6-(3,4-dimethoxy)phenyl-6H-dibenzo(b,d)pyran-8-yl)-N-(cyclopropylmethyl)aniline,
(1-methoxy-6-(3,4-dimethoxy)phenyl-6H-dibenzo(b,d)pyran-8-yl)-N-benzylaniline,
(1-methoxy-6-(3,4-dimethoxy)phenyl-6H-dibenzo(b,d)pyran-8-yl)benzenesulfonamide,
(1-methoxy-6-(3,4-dimethoxy)phenyl-6H-dibenzo(b,d)pyran-8-yl)ethanesulfonamide,
(1-methoxy-6-(3,4-dimethoxy)phenyl-6H-dibenzo(b,d)pyran-8-yl)isopropanesulfonamide,
(1-methoxy-6-(3,4-dimethoxy)phenyl-6H-dibenzo(b,d)pyran-8-yl)-(2-fluorobenzene)sulfonamide,
(1-methoxy-6-(3,4-dimethoxy)phenyl-6H-dibenzo(b,d)pyran-8-yl)-thiophene-2-sulfonamide,
(1-methoxy-6-(5-bromothien-2-yl)-6H-dibenzo(b,d)pyran-8-yl)acetamide,
(1-methoxy-6-(5-bromothien-2-yl)-6H-dibenzo(b,d)pyran-8-yl)propionamide,
(1-methoxy-6-(5-bromothien-2-yl)-6H-dibenzo(b,d)pyran-8-yl)-(2-methyl)propionamide,
(1-methoxy-6-(5-bromothien-2-yl)-6H-dibenzo(b,d)pyran-8-yl)benzamide,
(1-methoxy-6-(5-bromothien-2-yl)-6H-dibenzo(b,d)pyran-8-yl)cyclopropanamide,
(1-methoxy-6-(5-bromothien-2-yl)-6H-dibenzo(b,d)pyran-8-yl)-(2-methoxy)acetamide,
(1-methoxy-6-(5-bromothien-2-yl)-6H-dibenzo(b,d)pyran-8-yl)trifluoroacetamide,
(1-methoxy-6-(5-bromothien-2-yl)-6H-dibenzo(b,d)pyran-8-yl)-N,N-dimethylurea,
(1-methoxy-6-(5-bromothien-2-yl)-6H-dibenzo(b,d)pyran-8-yl)-N,N-dimethylthiourea,
(1-methoxy-6-(5-bromothien-2-yl)-6H-dibenzo(b,d)pyran-8-yl)-N,N-dimethylsulfonylurea,
(1-methoxy-6-(5-bromothien-2-yl)-6H-dibenzo(b,d)pyran-8-yl)-N,N-diethylsulfonylurea,
(1-methoxy-6-(5-bromothien-2-yl)-6H-dibenzo(b,d)pyran-8-yl)-N-methyl-N-ethylsulfonylurea,
(1-methoxy-6-(5-bromothien-2-yl)-6H-dibenzo(b,d)pyran-8-yl)aniline,
(1-methoxy-6-(5-bromothien-2-yl)-6H-dibenzo(b,d)pyran-8-yl)-N-ethylaniline,
(1-methoxy-6-(5-bromothien-2-yl)-6H-dibenzo(b,d)pyran-8-yl)-N-methylaniline,
(1-methoxy-6-(5-bromothien-2-yl)-6H-dibenzo(b,d)pyran-8-yl)-N-(cyclopropylmethyl)aniline,
(1-methoxy-6-(5-bromothien-2-yl)-6H-dibenzo(b,d)pyran-8-yl)-N-benzylaniline,
(1-methoxy-6-(5-bromothien-2-yl)-6H-dibenzo(b,d)pyran-8-yl)benzenesulfonamide,
(1-methoxy-6-(5-bromothien-2-yl)-6H-dibenzo(b,d)pyran-8-yl)ethanesulfonamide,
(1-methoxy-6-(5-bromothien-2-yl)-6H-dibenzo(b,d)pyran-8-yl)isopropanesulfonamide,
(1-methoxy-6-(5-bromothien-2-yl)-6H-dibenzo(b,d)pyran-8-yl)-(2-fluorobenzene)sulfonamide, (1-methoxy-6-(-bromothien-2-yl)-6H-dibenzo(b,d)pyran-8-yl)-thiophene-2-sulfonamide,
(1-difluoromethoxy-6-allyl-6H-dibenzo(b,d)pyran-8-yl)acetamide,
(1-difluoromethoxy-6-allyl-6H-dibenzo(b,d)pyran-8-yl)propionamide,
(1-difluoromethoxy-6-allyl-6H-dibenzo(b,d)pyran-8-yl)-(2-methyl)propionamide,
(1-difluoromethoxy-6-allyl-6H-dibenzo(b,d)pyran-8-yl)benzamide,
(1-difluoromethoxy-6-allyl-6H-dibenzo(b,d)pyran-8-yl)cyclopropanamide,
(1-difluoromethoxy-6-allyl-6H-dibenzo(b,d)pyran-8-yl)-(2-methoxy)acetamide,
(1-difluoromethoxy-6-allyl-6H-dibenzo(b,d)pyran-8-yl)trifluoroacetamide,
(1-difluoromethoxy-6-allyl-6H-dibenzo(b,d)pyran-8-yl)-N,N-dimethylurea,
(1-difluoromethoxy-6-allyl-6H-dibenzo(b,d)pyran-8-yl)-N,N-dimethylthiourea,
(1-difluoromethoxy-6-allyl-6H-dibenzo(b,d)pyran-8-yl)-N,N-dimethylsulfonylurea,
(1-difluoromethoxy-6-allyl-6H-dibenzo(b,d)pyran-8-yl)-N,N-diethylsulfonylurea,
(1-difluoromethoxy-6-allyl-6H-dibenzo(b,d)pyran-8-yl)-N-methyl-N-ethylsulfonylurea,
(1-difluoromethoxy-6-allyl-6H-dibenzo(b,d)pyran-8-yl)aniline,
(1-difluoromethoxy-6-allyl-6H-dibenzo(b,d)pyran-8-yl)-N-ethylaniline,
(1-difluoromethoxy-6-allyl-6H-dibenzo(b,d)pyran-8-yl)-N-methylaniline,
(1-difluoromethoxy-6-allyl-6H-dibenzo(b,d)pyran-8-yl)-N-(cyclopropylmethyl)aniline,
(1-difluoromethoxy-6-allyl-6H-dibenzo(b,d)pyran-8-yl)-N-benzylaniline,
(1-difluoromethoxy-6-allyl-6H-dibenzo(b,d)pyran-8-yl)benzenesulfonamide,
(1-difluoromethoxy-6-allyl-6H-dibenzo(b,d)pyran-8-yl)ethanesulfonamide,
(1-difluoromethoxy-6-allyl-6H-dibenzo(b,d)pyran-8-yl)isopropanesulfonamide,
(1-difluoromethoxy-6-allyl-6H-dibenzo(b,d)pyran-8-yl)-(2-fluorobenzene)sulfonamide,
(1-difluoromethoxy-6-allyl-6H-dibenzo(b,d)pyran-8-yl)-thiophene-2-sulfonamide,
(1-difluoromethoxy-6-phenyl-6H-dibenzo(b,d)pyran-8-yl)acetamide,
(1-difluoromethoxy-6-phenyl-6H-dibenzo(b,d)pyran-8-yl)propionamide,
(1-difluoromethoxy-6-phenyl-6H-dibenzo(b,d)pyran-8-yl)-(2-methyl)propionamide,
(1l-difluoromethoxy-6-phenyl-6H-dibenzo(b,d)pyran-8-yl)benzamide,
(1-difluoromethoxy-6-phenyl-6H-dibenzo(b,d)pyran-8-yl)cyclopropanamide,
(1-difluoromethoxy-6-phenyl-6H-dibenzo(b,d)pyran-8-yl)-(2-methoxy)acetamide,
(1-difluoromethoxy-6-phenyl-6H-dibenzo(b,d)pyran-8-yl)trifluoroacetamide,
(1-difluoromethoxy-6-phenyl-6H-dibenzo(b,d)pyran-8-yl)-N,N-dimethylurea,
(1-difluoromethoxy-6-phenyl-6H-dibenzo(b,d)pyran-8-yl)-N,N-dimethylthiourea,
(1-difluoromethoxy-6-phenyl-6H-dibenzo(b,d)pyran-8-yl)-N,N-dimethylsulfonylurea,
(1-difluoromethoxy-6-phenyl-6H-dibenzo(b,d)pyran-8-yl)-N,N-diethylsulfonylurea,
(1-difluoromethoxy-6-phenyl-6H-dibenzo(b,d)pyran-8-yl)-N-methyl-N-ethylsulfonylurea,
(1-difluoromethoxy-6-phenyl-6H-dibenzo(b,d)pyran-8-yl)aniline,
(1-difluoromethoxy-6-phenyl-6H-dibenzo(b,d)pyran-8-yl)-N-ethylaniline,
(1-difluoromethoxy-6-phenyl-6H-dibenzo(b,d)pyran-8-yl)-N-methylaniline,
(1-difluoromethoxy-6-phenyl-6H-dibenzo(b,d)pyran-8-yl)-N-(cyclopropylmethyl)aniline,
(1-difluoromethoxy-6-phenyl-6H-dibenzo(b,d)pyran-8-yl)-N-benzylaniline,
(1-difluoromethoxy-6-phenyl-6H-dibenzo(b,d)pyran-8-yl)benzenesulfonamide,
(1-difluoromethoxy-6-phenyl-6H-dibenzo(b,d)pyran-8-yl)ethanesulfonamide,
(1-difluoromethoxy-6-phenyl-6H-dibenzo(b,d)pyran-8-yl)isopropanesulfonamide,
(1-difluoromethoxy-6-phenyl-6H-dibenzo(b,d)pyran-8-yl)-(2-fluorobenzene)sulfonamide,
(1-difluoromethoxy-6-phenyl-6H-dibenzo(b,d)pyran-8-yl)-thiophene-2-sulfonamide,
(1-difluoromethoxy-6-(3-chlorophenyl)-6H-dibenzo(b,d)pyran-8-yl)acetamide,
(1-difluoromethoxy-6-(3-chlorophenyl)-6H-dibenzo(b,d)pyran-8-yl)propionamide,
(1-difluoromethoxy-6-(3-chlorophenyl)-6H-dibenzo(b,d)pyran-8-yl)-(2-methyl)propionamide,
(1-difluoromethoxy-6-(3-chlorophenyl)-6H-dibenzo(b,d)pyran-8-yl)-benzamide,
(1-difluoromethoxy-6-(3-chlorophenyl)-6H-dibenzo(b,d)pyran-8-yl)cyclopropanamide,
(1-difluoromethoxy-6-(3-chlorophenyl)-6H-dibenzo(b,d)pyran-8-yl)-(2-methoxy)acetamide,
(1-difluoromethoxy-6-(3-chlorophenyl)-6H-dibenzo(b,d)pyran-8-yl)trifluoroacetamide,
(1-difluoromethoxy-6-(3-chlorophenyl)-6H-dibenzo(b,d)pyran-8-yl)-N,N-dimethylurea,
(1-difluoromethoxy-6-(3-chlorophenyl)-6H-dibenzo(b,d)pyran-8-yl)-N,N-dimethylthiourea,
(1-difluoromethoxy-6-(3-chlorophenyl)-6H-dibenzo(b,d)pyran-8-yl)-N,N-dimethylsulfonylurea,
(1-difluoromethoxy-6-(3-chlorophenyl)-6H-dibenzo(b,d)pyran-8-yl)-N,N-diethylsulfonylurea,
(1-difluoromethoxy-6-(3-chlorophenyl)-6H-dibenzo(b,d)pyran-8-yl)-N-methyl-N-ethylsulfonylurea,
(1-difluoromethoxy-6-(3-chlorophenyl)-6H-dibenzo(b,d)pyran-8-yl)aniline,
(1-difluoromethoxy-6-(3-chlorophenyl)-6H-dibenzo(b,d)pyran-8-yl)-N-ethylaniline,
(1-difluoromethoxy-6-(3-chlorophenyl)-6H-dibenzo(b,d)pyran-8-yl)-N-methylaniline,
(1-difluoromethoxy-6-(3-chlorophenyl)-6H-dibenzo(b,d)pyran-8-yl)-N-(cyclopropylmethyl)aniline,
(1-difluoromethoxy-6-(3-chlorophenyl)-6H-dibenzo(b1d)pyran-8-yl)-N-benzylaniline, (1-difluoromethoxy-6-(3-chlorophenyl)-6H-dibenzo(b,d)pyran-8-yl)benzenesulfonamide,
(1-difluoromethoxy-6-(3-chlorophenyl)-6H-dibenzo(b,d)pyran-8-yl)ethanesulfonamide,
(1-difluoromethoxy-6-(3-chlorophenyl)-6H-dibenzo(b,d)pyran-8-yl)isopropanesulfonamide,
(1-difluoromethoxy-6-(3-chlorophenyl)-6H-dibenzo(b,d)pyran-8-yl)-(2-fluorobenzene)sulfonamide,
(1-difluoromethoxy-6-(3-chlorophenyl)-6H-dibenzo(b,d)pyran-8-yl)-thiophene-2-sulfonamide,
(1-difluoromethoxy-6-(3-fluorophenyl)-6H-dibenzo(b,d)pyran-8-yl)acetamide,
(1-difluoromethoxy-6-(3-fluorophenyl)-6H-dibenzo(b,d)pyran-8-yl)propionamide
(1-difluoromethoxy-6-(3-fluorophenyl)-6H-dibenzo(b,d)pyran-8-yl)-(2-methyl)propionamide,
(1-difluoromethoxy-6-(3-fluorophenyl)-6H-dibenzo(b,d)pyran-8-yl)benzamide,
(1-difluoromethoxy-6-(3-fluorophenyl)-6H-dibenzo(b,d)pyran-8-yl)cyclopropanamide,
(1-difluoromethoxy-6-(3-fluorophenyl)-6H-dibenzo(b,d)pyran-8-yl)-(2-methoxy)acetamide,
(1-difluoromethoxy-6-(3-fluorophenyl)-6H-dibenzo(b,d)pyran-8-yl)trifluoroacetamide,
(1-difluoromethoxy-6-(3-fluorophenyl)-6H-dibenzo(b,d)pyran-8-yl)-N,N-dimethylurea,
(1-difluoromethoxy-6-(3-fluorophenyl)-6H-dibenzo(b,d)pyran-8-yl)-N,N-dimethylthiourea,
(1-difluoromethoxy-6-(3-fluorophenyl)-6H-dibenzo(b,d)pyran-8-yl)-N,N-dimethylsulfonylurea,
(1-difluoromethoxy-6-(3-fluorophenyl)-6H-dibenzo(b,d)pyran-8-yl)-N,N-diethylsulfonylurea,
(1-difluoromethoxy-6-(3-fluorophenyl)-6H-dibenzo(b,d)pyran-8-yl)-N-methyl-N-ethylsulfonylurea,
(1-difluoromethoxy-6-(3-fluorophenyl)-6H-dibenzo(b,d)pyran-8-yl)aniline,
(1-difluoromethoxy-6-(3-fluorophenyl)-6H-dibenzo(b,d)pyran-8-yl)-N-ethylaniline,
(1-difluoromethoxy-6-(3-fluorophenyl)-6H-dibenzo(b,d)pyran-8-yl)-N-methylaniline,
(1-difluoromethoxy-6-(3-fluorophenyl)-6H-dibenzo(b,d)pyran-8-yl)-N-(cyclopropylmethyl)aniline,
(1-difluoromethoxy-6-(3-fluorophenyl)-6H-dibenzo(b,d)pyran-8-yl)-N-benzylaniline,
(1-difluoromethoxy-6-(3-fluorophenyl)-6H-dibenzo(b,d)pyran-8-yl)benzenesulfonamide,
(1-difluoromethoxy-6-(3-fluorophenyl)-6H-dibenzo(b,d)pyran-8-yl)ethanesulfonamide,
(1-difluoromethoxy-6-(3-fluorophenyl)-6H-dibenzo(b,d)pyran-8-yl)isopropanesulfonamide,
(1-difluoromethoxy-6-(3-fluorophenyl)-6H-dibenzo(b,d)pyran-8-yl)-(2-fluorobenzene)sulfonamide,
(1-difluoromethoxy-6-(3-fluorophenyl)-6H-dibenzo(bud)pyran-8-yl)-thiophene-2-sulfonamide,
(1-difluoromethoxy-6-(3-methoxyphenyl)-6H-dibenzo(b,d)pyran-8-yl)acetamide,
(1-difluoromethoxy-6-(3-methoxyphenyl)-6H-dibenzo(b,d)pyran-8-yl)propionamide,
(1-difluoromethoxy-6-(3-methoxyphenyl)-6H-dibenzo(b,d)pyran-8-yl)-(2-methyl)propionamide,
(1-difluoromethoxy-6-(3-methoxyphenyl)-6H-dibenzo(b,d)pyran-8-yl)benzamide,
(1-difluoromethoxy-6-(3-methoxyphenyl)-6H-dibenzo(b,d)pyran-8-yl)cyclopropanamide,
(1-difluoromethoxy-6-(3-methoxyphenyl)-6H-dibenzo(b,d)pyran-8-yl)-(2-methoxy)acetamide,
(1-difluoromethoxy-6-(3-methoxyphenyl)-6H-dibenzo(b,d)pyran-8-yl)trifluoroacetamide,
(1-difluoromethoxy-6-(3-methoxyphenyl)-6H-dibenzo(b,d)pyran-8-yl)-N,N-dimethylurea,
(1-difluoromethoxy-6-(3-methoxyphenyl)-6H-dibenzo(b,d)pyran-8-yl)-N,N-dimethylthiourea,
(1-difluoromethoxy-6-(3-methoxyphenyl)-6H-dibenzo(b,d)pyran-8-yl)-N,N-dimethylsulfonylurea,
(1-difluoromethoxy-6-(3-methoxyphenyl)-6H-dibenzo(b,d)pyran-8-yl)-N,N-diethylsulfonylurea,
(1-difluoromethoxy-6-(3-methoxyphenyl)-6H-dibenzo(b,d)pyran-8-yl)-N-methyl-N-ethylsulfonylurea,
(1-difluoromethoxy-6-(3-methoxyphenyl)-6H-dibenzo(b,d)pyran-8-yl)aniline,
(1-difluoromethoxy-6-(3-methoxyphenyl)-6H-dibenzo(b,d)pyran-8-yl)-N-ethylaniline,
(1-difluoromethoxy-6-(3-methoxyphenyl)-6H-dibenzo(b,d)pyran-8-yl)-N-methylaniline,
(1-difluoromethoxy-6-(3-methoxyphenyl)-6H-dibenzo(b,d)pyran-8-yl)-N-(cyclopropylmethyl)aniline,
(1-difluoromethoxy-6-(3-methoxyphenyl)-6H-dibenzo(b,d)pyran-8-yl)-N-benzylaniline,
(1-difluoromethoxy-6-(3-methoxyphenyl)-6H-dibenzo(b,d)pyran-8-yl)benzenesulfonamide,
(1-difluoromethoxy-6-(3-methoxyphenyl)-6H-dibenzo(b,d)pyran-8-yl)ethanesulfonamide,
(1-difluoromethoxy-6-(3-methoxyphenyl)-6H-dibenzo(b,d)pyran-8-yl)isopropanesulfonamide,
(1-difluoromethoxy-6-(3-methoxyphenyl)-6H-dibenzo(b,d)pyran-8-yl)-(2-fluorobenzene)sulfonamide,
(1-difluoromethoxy-6-(3-methoxyphenyl)-6H-dibenzo(b,d)pyran-8-yl)-thiophene-2-sulfonamide,
(1-difluoromethoxy-6-(3,4-dimethoxy)phenyl-6H-dibenzo(b,d)pyran-8-yl)acetamide,
(1-difluoromethoxy-6-(3,4-dimethoxy)phenyl-6H-dibenzo(b,d)pyran-8-yl)propionamide,
(1-difluoromethoxy-6-(3,4-dimethoxy)phenyl-6H-dibenzo(b,d)pyran-8-yl)-(2-methyl)propionamide,
(1-difluoromethoxy-6-(3,4-dimethoxy)phenyl-6H-dibenzo(b,d)pyran-8-yl)benzamide,
(1-difluoromethoxy-6-(3,4-dimethoxy)phenyl-6H-dibenzo(b,d)pyran-8-yl)cyclopropanamide,
(1-difluoromethoxy-6-(3,4-dimethoxy)phenyl-6H-dibenzo(b,d)pyran-8-yl)-(2-methoxy)acetamide,
(1-difluoromethoxy-6-(3,4-dimethoxy)phenyl-6H-dibenzo(b,d)pyran-8-yl)trifluoroacetamide,
(1-difluoromethoxy-6-(3,4-dimethoxy)phenyl-6H-dibenzo(b,d)pyran-8-yl)-N,N-dimethylurea,
(1-difluoromethoxy-6-(3,4-dimethoxy)phenyl-6H-dibenzo(b,d)pyran-8-yl)-N,N-dimethylthiourea,
(1-difluoromethoxy-6-(3,4-dimethoxy)phenyl-6H-dibenzo(b,d)pyran-8-yl)-N,N-dimethylsulfonylurea,
(1-difluoromethoxy-6-(3,4-dimethoxy)phenyl-6H-dibenzo(b,d)pyran-8-yl)-N,N-diethylsulfonylurea,
(1-difluoromethoxy-6-(3,4-dimethoxy)phenyl-6H-dibenzo(b,d)pyran-8-yl)-N-methyl-N-ethylsulfonylurea,
(1-difluoromethoxy-6-(3,4-dimethoxy)phenyl-6H-dibenzo(b,d)pyran-8-yl)aniline, (1-difluoromethoxy-6-(3,4-dimethoxy)phenyl-6H-dibenzo(b,d)pyran-8-yl)-N-ethylaniline,
(1-difluoromethoxy-6-(3,4-dimethoxy)phenyl-6H-dibenzo(b,d)pyran-8-yl)-N-methylaniline,
(1-difluoromethoxy-6-(3,4-dimethoxy)phenyl-6H-dibenzo(b,d)pyran-8-yl)-N-(cyclopropylmethyl)aniline,
(1-difluoromethoxy-6-(3,4-dimethoxy)phenyl-6H-dibenzo(b,d)pyran-8-yl)-N-benzylaniline,
(1-difluoromethoxy-6-(3,4-dimethoxy)phenyl-6H-dibenzo(b,d)pyran-8-yl)benzenesulfonamide,
(1-difluoromethoxy-6-(3,4-dimethoxy)phenyl-6H-dibenzo(b,d)pyran-8-yl)ethanesulfonamide,
(1-difluoromethoxy-6-(3,4-dimethoxy)phenyl-6H-dibenzo(b,d)pyran-8-yl)isopropanesulfonamide,
(1-difluoromethoxy-6-(3,4-dimethoxy)phenyl-6H-dibenzo(b,d)pyran-8-yl)-(2-fluorobenzene)sulfonamide,
(1-difluoromethoxy-6-(3,4-dimethoxy)phenyl-6H-dibenzo(b,d)pyran-8-yl)-thiophene-2-sulfonamide,
(1-difluoromethoxy-6-(5-bromothien-2-yl)-6H-dibenzo(b,d)pyran-8-yl)acetamide,
(1-difluoromethoxy-6-(5-bromothien-2-yl)-6H-dibenzo(b,d)pyran-8-yl)propionamide,
(1-difluoromethoxy-6-(5-bromothien-2-yl)-6H-dibenzo(b,d)pyran-8-yl)-(2-methyl)propionamide,
(1-difluoromethoxy-6-(5-bromothien-2-yl)-6H-dibenzo(b,d)pyran-8-yl)benzamide,
(1-difluoromethoxy-6-(5-bromothien-2-yl)-6H-dibenzo(b,d)pyran-8-yl)cyclopropanamide,
(1-difluoromethoxy-6-(5-bromothien-2-yl)-6H-dibenzo(b,d)pyran-8-yl)-(2-methoxy)acetamide,
(1-difluoromethoxy-6-(5-bromothien-2-yl)-6H-dibenzo(b,d)pyran-8-yl)trifluoroacetamide,
(1-difluoromethoxy-6-(5-bromothien-2-yl)-6H-dibenzo(b,d)pyran-8-yl)-N,N-dimethylurea,
(1-difluoromethoxy-6-(5-bromothien-2-yl)-6H-dibenzo(b,d)pyran-8-yl)-N,N-dimethylthiourea,
(1-difluoromethoxy-6-(5-bromothien-2-yl)-6H-dibenzo(b,d)pyran-8-yl)-N,N-dimethylsulfonylurea,
(1-difluoromethoxy-6-(5-bromothien-2-yl)-6H-dibenzo(b,d)pyran-8-yl)-N,N-diethylsulfonylurea,
(1-difluoromethoxy-6-(5-bromothien-2-yl)-6H-dibenzo(b,d)pyran-8-yl)-N-methyl-N-ethylsulfonylurea,
(1-difluoromethoxy-6-(5-bromothien-2-yl)-6H-dibenzo(bad)pyran-8-yl)aniline,
(1-difluoromethoxy-6-(5-bromothien-2-yl)-6H-dibenzo(b,d)pyran-8-yl)-N-ethylaniline,
(1-difluoromethoxy-6-(5-bromothien-2-yl)-6H-dibenzo(b,d)pyran-8-yl)-N-methylaniline,
(1-difluoromethoxy-6-(5-bromothien-2-yl)-6H-dibenzo(b,d)pyran-8-yl)-N-(cyclopropylmethyl)aniline,
(1-difluoromethoxy-6-(5-bromothien-2-yl)-6H-dibenzo(b,d)pyran-8-yl)-N-benzylaniline,
(1-difluoromethoxy-6-(5-bromothien-2-yl)-6H-dibenzo(b,d)pyran-8-yl)benzenesulfonamide,
(1-difluoromethoxy-6-(5-bromothien-2-yl)-6H-dibenzo(b,d)pyran-8-yl)ethanesulfonamide,
(1-difluoromethoxy-6-(5-bromothien-2-yl)-6H-dibenzo(b,d)pyran-8-yl)isopropanesulfonamide,
(1-difluoromethoxy-6-(5-bromothien-2-yl)-6H-dibenzo(b,d)pyran-8-yl)-(2-fluorobenzene)sulfonamide, and
(1-difluoromethoxy-6-(S-bromothien-2-yl)-6H-dibenzo(b,d)pyran-8-yl)-thiophene-2-sulfonamide.

Compounds of the present invention can be evaluated for biological activity as demonstrated below:

Methods for Radioligand Binding Studies with Human Glucocorticoid and Progesterone Receptor Cytosol $^3$(H)-dexamethasone (TRK 645) hereafter referred to as $^3$(H)-dex was purchased from Pharmacia Amersham, Uppsala, Sweden. Dexamethasone hereafter referred to as dex was purchased from SIGMA. The Costar 96-well polypropylene plates (3794 or 3365) were purchased from Life Technologies AB, Täby, Sweden. The GF/B filter (1450-521), filter cassette (1450-104), MeltiLex scintillating wax (1450-441), sample bag (1450-42), Microbeta™ 1450-PLUS and Microsealer 1495-021 were all purchased from Wallac Oy, Turkku, Finland. Human glucocorticoid receptors were extracted from Sf9 cells infected with a recombinant baculovirus transfer vector containing the cloned hGR genes. Recombinant baculovirus was generated utilizing the BAC-TO-BAC expression system (Life Technologies) in accordance to instruction from the supplier. The hGR coding sequences were cloned into a baculovirus transfer vector by standard techniques. The recombinant baculovi, uses expressing hGR were amplified and used to infect Sf9 cells. Infected cells were harvested 48 hrs post infection. The receptors were extracted from the cell pellet with a phosphate buffer (1 mM EDTA, 20 mM $KPO_4$ (pH8), 8.6% Glycerol, 12 mM MTG, 20 mM $Na_2MoO_4$). The concentration of hGR in the extract was measured as specific $^3$(H)-dex binding with the G25-assay as described in J. Steroid Biochem. Molec. Biol. 50, No. 5/6, 313–318, 1994 and estimated to approximately 25 nM. The extract was aliquoted and stored at −70° C.

The filter binding assay: Dilution series of the test compounds and dex as reference were made from 10 mM (1 mM dex) stock solutions in DMSO. 10 µl of the dilutions was added in duplicates to the wells. The cell extracts were diluted 10 fold in EPMo +MTG buffer (1 mM EDTA, $HPO_4$ 20 mM (pH8), 6 mM MTG). The diluted extract was added to the wells (110 µl). $^3$(H)-dex were diluted from the stock solution to 10–10.8nM in EPMo+MTG buffer. 110 µl of the diluted $^3$(H)-dex were added to the wells. The final concentration of hGR in the experiment was estimated to 1 nM. All preparations were made in ambient temperature (20–25° C.) on ice and with +4° C. temperated buffers. The plates were incubated over night at +4° C. (15–20hrs).

The incubation was stopped by filtration through GF/B filter on the Tomtec Cellharvester. The filtration on the Tomtec Cellharvester was programmed as follows: 1) Preparation before filtration with EP buffer (1 mM EDTA 20 mM $HPO_4$ (pH8)) 2×(Wash/Asp 0.6 sec., Asp 0.5 sec.); 2) Prewet of GF/B filter with EP+PEI buffer (EP buffer, 0.3% Polyesthylenimine) (Asp 0.8 sec.). 3) Filtration/harvesting of the 96-well incubation plate 3×(Wash/Asp 0.6 sec., Asp 0.5 sec.). The GF/B filter was dried for at least 1 hr at 65° C. A MeltiLex scintillation wax was melted onto the filter with the Microsealer. The filter was placed in a samplebag, which was thereafter trimmed with scissors to fit the filter cassette. The cassette were placed in the Microbeta and measured for 1 min/position, returning ccpm (corrected counts per minute).

For compounds able to displace the $^3$(H)-dex from the receptor an $IC_{50}$-value (the concentration required to inhibit 50% of the binding of (H)-dex was determined by a non-linear four parameter logistic model;

$$b=((b_{max}-b_{min})/(1+(I/IC_{50})^S))+b_{min}I$$

is added concentration of binding inhibitor, $IC_{50}$ is the concentration for inhibitor at half maximal binding and S is a slope factor.[1] For determinations of the concentration of $^3$(H)-dex in the solutions, regular scintillation counting in a Wallac Rackbeta 1214 was performed using the scintillation cocktail Supermix™ (Wallac).

[1] Haggblad, J., Carlsson, B., Kivelä, P., Siitari H., (1995) Biotechniques 18, 146–151

The Microbeta-instrument generates the mean cpm (counts per minute) value/minute and corrects for individual variations between the detectors thus generating corrected cpm values. It was found that the counting efficiency between detectors differed with less than five percent.

A similar protocol was employed to measure affinity of the compounds of the present invention for progesterone receptor (PR).

Compounds of the present invention demonstrate binding affinity for glucocorticoid receptor, and selectivity for GR over PR, as indicated below:

| EXAMPLE # | GR BINDING (% Inhibition @ 1.7 μM) | PR BINDING ($IC_{50}$, nM) |
|---|---|---|
| 1 | 82.1 | 5630 |
| 2 | 67.2 | >10,000 |
| 3 | 69.7 | >10,000 |
| 4 | 87.5 | 460 |
| 5 | 93.1 | 3350 |
| 6 | 85.0 | — |
| 7 | 90.6 | — |
| 8 | 87.9 | — |
| 9 | 93.1 | 1000 |
| 10 | 90.8 | 1000 |
| 11 | 57.8 | — |
| 12 | 86.1 | — |
| 13 | 85.4 | — |
| 14 | 85.1 | — |
| 15 | 72.8 | — |
| 16 | 74.3 | — |
| 17 | 66.0 | — |
| 18 | 81.3 | >10,000 |
| 19 | 66.0 | — |
| 20 | 54.4 | — |
| 21 | 39.1 | — |
| 22 | 87.9 | — |
| 23 | 36.9 | — |
| 24 | 88.9 | 800 |
| 25 | 92.7 | 370 |
| 26 | 92.2 | 29 |
| 27 | 86.8 | — |
| 28 | 36.6 | 4460 |
| 29 | 55.0 | — |
| 30 | 85.6 | 1280 |
| 31 | 90.0 | 79 |
| 32 | 89.9 | >10,000 |
| 33 | 87.5 | 5490 |
| 34 | 81.6 | — |
| 35 | 72.4 | — |
| 36 | 95.0 | 2240 |
| 37 | 94.8 | — |
| 38 | 58.9 | — |
| 39 | 90.6 | — |
| 40 | 69.3 | — |
| 41 | 88.7 | — |
| 42 | 55.2 | — |
| 43 | 90.6 | 730 |
| 44 | 91.8 | 6900 |
| 45 | 91.2 | 2160 |
| 46 | 84.6 | — |
| 47 | 94.5 | 3480 |
| 48 | 90.8 | >10,000 |
| 49 | 75.1 | — |
| 50 | 93.7 | 1050 |
| 51 | 94.0 | >10,000 |
| 52 | 92.2 | >10,000 |
| 53 | 92.9 | 1420 |
| 54 | 94.1 | 450 |
| 55 | 93.4 | 1000 |
| 56 | 68.7 | — |
| 57 | 94.9 | 1090 |
| 58 | 94.6 | 524 |
| 59 | 94.7 | 2110 |
| 60 | 95.0 | 500 |
| 61 | 91.3 | 3990 |
| 62 | 94.5 | 172 |
| 63 | 98.5 | 1200 |
| 64 | 44.3 | — |
| 65 | 94.9 | 2840 |
| 66 | 91.6 | 222 |
| 67 | 49.3 | — |
| 68 | 88.1 | >10,000 |
| 69 | 49.5 | — |
| 70 | 72.4 | — |
| 71 | 89.5 | 340 |
| 72 | 58.8 | — |
| 73 | 88.3 | >1,000 |
| 74 | 86.7 | 970 |
| 75 | 90.1 | 1850 |
| 76 | 89.7 | 670 |
| 77 | 90.4 | 480 |
| 78 | 77.9 | — |
| 79 | 66.1 | — |
| 80 | 88.6 | 620 |
| 81 | 84.5 | 9360 |
| 82 | 91.4 | 300 |
| 83 | 92.2 | 3630 |
| 84 | 91.8 | — |
| 85 | 81.6 | — |
| 86 | 90.4 | 77 |
| 87 | 86.3 | 210 |
| 88 | 85.6 | — |
| 89 | 86.1 | — |
| 90 | 55.1 | — |
| 91 | 90.1 | >1000 |
| 92 | 90.4 | 51 |
| 93 | 88.6 | >1000 |
| 94 | 79.6 | — |
| 95 | 90.0 | >1000 |
| 96 | 91.6 | 120 |
| 97 | 89.8 | 180 |
| 98 | 86.7 | 92 |
| 99 | 91.3 | >1000 |
| 100 | 95.4 | 250 |
| 101 | 91.3 | — |
| 102 | 18.1 | >1000 |
| 103 | 93.6 | 180 |
| 104 | 86.8 | — |
| 105 | 83.5 | — |
| 106 | 42.7 | — |
| 107 | 93.9 | 60 |
| 108 | 95.3 | 170 |
| 109 | 93.6 | 250 |
| 110 | 74.8 | — |
| 111 | 87.4 | — |
| 112 | 91.7 | — |
| 113 | 87.7 | — |
| 114 | 89.2 | 290 |
| 115 | 83.5 | — |
| 116 | 92.8 | 1050 |
| 117 | 86.1 | 430 |
| 118 | 94.2 | 610 |
| 119 | 90.3 | 1960 |
| 120 | 88.6 | 500 |
| 121 | 76.6 | — |
| 122 | 63.8 | — |
| 123 | 91.2 | >10000 |
| 124 | 88.7 | >10000 |
| 125 | 91.6 | >10000 |
| 126 | 93.6 | >10000 |
| 127 | 89.2 | >10000 |
| 128 | 91.7 | 880 |
| 129 | 93.4 | >10000 |
| 130 | 97.2 | >10000 |
| 131 | 93.7 | >10000 |

-continued

| EXAMPLE # | GR BINDING (% Inhibition @ 1.7 μM) | PR BINDING (IC$_{50}$, nM) |
|---|---|---|
| 132 | 91.1 | >10000 |
| 133 | 92.0 | >10000 |
| 134 | 88.8 | — |
| 135 | 83.7 | — |
| 136 | 91.1 | >10000 |
| 137 | 94.2 | >10000 |
| 138 | 92.5 | 280 |
| 139 | 90.6 | >1000 |
| 140 | 84.1 | — |
| 141 | 93.6 | — |
| 142 | 78.2 | — |
| 143 | 91.8 | 220 |
| 144 | 93.9 | 140 |
| 145 | 95.2 | 390 |
| 146 | 93.3 | 260 |
| 147 | 96.8 | 530 |
| 148 | 82.7 | — |
| 149 | 69.0 | — |
| 150 | 90.8 | — |
| 151 | 69.5 | — |
| 152 | 87.5 | 10000 |
| 153 | 92.8 | >10000 |
| 154 | 94.8 | 680 |

[1]Haggblad, J., Carlsson, B., Kivelä, P., Siitari H., (1995) Biotechniques 18, 146–151

These data indicate that the compounds of the present invention are uniquely selective for binding to GR over PR, and thus can be useful for the treatment of type II diabetes, obesity, hyperglycemia, inadequate glucose clearance, hyperinsulinemia, hypertriglyceridemia, and high-circulating glucocorticoid levels.

We claim:

1. A compound having formula I

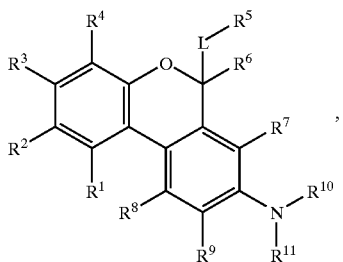

or a pharmaceutically acceptable salt or prodrug thereof, wherein $R^1$ is selected from the group consisting of
(1) alkanoyl, cyano, halo, hydroxy;
(2) alkyl, alkenyl, alkynyl, alkoxy, alkanoyloxy;
wherein each group defining (2) can be optionally substituted with 1–4 substituents independently selected from alkoxy, alkoxycarbonyl, amino, carboxamido, cyano, halo, hydroxy, oxo, unsubstituted or substituted aryl, unsubstituted or substituted heteroaryl, and unsubstituted or substituted heterocyclyl;
wherein the substituted aryl, substituted heteroaryl, and the substituted heterocyclyl groups are optionally substituted with 1–5 substituents independently selected from alkyl, alkenyl, alkynyl, alkoxy, alkoxyalkyl, alkoxycarbonyl, alkoxycarbonylalkyl, amino, aminoalkyl, carboxamido, carboxamidoalkyl, carboxy, carboxyalkyl, cyano, cyanoalkyl, hydroxy, hydroxyalkyl, hydroxyalkoxy, halo, haloalkyl, perfluoroalkyl, and perfluoroalkoxy;
(3) cycloalkyl, aryl, heteroaryl, heterocyclyl;
wherein each group defining (3) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, carboxamido, carboxamidoalkyl, carboxy, carboxy, alkyl, cyano, cyanoalkyl, hydroxy, hydroxyalkyl, hydroxyalkoxy, halo, haloalkyl, oxo, perfluoroalkyl, and perfluoroalkoxy;
(4) $CO_2R^{12}$, $OR^{12}$, $SR^{12}$, $S(O)R^{12}$, and $SO_2R^{12}$;
wherein $R^{12}$ is selected from the group consisting of alkyl, cycloalkyl, aryl, heteroaryl, and heterocyclyl;
wherein each group can be optionally substituted with 1–5 substituents independently selected from alkyl, alkenyl, alkoxyalkoxy, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;

$R_2$ is selected from hydrogen and $R_1$; or
$R_1$ and $R_2$ together are —$X^1$—$Y^1$—$Z^1$—, wherein $X^1$ is selected from a covelent bond, O and $CH_2$;
$Y^1$ is selected from C(O), alkylene, and alkenylene; and $Z^1$ is selected from $CH_2$, $CH_2O$, $CH_2NR^{13}$, $NR^{13}$, and O;
wherein $R^{13}$ is selected from
(1) hydrogen;
(2) alkyl;
wherein the alkyl can be optionally substituted with 1–4 substituents independently selected from alkenyl, alkoxy, cycloalkyl, aryl, halo; and
(3) aryl;

$R^3$, $R^4$, $R^7$, $R^8$, and $R^9$ are independently selected from hydrogen and $R_1$;

L is selected from a covalent bond and alkylene;

$R^5$ is selected from;
(1) alkanoyl, alkoxy, alkenyloxy, alkynyloxy, alkoxycarbonyl, cyano;
(2) aryl, arylalkyl, heteroaryl, and heterocyclyl;
wherein each group defining (2) can be optionally substituted with 1–5 substituents independently selected from alkanoylamino, alkanoylaryloxy, alkyl, alkylsulfonamido, alkenyl, alkenyloxy, alkynyl, alkoxy, alkoxyalkoxy, alkoxyalkyl, alkoxyalkynyl, alkoxyaryl, alkoxycarbonyl, alkoxycarbonylalkyl, alkoxycarbonylalkenyloxy, amino, aminoalkyl, aminoaryl, aryl, arylalkyl, arylalkenyl, arylalkynyl, aryloxy, arylsulfonamido, carboxamido, carboxamidoalkyl, carboxy, carboxyalkyl, carboxyaryl, cyano, cyanoalkyl, heteroaryl, (heteroaryl)heteroarylsulfonamido, heteroaryl, heterocyclyl, hydroxy, hydroxyalkyl, hydroxyalkoxy, hydroxyalkynyl, halo, haloalkyl, haloalkylsulfonamido, nitro, oxo, perfluoroalkyl, perfluoroalkoxy and trialkylsilylalkyl;
(3) alkyl, alkenyl, alkynyl, cycloalkyl;
wherein each group defining (3) can be optionally substituted with 1–4 substituents independently selected from alkoxy, alkenyloxy, alkoxycarbonyl, amino, aryl, carboxamido, carboxy, cyano, halo, hydroxy, and oxo;

$R^6$ is selected from hydrogen and alkyl; or

-L-$R^5$ and $R^6$ together are selected from (1)

wherein d is 1–4 and A is selected from $CH_2$, O, S, $SO_2$, and $NR^{13}$ and

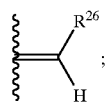
(2)

wherein the carbon—carbon double bond of (2) can be in the E or Z configuration and $R^{26}$ is selected from;
(1) alkyl;
wherein the alkyl can be optionally substituted with 1–4 substituents independently selected from alkenyl, alkynyl, alkoxy, alkoxycarbonyl, amino, aryl, carboxamido, carboxy, cyano, heteroaryl, heterocyclyl, hydroxy, and halo;
(2) aryl, heteroaryl, heterocyclyl, cycloalkyl, and cycloalkenyl;
wherein each group defining (2) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;
$R_{10}$ and $R_{11}$ are independently selected from;
(1) hydrogen;
(2) alkyl;
wherein the alkyl can be optionally substituted with 1–4 substituents independently selected from (a) alkenyl, (b) alkynyl, (c) alkoxy, (d) aryl, (e) cycloalkyl, (f) heteroaryl, (g) heterocyclyl, (h) alkoxycarbonyl, (i) carboxy, and () halo;
wherein (a)–(c) can be optionally substituted with 1–4 substituents independently selected from aryl, alkoxy, cycloalkyl, heteroaryl, heterocyclyl, alkoxycarbonyl, carboxy, and halo; and
wherein (d)–(g) can be optionally substituted with 1–5 substituents independently selected from alkyl, alkenyl, alkynyl, alkoxy, alkoxyalkyl, alkoxycarbonyl; alkoxycarbonylalkyl, amino, aminoalkyl, aryl, carboxamido, carboxamidoalkyl, carboxy, carboxyalkyl, cyano, heteroaryl, heterocyclyl, hydroxy, hydroxyalkyl, hydroxyalkoxy, halo, haloalkyl, nitro, perfluoroalkyl, and perfluoroalkoxy;
(3) aryl, cycloalkyl, heteroaryl, heterocyclyl;
wherein each group defining (3) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;
(4) —$SO_2R^{35}$ and —$C(O)R^{36}$;
wherein $R^{35}$ and $R^{36}$ are independently selected from
(a) alkoxy, amino;
(b) alkyl, alkenyl;
wherein each group defining (b) can be optionally substituted with 1–4 substituents independently selected from (i) alkenyl, (ii) alkynyl, (iii) alkoxy, (iv) aryl, (v) cycloalkyl, (vi) heteroaryl, (vii) heterocyclyl, (viii) alkoxycarbonyl, (ix) carboxy, and (x) halo;
wherein (i)–(iii) can be optionally substituted with 1–4 substituents independently selected from aryl, alkoxy, cycloalkyl, heteroaryl, heterocyclyl, alkoxycarbonyl, carboxy, and halo; and
wherein (iv)-(vii) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxyalkoxy, halo, haloalkyl, nitro, perfluoroalkyl, and perfluoroalkoxy;
(c) aryl, cycloalkyl, heteroaryl, heterocyclyl;
wherein each group defining (c) can be optionally substituted with 1–5 substituents independently selected from alkyl, alkenyl, alkynyl, alkoxy, alkoxyalkyl, alkoxycarbonyl, alkoxycarbonylalkyl, amino, aminoalkyl, aryl, carboxamido, carboxamidoalkyl, carboxy, carboxyalkyl, cyano, cyanoalkyl, heteroaryl, heterocyclyl, hydroxy, hydroxyalkyl, hydroxy, alkoxy, halo, haloalkyl, nitro, perfluoroalkyl, and perfluoroalkoxy.

2. A compound according to claim 1 wherein $R^1$ is $OR^{12}$; wherein $R^{12}$ is alkyl, and the alkyl is unsubstituted or substituted as set forth therein.

3. A compound according to claim 1 wherein $R^1$ is $OR^{12}$; wherein $R^{12}$ is alkyl, and the alkyl is unsubstituted or substituted with one, two, or three fluoro substituents.

4. A compound according to claim 3 wherein $R^1$ is selected from methoxy, ethoxy, and difluoromethoxy.

5. A compound according to claim 4 selected from the group consisting of
(1-methoxy-6-(3-trifluoromethyl)phenyl-7-methyl-6H-dibenzo(b,d)pyran-8-yl)methanesulfonamide;
(1-methoxy-6-phenyl-7-bromo-6H-dibenzo(b,d)pyran-8-yl)methanesulfonamide;
(1-methoxy-6-(3-trifluoromethyl)phenyl-7-vinyl-6H-dibenzo(b,d)pyran-8-yl)methanesulfonamide;
(1-difluoromethoxy-6-phenyl-7-bromo-6H-dibenzo(b,d)pyran-8-yl)amine;
(1-methoxy-6-phenyl-6H-dibenzo(b,d)pyran-8-yl)methanesulfonamide;
(1-methoxy-6-phenyl-6H-dibenzo(b,d)pyran-8-yl)benzenesulfonamide;
(1-methoxy-6-phenyl-6H-dibenzo(b,d)pyran-8-yl)ethanesulfonamide;
(1-methoxy-6-phenyl-6H-dibenzo(b,d)pyran-8-yl)isopropanesulfonamide;
(1-methoxy-6-phenyl-6H-dibenzo(b,d)pyran-8-yl)-(2-thienyl)sulfonamide;
(1-methoxy-6-phenyl-6H-dibenzo(b,d)pyran-8-yl)-(N,N-dimethyl)sulfonylurea;
(1-methoxy-6-phenyl-6H-dibenzo(b,d)pyran-8-yl)-(2-phenyl-E-ethenyl)sulfonamide;
(1-methoxy-6-phenyl-6H-dibenzo(b,d)pyran-8-yl)acetamide;
(1-methoxy-6-phenyl-6H-dibenzo(b,d)pyran-8-yl)propionamide;
(1-methoxy-6-phenyl-6H-dibenzo(b,d)pyran-8-yl)-(2-methyl)propionamide;
(1-methoxy-6-phenyl-6H-dibenzo(b,d)pyran-8-yl)benzamide;

(1-methoxy-6-phenyl-6H-dibenzo(b,d)pyran-8-yl) cyclopropanamide;
(1-methoxy-6-phenyl-6H-dibenzo(b,d)pyran-8-yl)-(2-methoxy)acetamide;
(1-methoxy-6-phenyl-6H1-dibenzo(b,d)pyran-8-yl) ethylamine;
(1-methoxy-6-phenyl-6H-dibenzo(b,d)pyran-8-yl) cyclopropylmethylamine;
(1-methoxy-6-phenyl-6H-dibenzo(b,d)pyran-8-yl) benzylaniline;
(1-methoxy-6-phenyl-6H-dibenzo(b,d)pyran-8-yl) trifluoroacetamide;
6R-(1-methoxy-6-phenyl-6H-dibenzo(b,d)pyran-8-yl) methanesulfonamide;
6S-(1-methoxy-6-phenyl-6H-dibenzo(b,d)pyran-8-yl) methanesulfonamide;
(1-difluoromethoxy-6-phenyl-6H-dibenzo(b,d)pyran-8-yl) (2thienyl)sulfonamide;
(1-difluoromethoxy-6-propyl-6H-dibenzo(b,d)pyran-8-yl) methanesulfonamide;
(1-difluoromethoxy-6-(4-(N-methylamino)phenyl)-7-bromo-6H-dibenzo(b,d)pyran-8-yl)amine;
(1-difluoromethoxy-6-(4-(N-propyl-N-methylamino) phenyl)-7-bromo-6H-dibenzo(b,d)pyran-8-yl)amine;
(1-difluoromethoxy-6-(4-(N-allyl-N-methylamino) phenyl)-6H-dibenzo(b,d)pyran-8-yl) methanesulfonamide;
(1-difluoromethoxy-6-allyl-6H-dibenzo(b,d)pyran-8-yl)-methanesulfonamide;
(1-methoxy-6-(4-allyloxy)phenyl-6H-dibenzo(b,d)pyran-8-yl)-methanesulfonamide;
(1-methoxy-6-(3-allyloxy)phenyl-6H-dibenzo(b,d)pyran-8-yl)-methanesulfonamide;
(1-methoxy-6-(3-hydroxy)phenyl-6H-dibenzo(b,d)pyran-8-yl)-methanesulfonamide;
(1-ethoxy-6-phenyl-6H-dibenzo(b,d)pyran-8-yl) methanesulfonamide;
(1-methoxy-6-(2-carboethoxyethyl)-6H-dibenzo(b,d)pyran-8-yl)-methanesulfonamide;
(1-methoxy-6-(4-cyanophenyl)-6H-dibenzo(b,d)pyran-8-yl)methanesulfonamide;
(1-methoxy-6-(6-cyanohexyl)-6H-dibenzo(b,d)pyran-8-yl)methanesulfonamide;
(1-methoxy-6-(3-cyanobenzyl)-6H-dibenzo(b,d)pyran-8-yl)methanesulfonamide;
(1-methoxy-6-(3-cyanophenyl)-6H-dibenzo(b,d)pyran-8-yl)methanesulfonamide;
(1-methoxy-6-(3-carboethoxyphenyl)-6H-dibenzo(b,d)pyran-8-yl)methanesulfonamide;
(1-methoxy-6-(4-carboethoxyphenyl)-6H-dibenzo(b,d)pyran-8-yl)methanesulfonamide;
(1-methoxy-6-allyl-6H-dibenzo(b,d)pyran-8-yl) methanesulfonamide;
(1-methoxy-6-(2-thienyl)-6H-dibenzo(b,d)pyran-8-yl) methanesulfonamide;
(1-methoxy-6-cyclohexyl-6H-dibenzo(b,d)pyran-8-yl) methanesulfonamide;
(1-methoxy-6-(4-ethoxybenzyl)-6H-dibenzo(b,d)pyran-8-yl)methanesulfonamide;
(1-methoxy-6-(4-chlorobutyl)-6H-dibenzo(b,d)pyran-8-yl)methanesulfonamide;
(1-methoxy-6-(5-chlorothien-2-yl)-6H-dibenzo(b,d) pyran-8-yl)methanesulfonamide;
(1-methoxy-6-(3-methoxyphenyl)-6H-dibenzo(b,d) pyran-8-yl)methanesulfonamide;
(1-methoxy-6-(3-chlorophenyl)-6H-dibenzo(b,d)pyran-8-yl)methanesulfonamide;
(1-methoxy-6-(4-chlorophenyl)-6H-dibenzo(b,d)pyran-8-yl)methanesulfonamide;
(1-methoxy-6-(5-bromothien-2-yl)-6H-dibenzo(b,d) pyran-8-yl)methanesulfonamide;
(1-methoxy-6-(3,4-dichlorophenyl)-6H-dibenzo(b,d) pyran-8-yl)methanesulfonamide;
(1-methoxy-6-(3-(2-methoxyethyl)aminocarbonyl) phenyl-6H-dibenzo(b,d)pyran-8-yl)-methanesulfonamide;
(1-methoxy-2-hydroxy-6-phenyl-6H-dibenzo(b,d)pyran-8-yl)methanesulfonamide;
(1-methoxy-3-methyl-6-phenyl-6H-dibenzo(b,d)pyran-8-yl)methanesulfonamide,
(1-methoxy-4-methyl-6-phenyl-6H-dibenzo(b,d)pyran-8-yl)methanesulfonamide;
(1-methoxy-6-(2-pyridyl)-6H-dibenzo(b,d)pyran-8-yl) methanesulfonamide;
(1-methoxy-6-(3-pyridyl)-6H-dibenzo(b,d)pyran-8-yl) methanesulfonamide;
(1-methoxy-6-(2-bromoprop-2-en-1-yl)-6H-dibenzo(b,d) pyran-8-yl)methanesulfonamide;
(1-methoxy-6-(2-(1-oxocyclohexyl))-6H-dibenzo(b,d) pyran-8-yl)methanesulfonamide;
(1-methoxy-6-(3-chloroprop-2-en-1-yl)-6H-dibenzo(b,d) pyran-8-yl)methanesulfonamide;
(1-methoxy-6-(inden-3-yl)-6H-dibenzo(b,d)pyran-8-yl) methanesulfonamide;
(1-methoxy-6-(5-chloropent-1l-yl)-6H-dibenzo(b,d) pyran-8-yl)methanesulfonamide;
(1-methoxy-6-(4-methylphenyl)-6H-dibenzo(b,d)pyran-8-yl)methanesulfonamide; and
(1-methoxy-6-(3-fluorophenyl)-6H-dibenzo(b,d)pyran-8-yl)methanesulfonamide.

6. A compound according to claim 4 selected from the group consisting of ethyl6-{1-methoxy-8-[(methylsulfonyl)amino]-6H-benzo[c]chromen-6-yl}hexanoate;
N-(6-{3-[allyl(methyl)amino]phenyl}-1-methoxy-6H-benzo[c]chromen-8-yl}methanesulfonamide;
N-{1-methoxy-6-[3-(methylamino)phenyl]-6H-benzo[c]chromen-8-yl}methanesulfonamide;
N-[6-(3-bromophenyl)-1-methoxy-6H-benzo[c]chromen-8-yl]methanesulfonamide;
N-(1-methoxy-6-{3-[methyl(methylsulfonyl)amino] phenyl}-6H-benzo[c]chromen-8-yl) methanesulfonamide;
N-(1-methoxy-6-pentyl-6H-benzo[c]chromen-8-yl) methanesulfonamide;
N-[6-(3,5-difluorobenzyl)-1-methoxy-6H-benzo[c]chromen-8-yl]methanesulfonamide;
N-[1-methoxy-6-(4-phenoxyphenyl)-6H-benzo[c]chromen-8-yl]methanesulfonamide;
N-{1-methoxy-6-[(E)-2-phenylethenyl]-6H-benzo[c]chromen-8-yl}methanesulfonamide;
N-(6-cyano-1-methoxy-6H-benzo[c]chromen-8-yl) methanesulfonamide;
N-{1-methoxy-6-[3-(phenylethynyl)phenyl]-6H-benzo[c]chromen-8-yl}methanesulfonamide;

N-{1-methoxy-6-[5-(3-methoxy-1-propynyl)-2-thienyl]-6H-benzo[c]chromen-8-yl}methanesulfonamide;

N-{1-methoxy-6-[5-(phenylethynyl)-2-thienyl]-6H-benzo[c]chromen-8-yl}methanesulfonamide;

ethyl(2E)-4-(3-{1-methoxy-8-[(methylsulfonyl)amino]-6H-benzo[c]chromen-6-yl}phenoxy)-2-butanoate;

N-{1-methoxy-6-[3-(4-methoxybutoxy)phenyl]-6H-benzo[c]chromen-8-yl}methanesulfonamide;

N-[6-(5-bromo-2-thienyl)-1-(difluoromethoxy)-6H-benzo[c]chromen-8-yl]methanesulfonamide;

N-[1-methoxy-6-(3-thienyl)-6H-benzo[c]chromen-8-yl]methanesulfonamide;

N-{6-[(1E)-1-heptenyl]-1-methoxy-6H-benzo[c]chromen-8-yl}methanesulfonamide;

N-(1-methoxy-6-{3-[(E)-2-phenylethenyl]phenyl}-6H-benzo[c]chromen-8-yl)methanesulfonamide;

N-[1-methoxy-6-(5-phenyl-2-thienyl)-6H-benzo[c]chromen-8-yl]methanesulfonamide;

N-(1-methoxy-6-{5-[(E)-2-phenylethenyl]-2-thienyl}-6H-benzo[c]chromen-8-yl)methanesulfonamide;

N-{6-[5-(5-hydroxy-1-pentynyl)-2-thienyl]-1-methoxy-6H-benzo[c]chromen-8-yl}methanesulfonamide;

N-[6-(3-bromophenyl)-1-(difluoromethoxy)-6H-benzo[c]chromen-8-yl]methanesulfonamide;

N-[2-(allyloxy)-1-methoxy-6-phenyl-6H-benzo[c]chromen-8-yl]methanesulfonamide;

N-{1-methoxy-2-[(2-methoxyethoxy)methoxy]-6-phenyl-6H-benzo[c]chromen-8-yl}methanesulfonamide;

N-[1-(difluoromethoxy)-6-(3-methoxyphenyl)-6H-benzo[c]chromen-8-yl]methanesulfonamide;

N-[6-(4-bromophenyl)-1-(difluoromethoxy)-6H-benzo[c]chromen-8-yl]methanesulfonamide;

N-(3-{1-methoxy-8-[(methylsulfonyl)amino]-6H-benzo[c]chromen-6-yl}phenyl)-N-methylacetamide;

N-{1-methoxy-6-[3-(4-pentenyl)phenyl]-6H-benzo[c]chromen-8-yl}methanesulfonamide;

N-{6-[3-(3-cyanopropyl)phenyl]-1-methoxy-6H-benzo[c]chromen-8-yl}methanesulfonamide;

N-{6-[3-(4-cyanobutyl)phenyl]-1-methoxy-6H-benzo[c]chromen-8-yl}methanesulfonamide;

ethyl3-{1-(difluoromethoxy)-8-[(methylsulfonyl)amino]-6H-benzo[c]chromen-6-yl}benzoate;

ethyl4-(3-{1-(difluoromethoxy)-8-[(methylsulfonyl)amino]-6H-benzo[c]chromen-6-yl}phenyl)butanoate;

N-[6-[3-(allyloxy)phenyl]-1-(difluoromethoxy)-6H-benzo[c]chromen-8-yl]methanesulfonamide;

N-1{-(difluoromethoxy)-6-[3-(3-methoxypropyl)phenyl]-6H-benzo[c]chromen-8-yl}methanesulfonamide;

ethyl3-(3-{1-(difluoromethoxy)-8-[(methylsulfonyl)amino]-6H-benzo[c]chromen-6-yl}phenyl)propanoate;

ethyl6-(3-{1-(difluoromethoxy)-8-[(methylsulfonyl)amino]-6H-benzo[c]chromen-6-yl}phenyl)hexanoate;

N-{1-(difluoromethoxy)-6-[3-(3-ethoxypropyl)phenyl]-6H-benzo[c]chromen-8-yl}methanesulfonamide;

4-(3-{1-(difluoromethoxy)-8-[(methylsulfonyl)amino]-6H-benzo[c]chromen-6-yl}phenyl)butanoic acid;

3'-{1-methoxy-8-[(methylsulfonyl)amino]-6H-benzo[c]chromen-6-yl}[1,1'-biphenyl]-4-carboxylicacid;

N-[1-methoxy-6-(4'-methyl[1,1'-biphenyl]-3-yl)-6H-benzo[c]chromen-8-yl]methanesulfonamide;

N-[1-methoxy-6-(3'-methoxy[1,1'-biphenyl]-3-yl)-6H-benzo[c]chromen-8-yl]methanesulfonamide;

N-[1-methoxy-6-(4'-methoxy[1,1'-biphenyl]-3-yl)-6H-benzo[c]chromen-8-yl]methanesulfonamide;

N-[6-(4'-chloro[1,1'-biphenyl]-3-yl)-1-methoxy-6H-benzo[c]chromen-8-yl]methanesulfonamide;

N-[6-(3',4'-dichloro[1,1'-biphenyl]-3-yl)-1-methoxy-6H-benzo[c]chromen-8-yl]methanesulfonamide;

N-[6-(4'-hydroxy-[1,1'-biphenyl]-3-yl)-1-methoxy-6H-benzo[c]chromen-8-yl]methanesulfonamide;

N-(3-{1-methoxy-8-[(methylsulfonyl)amino]-6H-benzo[c]chromen-6-yl}phenyl)-N-methylbenzenesulfonamide;

3-chloro-N-(3-{1-methoxy-8-[(methylsulfonyl)amino]-6H-benzo[c]chromen-6-yl}phenyl)-N-methyl-1-propanesulfonamide;

N-(3-{1-methoxy-8-[(methylsulfonyl)amino]-6H-benzo[c]chromen-6-yl}phenyl)-N-methylethanesulfonamide;

N-(3-{1-methoxy-8-[(methylsulfonyl)amino]-6H-benzo[c]chromen-6-yl}phenyl)-N-methyl-1-propanesulfonamide;

N-{6-[4'-(dimethylamino)[1,1'-biphenyl]-3-yl]-1-methoxy-6H-benzo[c]chromen-8-yl}methanesulfonamide;

N-(1-(difluoromethoxy)-6-{3-[3-(trimethylsilyl)propyl]phenyl}-6H-benzo[c]chromen-8-yl)methanesulfonamide;

ethyl5-(3-{1-(difluoromethoxy)-8-[(methylsulfonyl)amino]-6H-benzo[c]chromen-6-yl}phenyl)-2-methylpentanoate;

N-{1-(difluoromethoxy)-6-[3-(4-phenylbutyl)phenyl]-6H-benzo[c]chromen-8-yl}methanesulfonamide;

N-[6-[3-(6-cyanohexyl)phenyl]-1-(difluoromethoxy)-6H-benzo[c]chromen-8-yl]methanesulfonamide;

N-{1-methoxy-6-[5-(3-methoxypropyl)-2-thienyl]-6H-benzo[c]chromen-8-yl}methanesulfonamide;

N-[1-methoxy-6-(3-phenoxyphenyl)-6H-benzo[c]chromen-8-yl]methanesulfonamide;

N-{6-[3-(4-acetylphenoxy)phenyl]-1-methoxy-6H-benzo[c]chromen-8-yl}methanesulfonamide;

N-{1-(difluoromethoxy)-6-[3-(6-methoxyhexyl)phenyl]-6H-benzo[c]chromen-8-yl}methanesulfonamide;

N-(1-methoxy-6-{3-[4-oxo-4-(1-piperidinyl)butyl]phenyl}-6H-benzo[c]chromen-8-yl)methanesulfonamide;

N[6-(4'-chloro[1,1'-biphenyl]-3-yl)-1-(difluoromethoxy)-6H-benzo[c]chromen-8-yl]methanesulfonamide;

N-[1-(difluoromethoxy)-6-(4'-fluoro[1,1'-biphenyl]-3-yl)-6H-benzo[c]chromen-8-yl]methanesulfonamide;

N-[1-(difluoromethoxy)-6-(4'-methoxy[1,1'-biphenyl]-3-yl)-6H-benzo[c]chromen-8-yl]methanesulfonamide;

N-[6-(2'-chloro[1,1'-biphenyl]-3-yl)-1-(difluoromethoxy)-6H-benzo[c]chromen-8-yl]methanesulfonamide;

N-[1-(difluoromethoxy)-6-(4'-methyl[1,1'-biphenyl]-3-yl)-6H-benzo[c]chromen-8-yl]methanesulfonamide;

4-methoxy-N-(3-{1-methoxy-8-[(methylsulfonyl)amino]-6H-benzo[c]chromen-6-yl}phenyl)-N-methylbenzenesulfonamide;

5-(3-isoxazolyl)-N-(3-{1-methoxy-8-[(methylsulfonyl)amino]-6H-benzo[c]chromen-6-yl}phenyl)-N-methyl-2-thiophenesulfonamide;

ethyl4-(3-{1-methoxy-8-[(methylsulfonyl)amino]-6H-benzo[c]chromen-6-yl}phenyl)butanoate;

4-(3-{1-methoxy-8-[(methylsulfonyl)amino]-6H-benzo[c]chromen-6-yl}phenyl)butanoicacid;

4-bromo-N-(3-{1-methoxy-8-[(methylsulfonyl)amino]-6H-benzo[c]chromen-6-yl}phenyl)-N-methylbenzenesulfonamide;

N-{6-[4-(4-bromophenoxy)phenyl]-1-methoxy-6H-benzo[c]chromen-8-yl}methanesulfonamide; and N-(4-bromo-1-methoxy-6-phenyl-6H-benzo[c]chromen-8-yl)methanesulfonamide.

7. A compound according to claim 4 selected from the group consisting of (1-difluoromethoxy-6-phenyl-6H-dibenzo(b,d)pyran-8-yl)methanesulfonamide; N-[1-methoxy-6-(3-methylphenyl)-6H-benzo[c]chromen-8-yl]methanesulfonamide;

N-[6-(3,5-dimethylphenyl)-1-methoxy-6H-benzo[c]chromen-8-yl]methanesulfonamide; and N-[1-(difluoromethoxy)-6-(3-fluorophenyl)-6H-benzo[c]chromen-8-yl]methanesulfonamide.

8. A compound according to claim 4 wherein L is a covalent bond.

9. A compound according to claim 4 wherein $R^{11}$ is $-SO_2R^{35}$ and $R^{35}$ is selected from the group consisting of alkyl, alkenyl, aryl and heteroaryl.

10. A compound according to claim 4 wherein $R_3$, $R_4$, $R_7$, $R_8$ and $R_9$ are hydrogen or alkyl.

11. A compound according to claim 1 wherein $R^1$ is heteroaryl, and the heteroaryl is unsubstituted or substituted as set forth therein.

12. A compound according to claim 11 wherein $R^1$ is thienyl.

13. A compound according to claim 12 that is (1-(2-thienyl)-6-phenyl-6H-dibenzo(b,d)pyran-8-yl)-methanesulfonamide.

14. A compound according to claim 11 wherein $R^1$ is furanyl.

15. A compound according to claim 14 that is (1-(2-furanyl)-6-phenyl-6H-dibenzo(b,d)pyran-8-yl)methanesulfonamide.

16. A compound according to claim 1 wherein $R^1$ is alkynyl.

17. A compound according to claim 16 selected from the group consisting of (1-ethynyl-6-phenyl-6H-dibenzo(b,d)pyran-8-yl)methanesulfonamide; and (1-(propyn-1-yl)-6-phenyl-6H-dibenzo(b,d)pyran-8-yl)methanesulfonamide.

18. A compound according to claim 1 wherein $R^1$ is alkenyl.

19. A compound according to claim 18 selected from the group consisting of (1-vinyl-6-phenyl-6H-dibenzo(b,d)pyran-8-yl)methanesulfonamide; and (1-allyl-6-phenyl-6H-dibenzo(b,d)pyran-8-yl)methanesulfonamide.

20. A compound according to claim 1 wherein $R^1$ is alkanoyl.

21. A compound according to claim 20 that is (1-acetyl-6-phenyl-6H-dibenzo(b,d)pyran-8-yl)methanesulfonamide.

22. A compound according to claim 1 wherein $R^1$ is alkenyloxy.

23. A compound according to claim 22 that is

N-[1-(allyloxy)-6-phenyl-6H-benzo[c]chromen-8-yl]methanesulfonamide.

24. A compound according to claim 1 wherein $R^1$ is hydroxyalkyl.

25. A compound according to claim 24 that is

N-[1-(hydroxymethyl)-6-phenyl-6H-benzo[c]chromen-8-yl]methanesulfonamide.

26. A compound according to claim 1 wherein $R^1$ is alkynyloxy.

27. A compound according to claim 26 that is (1-(2-propynyl)oxy-6-phenyl-6H-dibenzo(b,d)pyran-8-yl)methanesulfonamide.

28. A compound according to claim 1 wherein $R^1$ is alkyloxycarbonyl.

29. A compound according to claim 28 that is (1-carbomethoxy-6-phenyl-6H-dibenzo(b,d)pyran-8-yl)methanesulfonamide.

30. A compound according to claim 1 wherein $R^1$ is cyano.

31. A compound according to claim 30 that is (1-cyano-6-phenyl-6H-dibenzo(b,d)pyran-8-yl)methanesulfonamide.

32. A compound according to claim 1 wherein $R^1$ and $R^2$ together are $-X^1-Y^1-Z^1-$ wherein $X^1$ and $Z^1$ are O and $Y^1$ is methylene.

33. A compound according to claim 32 that is (1,2-methylenedioxy-6-phenyl-6H-dibenzo(b,d)pyran-8-yl)methanesulfonamide.

34. A compound according to claim 1 wherein L is a covalent bond.

35. A compound according to claim 1 wherein $R^{10}$ is hydrogen.

36. A compound according to claim 1 wherein $R^{11}$ is $-SO_2R^{35}$.

37. A compound according to claim 1 wherein $R^{10}$ is hydrogen and $R^{11}$ is $SO_2R^{35}$.

38. A compound according to claim 1 wherein $R^3$, $R^4$, $R^7$, $R^8$, and $R^9$ are hydrogen or alkyl.

39. A compound according to claim 1 wherein $R^3$, $R^4$, $R^7$, $R^8$, and $R^9$ are hydrogen or alkyl;

$R^{10}$ is hydrogen and $R^{11}$ is $SO_2R_{35}$.

40. A compound according to claim 1 wherein $R^{11}$ is $-C(O)R^{36}$.

41. A compound according to claim 1 wherein $R^{11}$ is alkyl wherein the alkyl is unsubstituted or substituted as set forth therein.

42. A compound according to claim 41 wherein the alkyl is substituted with a substituent selected from aryl and cycloalkyl.

43. A method of selectively modulating the antagonism effects of the glucocorticoid receptor in a mammal comprising administering an effective amount of a compound of claim 1.

44. A method of treating diabetes in a mammal comprising administering an effective amount of a glucocorticoid receptor antagonist.

45. A method of treating diabetes in a mammal comprising administering an effective amount of a compound of claim 1.

46. A compound selected from the group consisting of (1-methoxy-6-allyl-6H-dibenzo(b,d)pyran-8-yl)methanesulfonamide, (1-methoxy-6-phenyl-6H-dibenzo(b,d)pyran-8-yl)methanesulfonamide, (1-methoxy-6-(3-chlorophenyl)-6H-dibenzo(b,d)pyran-8-yl)methanesulfonamide,
(1-methoxy-6-(3-fluorophenyl)-6H-dibenzo(b,d)pyran-8-yl)methanesulfonamide,
(1-methoxy-6-(3-methoxyphenyl)-6H-dibenzo(b,d)pyran-8-yl)methanesulfonamide,
(1-methoxy-6-(3,4-dimethoxy)phenyl-6H-dibenzo(b,d)pyran-8-yl)methanesulfonamide,
(1-methoxy-6-(5-bromothien-2-yl)-6H-dibenzo(b,d)pyran-8-yl)methanesulfonamide,
(1-difluoromethoxy-6-allyl-6H-dibenzo(b,d)pyran-8-yl)methanesulfonamide,
(1-difluoromethoxy-6-phenyl-6H-dibenzo(b,d)pyran-8-yl)methanesulfonamide,
(1-difluoromethoxy-6-(3-chlorophenyl)-6H-dibenzo(b,d)pyran-8-yl)methanesulfonamide,
(1-difluoromethoxy-6-(3-fluorophenyl)-6H-dibenzo(b,d)pyran-8-yl)methanesulfonamide,
(1-difluoromethoxy-6-(31-methoxyphenyl)-6H-dibenzo(b,d)pyran-8-yl)methanesulfonamide,
(1-difluoromethoxy-6-(3,4-dimethoxy)phenyl-6H-dibenzo(b,d)pyran-8-yl)methanesulfonamide,
(1-difluoromethoxy-6-(5-bromothien-2-yl)-6H-dibenzo(b,d)pyran-8-yl)methanesulfonamide,
(1-trifluoromethyl-6-allyl-6H-dibenzo(b,d)pyran-8-yl)methanesulfonamide,
(1-trifluoromethyl-6-phenyl-6H-dibenzo(b,d)pyran-8-yl)methanesulfonamide,
(1-trifluoromethyl-6-(3-chlorophenyl)-6H-dibenzo(b,d)pyran-8-yl)methanesulfonamide,
(1-trifluoromethyl-6-(3-fluorophenyl)-6H-dibenzo(b,d)pyran-8-yl)methanesulfonamide,
(1-trifluoromethyl-6-(3-methoxyphenyl)-6H-dibenzo(b,d)pyran-8-yl)methanesulfonamide,
(1-trifluoromethyl-6-(3,4-dimethoxy)phenyl-6H-dibenzo(b,d)pyran-8-yl)methanesulfonamide,
(1-trifluoromethyl-6-(5-bromothien-2-yl)-6H-dibenzo(b,d)pyran-8-yl)methanesulfonamide,
(1-trifluoromethoxy-6-allyl-6H-dibenzo(b,d)pyran-8-yl)methanesulfonamide,
(1-trifluoromethoxy-6-phenyl-6H-dibenzo(b,d)pyran-8-yl)methanesulfonamide,
(1-trifluoromethoxy-6-(3-chlorophenyl)-6H-dibenzo(b,d)pyran-8-yl)methanesulfonamide,
(1-trifluoromethoxy-6-(3-fluorophenyl)-6H-dibenzo(b,d)pyran-8-yl)methanesulfonamide,
(1-trifluoromethoxy-6-(3-methoxyphenyl)-6H-dibenzo(b,d)pyran-8-yl)methanesulfonamide,
(1-trifluoromethoxy-6-(3,4-dimethoxy)phenyl-6H-dibenzo(b,d)pyran-8-yl)methanesulfonamide,
(1-trifluoromethoxy-6-(5-bromothien-2-yl)-6H-dibenzo(b,d)pyran-8-yl)methanesulfonamide,
(1-methylthio-6-allyl-6H-dibenzo(b,d)pyran-8-yl)methanesulfonamide,
(1-methylthio-6-phenyl-6H-dibenzo(b,d)pyran-8-yl)methanesulfonamide,
(1-methylthio-6-(31-chlorophenyl)-6H-dibenzo(b,d)pyran-8-yl)methanesulfonamide,
(1-methylthio-6-(3-fluorophenyl)-6H-dibenzo(b,d)pyran-8-yl)methanesulfonamide,
(1-methylthio-6-(3-methoxyphenyl)-6H-dibenzo(b,d)pyran-8-yl)methanesulfonamide,
(1-methylthio-6-(3,4-dimethoxy)phenyl-6H-dibenzo(b,d)pyran-8-yl)methanesulfonamide,
(1-methylthio-6-(5-bromothien-2-yl)-6H-dibenzo(b,d)pyran-8-yl)methanesulfonamide,
(1-ethylthio-6-allyl-6H-dibenzo(b,d)pyran-8-yl)methanesulfonamide,
(1-ethylthio-6-phenyl-6H-dibenzo(b,d)pyran-8-yl)methanesulfonamide,
(1-ethylthio-6-(3-chlorophenyl)-6H-dibenzo(b,d)pyran-8-yl)methanesulfonamide,
(1-ethylthio-6-(3-fluorophenyl)-6H-dibenzo(b,d)pyran-8-yl)methanesulfonamide,
(1-ethylthio-6-(3-methoxyphenyl)-6H-dibenzo(b,d)pyran-8-yl)methanesulfonamide,
(1-ethylthio-6-(3,4-dimethoxy)phenyl-6H-dibenzo(b,d)pyran-8-yl)methanesulfonamide,
(1-ethylthio-6-(5-bromothien-2-yl)-6H-dibenzo(b,d)pyran-8-yl)methanesulfonamide,
(1-trifluoromethylthio-6-allyl-6H-dibenzo(b,d)pyran-8-yl)methanesulfonamide,
(1-trifluoromethylthio-6-phenyl-6H-dibenzo(b,d)pyran-8-yl)methanesulfonamide,
(1-trifluoromethylthio-6-(3-chlorophenyl)-6H-dibenzo(b,d)pyran-8-yl)methanesulfonamide,
(1-trifluoromethylthio-6-(3-fluorophenyl)-6H-dibenzo(b,d)pyran-8-yl)methanesulfonamide,
(1-trifluoromethylthio-6-(3-methoxyphenyl)-6H-dibenzo(b,d)pyran-8-yl)methanesulfonamide,
(1-trifluoromethylthio-6-(3,4-dimethoxy)phenyl-6H-dibenzo(b,d)pyran-8-yl)methanesulfonamide,
(1-trifluoromethylthio-6-(5-bromothien-2-yl)-6H-dibenzo(b,d)pyran-8-yl)methanesulfonamide,
(1-ethoxy-6-allyl-6H-dibenzo(b,d)pyran-8-yl)methanesulfonamide,
(1-ethoxy-6-phenyl-6H-dibenzo(b,d)pyran-8-yl)methanesulfonamide,
(1-ethoxy-6-(3-chlorophenyl)-6H-dibenzo(b,d)pyran-8-yl)methanesulfonamide,
(1-ethoxy-6-(3-fluorophenyl)-6H-dibenzo(b,d)pyran-8-yl)methanesulfonamide,
(1-ethoxy-6-(3-methoxyphenyl)-6H-dibenzo(b,d)pyran-8-yl)methanesulfonamide,
(1-ethoxy-6-(3,4-dimethoxy)phenyl-6H-dibenzo(b,d)pyran-8-yl)methanesulfonamide,
(1-ethoxy-6-(5-bromothien-2-yl)-6H-dibenzo(b,d)pyran-8-yl)methanesulfonamide,
(1-methanesulfinyl-6-allyl-6H-dibenzo(b,d)pyran-8-yl)methanesulfonamide,
(1-methanesulfinyl-6-phenyl-6H-dibenzo(b,d)pyran-8-yl)methanesulfonamide,
(1-methanesulfinyl-6-(3-chlorophenyl)-6H-dibenzo(b,d)pyran-8-yl)methanesulfonamide,
(1-methanesulfinyl-6-(3-fluorophenyl)-6H-dibenzo(b,d)pyran-8-yl)methanesulfonamide,
(1-methanesulfinyl-6-(3-methoxyphenyl)-6H-dibenzo(b,d)pyran-8-yl)methanesulfonamide,
(1-methanesulfinyl-6-(3,4-dimethoxy)phenyl-6H-dibenzo(bed)pyran-8-yl)methanesulfonamide,
(1-methanesulfinyl-6-(5-bromothien-2-yl)-6H-dibenzo(b,d)pyran-8-yl)methanesulfonamide,
(1-methanesulfinyl-6-allyl-6H-dibenzo(b,d)pyran-8-yl)methanesulfonamide, (1-ethanesulfinyl-6-phenyl-6H-dibenzo(b,d)pyran-8-yl)methanesulfonamide,
(1-ethanesulfinyl-6-(3-chlorophenyl)-6H-dibenzo(b,d)pyran-8-yl)methanesulfonamide,
(1-ethanesulfinyl-6-(3-fluorophenyl)-6H-dibenzo(b,d)pyran-8-yl)methanesulfonamide,
(1-ethanesulfinyl-6-(3-methoxyphenyl)-6H-dibenzo(b,d)pyran-8-yl)methanesulfonamide,
(1-ethanesulfinyl-6-(3,4-dimethoxy)phenyl-6H-dibenzo(b,d)pyran-8-yl)methanesulfonamide,
(1-ethanesulfinyl-6-(5-bromothien-2-yl)-6H-dibenzo(b,d)pyran-8-yl)methanesulfonamide,
(1-methanesulfonyl-6-allyl-6H-dibenzo(b,d)pyran-8-yl)methanesulfonamide,
(1-methanesulfonyl-6-phenyl-6H-dibenzo(b,d)pyran-8-yl)methanesulfonamide,
(1-methanesulfonyl-6-(3-chlorophenyl)-6H-dibenzo(b,d)pyran-8-yl)methanesulfonamide,
(1-methanesulfonyl-6-(3-fluorophenyl)-6H-dibenzo(b,d)pyran-8-yl)methanesulfonamide,
(1-methanesulfonyl-6-(3-methoxyphenyl)-6H-dibenzo(b,d)pyran-8-yl)methanesulfonamide,
(1-methanesulfonyl-6-(3,4-dimethoxy)phenyl-6H-dibenzo(b,d)pyran-8-yl)methanesulfonamide,
(1-methanesulfonyl-6-(5-bromothien-2-yl)-6H-dibenzo(b,d)pyran-8-yl)methanesulfonamide,
(1-ethanesulfonyl-6-allyl-6H-dibenzo(b,d)pyran-8-yl)methanesulfonamide,
(1-ethanesulfonyl-6-phenyl-6H-dibenzo(b,d)pyran-8-yl)methanesulfonamide,
(1-ethanesulfonyl-6-(3-chlorophenyl)-6H-dibenzo(b,d)pyran-8-yl)methanesulfonamide,
(1-ethanesulfonyl-6-(3-fluorophenyl)-6H-dibenzo(b,d)pyran-8-yl)methanesulfonamide,
(1-ethanesulfonyl-6-(3-methoxyphenyl)-6H-dibenzo(b,d)pyran-8-yl)methanesulfonamide,
(1-ethanesulfonyl-6-(3,4-dimethoxy)phenyl-6H-dibenzo(b,d)pyran-8-yl)methanesulfonamide,
(1-ethanesulfonyl-6-(5-bromothien-2-yl)-6H-dibenzo(b,d)pyran-8-yl)methanesulfonamide,
(1-bromo-6-allyl-6H-dibenzo(b,d)pyran-8-yl)methanesulfonamide,
(1-bromo-6-phenyl-6H-dibenzo(b,d)pyran-8-yl)methanesulfonamide,
(1-bromo-6-(3-chlorophenyl)-6H-dibenzo(b,d)pyran-8-yl)methanesulfonamide,
(1-bromo-6-(3-fluorophenyl)-6H-dibenzo(b,d)pyran-8-yl)methanesulfonamide,
(1-bromo-6-(3-methoxyphenyl)-6H-dibenzo(b,d)pyran-8-yl)methanesulfonamide,
(1-bromo-6-(3,4-dimethoxy)phenyl-6H-dibenzo(b,d)pyran-8-yl)methanesulfonamide,
(1-bromo-6-(3-dimethoxyphenyl)-6H-dibenzo(b,d)pyran-8-yl)methanesulfonamide,
(1-dimethylamino-6-allyl-6H-dibenzo(b,d)pyran-8-yl)methanesulfonamide,
(1-dimethylamino-6-phenyl-6H-dibenzo(b,d)pyran-8-yl)methanesulfonamide,
(1-dimethylamino-6-(3-chlorophenyl)-6H-dibenzo(b,d)pyran-8-yl)methanesulfonamide,
(1-dimethylamino-6-(3-fluorophenyl)-6H-dibenzo(b,d)pyran-8-yl)methanesulfonamide,
(1-dimethylamino-6-(3-methoxyphenyl)-6H-dibenzo(b,d)pyran-8-yl)methanesulfonamide,
(1-dimethylamino-6-(3,4-dimethoxy)phenyl-6H-dibenzo(b,d)pyran-8-yl)methanesulfonamide,
(1-dimethylamino-6-(-bromothien-2-yl)-6H-dibenzo(b,d)pyran-8-yl)methanesulfonamide,
(1-diethylamino-6-allyl-6H-dibenzo(b,d)pyran-8-yl)methanesulfonamide,
(1-diethylamino-6-phenyl-6H-dibenzo(b,d)pyran-8-yl)methanesulfonamide,
(1-diethylamino-6-(3-chlorophenyl)-6H-dibenzo(bud)pyran-8-yl)methanesulfonamide,
(1-diethylamino-6-(3-fluorophenyl)-6H-dibenzo(b,d)pyran-8-yl)methanesulfonamide,
(1-diethylamino-6-(3-methoxyphenyl)-6H-dibenzo(b,d)pyran-8-yl)methanesulfonamide,
(1-diethylamino-6-(3,4-dimethoxy)phenyl-6H-dibenzo(b,d)pyran-8-yl)methanesulfonamide,
(1-diethylamino-6-(5-bromothien-2-yl)-6H-dibenzo(b,d)pyran-8-yl)methanesulfonamide,
(1-(N-methyl-N-ethylamino)-6-allyl-6H-dibenzo(b,d)pyran-8-yl)methanesulfonamide,
(1-(N-methyl-N-ethylamino)-6-phenyl-6H-dibenzo(b,d)pyran-8-yl)methanesulfonamide,
(1-(N-methyl-N-ethylamino)-6-(3-chlorophenyl)-6H-dibenzo(b,d)pyran-8-yl)methanesulfonamide,
(1-(N-methyl-N-ethylamino)-6-(3-fluorophenyl)-6H-dibenzo(b,d)pyran-8-yl)methanesulfonamide,
(1-(N-methyl-N-ethylamino)-6-(3-methoxyphenyl)-6H-dibenzo(b,d)pyran-8-yl)methanesulfonamide,
(1-(N-methyl-N-ethylamino)-6-(3,4-dimethoxy)phenyl-6H-dibenzo(b,d)pyran-8-yl)methanesulfonamide,
(1-(N-methyl-N-ethylamino)-6-(5-bromothien-2-yl)-6H-dibenzo(b,d)pyran-8-yl)methanesulfonamide,
(1-(2-thienyl)-6-allyl-6H-dibenzo(b,d)pyran-8-yl)methanesulfonamide,
(1-(2-thienyl)-6-phenyl-6H-dibenzo(b,d)pyran-8-yl)methanesulfonamide,
(1-(2-thinyl)-6-(3-chlorophenyl)-6H-dibenzo(b,d)pyran-8-yl)methanesulfonamide,
(1-(2-thienyl)-6-(3-fluorophenyl)-6H-dibenzo(b,d)pyran-8-yl)methanesulfonamide,
(1-(2-thienyl)-6-(3-methoxyphenyl)-6H-dibenzo(b,d)pyran-8-yl)methanesulfonamide,
(1-(2-thienyl)-6-(3,4-dimethoxy)phenyl-6H-dibenzo(b,d)pyran-8-yl)methanesulfonamide,
(1-(2-thienyl)-6-(5-bromothien-2-yl)-6H-dibenzo(b,d)pyran-8-yl)methanesulfonamide,
(1-(2-furanyl)-6-allyl-6H-dibenzo(b,d)pyran-8-yl)methanesulfonamide,
(1-(2-furanyl)-6-phenyl-6H-dibenzo(b,d)pyran-8-yl)methanesulfonamide,
(1-(2-furanyl)-6-(3-chlorophenyl)-6H-dibenzo(b,d)pyran-8-yl)methanesulfonamide,
(1-(2-furanyl)-6-(3-fluorophenyl)-6H-dibenzo(b,d)pyran-8-yl)methanesulfonamide,
(1-(2-furanyl)-6-(3-methoxyphenyl)-6H-dibenzo(b,d)pyran-8-yl)methanesulfonamide,
(1-(2-furanyl)-6-(3,4-dimethoxy)phenyl-6H-dibenzo(b,d)pyran-8-yl)methanesulfonamide,
(1-(2-furanyl)-6-(5-bromothien-2-yl)-6H-dibenzo(b,d)pyran-8-yl)methanesulfonamide, (1-ethynyl-6-allyl-6H-dibenzo(b,d)pyran-8-yl)methanesulfonamide,
(1-ethynyl-6-phenyl-6H-dibenzo(b,d)pyran-8-yl)methanesulfonamide,
(1-ethnyl-6-(3-chlorophenyl)-6H-dibenzo(b,d)pyran-8-yl)methanesulfonamide,
(1-ethynyl-6-(3-fluorophenyl)-6H-dibenzo(b,d)pyran-8-yl)methanesulfonamide,
(1-ethnyl-6-(3-methoxyphenyl)-6H-dibenzo(b,d)pyran-8-yl)methanesulfonamide,
(1-ethynyl-6-(3,4-dimethoxy)phenyl-6H-dibenzo(b,d)pyran-8-yl)methanesulfonamide,
(1-ethynyl-6-(5-bromothien-2-yl)-6H-dibenzo(b,d)pyran-8-yl)methanesulfonamide,
(1-propyn-1-yl-6-allyl-6H-dibenzo(b,d)pyran-8-yl)methanesulfonamide,
(1-propyn-1-yl-6-phenyl-6H-dibenzo(b,d)pyran-8-yl)methanesulfonamide,
(1-propyn-1-yl-6-(3-chlorophenyl)-6H-dibenzo(b,d)pyran-8-yl)methanesulfonamide,
(1-propyn-1-yl-6-(3-fluorophenyl)-6H-dibenzo(b,d)pyran-8-yl)methanesulfonamide,
(1-propyn-1-yl-6-(3-methoxyphenyl)-6H-dibenzo(b,d)pyran-8-yl)methanesulfonamide,
(1-propyn-1-yl-6-(3,4-dimethoxy)phenyl-6H-dibenzo(b,d)pyran-8-yl)methanesulfonamide,
(1-propyn-1-yl-6-(5-bromothien-2-yl)-6H-dibenzo(b,d)pyran-8-yl)methanesulfonamide,
(1-vinyl-6-allyl-6H-dibenzo(b,d)pyran-8-yl)methanesulfonamide,
(1-vinyl-6-phenyl-6H-dibenzo(b,d)pyran-8-yl)methanesulfonamide,
(1-vinyl-6-(3-chlorophenyl)-6H-dibenzo(b,d)pyran-8-yl)methanesulfonamide,
(1-vinyl-6-(3-fluorophenyl)-6H-dibenzo(b,d)pyran-8-yl)methanesulfonamide,
(1-vinyl-6-(3-methoxyphenyl)-6H-dibenzo(b,d)pyran-8-yl)methanesulfonamide,
(1-vinyl-6-(3,4-dimethoxy)phenyl-6H-dibenzo(b,d)pyran-8-yl)methanesulfonamide,
(1-vinyl-6-(5-bromothien-2-yl)-6H-dibenzo(b,d)pyran-8-yl)methanesulfonamide,
(1-(propyn-2-yl)oxy-6-allyl-6H-dibenzo(b,d)pyran-8-yl)methanesulfonamide,
(1-(propyn-2-yl)oxy-6-phenyl-6H-dibenzo(b,d)pyran-8-yl)methanesulfonamide,
(1-(propyn-2-yl)oxy-6-(3-chlorophenyl)-6H-dibenzo(b,d)pyran-8-yl)methanesulfonamide,
(1-(propyn-2-yl)oxy-6-(3-fluorophenyl)-6H-dibenzo(b,d)pyran-8-yl)methanesulfonamide,
(1-(propyn-2-yl)oxy-6-(3-methoxyphenyl)-6H-dibenzo(b,d)pyran-8-yl)methanesulfonamide,
(1-(propyn-2-yl)oxy-6-(3,4-dimethoxy)phenyl-6H-dibenzo(b,d)pyran-8-yl)methanesulfonamide,
(1-(propyn-2-yl)oxy-6-(-bromothien-2-yl)-6H-dibenzo(b,d)pyran-8-yl)methanesulfonamide,
(1-cyano-6-allyl-6H-dibenzo(b,d)pyran-8-yl)methanesulfonamide,
(1-cyano-6-phenyl-6H-dibenzo(b,d)pyran-8-yl)methanesulfonamide,
(1-cyano-6-(3-chlorophenyl)-6H-dibenzo(b,d)pyran-8-yl)methanesulfonamide,
(1-cyano-6-(3-fluorophenyl)-6H-dibenzo(b,d)pyran-8-yl)methanesulfonamide,
(1-cyano-6-(3-methoxyphenyl)-6H-dibenzo(b,d)pyran-8-yl)methanesulfonamide,
(1-cyano-6-(3,4-dimethoxyphenyl)-6H-dibenzo(b,d)pyran-8-yl)methanesulfonamide,
(1-hydroxymethyl-6-allyl-6H-dibenzo(b,d)pyran-8-yl)methanesulfonamide,
(1-hydroxymethyl-6-phenyl-6H-dibenzo(b,d)pyran-8-yl)methanesulfonamide,
(1-hydroxymethyl-6-(3-chlorophenyl)-6H-dibenzo(b,d)pyran-8-yl)methanesulfonamide,
(1-hydroxymethyl-6-(3-fluorophenyl)-6H-dibenzo(b,d)pyran-8-yl)methanesulfonamide,
(1-hydroxymethyl-6-(3-methoxyphenyl)-6H-dibenzo(b,d)pyran-8-yl)methanesulfonamide,
(1-hydroxymethyl-6-(3,4-dimethoxy)phenyl-6H-dibenzo(b,d)pyran-8-yl)methanesulfonamide,
(1-hydroxymethyl-6-(5-bromothien-2-yl)-6H-dibenzo(b,d)pyran-8-yl)methanesulfonamide,
(1-formyl-6-allyl-6H-dibenzo(b,d)pyran-8-yl)methanesulfonamide,
(1-formyl-6-phenyl-6H-dibenzo(b,d)pyran-8-yl)methanesulfonamide,
(1-formyl-6-(3-chlorophenyl)-6H-dibenzo(b,d)pyran-8-yl)methanesulfonamide,
(1-formyl-6-(3-fluorophenyl)-6H-dibenzo(b,d)pyran-8-yl)methanesulfonamide,
(1-formyl-6-(3-methoxyphenyl)-6H-dibenzo(b,d)pyran-8-yl)methanesulfonamide,
(1-formyl-6-(3,4-dimethoxy)phenyl-6H-dibenzo(b,d)pyran-8-yl)methanesulfonamide,
(1-formyl-6-(5-bromothien-2-yl)-6H-dibenzo(b,d)pyran-8-yl)methanesulfonamide,
(1-formaldoximino-6-allyl-6H-dibenzo(b,d)pyran-8-yl)methanesulfonamide,
(1-formaldoximino-6-phenyl-6H-dibenzo(b,d)pyran-8-yl)methanesulfonamide,
(1-formaldoximino-6-(3-chlorophenyl)-6H-dibenzo(b,d)pyran-8-yl)methanesulfonamide,
(1-formaldoximino-6-(3-fluorophenyl)-6H-dibenzo(b,d)pyran-8-yl)methanesulfonamide,
(1-formaldoximino-6-(3-methoxyphenyl)-6H-dibenzo(b,d)pyran-8-yl)methanesulfonamide,
(1-formaldoximino-6-(3,4-dimethoxy)phenyl-6H-dibenzo(b,d)pyran-8-yl)methanesulfonamide,
(1-formaldoximino-6-(5-bromothien-2-yl)-6H-dibenzo(b,d)pyran-8-yl)methanesulfonamide,
(1-methoxymethyl-6-allyl-6H-dibenzo(b,d)pyran-8-yl)methanesulfonamide,
(1-methoxymethyl-6-phenyl-6H-dibenzo(b,d)pyran-8-yl)methanesulfonamide,
(1-methoxymethyl-6-(3-chlorophenyl)-6H-dibenzo(b,d)pyran-8-yl)methanesulfonamide,
(1-methoxymethyl-6-(3-fluorophenyl)-6H-dibenzo(b,d)pyran-8-yl)methanesulfonamide,
(1-methoxymethyl-6-(3-methoxyphenyl)-6H-dibenzo(b,d)pyran-8-yl)methanesulfonamide,
(1-methoxymethyl-6-(3,4-dimethoxy)phenyl-6H-dibenzo(b,d)pyran-8-yl)methanesulfonamide,
(1-methoxymethyl-6-(5-bromothien-2-yl)-6H-dibenzo(b,d)pyran-8-yl)methanesulfonamide, (1-chloro-6-allyl-6H-dibenzo(b,d)pyran-8-yl)methanesulfonamide,
(1-chloro-6-phenyl-6H-dibenzo(b,d)pyran-8-yl)methanesulfonamide,
(1-chloro-6-(3-chlorophenyl)-6H-dibenzo(b,d)pyran-8-yl)methanesulfonamide,
(1-chloro-6-(3-fluorophenyl)-6H-dibenzo(b,d)pyran-8-yl)methanesulfonamide,
(1-chloro-6-(3-methoxyphenyl)-6H-dibenzo(b,d)pyran-8-yl)methanesulfonamide,
(1-chloro-6-(3,4-dimethoxy)phenyl-6H-dibenzo(b,d)pyran-8-yl)methanesulfonamide,
(1-chloro-6-(5-bromothien-2-yl)-6H-dibenzo(b,d)pyran-8-yl)methanesulfonamide,
(1-ethyl-6-allyl-6H-dibenzo(b,d)pyran-8-yl)methanesulfonamide,
(1-ethyl-6-phenyl-6H-dibenzo(b,d)pyran-8-yl)methanesulfonamide,
(1-ethyl-6-(3-chlorophenyl)-6H-dibenzo(b,d)pyran-8-yl)methanesulfonamide,
(1-ethyl-6-(3-fluorophenyl)-6H-dibenzo(b,d)pyran-8-yl)methanesulfonamide,
(1-ethyl-6-(3-methoxyphenyl)-6H-dibenzo(b,d)pyran-8-yl)methanesulfonamide,
(1-ethyl-6-(3,4-dimethoxy)phenyl-6H-dibenzo(b,d)pyran-8-yl)methanesulfonamide,
(1–1-ethyl-6-(5-bromothien-2-yl)-6H-dibenzo(b,d)pyran-8-yl)methanesulfonamide,
(1-methoxy-2-hydroxy-6-allyl-6H-dibenzo(b,d)pyran-8-yl)methanesulfonamide,
(1-methoxy-2-hydroxy-6-phenyl-6H-dibenzo(b,d)pyran-8-yl)methanesulfonamide,
(1-methoxy-2-hydroxy-6-(3-chlorophenyl)-6H-dibenzo(b,d)pyran-8-yl)methanesulfonamide,
(1-methoxy-2-hydroxy-6-(3-fluorophenyl)-6H-dibenzo(b,d)pyran-8-yl)methanesulfonamide,
(1-methoxy-2-hydroxy-6-(3-methoxyphenyl)-6H-dibenzo(b,d)pyran-8-yl)methanesulfonamide,
(1-methoxy-2-hydroxy-6-(3,4-dimethoxy)phenyl-6H-dibenzo(b,d)pyran-8-yl)methanesulfonamide,
(1-methoxy-2-hydroxy-6-(5-bromothien-2-yl)-6H-dibenzo(b,d)pyran-8-yl)methanesulfonamide,
(1-methoxy-2-chloro-6-allyl-6H-dibenzo(b,d)pyran-8-yl)methanesulfonamide,
(1-methoxy-2-chloro-6-phenyl-6H-dibenzo(b,d)pyran-8-yl)methanesulfonamide,
(1-methoxy-2-chloro-6-(3-chlorophenyl)-6H-dibenzo(b,d)pyran-8-yl)methanesulfonamide,
(1-methoxy-2-chloro-6-(3-fluorophenyl)-6H-dibenzo(b,d)pyran-8-yl)methanesulfonamide,
(1-methoxy-2-chloro-6-(3-methoxyphenyl)-6H-dibenzo(b,d)pyran-8-yl)methanesulfonamide,
(1-methoxy-2-chloro-6-(3,4-dimethoxy)phenyl-6H-dibenzo(b,d)pyran-8-yl)methanesulfonamide,
(1-methoxy-2-chloro-6-(5-bromothien-2-yl)-6H-dibenzo(b,d)pyran-8-yl)methanesulfonamide,
(1-methoxy-2-bromo-6-allyl-6H-dibenzo(b,d)pyran-8-yl)methanesulfonamide,
(1-methoxy-2-bromo-6-phenyl-6H-dibenzo(b,d)pyran-8-yl)methanesulfonamide,
(1-methoxy-2-bromo-6-(3-chlorophenyl)-6H-dibenzo(b,d)pyran-8-yl)methanesulfonamide,
(1-methoxy-2-bromo-6-(3-fluorophenyl)-6H-dibenzo(b,d)pyran-8-yl)methanesulfonamide,
(1-methoxy-2-bromo-6-(3-methoxyphenyl)-6H-dibenzo(b,d)pyran-8-yl)methanesulfonamide,
(1-methoxy-2-bromo-6-(3,4-dimethoxy)phenyl-6H-dibenzo(b,d)pyran-8-yl)methanesulfonamide,
(1-methoxy-2-bromo-6-(5-bromothien-2-yl)-6H-dibenzo(b,d)pyran-8-yl)methanesulfonamide,
(1-methoxy-2-fluoro-6-allyl-6H-dibenzo(b,d)pyran-8-yl)methanesulfonamide,
(1-methoxy-2-fluoro-6-phenyl-6H-dibenzo(bud)pyran-8-yl)methanesulfonamide,
(1-methoxy-2-fluoro-6-(3-chlorophenyl)-6H-dibenzo(b,d)pyran-8-yl)methanesulfonamide,
(1-methoxy-2-fluoro-6-(3-fluorophenyl)-6H-dibenzo(b,d)pyran-8-yl)methanesulfonamide,
(1-methoxy-2-fluoro-6-(3-methoxyphenyl)-6H-dibenzo(b,d)pyran-8-yl)methanesulfonamide,
(1-methoxy-2-fluoro-6-(3,4-dimethoxy)phenyl-6H-dibenzo(b,d)pyran-8-yl)methanesulfonamide,
(1-methoxy-2-fluoro-6-(5-bromothien-2-yl)-6H-dibenzo(b,d)pyran-8-yl)methanesulfonamide,
(1-methoxy-2-methyl-6-allyl-6H-dibenzo(b,d)pyran-8-yl)methanesulfonamide,
(1-methoxy-2-methyl-6-phenyl-6H-dibenzo(b,d)pyran-8-yl)methanesulfonamide,
(1-methoxy-2-methyl-6-(3-chlorophenyl)-6H-dibenzo(b,d)pyran-8-yl)methanesulfonamide,
(1-methoxy-2-methyl-6-(3-fluorophenyl)-6H-dibenzo(b,d)pyran-8-yl)methanesulfonamide,
(1-methoxy-2-methyl-6-(3-methoxyphenyl)-6H-dibenzo(b,d)pyran-8-yl)methanesulfonamide,
(1-methoxy-2-methyl-6-(3,4-dimethoxy)phenyl-6H-dibenzo(b,d)pyran-8-yl)methanesulfonamide,
(1-methoxy-2-methyl-6-(5-bromothien-2-yl)-6H-dibenzo(b,d)pyran-8-yl)methanesulfonamide,
(1-methoxy-2-allyloxy-6-allyl-6H-dibenzo(b,d)pyran-8-yl)methanesulfonamide,
(1-methoxy-2-allyloxy-6-phenyl-6H-dibenzo(b,d)pyran-8-yl)methanesulfonamide,
(1-methoxy-2-allyloxy-6-(3-chlorophenyl)-6H-dibenzo(b,d)pyran-8-yl)methanesulfonamide,
(1-methoxy-2-allyloxy-6-(3-fluorophenyl)-6H-dibenzo(b,d)pyran-8-yl)methanesulfonamide,
(1-methoxy-2-allyloxy-6-(3-methoxyphenyl)-6H-dibenzo(b,d)pyran-8-yl)methanesulfonamide,
(1-methoxy-2-allyloxy-6-(3,4-dimethoxy)phenyl-6H-dibenzo(b,d)pyran-8-yl)methanesulfonamide,
(1-methoxy-2-allyloxy-6-(5-bromothien-2-yl)-6H-dibenzo(b,d)pyran-8-yl)methanesulfonamide,
(1-methoxy-2-(2-allyloxy)ethoxy-6-allyl-6H-dibenzo(b,d)pyran-8-yl)methanesulfonamide,
(1-methoxy-2-(2-allyloxy)ethoxy-6-phenyl-6H-dibenzo(b,d)pyran-8-yl)methanesulfonamide,
(1-methoxy-2-(2-allyloxy)ethoxy-6-(3-chlorophenyl)-6H-dibenzo(b,d)pyran-8-yl)methanesulfonamide,
(1-methoxy-2-(2-allyloxy)ethoxy-6-(3-fluorophenyl)-6H-dibenzo(b,d)pyran-8-yl)methanesulfonamide,
(1-methoxy-2-(2-allyloxy)ethoxy-6-(3-methoxyphenyl)-6H-dibenzo(b,d)pyran-8-yl)methanesulfonamide,
(1-methoxy-2-(2-allyloxy)ethoxy-6-(3,4-dimethoxy)phenyl-6H-dibenzo(b,d)pyran-8-yl)methanesulfonamide, (1-methoxy-2-(2-allyloxy)ethoxy-6-(5-bromothien-2-yl)-6H-dibenzo(b,d)pyran-8-yl)methanesulfonamide,
(1-methoxy-2-(2-(2-methoxyethoxy)ethoxy)-6-allyl-6H-dibenzo(b,d)pyran-8-yl)methanesulfonamide,
(1-methoxy-2-(2-(2-methoxyethoxy)ethoxy)-6-phenyl-6H-dibenzo(b,d)pyran-8-yl)methanesulfonamide,
(1-methoxy-2-(2-(2-methoxyethoxy)ethoxy)-6-phenyl-6H-dibenzo(b,d)pyran-8-yl)methanesulfonamide,
(1-methoxy-2-(2-(2-methoxyethoxy)ethoxy)-6-(3-fluorophenyl)-6H-dibenzo(b,d)pyran-8-yl)methanesulfonamide,
(1-methoxy-2-(2-(2-methoxyethoxy)ethoxy)-6-(3-methoxyphenyl)-6H-dibenzo(b,d)pyran-8-yl)methanesulfonamide,
(1-methoxy-2-(2-(2-methoxyethoxy)ethoxy)-6-(3,4-dimethoxy)phenyl-6H-dibenzo(b,d)pyran-8-yl)methanesulfonamide,
(1-methoxy-2-(2-(2-methoxyethoxy)ethoxy)-6-(5-bromothien-2-yl)-6H-dibenzo(b,d)pyran-8-yl)methanesulfonamide,
(1-difluoromethoxy-2-hydroxy-6-allyl-6H-dibenzo(b,d)pyran-8-yl)methanesulfonamide,
(1-difluoromethoxy-2-hydroxy-6-phenyl-6H-dibenzo(b,d)pyran-8-yl)methanesulfonamide,
(1-difluoromethoxy-2-hydroxy-6-(3-chlorophenyl)-6H-dibenzo(b,d)pyran-8-yl)methanesulfonamide,
(1-difluoromethoxy-2-hydroxy-6-(3-fluorophenyl)-6H-dibenzo(b,d)pyran-8-yl)methanesulfonamide,
(1-difluoromethoxy-2-hydroxy-6-(3-methoxyphenyl)-6H-dibenzo(b,d)pyran-8-yl)methanesulfonamide,
(1-difluoromethoxy-2-hydroxy-6-(3,4-dimethoxy)phenyl-6H-dibenzo(b,d)pyran-8-yl)methanesulfonamide,
(1-difluoromethoxy-2-hydroxy-6-(5-bromothien-2-yl)-6H-dibenzo(b,d)pyran-8-yl)methanesulfonamide,
(1-difluoromethoxy-2-chloro-6-allyl-6H-dibenzo(b,d)pyran-8-yl)methanesulfonamide,
(1-difluoromethoxy-2-chloro-6-phenyl-6H-dibenzo(b,d)pyran-8-yl)methanesulfonamide,
(1-difluoromethoxy-2-chloro-6-(3-chlorophenyl)-6H-dibenzo(b,d)pyran-8-yl)methanesulfonamide,
(1-difluoromethoxy-2-chloro-6-(3-fluorophenyl)-6H-dibenzo(b,d)pyran-8-yl)methanesulfonamide,
(1-difluoromethoxy-2-chloro-6-(3-methoxyphenyl)-6H-dibenzo(b,d)pyran-8-yl)methanesulfonamide,
(1-difluoromethoxy-2-chloro-6-(3,4-dimethoxy)phenyl-6H-dibenzo(b,d)pyran-8-yl)methanesulfonamide,
(1-difluoromethoxy-2-chloro-6-(5-bromothien-2-yl)-6H-dibenzo(b,d)pyran-8-yl)methanesulfonamide,
(1-difluoromethoxy-2-bromo-6-allyl-6H-dibenzo(b,d)pyran-8-yl)methanesulfonamide,
(1-difluoromethoxy-2-bromo-6-phenyl-6H-dibenzo(b,d)pyran-8-yl)methanesulfonamide,
(1-difluoromethoxy-2-bromo-6-(3-chlorophenyl)-6H-dibenzo(b,d)pyran-8-yl)methanesulfonamide,
(1-difluoromethoxy-2-bromo-6-(3-fluorophenyl)-6H-dibenzo(b,d)pyran-8-yl)methanesulfonamide,
(1-difluoromethoxy-2-bromo-6-(3-methoxyphenyl)-6H-dibenzo(b,d)pyran-8-yl)methanesulfonamide,
(1-difluoromethoxy-2-bromo-6-(3,4-dimethoxy)phenyl-6H-dibenzo(b,d)pyran-8-yl)methanesulfonamide,
(1-difluoromethoxy-2-bromo-6-(5-bromothien-2-yl)-6H-dibenzo(b,d)pyran-8-yl)methanesulfonamide,
(1-difluoromethoxy-2-fluoro-6-allyl-6H-dibenzo(b,d)pyran-8-yl)methanesulfonamide,
(1-difluoromethoxy-2-fluoro-6-phenyl-6H-dibenzo(bud)pyran-8-yl)methanesulfonamide,
(1-difluoromethoxy-2-fluoro-6-(3-chlorophenyl)-6H-dibenzo(b,d)pyran-8-yl)methanesulfonamide,
(1-difluoromethoxy-2-fluoro-6-(3-fluorophenyl)-6H-dibenzo(b,d)pyran-8-yl)methanesulfonamide,
(1-difluoromethoxy-2-fluoro-6-(3-methoxyphenyl)-6H-dibenzo(b,d)pyran-8-yl)methanesulfonamide,
(1-difluoromethoxy-2-fluoro-6-(3,4-dimethoxy)phenyl-6H-dibenzo(b,d)pyran-8-yl)methanesulfonamide,
(1-difluoromethoxy-2-fluoro-6-(5-bromothien-2-yl)-6H-dibenzo(b,d)pyran-8-yl)methanesulfonamide,
(1-difluoromethoxy-2-methyl-6-allyl-6H-dibenzo(b,d)pyran-8-yl)methanesulfonamide,
(1-difluoromethoxy-2-methyl-6-phenyl-6H-dibenzo(b,d)pyran-8-yl)methanesulfonamide,
(1-difluoromethoxy-2-methyl-6-(3-chlorophenyl)-6H-dibenzo(b,d)pyran-8-yl)methanesulfonamide,
(1-difluoromethoxy-2-methyl-6-(3-fluorophenyl)-6H-dibenzo(b,d)pyran-8-yl)methanesulfonamide,
(1-difluoromethoxy-2-methyl-6-(3-methoxyphenyl)-6H-dibenzo(b,d)pyran-8-yl)methanesulfonamide,
(1-difluoromethoxy-2-methyl-6-(3,4-dimethoxy)phenyl-6H-dibenzo(b,d)pyran-8-yl)methanesulfonamide,
(1-difluoromethoxy-2-methyl-6-(5-bromothien-2-yl)-6H-dibenzo(b,d)pyran-8-yl)methanesulfonamide,
(1-difluoromethoxy-2-allyloxy-6-allyl-6H-dibenzo(b,d)pyran-8-yl)methanesulfonamide,
(1-difluoromethoxy-2-allyloxy-6-phenyl-6H-dibenzo(b,d)pyran-8-yl)methanesulfonamide,
(1-difluoromethoxy-2-allyloxy-6-(3-chlorophenyl)-6H-dibenzo(b,d)pyran-8-yl)methanesulfonamide,
(1-difluoromethoxy-2-allyloxy-6-(3-fluorophenyl)-6H-dibenzo(b,d)pyran-8-yl)methanesulfonamide,
(1-difluoromethoxy-2-allyloxy-6-(3-methoxyphenyl)-6H-dibenzo(b,d)pyran-8-yl)methanesulfonamide,
(1-difluoromethoxy-2-allyloxy-6-(3,4-dimethoxy)phenyl-6H-dibenzo(b,d)pyran-8-yl)methanesulfonamide,
(1-difluoromethoxy-2-allyloxy-6-(5-bromothien-2-yl)-6H-dibenzo(b,d)pyran-8-yl)methanesulfonamide,
(1-difluoromethoxy-2-(2-allyloxy)ethoxy-6-allyl-6H-dibenzo(b,d)pyran-8-yl)methanesulfonamide,
(1-difluoromethoxy-2-(2-allyloxy)ethoxy-6-phenyl-6H-dibenzo(b,d)pyran-8-yl)methanesulfonamide,
(1-difluoromethoxy-2-(2-allyloxy)ethoxy-6-(3-chlorophenyl)-6H-dibenzo(b,d)pyran-8-yl)methanesulfonamide,
(1-difluoromethoxy-2-(2-allyloxy)ethoxy-6-(3-fluorophenyl)-6H-dibenzo(b,d)pyran-8-yl)methanesulfonamide,
(1-difluoromethoxy-2-(2-allyloxy)ethoxy-6-(3-methoxyphenyl)-6H-dibenzo(b,d)pyran-8-yl)methanesulfonamide,
(1-difluoromethoxy-2-(2-allyloxy)ethoxy-6-(3,4-dimethoxy)phenyl-6H-dibenzo(b,d)pyran-8-yl)methanesulfonamide,
(1-difluoromethoxy-2-(2-allyloxy)ethoxy-6-(5-bromothien-2-yl)-6H-dibenzo(b,d)pyran-8-yl)methanesulfonamide, (1-difluoromethoxy-2-(2-(2-methoxyethoxy)ethoxy)-6-allyl-6H-dibenzo(b,d)pyran-8-yl)methanesulfonamide,
(1-difluoromethoxy-2-(2-(2-methoxyethoxy)ethoxy)-6-phenyl-6H-dibenzo(b,d)pyran-8-yl)methanesulfonamide,
(1-difluoromethoxy-2-(2-(2-methoxyethoxy)ethoxy)-6-(3-chlorophenyl)-6H-dibenzo(b,d)pyran-8-yl)methanesulfonamide,
(1-difluoromethoxy-2-(2-(2-methoxyethoxy)ethoxy)-6-(3-fluorophenyl)-6H-dibenzo(b,d)pyran-8-yl)methanesulfonamide,
(1-difluoromethoxy-2-(2-(2-methoxyethoxy)ethoxy)-6-(3-methoxyphenyl)-6H-dibenzo(b,d)pyran-8-yl)methanesulfonamide,
(1-difluoromethoxy-2-(2-(2-methoxyethoxy)ethoxy)-6-(3,4-dimethoxy)phenyl-6H-dibenzo(b,d)pyran-8-yl)methanesulfonamide,
(1-difluoromethoxy-2-(2-(2-methoxyethoxy)ethoxy)-6-(5-bromothien-2-yl)-6H-dibenzo(b,d)pyran-8-yl)methanesulfonamide,
(1-methoxy-3-bromo-6-allyl-6H-dibenzo(b,d)pyran-8-yl)methanesulfonamide,
(1-methoxy-3-bromo-6-phenyl-6H-dibenzo(b,d)pyran-8-yl)methanesulfonamide,
(1-methoxy-3-bromo-6-(3-chlorophenyl)-6H-dibenzo(b,d)pyran-8-yl)methanesulfonamide,
(1-methoxy-3-bromo-6-(3-fluorophenyl)-6H-dibenzo(b,d)pyran-8-yl)methanesulfonamide,
(1-methoxy-3-bromo-6-(3-methoxyphenyl)-6H-dibenzo(b,d)pyran-8-yl)methanesulfonamide,
(1-methoxy-3-bromo-6-(3,4-dimethoxy)phenyl-6H-dibenzo(b,d)pyran-8-yl)methanesulfonamide,
(1-methoxy-3-bromo-6-(5-bromothien-2-yl)-6H-dibenzo(b,d)pyran-8-yl)methanesulfonamide,
(1-methoxy-3-chloro-6-allyl-6H-dibenzo(b,d)pyran-8-yl)methanesulfonamide,
(1-methoxy-3-chloro-6-phenyl-6H-dibenzo(b,d)pyran-8-yl)methanesulfonamide,
(1-methoxy-3-chloro-6-(3-chlorophenyl)-6H-dibenzo(b,d)pyran-8-yl)methanesulfonamide,
(1-methoxy-3-chloro-6-(3-fluorophenyl)-6H-dibenzo(b,d)pyran-8-yl)methanesulfonamide,
(1-methoxy-3-chloro-6-(3-methoxyphenyl)-6H-dibenzo(b,d)pyran-8-yl)methanesulfonamide,
(1-methoxy-3-chloro-6-(3,4-dimethoxy)phenyl-6H-dibenzo(b,d)pyran-8-yl)methanesulfonamide,
(1-methoxy-3-chloro-6-(5-bromothien-2-yl)-6H-dibenzo(b,d)pyran-8-yl)methanesulfonamide,
(1-methoxy-3-fluoro-6-allyl-6H-dibenzo(b,d)pyran-8-yl)methanesulfonamide,
(1-methoxy-3-fluoro-6-phenyl-6H-dibenzo(b,d)pyran-8-yl)methanesulfonamide,
(1-methoxy-3-fluoro-6-(3-chlorophenyl)-6H-dibenzo(b,d)pyran-8-yl)methanesulfonamide,
(1-methoxy-3-fluoro-6-(3-fluorophenyl)-6H-dibenzo(b,d)pyran-8-yl)methanesulfonamide,
(1-methoxy-3-fluoro-6-(3-methoxyphenyl)-6H-dibenzo(b,d)pyran-8-yl)methanesulfonamide,
(1-methoxy-3-fluoro-6-(3,4-dimethoxy)phenyl-6H-dibenzo(b,d)pyran-8-yl)methanesulfonamide,
(1-methoxy-3-fluoro-6-(5-bromothien-2-yl)-6H-dibenzo(b,d)pyran-8-yl)methanesulfonamide,
(1-methoxy-3-methyl-6-allyl-6H-dibenzo(b,d)pyran-8-yl)methanesulfonamide,
(1-methoxy-3-methyl-6-phenyl-6H-dibenzo(b,d)pyran-8-yl)methanesulfonamide,
(1-methoxy-3-methyl-6-ethynyl)-6H-dibenzo(b,d)pyran-8-yl)methanesulfonamide,
(1-methoxy-3-methyl-6-(3-fluorophenyl)-6H-dibenzo(b,d)pyran-8-yl)methanesulfonamide,
(1-methoxy-3-methyl-6-(3-methoxyphenyl)-6H-dibenzo(b,d)pyran-8-yl)methanesulfonamide,
(1-methoxy-3-methyl-6-(3,4-dimethoxy)phenyl-6H-dibenzo(b,d)pyran-8-yl)methanesulfonamide,
(1-methoxy-3-methyl-6-(5-bromothien-2-yl)-6H-dibenzo(b,d)pyran-8-yl)methanesulfonamide,
(1-difluoromethoxy-3-bromo-6-allyl-6H-dibenzo(b,d)pyran-9-yl)methanesulfonamide,
(1-difluoromethoxy-3-bromo-6-phenyl-6H-dibenzo(b,d)pyran-8-yl)methanesulfonamide,
(1-difluoromethoxy-3-bromo-6-(3-chlorophenyl)-6H-dibenzo(b,d)pyran-8-yl)methanesulfonamide,
(1-difluoromethoxy-3-bromo-6-(3-fluorophenyl)-6H-dibenzo(b,d)pyran-8-yl)methanesulfonamide,
(1-difluoromethoxy-3-bromo-6-(3-methoxyphenyl)-6H-dibenzo(b,d)pyran-8-yl)methanesulfonamide,
(1-difluoromethoxy-3-bromo-6-(3,4-dimethoxy)phenyl-6H-dibenzo(b,d)pyran-8-yl)methanesulfonamide,
(1-difluoromethoxy-3-bromo-6-(5-bromothien-2-yl)-6H-dibenzo(b,d)pyran-8-yl)methanesulfonamide,
(1-difluoromethoxy-3-chloro-6-allyl-6H-dibenzo(b,d)pyran-8-yl)methanesulfonamide,
(1-difluoromethoxy-3-chloro-6-phenyl-6H-dibenzo(b,d)pyran-8-yl)methanesulfonamide,
(1-difluoromethoxy-3-chloro-6-(3-chlorophenyl)-6H-dibenzo(b,d)pyran-8-yl)methanesulfonamide,
(1-difluoromethoxy-3-chloro-6-(3-fluorophenyl)-6H-dibenzo(b,d)pyran-8-yl)methanesulfonamide,
(1-difluoromethoxy-3-chloro-6-(3-methoxyphenyl)-6H-dibenzo(b,d)pyran-8-yl)methanesulfonamide,
(1-difluoromethoxy-3-chloro-6-(3,4-dimethoxy)phenyl-6H-dibenzo(b,d)pyran-8-yl)methanesulfonamide,
(1-difluoromethoxy-3-chloro-6-(5-bromothien-2-yl)-6H-dibenzo(b,d)pyran-8-yl)methanesulfonamide,
(1-difluoromethoxy-3-fluoro-6-allyl-6H-dibenzo(b,d)pyran-8-yl)methanesulfonamide,
(1-difluoromethoxy-3-fluoro-6-phenyl-6H-dibenzo(b,d)pyran-8-yl)methanesulfonamide,
(1-difluoromethoxy-3-fluoro-6-(3-chlorophenyl)-6H-dibenzo(b,d)pyran-8-yl)methanesulfonamide,
(1-difluoromethoxy-3-fluoro-6-(3-fluorophenyl)-6H-dibenzo(b,d)pyran-8-yl)methanesulfonamide,
(1-difluoromethoxy-3-fluoro-6-(3-methoxyphenyl)-6H-dibenzo(b,d)pyran-8-yl)methanesulfonamide,
(1-difluoromethoxy-3-fluoro-6-(3,4-dimethoxy)phenyl-6H-dibenzo(b,d)pyran-8-yl)methanesulfonamide,
(1-difluoromethoxy-3-fluoro-6-(5-bromothien-2-yl)-6H-dibenzo(b,d)pyran-8-yl)methanesulfonamide,
(1-difluoromethoxy-3-methyl-6-allyl-6H-dibenzo(b,d)pyran-8-yl)methanesulfonamide,
(1-difluoromethoxy-3-methyl-6-phenyl-6H-dibenzo(b,d)pyran-8-yl)methanesulfonamide,
(1-difluoromethoxy-3-methyl-6-(3-chlorophenyl)-6H-dibenzo(b,d)pyran-8-yl)methanesulfonamide, (1-difluoromethoxy-3-methyl-6-(3-fluorophenyl)-6H-dibenzo(b,d)pyran-8-yl)methanesulfonamide,
(1-difluoromethoxy-3-methyl-6-(3-methoxyphenyl)-6H-dibenzo(b,d)pyran-8-yl)methanesulfonamide,
(1-difluoromethoxy-3-methyl-6-(3,4-dimethoxy)phenyl-6H-dibenzo(b,d)pyran-8-yl)methanesulfonamide,
(1-difluoromethoxy-3-methyl-6-(5-bromothien-2-yl)-6H-dibenzo(b,d)pyran-8-yl)methanesulfonamide,
(1-methoxy-3-bromo-6-allyl-6H-dibenzo(b,d)pyran-8-yl)methanesulfonamide,
(1-methoxy-3-bromo-6-phenyl-6H-dibenzo(b,d)pyran-8-yl)methanesulfonamide,
(1-methoxy-3-bromo-6-(3-chlorophenyl)-6H-dibenzo(bud)pyran-8-yl)methanesulfonamide,
(1-methoxy-3-bromo-6-(3-fluorophenyl)-6H-dibenzo(b,d)pyran-8-yl)methanesulfonamide,
(1-methoxy-3-bromo-6-(3-methoxyphenyl)-6H-dibenzo(b,d)pyran-8-yl)methanesulfonamide,
(1-methoxy-3-bromo-6-(3,4-dimethoxy)phenyl-6H-dibenzo(b,d)pyran-8-yl)methanesulfonamide,
(1-methoxy-3-bromo-6-(5-bromothien-2-yl)-6H-dibenzo(b,d)pyran-8-yl)methanesulfonamide,
(1-methoxy-3-chloro-6-allyl-6H-dibenzo(b,d)pyran-8-yl)methanesulfonamide,
(1-methoxy-3-chloro-6-phenyl-6H-dibenzo(b,d)pyran-8-yl)methanesulfonamide,
(1-methoxy-3-chloro-6-(3-chlorophenyl)-6H-dibenzo(b,d)pyran-8-yl)methanesulfonamide,
(1-methoxy-3-chloro-6-(3-fluorophenyl)-6H-dibenzo(b,d)pyran-8-yl)methanesulfonamide,
(1-methoxy-3-chloro-6-(3-methoxyphenyl)-6H-dibenzo(b,d)pyran-8-yl)methanesulfonamide,
(1-methoxy-3-chloro-6-(3,4-dimethoxy)phenyl-6H-dibenzo(b,d)pyran-8-yl)methanesulfonamide,
(1-methoxy-3-chloro-6-(5-bromothien-2-yl)-6H-dibenzo(b,d)pyran-8-yl)methanesulfonamide,
(1-methoxy-3-fluoro-6-allyl-6H-dibenzo(b,d)pyran-9-yl)methanesulfonamide,
(1-methoxy-3-fluoro-6-phenyl-6H-dibenzo(b,d)pyran-8-yl)methanesulfonamide,
(1-methoxy-3-fluoro-6-(3-chlorophenyl)-6H-dibenzo(b,d)pyran-8-yl)methanesulfonamide,
(1-methoxy-3-fluoro-6-(3-fluorophenyl)-6H-dibenzo(b,d)pyran-8-yl)methanesulfonamide,
(1-methoxy-3-fluoro-6-(3-methoxyphenyl)-6H-dibenzo(b,d)pyran-8-yl)methanesulfonamide,
(1-methoxy-3-fluoro-6-(3,4-dimethoxy)phenyl-6H-dibenzo(b,d)pyran-8-yl)methanesulfonamide,
(1-methoxy-3-fluoro-6-(5-bromothien-2-yl)-6H-dibenzo(b,d)pyran-8-yl)methanesulfonamide,
(1-methoxy-3-methyl-6-allyl-6H-dibenzo(b,d)pyran-8-yl)methanesulfonamide,
(1-methoxy-3-methyl-6-phenyl-6H-dibenzo(b,d)pyran-8-yl)methanesulfonamide,
(1-methoxy-3-methyl-6-(3-chlorophenyl)-6H-dibenzo(b,d)pyran-8-yl)methanesulfonamide,
(1-methoxy-6-(3-fluorophenyl)-6H-dibenzo(b,d)pyran-8-yl)methanesulfonamide,
(1-methoxy-3-methyl-6-(3-methoxyphenyl)-6H-dibenzo(b,d)pyran-8-yl)methanesulfonamide,
(1-methoxy-3-methyl-6-(3,4-dimethoxy)phenyl-6H-dibenzo(b,d)pyran-8-yl)methanesulfonamide,
(1-methoxy-3-methyl-6-(5-bromothien-2-yl)-6H-dibenzo(b,d)pyran-8-yl)methanesulfonamide,
(1-difluoromethoxy-3-bromo-6-allyl-6H-dibenzo(b,d)pyran-8-yl)methanesulfonamide,
(1-difluoromethoxy-3-bromo-6-phenyl-6H-dibenzo(b,d)pyran-8-yl)methanesulfonamide,
(1-difluoromethoxy-3-bromo-6-(3-chlorophenyl)-6H-dibenzo(b,d)pyran-8-yl)methanesulfonamide,
(1-difluoromethoxy-3-bromo-6-(3-fluorophenyl)-6H-dibenzo(b,d)pyran-8-yl)methanesulfonamide,
(1-difluoromethoxy-3-bromo-6-(3-methoxyphenyl)-6H-dibenzo(b,d)pyran-8-yl)methanesulfonamide,
(1-difluoromethoxy-3-bromo-6-(3,4-dimethoxy)phenyl-6H-dibenzo(bud)pyran-8-yl)methanesulfonamide,
(1-difluoromethoxy-3-bromo-6-(5-bromothien-2-yl)-6H-dibenzo(b,d)pyran-8-yl)methanesulfonamide,
(1-difluoromethoxy-3-chloro-6-allyl-6H-dibenzo(b,d)pyran-8-yl)methanesulfonamide,
(1-difluoromethoxy-3-chloro-6-phenyl-6H-dibenzo(b,d)pyran-8-yl)methanesulfonamide,
(1-difluoromethoxy-3-chloro-6-(3-chlorophenyl)-6H-dibenzo(b,d)pyran-8-yl)methanesulfonamide,
(1-difluoromethoxy-3-chloro-6-(3-fluorophenyl)-6H-dibenzo(b,d)pyran-8-yl)methanesulfonamide,
(1-difluoromethoxy-3-chloro-6-(3-methoxyphenyl)-6H-dibenzo(b,d)pyran-8-yl)methanesulfonamide,
(1-difluoromethoxy-3-chloro-6-(3,4-dimethoxy)phenyl-6H-dibenzo(b,d)pyran-8-yl)methanesulfonamide,
(1-difluoromethoxy-3-chloro-6-(5-bromothien-2-yl)-6H-dibenzo(b,d)pyran-8-yl)methanesulfonamide,
(1-difluoromethoxy-3-fluoro-6-allyl-6H-dibenzo(b,d)pyran-8-yl)methanesulfonamide,
(1-difluoromethoxy-3-fluoro-6-phenyl-6H1-dibenzo(b,d)pyran-8-yl)methanesulfonamide,
(1-difluoromethoxy-3-fluoro-6-(3-chlorophenyl)-6H-dibenzo(b,d)pyran-8-yl)methanesulfonamide,
(1-difluoromethoxy-3-fluoro-6-(3-fluorophenyl)-6H-dibenzo(b,d)pyran-8-yl)methanesulfonamide,
(1-difluoromethoxy-3-fluoro-6-(3-methoxyphenyl)-6H-dibenzo(b,d)pyran-8-yl)methanesulfonamide,
(1-difluoromethoxy-3-fluoro-6-(3,4-dimethoxy)phenyl-6H-dibenzo(b,d)pyran-8-yl)methanesulfonamide,
(1-difluoromethoxy-3-fluoro-6-(5-bromothien-2-yl)-6H-dibenzo(b,d)pyran-8-yl)methanesulfonamide,
(1-difluoromethoxy-3-methyl-6-allyl-6H-dibenzo(b,d)pyran-8-yl)methanesulfonamide,
(1-difluoromethoxy-3-methyl-6-phenyl-6H-dibenzo(b,d)pyran-8-yl)methanesulfonamide,
(1-difluoromethoxy-3-methyl-6-(3-chlorophenyl)-6H-dibenzo(b,d)pyran-8-yl)methanesulfonamide,
(1-difluoromethoxy-3-methyl-6-(3-fluorophenyl)-6H-dibenzo(b,d)pyran-8-yl)methanesulfonamide,
(1-difluoromethoxy-3-methyl-6-(3-methoxyphenyl)-6H-dibenzo(b,d)pyran-8-yl)methanesulfonamide,
(1-difluoromethoxy-3-methyl-6-(3,4-dimethoxy)phenyl-6H-dibenzo(b,d)pyran-8-yl)methanesulfonamide,
(1-difluoromethoxy-3-methyl-6-(5-bromothien-2-yl)-6H-dibenzo(b,d)pyran-8-yl)methanesulfonamide,
(1-methoxy-6-cyclohexyl-6H-dibenzo(b,d)pyran-8-yl)methanesulfonamide,
(1-methoxy-6-propyl-6H-dibenzo(b,d)pyran-8-yl)methanesulfonamide, (1-methoxy-6-(4-chlorobutyl)-6H-dibenzo(b,d)pyran-8-yl)methanesulfonamide,
(1-methoxy-6-(6-cyanohexyl)-6H-dibenzo(b,d)pyran-8-yl)methanesulfonamide,
(1-methoxy-6-(4-methoxy-2-buten-1-yl)-6H-dibenzo(b,d)pyran-8-yl)methanesulfonamide,
(1-methoxy-6-(4-hydroxy-2-buten-1-yl)-6H-dibenzo(b,d)pyran-8-yl)methanesulfonamide,
(1-methoxy-6-(4-(but-3-en-1-yloxy)-2-buten-1-yl)-6H-dibenzo(b,d)pyran-8-yl)methanesulfonamide,
(1-methoxy-6-(4-(3-methoxypropoxy)-2-buten-1-yl)-6H-dibenzo(b,d)pyran-8-yl)methanesulfonamide,
(1-methoxy-6-(4-allyloxybenzyl)-6H-dibenzo(b,d)pyran-8-yl)methanesulfonamide,
(1-methoxy-6-(2-carboxyethyl)-6H-dibenzo(b,d)pyran-8-yl)methanesulfonamide,
(1-methoxy-6-(3-carboxypropyl)-6H-dibenzo(b,d)pyran-8-yl)methanesulfonamide,
(1-methoxy-6-(4-carboxybutyl)-6H-dibenzo(b,d)pyran-8-yl)methanesulfonamide,
(1-methoxy-6-(5-carboxypentyl)-6H-dibenzo(b,d)pyran-8-yl)methanesulfonamide,
(1-methoxy-6-(2-carbomethoxyethyl)-6H-dibenzo(b,d)pyran-8-yl)methanesulfonamide,
(1-methoxy-6-(3-carbomethoxypropyl)-6H-dibenzo(b,d)pyran-8-yl)methanesulfonamide,
(1-methoxy-6-(4-carbomethoxybutyl)-6H-dibenzo(b,d)pyran-8-yl)methanesulfonamide,
(1-methoxy-6-(5-carbomethoxypentyl)-6H-dibenzo(b,d)pyran-8-yl)methanesulfonamide,
(1-methoxy-6-(2-carboethoxyethyl)-6H-dibenzo(b,d)pyran-8-yl)methanesulfonamide,
(1-methoxy-6-(3-carboethoxypropyl)-6H-dibenzo(b,d)pyran-8-yl)methanesulfonamide,
(1-methoxy-6-(4-carboethoxybutyl)-6H-dibenzo(b,d)pyran-8-yl)methanesulfonamide,
(1-methoxy-6-(5-carboethoxypentyl)-6H-dibenzo(b,d)pyran-8-yl)methanesulfonamide,
(1-methoxy-6-(2,2-dimethyl-2-carboxyethyl)-6H-dibenzo(b,d)pyran-8-yl)methanesulfonamide,
(1-methoxy-6-(3,3-dimethyl-3-carboxypropyl)-6H-dibenzo(b,d)pyran-8-yl)methanesulfonamide,
(1-methoxy-6-(4,4-dimethyl-4-carboxybutyl)-6H-dibenzo(b,d)pyran-8-yl)methanesulfonamide,
(1-methoxy-6-(5,5-dimethyl-5-carboxypentyl)-6H-dibenzo(b,d)pyran-8-yl)methanesulfonamide,
(1-methoxy-6-(2,2-dimethyl-2-carbomethoxyethyl)-6H-dibenzo(b,d)pyran-8-yl)methanesulfonamide,
(1-methoxy-6-(3,3-dimethyl-3-carbomethoxypropyl)-6H-dibenzo(b,d)pyran-8-yl)methanesulfonamide,
(1-methoxy-6-(4,4-dimethyl-4-carbomethoxybutyl)-6H-dibenzo(b,d)pyran-8-yl)methanesulfonamide,
(1-methoxy-6-(5,5-dimethyl-5-carbomethoxypentyl)-6H-dibenzo(b,d)pyran-8-yl)methanesulfonamide,
(1-methoxy-6-(2,2-dimethyl-2-carboethoxyethyl)-6H-dibenzo(b,d)pyran-8-yl)methanesulfonamide,
(1-methoxy-6-(3,3-dimethyl-3-carboethoxypropyl)-6H-dibenzo(b,d)pyran-8-yl)methanesulfonamide,
(1-methoxy-6-(4,4-dimethyl-4-carboethoxybutyl)-6H-dibenzo(b,d)pyran-8-yl)methanesulfonamide,
(1-methoxy-6-(5,5-dimethyl-5-carboethoxypentyl)-6H-dibenzo(b,d)pyran-8-yl)methanesulfonamide,
(1-methoxy-6-(5-carboethoxypentyl)-6H-dibenzo(b,d)pyran-8-yl)methanesulfonamide,
(1-methoxy-6-(6-hydroxyhexyl)-6H-dibenzo(b,d)pyran-8-yl)methanesulfonamide,
(1-methoxy-6-(6-oxohexyl)-6H-dibenzo(b,d)pyran-8-yl)methanesulfonamide,
(1-methoxy-6-(6-oxyhexyl)-6H-dibenzo(b,d)pyran-8-yl)methanesulfonamide,
(1-methoxy-6-(8-methoxyoctyl)-6H-dibenzo(b,d)pyran-8-yl)methanesulfonamide,
(1-methoxy-6-(5-(N-(2-methoxyethyl)aminocarbonyl)pentyl)-6H-dibenzo(b,d)pyran-8-yl)methanesulfonamide,
(1-methoxy-6-(5-(N-methyl-N-(2-methoxyethyl)aminocarbonyl)pentyl)-6H-dibenzo(b,d)pyran-8-yl)methanesulfonamide,
(1-methoxy-6-(3-(2-carboxyethyl)phenyl)-6H-dibenzo(b,d)pyran-8-yl)methanesulfonamide,
(1-methoxy-6-(3-(3-carboxypropyl)phenyl)-6H-dibenzo(b,d)pyran-8-yl)methanesulfonamide,
(1-methoxy-6-(3-(4-carboxybutyl)phenyl)-6H-dibenzo(b,d)pyran-8-yl)methanesulfonamide,
(1-methoxy-6-(3-(5-carboxypentyl)phenyl)-6H-dibenzo(bed)pyran-8-yl)methanesulfonamide,
(1-methoxy-6-(3-(2-carbomethoxyethyl)phenyl)-6H-dibenzo(b,d)pyran-8-yl)methanesulfonamide,
(1-methoxy-6-(3-(3-carbomethoxypropyl)phenyl)-6H-dibenzo(b,d)pyran-8-yl)methanesulfonamide,
(1-methoxy-6-(3-(4-carbomethoxybutyl)phenyl)-6H-dibenzo(b,d)pyran-8-yl)methanesulfonamide,
(1-methoxy-6-(3-(5-carbomethoxypentyl)phenyl)-6H-dibenzo(b,d)pyran-8-yl)methanesulfonamide,
(1-methoxy-6-(3-(2-carboethoxyethyl)phenyl)-6H-dibenzo(b,d)pyran-8-yl)methanesulfonamide,
(1-methoxy-6-(3-(3-carboethoxypropyl)phenyl)-6H-dibenzo(b,d)pyran-8-yl)methanesulfonamide,
(1-methoxy-6-(3-(4-carboethoxybutyl)phenyl)-6H-dibenzo(b,d)pyran-8-yl)methanesulfonamide,
(1-methoxy-6-(3-(5-carboethoxypentyl)phenyl)-6H-dibenzo(b,d)pyran-8-yl)methanesulfonamide,
(1-methoxy-6-(3-(2,2-dimethyl-2-carboxyethyl)phenyl)-6H-dibenzo(b,d)pyran-8-yl)methanesulfonamide,
(1-methoxy-6-(3-(3,3-dimethyl-3-carboxypropyl)phenyl)-6H-dibenzo(b,d)pyran-8-yl)methanesulfonamide,
(1-methoxy-6-(3-(4,4-dimethyl-4-carboxybutyl)phenyl)-6H-dibenzo(b,d)pyran-8-yl)methanesulfonamide,
(1-methoxy-6-(3-(5,5-dimethyl-5-carboxypentyl)phenyl)-6H-dibenzo(b,d)pyran-8-yl)methanesulfonamide,
(1-methoxy-6-(3-(2,2-dimethyl-2-carbomethoxyethyl)phenyl)-6H-dibenzo(b,d)pyran-8-yl)methanesulfonamide,
(1-methoxy-6-(3-(3,3-dimethyl-3-carbomethoxypropylphenyl)-6H-dibenzo(b,d)pyran-8-yl)methanesulfonamide,
(1-methoxy-6-(3-(4,4-dimethyl-4-carbomethoxybutyl)phenyl)-6H-dibenzo(b,d)pyran-8-yl)methanesulfonamide,
(1-methoxy-6-(3-(5,5-dimethyl-5-carbomethoxypentyl)phenyl)-6H-dibenzo(b,d)pyran-8-yl)methanesulfonamide, (1-methoxy-6-(3-(2,2-dimethyl-2-carboethoxyethyl)phenyl)-6H-dibenzo(b,d)pyran-8-yl)methanesulfonamide, (1-methoxy-6-(3-(3,3-dimethyl-3-carboethoxypropyl)phenyl)-6H-dibenzo(b,d)pyran-8-yl)methanesulfonamide, (1-methoxy-6-(3-(4,4-dimethyl-4-carboethoxybutyl)phenyl)-6H-dibenzo(b,d)pyran-8-yl)methanesulfonamide, (1-methoxy-6-(3-(5,5-dimethyl-5-carboethoxypentyl)phenyl)-6H-dibenzo(b,d)pyran-8-yl)methanesulfonamide, (1-methoxy-6-(4-(2-carboxyethyl)phenyl)-6H-dibenzo(b,d)pyran-8-yl)methanesulfonamide, (1-methoxy-6-(4-(3-carboxypropyl)phenyl)-6H-dibenzo(b,d)pyran-8-yl)methanesulfonamide, (1-methoxy-6-(4-(4-carboxybutyl)phenyl)-6H-dibenzo(b,d)pyran-8-yl)methanesulfonamide, (1-methoxy-6-(4-(5-carboxypentyl)phenyl)-6H-dibenzo(b,d)pyran-8-yl)methanesulfonamide, (1-methoxy-6-(4-(2-carbomethoxyethyl)phenyl)-6H-dibenzo(b,d)pyran-8-yl)methanesulfonamide, (1-methoxy-6-(4-(3-carbomethoxypropyl)phenyl)-6H-dibenzo(b,d)pyran-8-yl)methanesulfonamide, (1-methoxy-6-(4-(4-carbomethoxybutyl)phenyl)-6H-dibenzo(b,d)pyran-8-yl)methanesulfonamide, (1-methoxy-6-(4-(5-carbomethoxypentyl)phenyl)-6H-dibenzo(b,d)pyran-8-yl)methanesulfonamide, (1-methoxy-6-(4-(2-carboethoxyethyl)phenyl)-6H-dibenzo(b,d)pyran-8-yl)methanesulfonamide, (1-methoxy-6-(4-(3-carboethoxypropyl)phenyl)-6H-dibenzo(b,d)pyran-8-yl)methanesulfonamide, (1-methoxy-6-(4-(4-carboethoxybutyl)phenyl)-6H-dibenzo(b,d)pyran-8-yl)methanesulfonamide, (1-methoxy-6-(4-(5-carboethoxypentyl)phenyl)-6H-dibenzo(b,d)pyran-8-yl)methanesulfonamide, (1-methoxy-6-(4-(2,2-dimethyl-2-carboxyethyl)phenyl)-6H-dibenzo(b,d)pyran-8-yl)methanesulfonamide, (1-methoxy-6-(4-(3,3-dimethyl-3-carboxypropyl)phenyl)-6H-dibenzo(b,d)pyran-8-yl)methanesulfonamide, (1-methoxy-6-(4-(4,4-dimethyl-4-carboxybutyl)phenyl)-6H-dibenzo(bud)pyran-8-yl)methanesulfonamide, (1-methoxy-6-(4-(5,5-dimethyl-5-carboxypentyl)phenyl)-6H-dibenzo(b,d)pyran-8-yl)methanesulfonamide, (1-methoxy-6-(4-(2,2-dimethyl-2-carbomethoxyethyl)phenyl)-6H-dibenzo(b,d)pyran-8-yl)methanesulfonamide, (1-methoxy-6-(4-(3,3-dimethyl-3-carbomethoxypropylphenyl)-6H-dibenzo(b,d)pyran-8-yl)methanesulfonamide, (1-methoxy-6-(4-(4,4-dimethyl-4-carbomethoxybutyl)phenyl)-6H-dibenzo(b,d)pyran-8-yl)methanesulfonamide, (1-methoxy-6-(4-(5,5-dimethyl-5-carbomethoxypentyl)phenyl)-6H-dibenzo(b,d)pyran-8-yl)methanesulfonamide, (1-methoxy-6-(4-(2,2-dimethyl-2-carboethoxyethyl)phenyl)-6H-dibenzo(b,d)pyran-8-yl)methanesulfonamide, (1-methoxy-6-(4-(3,3-dimethyl-3-carboethoxypropyl)phenyl)-6H-dibenzo(b,d)pyran-8-yl)methanesulfonamide, (1-methoxy-6-(4-(4,4-dimethyl-4-carboethoxybutyl)phenyl)-6H-dibenzo(b,d)pyran-8-yl)methanesulfonamide, (1-methoxy-6-(4-(5,5-dimethyl-5-carboethoxypentyl)phenyl)-6H-dibenzo(b,d)pyran-8-yl)methanesulfonamide, (1-methoxy-6-(3-(N-methyl-N-(N,N-dimethylaminocarbonyl)methylamino)phenyl)-6H-dibenzo(b,d)pyran-8-yl)methanesulfonamide, (1-methoxy-6-(3-(N-methyl-N-(N,N-diethylaminocarbonyl)methylamino)phenyl)-6H-dibenzo(b,d)pyran-8-yl)methanesulfonamide, (1-methoxy-6-(3-(2-(N-methyl-N-(N,N-dimethylaminocarbonyl)ethyl)amino)phenyl)-6H-dibenzo(b,d)pyran-8-yl)methanesulfonamide, (1-methoxy-6-(3-(2-(N-methyl-N-(N,N-diethylaminocarbonyl)ethyl)amino)phenyl)-6H-dibenzo(b,d)pyran-8-yl)methanesulfonamide, (1-methoxy-6-(3-(3-(N-methyl-N-(N,N-dimethylcarbonyl)propyl)amino)phenyl)-6H-dibenzo(b,d)pyran-8-yl)methanesulfonamide, (1-methoxy-6-(3-(3-(N-methyl-N-(N,N-diethylaminocarbonyl)propyl)amino)phenyl)-6H-dibenzo(b,d)pyran-8-yl)methanesulfonamide, (1-methoxy-6-(3-(N-methyl-N-acetyl)aminophenyl)-6H-dibenzo(b,d)pyran-8-yl)methanesulfonamide, (1-methoxy-6-(3-(N-methyl-N-propionyl)aminophenyl)-6H-dibenzo(b,d)pyran-8-yl)methanesulfonamide, (1-methoxy-6-(3-(N-methyl-N-methanesulfonyl)aminophenyl)-6H-dibenzo(b,d)pyran-8-yl)methanesulfonamide, (1-methoxy-6-(3-(N-methyl-N-ethanesulfonyl)aminophenyl)-6H-dibenzo(b,d)pyran-8-yl)methanesulfonamide, (1-methoxy-6-(4-chlorophenyl)-6H-dibenzo(b,d)pyran-8-yl)methanesulfonamide, (1-methoxy-6-(4-fluorophenyl)-6H-dibenzo(b,d)pyran-8-yl)methanesulfonamide, (1-methoxy-6-(4-methoxyphenyl)-6H-dibenzo(b,d)pyran-8-yl)methanesulfonamide, (1-methoxy-6-(3-hydroxyphenyl)-6H-dibenzo(b,d)pyran-8-yl)methanesulfonamide, (1-methoxy-6-(3-trifluoromethylphenyl)-6H-dibenzo(b,d)pyran-8-yl)methanesulfonamide, (1-methoxy-6-(3-methylphenyl)-6H-dibenzo(b,d)pyran-8-yl)methanesulfonamide, (1-methoxy-6-(3-bromophenyl)-6H-dibenzo(b,d)pyran-8-yl)methanesulfonamide, (1-methoxy-6-(4-bromophenyl)-6H-dibenzo(b,d)pyran-8-yl)methanesulfonamide, (1-methoxy-6-(3-cyanophenyl)-6H-dibenzo(b,d)pyran-8-yl)methanesulfonamide, (1-methoxy-6-(4-cyanophenyl)-6H-dibenzo(b,d)pyran-8-yl)methanesulfonamide, (1-methoxy-6-(3-carbomethoxyphenyl)-6H-dibenzo(b,d)pyran-8-yl)methanesulfonamide, (1-methoxy-6-(4-carbomethoxyphenyl)-6H-dibenzo(b,d)pyran-8-yl)methanesulfonamide, (1-methoxy-6-(3-carboethoxyphenyl)-6H-dibenzo(b,d)pyran-8-yl)methanesulfonamide, (1-methoxy-6-(4-carboethoxyphenyl)-6H-dibenzo(b,d)pyran-8-yl)methanesulfonamide, (1-methoxy-6-(3-ethoxyphenyl)-6H-dibenzo(b,d)pyran-8-yl)methanesulfonamide,
(1-methoxy-6-(4-ethoxyphenyl)-6H-dibenzo(b,d)pyran-8-yl)methanesulfonamide,
(1-methoxy-6-(3-allyloxyphenyl)-6H-dibenzo(b,d)pyran-8-yl)methanesulfonamide,
(1-methoxy-6-(4-allyloxyphenyl)-6H-dibenzo(b,d)pyran-8-yl)methanesulfonamide,
(1-methoxy-6-(3-allylphenyl)-6H-dibenzo(b,d)pyran-8-yl)methanesulfonamide,
(1-methoxy-6-(4-allylphenyl)-6H-dibenzo(b,d)pyran-8-yl)methanesulfonamide,
(1-methoxy-6-(thien-2-yl)-6H-dibenzo(b,d)pyran-8-yl)methanesulfonamide,
(1-methoxy-6-(-chlorothien-2-yl)-6H-dibenzo(b,d)pyran-8-yl)methanesulfonamide,
(1-methoxy-6-(5-(3-methoxypropen-1-yl)thien-2-yl)-6H-dibenzo(b,d)pyran-8-yl)methanesulfonamide,
(1-methoxy-6-(5-(3-methoxypropyl)thien-2-yl)-6H-dibenzo(b,d)pyran-8-yl)methanesulfonamide,
(1-methoxy-6-(furan-2-yl)-6H-dibenzo(b,d)pyran-8-yl)methanesulfonamide,
(1-methoxy-6-(pyridin-2-yl)-6H-dibenzo(b,d)pyran-8-yl)methanesulfonamide,
(1-methoxy-6-(pyridin-3-yl)-6H-dibenzo(b,d)pyran-8-yl)methanesulfonamide,
(1-methoxy-6-(pyridin-4-yl)-6H-dibenzo(b,d)pyran-8-yl)methanesulfonamide,
(1-methoxy-6-(5-bromopyridin-3-yl)-6H-dibenzo(b,d)pyran-8-yl)methanesulfonamide,
(1-methoxy-6-(5-(N-methyl-N-(2-methoxyethyl)amino)pyridin-3-yl)-6H-dibenzo(b,d)pyran-8-yl)methanesulfonamide,
(1-methoxy-6-(5-(3-methoxypropen-1-yl)pyridin-3-yl)-6H-dibenzo(b,d)pyran-8-yl)methanesulfonamide,
(1-methoxy-6-(4-(N-methylamino)phenyl)-6H-dibenzo(b,d)pyran-8-yl)methanesulfonamide,
(1-methoxy-6-(4-(N-allyl-N-methylamino)phenyl)-6H-dibenzo(b,d)pyran-8-yl)methanesulfonamide,
(1-methoxy-6-(4-(N-propyl-N-methylamino)phenyl)-6H-dibenzo(b,d)pyran-8-yl)methanesulfonamide,
(1-methoxy-6-(3-(N-methanesulfonylamino)phenyl)-6H-dibenzo(b,d)pyran-8-yl)methanesulfonamide,
(1-methoxy-6-(3-(N-methyl-N-propanesulfonylamino)phenyl)-6H-dibenzo(b,d)pyran-8-yl)methanesulfonamide,
(1-methoxy-6-(3-(4-methoxybutoxy)phenyl)-6H-dibenzo(b,d)pyran-8-yl)methanesulfonamide,
(1-methoxy-6-(3-(4-methoxybut-2-en-1-yloxy)phenyl)-6H-dibenzo(b,d)pyran-8-yl)methanesulfonamide,
(1-methoxy-6-(3-(4-hydroxybut-2-en-1-yloxy)phenyl)-6H-dibenzo(b,d)pyran-8-yl)methanesulfonamide,
(1-methoxy-6-(3-(3-carboethoxyprop-2-en-1-yloxy)phenyl)-6H-dibenzo(b,d)pyran-8-yl)methanesulfonamide,
(1-methoxy-6-(3-(2-(2-methoxyethoxy)ethoxy)phenyl)-6H-dibenzo(b,d)pyran-8-yl)methanesulfonamide,
(1-methoxy-6-(3-((N-methyl-N-(2-methoxyethyl)aminocarbonyl)phenyl)-6H-dibenzo(b,d)pyran-8-yl)methanesulfonamide,
(1-methoxy-6-(3-(methylthiomethoxy)phenyl)-6H-dibenzo(b,d)pyran-8-yl)methanesulfonamide,
(1-methoxy-6-(3-(2-hydroxyethyl)phenyl)-6H-dibenzo(b,d)pyran-8-yl)methanesulfonamide,
(1-methoxy-6-(3-(2-methoxyethyl)phenyl)-6H-dibenzo(b,d)pyran-8-yl)methanesulfonamide,
(1-methoxy-6-(3-(2-(but-3-en-1-yloxy)ethyl)phenyl)-6H-dibenzo(b,d)pyran-8-yl)methanesulfonamide,
(1-methoxy-6-(3-(2-(N,N-dimethylaminocarbonyloxy)ethyl)phenyl)-6H-dibenzo(b,d)pyran-8-yl)methanesulfonamide,
(1-methoxy-6-(3-(N,N-dimethylaminocarbonyloxy)phenyl)-6H-dibenzo(b,d)pyran-8-yl)methanesulfonamide,
(1-methoxy-6-(3-(3-bromoprop-2-en-1-yloxy)phenyl)-6H-dibenzo(b,d)pyran-8-yl)methanesulfonamide,
(1-methoxy-6-(3-fluoro-5-methoxyphenyl)-6H-dibenzo(b,d)pyran-8-yl)methanesulfonamide,
(1-methoxy-6-(3-fluoro-5-hydroxyphenyl)-6H-dibenzo(b,d)pyran-8-yl)methanesulfonamide,
(1-methoxy-6-(3-fluoro-5-allyloxyphenyl)-6H-dibenzo(b,d)pyran-8-yl)methanesulfonamide,
(1-methoxy-6-(3-fluoro-5-(2-methoxyethoxy)phenyl)-6H-dibenzo(b,d)pyran-8-yl)methanesulfonamide,
(1-methoxy-6-(3-fluoro-5-(2-(2-methoxyethoxy)ethoxy)phenyl)-6H-dibenzo(b,d)pyran-8-yl)methanesulfonamide,
(1-methoxy-6-(3-fluoro-5-(2-allyloxyethoxy)phenyl)-6H-dibenzo(b,d)pyran-8-yl)methanesulfonamide,
(1-difluoromethoxy-6-cyclohexyl-6H-dibenzo(b,d)pyran-8-yl)methanesulfonamide,
(1-difluoromethoxy-6-propyl-6H-dibenzo(b,d)pyran-8-yl)methanesulfonamide,
(1-difluoromethoxy-6-(4-chlorobutyl)-6H-dibenzo(b,d)pyran-8-yl)methanesulfonamide,
(1-difluoromethoxy-6-(6-cyanohexyl)-6H-dibenzo(b,d)pyran-8-yl)methanesulfonamide,
(1-difluoromethoxy-6-(4-methoxy-2-buten-1-yl)-6H-dibenzo(b,d)pyran-8-yl)methanesulfonamide,
(1-difluoromethoxy-6-(4-hydroxy-2-buten-1-yl)-6H-dibenzo(b,d)pyran-8-yl)methanesulfonamide,
(1-difluoromethoxy-6-(4-(but-3-en-1-yloxy)-2-buten-1-yl)-6H-dibenzo(b,d)pyran-8-yl)methanesulfonamide,
(1-difluoromethoxy-6-(4-(3-methoxypropoxy)-2-buten-1-yl)-6H-dibenzo(b,d)pyran-8-yl)methanesulfonamide,
(1-difluoromethoxy-6-(4-allyloxybenzyl)-6H-dibenzo(b,d)pyran-8-yl)methanesulfonamide,
(1-difluoromethoxy-6-(2-carboxyethyl)-6H-dibenzo(b,d)pyran-8-yl)methanesulfonamide,
(1-difluoromethoxy-6-(3-carboxypropyl)-6H-dibenzo(b,d)pyran-8-yl)methanesulfonamide,
(1-difluoromethoxy-6-(4-carboxybutyl)-6H-dibenzo(b,d)pyran-8-yl)methanesulfonamide,
(1-difluoromethoxy-6-(5-carboxypentyl)-6H-dibenzo(b,d)pyran-8-yl)methanesulfonamide,
(1-difluoromethoxy-6-(2-carbomethoxyethyl)-6H-dibenzo(b,d)pyran-8-yl)methanesulfonamide,
(1-difluoromethoxy-6-(3-carbomethoxypropyl)-6H-dibenzo(b,d)pyran-8-yl)methanesulfonamide,
(1-difluoromethoxy-6-(4-carbomethoxybutyl)-6H-dibenzo(b,d)pyran-8-yl)methanesulfonamide,
(1-difluoromethoxy-6-(5-carbomethoxypentyl)-6H-dibenzo(b,d)pyran-8-yl)methanesulfonamide, (1-difluoromethoxy-6-(2-carboethoxyethyl)-6H-dibenzo(b,d)pyran-8-yl)methanesulfonamide,
(1-difluoromethoxy-6-(3-carboethoxypropyl)-6H-dibenzo(b,d)pyran-8-yl)methanesulfonamide,
(1-difluoromethoxy-6-(4-carboethoxybutyl)-6H-dibenzo(b,d)pyran-8-yl)methanesulfonamide,
(1-difluoromethoxy-6-(5-carboethoxypentyl)-6H-dibenzo(b,d)pyran-8-yl)methanesulfonamide,
(1-difluoromethoxy-6-(2,2-dimethyl-2-carboxyethyl)-6H-dibenzo(b,d)pyran-8-yl)methanesulfonamide,
(1-difluoromethoxy-6-(3,3-dimethyl-3-carboxypropyl)-6H-dibenzo(b,d)pyran-8-yl)methanesulfonamide,
(1-difluoromethoxy-6-(4,4-dimethyl-4-carboxybutyl)-6H-dibenzo(b,d)pyran-8-yl)methanesulfonamide,
(1-difluoromethoxy-6-(5,5-dimethyl-5-carboxypentyl)-6H-dibenzo(b,d)pyran-8-yl)methanesulfonamide,
(1-difluoromethoxy-6-(2,2-dimethyl-2-carbomethoxyethyl)-6H-dibenzo(b,d)pyran-8-yl)methanesulfonamide,
(1-difluoromethoxy-6-(3,3-dimethyl-3-carbomethoxypropyl)-6H-dibenzo(b,d)pyran-8-yl)methanesulfonamide,
(1-difluoromethoxy-6-(4,4-dimethyl-4-carbomethoxybutyl)-6H-dibenzo(b,d)pyran-8-yl)methanesulfonamide,
(1-difluoromethoxy-6-(5,5-dimethyl-5-carbomethoxypentyl)-6H-dibenzo(b,d)pyran-8-yl)methanesulfonamide,
(1-difluoromethoxy-6-(2,2-dimethyl-2-carboethoxyethyl)-6H-dibenzo(b,d)pyran-8-yl)methanesulfonamide,
(1-difluoromethoxy-6-(3,3-dimethyl-3-carboethoxypropyl)-6H-dibenzo(b,d)pyran-8-yl)methanesulfonamide,
(1-difluoromethoxy-6-(4,4-dimethyl-4-carboethoxybutyl)-6H-dibenzo(b,d)pyran-8-yl)methanesulfonamide,
(1-difluoromethoxy-6-(5,5-dimethyl-5-carboethoxypentyl)-6H-dibenzo(b,d)pyran-8-yl)methanesulfonamide,
(1-difluoromethoxy-6-(5-carboethoxypentyl)-6H-dibenzo(b,d)pyran-8-yl)methanesulfonamide,
(1-difluoromethoxy-6-(6-hydroxyhexyl)-6H-dibenzo(b,d)pyran-8-yl)methanesulfonamide,
(1-difluoromethoxy-6-(6-oxohexyl)-6H-dibenzo(b,d)pyran-8-yl)methanesulfonamide,
(1-difluoromethoxy-6-(6-methoxyhexyl)-6H-dibenzo(b,d)pyran-8-yl)methanesulfonamide,
(1-difluoromethoxy-6-(8-methoxyoctyl)-6H-dibenzo(b,d)pyran-8-yl)methanesulfonamide,
(1-difluoromethoxy-6-(5-(N-(2-methoxyethyl)aminocarbonyl)pentyl)-6H-dibenzo(b,d)pyran-8-yl)methanesulfonamide,
(1-difluoromethoxy-6-(5-(N-methyl-N-(2-methoxyethyl)aminocarbonyl)pentyl)-6H-dibenzo(b,d)pyran-8-yl)methanesulfonamide,
(1-difluoromethoxy-6-(3-(2-carboxyethyl)phenyl)-6H-dibenzo(b,d)pyran-8-yl)methanesulfonamide,
(1-difluoromethoxy-6-(3-(3-carboxypropyl)phenyl)-6H-dibenzo(b,d)pyran-8-yl)methanesulfonamide,
(1-difluoromethoxy-6-(3-(4-carboxybutyl)phenyl)-6H-dibenzo(b,d)pyran-8-yl)methanesulfonamide,
(1-difluoromethoxy-6-(3-(5-carboxypentyl)phenyl)-6H-dibenzo(b,d)pyran-8-yl)methanesulfonamide,
(1-difluoromethoxy-6-(3-(2-carbomethoxyethyl)phenyl)-6H-dibenzo(b,d)pyran-8-yl)methanesulfonamide,
(1-difluoromethoxy-6-(3-(3-carbomethoxypropyl)phenyl)-6H-dibenzo(b,d)pyran-8-yl)methanesulfonamide,
(1-difluoromethoxy-6-(3-(4-carbomethoxybutyl)phenyl)-6H-dibenzo(b,d)pyran-8-yl)methanesulfonamide,
(1-difluoromethoxy-6-(3-(5-carbomethoxypentyl)phenyl)-6H-dibenzo(b,d)pyran-8-yl)methanesulfonamide,
(1-difluoromethoxy-6-(3-(2-carboethoxyethyl)phenyl)-6H-dibenzo(b,d)pyran-8-yl)methanesulfonamide,
(1-difluoromethoxy-6-(3-(3-carboethoxypropyl)phenyl)-6H-dibenzo(b,d)pyran-8-yl)methanesulfonamide,
(1-difluoromethoxy-6-(3-(4-carboethoxybutyl)phenyl)-6H-dibenzo(b,d)pyran-8-yl)methanesulfonamide,
(1-difluoromethoxy-6-(3-(5-carboethoxypentyl)phenyl)-6H-dibenzo(b,d)pyran-8-yl)methanesulfonamide,
(1-difluoromethoxy-6-(3-(2,2-dimethyl-2-carboxyethyl)phenyl)-6H-dibenzo(b,d)pyran-8-yl)methanesulfonamide,
(1-difluoromethoxy-6-(3-(3,3-dimethyl-3-carboxypropyl)phenyl)-6H-dibenzo(b,d)pyran-8-yl)methanesulfonamide,
(1-difluoromethoxy-6-(3-(4,4-dimethyl-4-carboxybutyl)phenyl)-6H-dibenzo(b,d)pyran-8-yl)methanesulfonamide,
(1-difluoromethoxy-6-(3-(5,5-dimethyl-5-carboxypentyl)phenyl)-6H-dibenzo(b,d)pyran-8-yl)methanesulfonamide,
(1-difluoromethoxy-6-(3-(2,2-dimethyl-2-carbomethoxyethyl)phenyl)-6H-dibenzo(b,d)pyran-8-yl)methanesulfonamide,
(1-difluoromethoxy-6-(3-(3,3-dimethyl-3-carbomethoxypropylphenyl)-6H-dibenzo(b,d)pyran-8-yl)methanesulfonamide,
(1-difluoromethoxy-6-(3-(4,4-dimethyl-4-carbomethoxybutyl)phenyl)-6H-dibenzo(b,d)pyran-8-yl)methanesulfonamide,
(1-difluoromethoxy-6-(3-(5,5-dimethyl-5-carbomethoxypentyl)phenyl)-6H-dibenzo(b,d)pyran-8-yl)methanesulfonamide,
(1-difluoromethoxy-6-(3-(2,2-dimethyl-2-carboethoxyethyl)phenyl)-6H-dibenzo(b,d)pyran-8-yl)methanesulfonamide,
(1-difluoromethoxy-6-(3-(3,3-dimethyl-3-carboethoxypropyl)phenyl)-6H-dibenzo(b,d)pyran-8-yl)methanesulfonamide,
(1-difluoromethoxy-6-(3-(4,4-dimethyl-4-carboethoxybutyl)phenyl)-6H-dibenzo(b,d)pyran-8-yl)methanesulfonamide,
(1-difluoromethoxy-6-(3-(5,5-dimethyl-5-carboethoxypentyl)phenyl)-6H-dibenzo(b,d)pyran-8-yl)methanesulfonamide,
(1-difluoromethoxy-6-(4-(2-carboxyethyl)phenyl)-6H-dibenzo(b,d)pyran-8-yl)methanesulfonamide,
(1-difluoromethoxy-6-(4-(3-carboxypropyl)phenyl)-6H-dibenzo(b,d)pyran-8-yl)methanesulfonamide,
(1-difluoromethoxy-6-(4-(4-carboxybutyl)phenyl)-6H-dibenzo(b,d)pyran-8-yl)methanesulfonamide,
(1-difluoromethoxy-6-(4-(5-carboxypentyl)phenyl)-6H-dibenzo(b,d)pyran-8-yl)methanesulfonamide, (1-difluoromethoxy-6-(4-(2-carbomethoxyethyl)phenyl)-6H-dibenzo(b,d)pyran-8-yl)methanesulfonamide,
(1-difluoromethoxy-6-(4-(3-carbomethoxypropyl)phenyl)-6H-dibenzo(b,d)pyran-8-yl)methanesulfonamide,
(1-difluoromethoxy-6-(4-(4-carbomethoxybutyl)phenyl)-6H-dibenzo(b,d)pyran-8-yl)methanesulfonamide,
(1-difluoromethoxy-6-(4-(5-carbomethoxypentyl)phenyl)-6H-dibenzo(b,d)pyran-8-yl)methanesulfonamide,
(1-difluoromethoxy-6-(4-(2-carboethoxyethyl)phenyl)-6H-dibenzo(b,d)pyran-8-yl)methanesulfonamide,
(1-difluoromethoxy-6-(4-(3-carboethoxypropyl)phenyl)-6H-dibenzo(b,d)pyran-8-yl)methanesulfonamide,
(1-difluoromethoxy-6-(4-(4-carboethoxybutyl)phenyl)-6H-dibenzo(b,d)pyran-8-yl)methanesulfonamide,
(1-difluoromethoxy-6-(4-(5-carboethoxypentyl)phenyl)-6H-dibenzo(b,d)pyran-8-yl)methanesulfonamide,
(1-difluoromethoxy-6-(4-(2,2-dimethyl-2-carboxyethyl)phenyl)-6H-dibenzo(b,d)pyran-8-yl)methanesulfonamide,
(1-difluoromethoxy-6-(4-(3,3-dimethyl-3-carboxypropyl)phenyl)-6H-dibenzo(b,d)pyran-8-yl)methanesulfonamide,
(1-difluoromethoxy-6-(4-(4,4-dimethyl-4-carboxybutyl)phenyl)-6H-dibenzo(b,d)pyran-8-yl)methanesulfonamide,
(1-difluoromethoxy-6-(4-(5,5-dimethyl-5-carboxypentyl)phenyl)-6H-dibenzo(b,d)pyran-8-yl)methanesulfonamide,
(1-difluoromethoxy-6-(4-(2,2-dimethyl-2-carbomethoxyethyl)phenyl)-6H-dibenzo(b,d)pyran-8-yl)methanesulfonamide,
(1-difluoromethoxy-6-(4-(3,3-dimethyl-3-carbomethoxypropylphenyl)-6H-dibenzo(b,d)pyran-8-yl)methanesulfonamide,
(1-difluoromethoxy-6-(4-(4,4-dimethyl-4-carbomethoxybutyl)phenyl)-6H-dibenzo(b,d)pyran-8-yl)methanesulfonamide,
(1-difluoromethoxy-6-(4-(5,5-dimethyl-5-carbomethoxypentyl)phenyl)-6H-dibenzo(b,d)pyran-8-yl)methanesulfonamide,
(1-difluoromethoxy-6-(4-(2,2-dimethyl-2-carboethoxyethyl)phenyl)-6H-dibenzo(b,d)pyran-8-yl)methanesulfonamide,
(1-difluoromethoxy-6-(4-(3,3-dimethyl-3-carboethoxypropyl)phenyl)-6H-dibenzo(b,d)pyran-8-yl)methanesulfonamide,
(1-difluoromethoxy-6-(4-(4,4-dimethyl-4-carboethoxybutyl)phenyl)-6H-dibenzo(b,d)pyran-8-yl)methanesulfonamide,
(1-difluoromethoxy-6-(4-(5,5-dimethyl-5-carboethoxypentyl)phenyl)-6H-dibenzo(b,d)pyran-8-yl)methanesulfonamide,
(1-difluoromethoxy-6-(3-(N-methyl-N-(N,N-dimethylaminocarbonyl)methylamino)phenyl)-6H-dibenzo(b,d)pyran-8-yl)methanesulfonamide,
(1-difluoromethoxy-6-(3-(N-methyl-N-(N,N-diethylaminocarbonyl)methylamino)phenyl)-6H-dibenzo(b,d)pyran-8-yl)methanesulfonamide,
(1-difluoromethoxy-6-(3-(2-(N-methyl-N-(N,N-dimethylaminocarbonyl)ethyl)amino)phenyl)-6H-dibenzo(b,d)pyran-8-yl)methanesulfonamide,
(1-difluoromethoxy-6-(3-(2-(N-methyl-N-(N,N-diethylaminocarbonyl)ethyl)amino)phenyl)-6H-dibenzo(b,d)pyran-8-yl)methanesulfonamide,
(1-difluoromethoxy-6-(3-(3-(N-methyl-N-(N,N-dimethylaminocarbonyl)propyl)amino)phenyl)-6H-dibenzo(b,d)pyran-8-yl)methanesulfonamide,
(1-difluoromethoxy-6-(3-(3-(N-methyl-N-(N,N-diethylaminocarbonyl)propyl)amino)phenyl)-6H-dibenzo(b,d)pyran-8-yl)methanesulfonamide,
(1-difluoromethoxy-6-(3-(N-methyl-N-acetyl)aminophenyl)-6H-dibenzo(b,d)pyran-8-yl)methanesulfonamide,
(1-difluoromethoxy-6-(3-(N-methyl-N-propionyl)aminophenyl)-6H-dibenzo(b,d)pyran-8-yl)methanesulfonamide,
(1-difluoromethoxy-6-(3-(N-methyl-N-methanesulfonyl)aminophenyl)-6H-dibenzo(b,d)pyran-8-yl)methanesulfonamide,
(1-difluoromethoxy-6-(3-(N-methyl-N-ethanesulfonyl)aminophenyl)-6H-dibenzo(b1d)pyran-8-yl)methanesulfonamide,
(1-difluoromethoxy-6-(4-chlorophenyl)-6H-dibenzo(b,d)pyran-8-yl)methanesulfonamide,
(1-difluoromethoxy-6-(4-fluorophenyl)-6H-dibenzo(b,d)pyran-8-yl)methanesulfonamide,
(1-difluoromethoxy-6-(4-methoxyphenyl)-6H-dibenzo(b,d)pyran-8-yl)methanesulfonamide,
(1-difluoromethoxy-6-(3-hydroxyphenyl)-6H-dibenzo(b,d)pyran-8-yl)methanesulfonamide,
(1-difluoromethoxy-6-(3-trifluoromethylphenyl)-6H-dibenzo(b,d)pyran-8-yl)methanesulfonamide,
(1-difluoromethoxy-6-(3-methylphenyl)-6H-dibenzo(b,d)pyran-8-yl)methanesulfonamide,
(1-difluoromethoxy-6-(3-bromophenyl)-6H-dibenzo(b,d)pyran-8-yl)methanesulfonamide,
(1-difluoromethoxy-6-(4-bromophenyl)-6H-dibenzo(b,d)pyran-8-yl)methanesulfonamide,
(1-difluoromethoxy-6-(3-cyanophenyl)-6H-dibenzo(b,d)pyran-8-yl)methanesulfonamide,
(1-difluoromethoxy-6-(4-cyanophenyl)-6H-dibenzo(b,d)pyran-9-yl)methanesulfonamide,
(1-difluoromethoxy-6-(3-carbomethoxyphenyl)-6H-dibenzo(b,d)pyran-8-yl)methanesulfonamide,
(1-difluoromethoxy-6-(4-carbomethoxyphenyl)-6H-dibenzo(b,d)pyran-8-yl)methanesulfonamide,
(1-difluoromethoxy-6-(3-carboethoxyphenyl)-6H-dibenzo(b,d)pyran-8-yl)methanesulfonamide,
(1-difluoromethoxy-6-(4-carboethoxyphenyl)-6H-dibenzo(b,d)pyran-8-yl)methanesulfonamide,
(1-difluoromethoxy-6-(3-ethoxyphenyl)-6H-dibenzo(b,d)pyran-8-yl)methanesulfonamide,
(1-difluoromethoxy-6-(4-ethoxyphenyl)-6H-dibenzo(b,d)pyran-8-yl)methanesulfonamide,
(1-difluoromethoxy-6-(3-allyloxyphenyl)-6H-dibenzo(b,d)pyran-8-yl)methanesulfonamide,
(1-difluoromethoxy-6-(4-allyloxyphenyl)-6H-dibenzo(b,d)pyran-8-yl)methanesulfonamide,
(1-difluoromethoxy-6-(3-allylphenyl)-6H-dibenzo(b,d)pyran-8-yl)methanesulfonamide,
(1-difluoromethoxy-6-(4-allylphenyl)-6H-dibenzo(b,d)pyran-8-yl)methanesulfonamide,
(1-difluoromethoxy-6-(thien-2-yl)-6H-dibenzo(b,d)pyran-8-yl)methanesulfonamide, (1-difluoromethoxy-6-(5-chlorothien-2-yl)-6H-dibenzo(b,d)pyran-8-yl)methanesulfonamide,
(1-difluoromethoxy-6-(5-(3-methoxypropen-1-yl)thien-2-yl)-6H-dibenzo(b,d)pyran-8-yl)methanesulfonamide,
(1-difluoromethoxy-6-(5-(3-methoxypropyl)thien-2-yl)-6H-dibenzo(b,d)pyran-8-yl)methanesulfonamide,
(1-difluoromethoxy-6-(furan-2-yl)-6H-dibenzo(b,d)pyran-8-yl)methanesulfonamide,
(1-difluoromethoxy-6-(pyridin-2-yl)-6H-dibenzo(b,d)pyran-8-yl)methanesulfonamide,
(1-difluoromethoxy-6-(pyridin-3-yl)-6H-dibenzo(b,d)pyran-8-yl)methanesulfonamide,
(1-difluoromethoxy-6-(pyridin-4-yl)-6H-dibenzo(b,d)pyran-8-yl)methanesulfonamide,
(1-difluoromethoxy-6-(5-bromopyridin-3-yl)-6H-dibenzo(b,d)pyran-8-yl)methanesulfonamide,
(1-difluoromethoxy-6-(5-(N-methyl-N-(2-methoxyethyl)amino)pyridin-3-yl)-6H-dibenzo(b,d)pyran-8-yl)methanesulfonamide,
(1-difluoromethoxy-6-(5-(3-methoxypropen-1-yl)pyridin-3-yl)-6H-dibenzo(b,d)pyran-8-yl)methanesulfonamide,
(1-difluoromethoxy-6-(4-(N-methylamino)phenyl)-6H-dibenzo(b,d)pyran-8-yl)methanesulfonamide,
(1-difluoromethoxy-6-(4-(N-allyl-N-methylamino)phenyl)-6H-dibenzo(b,d)pyran-8-yl)methanesulfonamide,
(1-difluoromethoxy-6-(4-(N-propyl-N-methylamino)phenyl)-6H-dibenzo(b,d)pyran-8-yl)methanesulfonamide,
(1-difluoromethoxy-6-(3-(N-methanesulfonylamino)phenyl)-6H-dibenzo(b,d)pyran-8-yl)methanesulfonamide,
(1-difluoromethoxy-6-(3-(N-methyl-N-propanesulfonylamino)phenyl)-6H-dibenzo(b,d)pyran-8-yl)methanesulfonamide,
(1-difluoromethoxy-6-(3-(4-methoxybutoxy)phenyl)-6H-dibenzo(b,d)pyran-8-yl)methanesulfonamide,
(1-difluoromethoxy-6-(3-(4-methoxybut-2-en-1-yloxy)phenyl)-6H-dibenzo(b,d)pyran-8-yl)methanesulfonamide,
(1-difluoromethoxy-6-(3-(4-hydroxybut-2-en-1-yloxy)phenyl)-6H-dibenzo(b,d)pyran-8-yl)methanesulfonamide,
(1-difluoromethoxy-6-(3-(3-carboethoxyprop-2-en-1-yloxy)phenyl)-6H-dibenzo(b,d)pyran-8-yl)methanesulfonamide,
(1-difluoromethoxy-6-(3-(2-(2-methoxyethoxy)ethoxy)phenyl)-6H-dibenzo(b,d)pyran-8-yl)methanesulfonamide,
(1-difluoromethoxy-6-(3-((N-methyl-N-(2-methoxyethyl)amino)carbonyl)phenyl)-6H-dibenzo(b,d)pyran-8-yl)methanesulfonamide,
(1-difluoromethoxy-6-(3-(methylthiomethoxy)phenyl)-6H-dibenzo(b,d)pyran-8-yl)methanesulfonamide,
(1-difluoromethoxy-6-(3-(2-hydroxyethyl)phenyl)-6H-dibenzo(b,d)pyran-8-yl)methanesulfonamide,
(1-difluoromethoxy-6-(3-(2-methoxyethyl)phenyl)-6H-dibenzo(b,d)pyran-8-yl)methanesulfonamide,
(1-difluoromethoxy-6-(3-(2-(but-3-en-1-yloxy)ethyl)phenyl)-6H-dibenzo(b,d)pyran-8-yl)methanesulfonamide,
(1-difluoromethoxy-6-(3-(2-(N,N-dimethylaminocarbonyloxy)ethyl)phenyl)-6H-dibenzo(b,d)pyran-8-yl)methanesulfonamide,
(1-difluoromethoxy-6-(3-(N,N-dimethylaminocarbonyloxy)phenyl)-6H-dibenzo(b,d)pyran-8-yl)methanesulfonamide,
(1-difluoromethoxy-6-(3-(3-bromoprop-2-en-1-yloxy)phenyl)-6H-dibenzo(b,d)pyran-8-yl)methanesulfonamide,
(1-difluoromethoxy-6-(3-fluoro-5-methoxyphenyl)-6H-dibenzo(b,d)pyran-8-yl)methanesulfonamide,
(1-difluoromethoxy-6-(3-fluoro-5-hydroxyphenyl)-6H-dibenzo(b,d)pyran-8-yl)methanesulfonamide,
(1-difluoromethoxy-6-(3-fluoro-5-allyloxyphenyl)-6H-dibenzo(b,d)pyran-8-yl)methanesulfonamide,
(1-difluoromethoxy-6-(3-fluoro-5-(2-methoxyethoxy)phenyl)-6H-dibenzo(b,d)pyran-8-yl)methanesulfonamide,
(1-difluoromethoxy-6-(3-fluoro-5-(2-(2-methoxyethoxy)ethoxy)phenyl)-6H-dibenzo(b,d)pyran-8-yl)methanesulfonamide,
(1-difluoromethoxy-6-(3-fluoro-5-(2-allyloxyethoxy)phenyl)-6H-dibenzo(b,d)pyran-8-yl)methanesulfonamide,
(1-methoxy-6-allyl-7-bromo-6H-dibenzo(b,d)pyran-8-yl)methanesulfonamide,
(1-methoxy-6-allyl-7-methyl-6H-dibenzo(b,d)pyran-8-yl)methanesulfonamide,
(1-methoxy-6-phenyl-7-bromo-6H-dibenzo(b,d)pyran-8-yl)methanesulfonamide,
(1-methoxy-6-phenyl-7-methyl-6H-dibenzo(b,d)pyran-8-yl)methanesulfonamide,
(1-methoxy-6-(3-chlorophenyl)-7-bromo-6H-dibenzo(b,d)pyran-8-yl)methanesulfonamide,
(1-methoxy-6-(3-chlorophenyl)-7-methyl-6H-dibenzo(b,d)pyran-8-yl)methanesulfonamide,
(1-methoxy-6-(3-fluorophenyl)-7-bromo-6H-dibenzo(b,d)pyran-8-yl)methanesulfonamide,
(1-methoxy-6-(3-fluorophenyl)-7-methyl-6H-dibenzo(b,d)pyran-8-yl)methanesulfonamide,
(1-methoxy-6-(3-methoxyphenyl)-7-bromo-6H-dibenzo(b,d)pyran-8-yl)methanesulfonamide,
(1-methoxy-6-(3-methoxyphenyl)-7-methyl-6H-dibenzo(b,d)pyran-8-yl)methanesulfonamide,
(1-methoxy-6-(3,4-dimethoxy)phenyl-7-bromo-6H-dibenzo(b,d)pyran-8-yl)methanesulfonamide,
(1-methoxy-6-(3,4-dimethoxy)phenyl-7-methyl-6H-dibenzo(b,d)pyran-8-yl)methanesulfonamide,
(1-methoxy-6-(5-bromothien-2-yl)-7-bromo-6H-dibenzo(b,d)pyran-8-yl)methanesulfonamide,
(1-methoxy-6-(5-bromothien-2-yl)-7-methyl-6H-dibenzo(b,d)pyran-8-yl)methanesulfonamide,
(1-difluoromethoxy-6-allyl-7-bromo-6H-dibenzo(b,d)pyran-8-yl)methanesulfonamide,
(1-difluoromethoxy-6-allyl-7-methyl-6H-dibenzo(b,d)pyran-8-yl)methanesulfonamide,
(1-difluoromethoxy-6-phenyl-7-bromo-6H-dibenzo(b,d)pyran-8-yl)methanesulfonamide,
(1-difluoromethoxy-6-phenyl-7-methyl-6H-dibenzo(b,d)pyran-8-yl)methanesulfonamide,
(1-difluoromethoxy-6-(3-chlorophenyl)-7-bromo-6H-dibenzo(b,d)pyran-8-yl)methanesulfonamide, (1-difluoromethoxy-6-(3-chlorophenyl)-7-methyl-6H-dibenzo(b,d)pyran-8-yl)methanesulfonamide,
(1-difluoromethoxy-6-(3-fluorophenyl)-7-bromo-6H-dibenzo(b,d)pyran-8-yl)methanesulfonamide,
(1-difluoromethoxy-6-(3-fluorophenyl)-7-methyl-6H-dibenzo(b,d)pyran-8-yl)methanesulfonamide,
(1-difluoromethoxy-6-(3-methoxyphenyl)-7-bromo-6H-dibenzo(b,d)pyran-8-yl)methanesulfonamide,
(1-difluoromethoxy-6-(3-methoxyphenyl)-7-methyl-6H-dibenzo(b,d)pyran-8-yl)methanesulfonamide,
(1-difluoromethoxy-6-(3,4-dimethoxy)phenyl-7-bromo-6H-dibenzo(b,d)pyran-8-yl)methanesulfonamide,
(1-difluoromethoxy-6-(3,4-dimethoxy)phenyl-7-methyl-6H-dibenzo(b,d)pyran-8-yl)methanesulfonamide,
(1-difluoromethoxy-6-(5-bromothien-2-yl)-7-bromo-6H-dibenzo(b,d)pyran-8-yl)methanesulfonamide,
(1-difluoromethoxy-6-(5-bromothien-2-yl)-7-methyl-6H-dibenzo(b,d)pyran-8-yl)methanesulfonamide,
(1-methoxy-6-allyl-8-methyl-6H-dibenzo(b,d)pyran-8-yl)methanesulfonamide,
(1-methoxy-6-phenyl-8-methyl-6H-dibenzo(b,d)pyran-8-yl)methanesulfonamide,
(1-methoxy-6-(3-chlorophenyl)-8-methyl-6H-dibenzo(b,d)pyran-8-yl)methanesulfonamide,
(1-methoxy-6-(3-fluorophenyl)-8-methyl-6H-dibenzo(b,d)pyran-8-yl)methanesulfonamide,
(1-methoxy-6-(3-methoxyphenyl)-8-methyl-6H-dibenzo(b,d)pyran-8-yl)methanesulfonamide,
(1-methoxy-6-(3,4-dimethoxy)phenyl-8-methyl-6H-dibenzo(b,d)pyran-8-yl)methanesulfonamide,
(1-methoxy-6-(5-bromothien-2-yl)-8-methyl-6H-dibenzo(b,d)pyran-8-yl)methanesulfonamide,
(1-difluoromethoxy-6-allyl-8-methyl-6H-dibenzo(b,d)pyran-8-yl)methanesulfonamide,
(1-difluoromethoxy-6-phenyl-8-methyl-6H-dibenzo(b,d)pyran-8-yl)methanesulfonamide,
(1-difluoromethoxy-6-(3-chlorophenyl)-8-methyl-6H-dibenzo(b,d)pyran-8-yl)methanesulfonamide,
(1-difluoromethoxy-6-(3-fluorophenyl)-8-methyl-6H-dibenzo(b,d)pyran-8-yl)methanesulfonamide,
(1-difluoromethoxy-6-(3-methoxyphenyl)-8-methyl-6H-dibenzo(b,d)pyran-8-yl)methanesulfonamide,
(1-difluoromethoxy-6-(3,4-dimethoxy)phenyl-8-methyl-6H-dibenzo(b,d)pyran-8-yl)methanesulfonamide,
(1-difluoromethoxy-6-(5-bromothien-2-yl)-8-methyl-6H-dibenzo(b,d)pyran-8-yl)methanesulfonamide,
(1-methoxy-6-allyl-9-allyl-6H-dibenzo(b,d)pyran-8-yl)methanesulfonamide,
(1-methoxy-6-phenyl-9-allyl-6H-dibenzo(b,d)pyran-8-yl)methanesulfonamide,
(1-methoxy-6-(3-chlorophenyl)-9-allyl-6H-dibenzo(b,d)pyran-8-yl)methanesulfonamide,
(1-methoxy-6-(3-fluorophenyl)-9-allyl-6H-dibenzo(b,d)pyran-8-yl)methanesulfonamide,
(1-methoxy-6-(3-methoxyphenyl)-9-allyl-6H-dibenzo(b,d)pyran-8-yl)methanesulfonamide,
(1-methoxy-6-(3,4-dimethoxy)phenyl-9-allyl-6H-dibenzo(b,d)pyran-8-yl)methanesulfonamide,
(1-methoxy-6-(-bromothien-2-yl)-9-allyl-6H-dibenzo(b,d)pyran-8-yl)methanesulfonamide,
(1-difluoromethoxy-6-allyl-9-allyl-6H-dibenzo(b,d)pyran-8-yl)methanesulfonamide,
(1-difluoromethoxy-6-phenyl-9-allyl-6H-dibenzo(b,d)pyran-8-yl)methanesulfonamide,
(1-difluoromethoxy-6-(3-chlorophenyl)-9-allyl-6H-dibenzo(b,d)pyran-8-yl)methanesulfonamide,
(1-difluoromethoxy-6-(3-fluorophenyl)-9-allyl-6H-dibenzo(b,d)pyran-8-yl)methanesulfonamide,
(1-difluoromethoxy-6-(3-methoxyphenyl)-9-allyl-6H-dibenzo(b,d)pyran-8-yl)methanesulfonamide,
(1-difluoromethoxy-6-(3,4-dimethoxy)phenyl-9-allyl-6H-dibenzo(b,d)pyran-8-yl)methanesulfonamide,
(1-difluoromethoxy-6-(5-bromothien-2-yl)-9-allyl-6H-dibenzo(b,d)pyran-8-yl)methanesulfonamide,
(1-methoxy-6-allyl-6H-dibenzo(b,d)pyran-8-yl)acetamide,
(1-methoxy-6-allyl-6H-dibenzo(b,d)pyran-8-yl)propionamide,
(1-methoxy-6-allyl-6H-dibenzo(b,d)pyran-8-yl)-(2-methyl)propionamide,
(1-methoxy-6-allyl-6H-dibenzo(b,d)pyran-8-yl)benzamide,
(1-methoxy-6-allyl-6H-dibenzo(b,d)pyran-8-yl)cyclopropanamide,
(1-methoxy-6-allyl-6H-dibenzo(b,d)pyran-8-yl)-(2-methoxy)acetamide,
(1-methoxy-6-allyl-6H-dibenzo(b,d)pyran-8-yl)trifluoroacetamide,
(1-methoxy-6-allyl-6H-dibenzo(b,d)pyran-8-yl)-N,N-dimethylurea,
(1-methoxy-6-allyl-6H-dibenzo(b,d)pyran-8-yl)-N,N-dimethylthiourea,
(1-methoxy-6-allyl-6H-dibenzo(b,d)pyran-8-yl)-N,N-dimethylsulfonylurea,
(1-methoxy-6-allyl-6H-dibenzo(b,d)pyran-8-yl)-N,N-diethylsulfonylurea,
(1-methoxy-6-allyl-6H-dibenzo(b,d)pyran-8-yl)-N-methyl-N-ethylsulfonylurea,
(1-methoxy-6-allyl-6H-dibenzo(b,d)pyran-8-yl)aniline,
(1-methoxy-6-allyl-6H-dibenzo(b,d)pyran-8-yl)-N-ethylaniline,
(1-methoxy-6-allyl-6H-dibenzo(b,d)pyran-8-yl)-N-methylaniline,
(1-methoxy-6-allyl-6H-dibenzo(b,d)pyran-8-yl)-N-(cyclopropylmethyl)aniline,
(1-methoxy-6-allyl-6H-dibenzo(b,d)pyran-8-yl)-N-benzylaniline,
(1-methoxy-6-allyl-6H-dibenzo(b,d)pyran-8-yl)benzenesulfonamide,
(1-methoxy-6-allyl-6H-dibenzo(b,d)pyran-8-yl)ethanesulfonamide,
(1-methoxy-6-allyl-6H-dibenzo(b,d)pyran-8-yl)isopropanesulfonamide,
(1-methoxy-6-allyl-6H-dibenzo(b,d)pyran-8-yl)-(2-fluorobenzene)sulfonamide,
(1-methoxy-6-allyl-6H-dibenzo(b,d)pyran-8-yl)-thiophene-2-sulfonamide,
(1-methoxy-6-phenyl-6H-dibenzo(b,d)pyran-8-yl)acetamide,
(1-methoxy-6-phenyl-6H-dibenzo(b,d)pyran-8-yl)propionamide,
(1-methoxy-6-phenyl-6H-dibenzo(b,d)pyran-8-yl)-(2-methyl)propionamide, (1-methoxy-6-phenyl-6H-dibenzo(b,d)pyran-8-yl) benzamide,
(1-methoxy-6-phenyl-6H-dibenzo(b,d)pyran-8-yl) cyclopropanamide,
(1-methoxy-6-phenyl-6H-dibenzo(b,d)pyran-8-yl)-(2-methoxy)acetamide,
(1-methoxy-6-phenyl-6H-dibenzo(b,d)pyran-8-yl) trifluoroacetamide,
(1-methoxy-6-phenyl-6H-dibenzo(b,d)pyran-8-yl)-N,N-dimethylurea,
(1-methoxy-6-phenyl-6H-dibenzo(b,d)pyran-8-yl)-N,N-dimethylthiourea,
(1-methoxy-6-phenyl-6H-dibenzo(b,d)pyran-8-yl)-N,N-dimethylsulfonylurea,
(1-methoxy-6-phenyl-6H-dibenzo(b,d)pyran-8-yl)-N,N-diethylsulfonylurea,
(1-methoxy-6-phenyl-6H-dibenzo(b,d)pyran-8-yl)-N-methyl-N-ethylsulfonylurea,
(1-methoxy-6-phenyl-6H-dibenzo(b,d)pyran-8-yl) aniline,
(1-methoxy-6-phenyl-6H-dibenzo(b,d)pyran-8-yl)-N-ethylaniline,
(1-methoxy-6-phenyl-6H-dibenzo(b,d)pyran-8-yl)-N-methylaniline,
(1-methoxy-6-phenyl-6H-dibenzo(b,d)pyran-8-yl)-N-benzylaniline,
(1-methoxy-6-phenyl-6H-dibenzo(b,d)pyran-8-yl) benzenesulfonamide,
(1-methoxy-6-phenyl-6H-dibenzo(b,d)pyran-8-yl) ethanesulfonamide,
(1-methoxy-6-phenyl-6H-dibenzo(b,d)pyran-8-yl) isopropanesulfonamide,
(1-methoxy-6-phenyl-6H-dibenzo(b,d)pyran-8-yl)-(2-fluorobenzene)sulfonamide,
(1-methoxy-6-phenyl-6H-dibenzo(b,d)pyran-8-yl)-thiophene-2-sulfonamide,
(1-methoxy-6-(3-chlorophenyl)-6H-dibenzo(b,d)pyran-8-yl)acetamide,
(1-methoxy-6-(3-chlorophenyl)-6H-dibenzo(b,d)pyran-8-yl)propionamide,
(1-methoxy-6-(3-chlorophenyl)-6H-dibenzo(b,d)pyran-8-yl)-(2-methyl)propionamide,
(1-methoxy-6-(3-chlorophenyl)-6H-dibenzo(b,d)pyran-8-yl)benzamide,
(1-methoxy-6-(3-chlorophenyl)-6H-dibenzo(b,d)pyran-8-yl)cyclopropanamide,
(1-methoxy-6-(3-chlorophenyl)-6H-dibenzo(b,d)pyran-8-yl)-(2-methoxy)acetamide,
(1-methoxy-6-(3-chlorophenyl)-6H-dibenzo(b,d)pyran-8-yl)trifluoroacetamide,
(1-methoxy-6-(3-chlorophenyl)-6H-dibenzo(b,d)pyran-8-yl)-N,N-dimethylurea,
(1-methoxy-6-(3-chlorophenyl)-6H-dibenzo(b,d)pyran-8-yl)-N,N-dimethylthiourea,
(1-methoxy-6-(3-chlorophenyl)-6H-dibenzo(b,d)pyran-8-yl)-N,N-dimethylsulfonylurea,
(1-methoxy-6-(3-chlorophenyl)-6H-dibenzo(b,d)pyran-8-yl)-N,N-diethylsulfonylurea,
(1-methoxy-6-(3-chlorophenyl)-6H-dibenzo(b,d)pyran-8-yl)-N-methyl-N-ethylsulfonylurea,
(1-methoxy-6-(3-chlorophenyl)-6H-dibenzo(b,d)pyran-8-yl)aniline,
(1-methoxy-6-(3-chlorophenyl)-6H-dibenzo(b,d)pyran-8-yl)-N-ethylaniline,
(1-methoxy-6-(3-chlorophenyl)-6H-dibenzo(b,d)pyran-8-yl)-N-methylaniline,
(1-methoxy-6-(3-chlorophenyl)-6H-dibenzo(b,d)pyran-8-yl)-N-(cyclopropylmethyl)aniline,
(1-methoxy-6-(3-chlorophenyl)-6H-dibenzo(b,d)pyran-8-yl)-N-benzylaniline,
(1-methoxy-6-(3-chlorophenyl)-6H-dibenzo(b,d)pyran-8-yl)benzenesulfonamide,
(1-methoxy-6-(3-chlorophenyl)-6H-dibenzo(b,d)pyran-8-yl)ethanesulfonamide,
(1-methoxy-6-(3-chlorophenyl)-6H-dibenzo(b,d)pyran-8-yl)isopropanesulfonamide,
(1-methoxy-6-(3-chlorophenyl)-6H-dibenzo(b,d)pyran-8-yl)-(2-fluorobenzene)sulfonamide,
(1-methoxy-6-(3-chlorophenyl)-6H-dibenzo(b,d)pyran-8-yl)-thiophene-2-sulfonamide,
(1-methoxy-6-(3-fluorophenyl)-6H-dibenzo(b,d)pyran-8-yl)acetamide,
(1-methoxy-6-(3-fluorophenyl)-6H-dibenzo(b,d)pyran-8-yl)propionamide,
(1-methoxy-6-(3-fluorophenyl)-6H-dibenzo(b,d)pyran-8-yl)-(2-methyl)propionamide,
(1-methoxy-6-(3-fluorophenyl)-6H-dibenzo(b,d)pyran-8-yl)benzamide,
(1-methoxy-6-(3-fluorophenyl)-6H-dibenzo(b,d)pyran-8-yl)(2methoxy)acetamide,
(1-methoxy-6-(3-fluorophenyl)-6H-dibenzo(b,d)pyran-8-yl)trifluoroacetamide,
(1-methoxy-6-(3-fluorophenyl)-6H-dibenzo(b,d)pyran-8-yl)-N,N-dimethylurea,
(1-methoxy-6-(3-fluorophenyl)-6H-dibenzo(b,d)pyran-8-yl)-N,N-dimethylthiourea,
(1-methoxy-6-(3-fluorophenyl)-6H-dibenzo(b,d)pyran-8-yl)-N,N-dimethylsulfonylurea,
(1-methoxy-6-(3-fluorophenyl)-6H-dibenzo(b,d)pyran-8-yl)-N,N-diethylsulfonylurea,
(1-methoxy-6-(3-fluorophenyl)-6H-dibenzo(b,d)pyran-8-yl)-N-methyl-N-ethylsulfonylurea,
(1-methoxy-6-(3-fluorophenyl)-6H-dibenzo(b,d)pyran-8-yl)aniline,
(1-methoxy-6-(3-fluorophenyl)-6H-dibenzo(b,d)pyran-8-yl)-N-ethylaniline,
(1-methoxy-6-(3-fluorophenyl)-6H-dibenzo(b,d)pyran-8-yl)-N-methylaniline,
(1-methoxy-6-(3-fluorophenyl)-6H-dibenzo(b,d)pyran-8-yl)-N-(cyclopropylmethyl)aniline,
(1-methoxy-6-(3-fluorophenyl)-6H-dibenzo(b,d)pyran-8-yl)-N-benzylaniline,
(1-methoxy-6-(3-fluorophenyl)-6H-dibenzo(b,d)pyran-8-yl)benzenesulfonamide,
(1-methoxy-6-(3-fluorophenyl)-6H-dibenzo(b,d)pyran-8-yl)ethanesulfonamide,
(1-methoxy-6-(3-fluorophenyl)-6H-dibenzo(b,d)pyran-8-yl)isopropanesulfonamide,
(1-methoxy-6-(3-fluorophenyl)-6H-dibenzo(b,d)pyran-8-yl)-(2-fluorobenzene)sulfonamide,
(1-methoxy-6-(3-fluorophenyl)-6H-dibenzo(b,d)pyran-8-yl)-thiophene-2-sulfonamide,
(1-methoxy-6-(3-methoxyphenyl)-6H-dibenzo(b,d)pyran-8-yl)acetamide, (1-methoxy-6-(3-methoxyphenyl)-6H-dibenzo(b,d pyran-8-yl)propionamide,
(1-methoxy-6-(3-methoxyphenyl)-6H-dibenzo(b,d)pyran-8-yl)-(2-methyl)propionamide,
(1-methoxy-6-(3-methoxyphenyl)-6H-dibenzo(b,d)pyran-8-yl)benzamide,
(1-methoxy-6-(3-methoxyphenyl)-6H-dibenzo(b,d)pyran-8-yl)cyclopropanamide,
(1-methoxy-6-(3-methoxyphenyl)-6H-dibenzo(b,d)pyran-8-yl)-(2-methoxy)acetamide,
(1-methoxy-6-(3-methoxyphenyl)-6H-dibenzo(b,d)pyran-8-yl)trifluoroacetamide,
(1-methoxy-6-(3-methoxyphenyl)-6H-dibenzo(b,d)pyran-8-yl)-N,N-dimethylurea,
(1-methoxy-6-(3-methoxyphenyl)-6H-dibenzo(b,d)pyran-8-yl)-N,N-dimethylthiourea,
(1-methoxy-6-(3-methoxyphenyl)-6H-dibenzo(b,d)pyran-8-yl)-N,N-dimethylsulfonylurea,
(1-methoxy-6-(3-methoxyphenyl)-6H-dibenzo(b,d)pyran-8-yl)-N,N-diethylsulfonylurea,
(1-methoxy-6-(3-methoxyphenyl)-6H-dibenzo(b,d)pyran-8-yl)-N-methyl-N-ethylsulfonylurea,
(1-methoxy-6-(3-methoxyphenyl)-6H-dibenzo(b,d)pyran-8-yl)aniline,
(1-methoxy-6-(3-methoxyphenyl)-6H-dibenzo(b,d)pyran-8-yl)-N-ethylaniline,
(1-methoxy-6-(3-methoxyphenyl)-6H-dibenzo(b,d)pyran-8-yl)-N-methylaniline,
(1-methoxy-6-(3-methoxyphenyl)-6H-dibenzo(b,d)pyran-8-yl)-N-(cyclopropylmethyl)aniline,
(1-methoxy-6-(3-methoxyphenyl)-6H-dibenzo(b,d)pyran-8-yl)-N-benzylaniline,
(1-methoxy-6-(3-methoxyphenyl)-6H-dibenzo(b,d)pyran-8-yl)benzenesulfonamide,
(1-methoxy-6-(3-methoxyphenyl)-6H-dibenzo(b,d)pyran-8-yl)ethanesulfonamide,
(1-methoxy-6-(3-methoxyphenyl)-6H-dibenzo(b,d)pyran-8-yl)isopropanesulfonamide,
(1-methoxy-6-(3-methoxyphenyl)-6H-dibenzo(b,d)pyran-8-yl)-(2-fluorobenzene)sulfonamide,
(1-methoxy-6-(3-methoxyphenyl)-6H-dibenzo(b,d)pyran-8-yl)-thiophene-2-sulfonamide,
(1-methoxy-6-(3,4-dimethoxy)phenyl-6H-dibenzo(b,d)pyran-8-yl)acetamide,
(1-methoxy-6-(3,4-dimethoxy)phenyl-6H-dibenzo(b,d)pyran-8-yl)propionamide,
(1-methoxy-6-(3,4-dimethoxy)phenyl-6H-dibenzo(b,d)pyran-8-yl)-(2-methyl)propionamide,
(1-methoxy-6-(3,4-dimethoxy)phenyl-6H-dibenzo(b,d)pyran-8-yl)benzamide,
(1-methoxy-6-(3,4-dimethoxy)phenyl-6H-dibenzo(b,d)pyran-8-yl)cyclopropanamide,
(1-methoxy-6-(3,4-dimethoxy)phenyl-6H-dibenzo(b,d)pyran-8-yl)-(2-methoxy)acetamide,
(1-methoxy-6-(3,4-dimethoxy)phenyl-6H-dibenzo(b,d)pyran-8-yl)trifluoroacetamide,
(1-methoxy-6-(3,4-dimethoxy)phenyl-6H-dibenzo(b,d)pyran-8-yl)-N,N-dimethylurea,
(1-methoxy-6-(3,4-dimethoxy)phenyl-6H-dibenzo(b,d)pyran-8-yl)-N,N-dimethylthiourea,
(1-methoxy-6-(3,4-dimethoxy)phenyl-6H-dibenzo(b,d)pyran-8-yl)-N,N-dimethylsulfonylurea,
(1-methoxy-6-(3,4-dimethoxy)phenyl-6H-dibenzo(b,d)pyran-8-yl)-N,N-diethylsulfonylurea,
(1-methoxy-6-(3,4-dimethoxy)phenyl-6H-dibenzo(b,d)pyran-8-yl)-N-methyl-N-ethylsulfonylurea,
(1-methoxy-6-(3,4-dimethoxy)phenyl-6H-dibenzo(b,d)pyran-8-yl)aniline,
(1-methoxy-6-(3,4-dimethoxy)phenyl-6H-dibenzo(b,d)pyran-8-yl)-N-ethylaniline,
(1-methoxy-6-(3,4-dimethoxy)phenyl-6H-dibenzo(b,d)pyran-8-yl)-N-methylaniline,
(1-methoxy-6-(3,4-dimethoxy)phenyl-6H-dibenzo(b,d)pyran-8-yl)-N-(cyclopropylmethyl)aniline,
(1-methoxy-6-(3,4-dimethoxy)phenyl-6H-dibenzo(b,d)pyran-8-yl)-N-benzylaniline,
(1-methoxy-6-(3,4-dimethoxy)phenyl-6H-dibenzo(b,d)pyran-8-yl)benzenesulfonamide,
(1-methoxy-6-(3,4-dimethoxy)phenyl-6H-dibenzo(b,d)pyran-8-yl)ethanesulfonamide,
(1-methoxy-6-(3,4-dimethoxy)phenyl-6H-dibenzo(b,d)pyran-8-yl)isopropanesulfonamide,
(1-methoxy-6-(3,4-dimethoxy)phenyl-6H-dibenzo(b,d)pyran-8-yl)-(2-fluorobenzene)sulfonamide,
(1-methoxy-6-(3,4-dimethoxy)phenyl-6H-dibenzo(b,d)pyran-8-yl)-thiophene-2-sulfonamide,
(1-methoxy-6-(5-bromothien-2-yl)-6H-dibenzo(b,d)pyran-8-yl)acetamide,
(1-methoxy-6-(5-bromothien-2-yl)-6H-dibenzo(b,d)pyran-8-yl)propionamide,
(1-methoxy-6-(5-bromothien-2-yl)-6H-dibenzo(b,d)pyran-8-yl)-(2-methyl)propionamide,
(1-methoxy-6-(5-bromothien-2-yl)-6H-dibenzo(b,d)pyran-8-yl)benzamide,
(1-methoxy-6-(5-bromothien-2-yl)-6H-dibenzo(b,d)pyran-8-yl)cyclopropanamide,
(1-methoxy-6-(5-bromothien-2-yl)-6H-dibenzo(b,d)pyran-8-yl)-(2-methoxy)acetamide,
(1-methoxy-6-(5-bromothien-2-yl)-6H-dibenzo(b,d)pyran-8-yl)trifluoroacetamide,
(1-methoxy-6-(5-bromothien-2-yl)-6H-dibenzo(b,d)pyran-8-yl)-N,N-dimethylurea,
(1-methoxy-6-(5-bromothien-2-yl)-6H-dibenzo(b,d)pyran-8-yl)-N,N-dimethylthiourea,
(1-methoxy-6-(5-bromothien-2-yl)-6H-dibenzo(b,d)pyran-8-yl)-N,N-dimethylsulfonylurea,
(1-methoxy-6-(5-bromothien-2-yl)-6H-dibenzo(b,d)pyran-8-yl)-N,N-diethylsulfonylurea,
(1-methoxy-6-(5-bromothien-2-yl)-6H-dibenzo(b,d)pyran-8-yl)-N-methyl-N-ethylsulfonylurea,
(1-methoxy-6-(5-bromothien-2-yl)-6H-dibenzo(b,d)pyran-8-yl)aniline,
(1-methoxy-6-(5-bromothien-2-yl)-6H-dibenzo(b,d)pyran-8-yl)-N-ethylaniline,
(1-methoxy-6-(5-bromothien-2-yl)-6H-dibenzo(b,d)pyran-8-yl)-N-methylaniline,
(1-methoxy-6-(5-bromothien-2-yl)-6H-dibenzo(b,d)pyran-8-yl)-N-(cyclopropylmethyl)aniline,
(1-methoxy-6-(5-bromothien-2-yl)-6H-dibenzo(b,d)pyran-8-yl)-N-benzylaniline,
(1-methoxy-6-(5-bromothien-2-yl)-6H-dibenzo(b,d)pyran-8-yl)benzenesulfonamide,
(1-methoxy-6-(5-bromothien-2-yl)-6H-dibenzo(b,d)pyran-8-yl)ethanesulfonamide, (1-methoxy-6-(5-bromothien-2-yl)-6H-dibenzo(b,d)pyran-8-yl)isopropanesulfonamide,
(1-methoxy-6-(5-bromothien-2-yl)-6H-dibenzo(b,d)pyran-8-yl)-(2-fluorobenzene)sulfonamide,
(1-methoxy-6-(5-bromothien-2-yl)-6H-dibenzo(b,d)pyran-8-yl)-thiophene-2-sulfonamide,
(1-difluoromethoxy-6-allyl-6H-dibenzo(b,d)pyran-8-yl)acetamide,
(1-difluoromethoxy-6-allyl-6H-dibenzo(b,d)pyran-8-yl)propionamide,
(1-difluoromethoxy-6-allyl-6H-dibenzo(b,d)pyran-8-yl)-(2-methyl)propionamide,
(1-difluoromethoxy-6-allyl-6H-dibenzo(b,d)pyran-8-yl)benzamide,
(1-difluoromethoxy-6-allyl-6H-dibenzo(b,d)pyran-8-yl)cyclopropanamide,
(1-difluoromethoxy-6-allyl-6H-dibenzo(b,d)pyran-8-yl)-(2-methoxy)acetamide,
(1-difluoromethoxy-6-allyl-6H-dibenzo(b,d)pyran-8-yl)trifluoroacetamide,
(1-difluoromethoxy-6-allyl-6H-dibenzo(b,d)pyran-8-yl)-N,N-dimethylurea,
(1-difluoromethoxy-6-allyl-6H-dibenzo(b,d)pyran-8-yl)-N,N-dimethylthiourea,
(1-difluoromethoxy-6-allyl-6H-dibenzo(b,d)pyran-8-yl)-N,N-dimethylsulfonylurea,
(1-difluoromethoxy-6-allyl-6H-dibenzo(b,d)pyran-8-yl)-N,N-diethylsulfonylurea,
(1-difluoromethoxy-6-allyl-6H-dibenzo(b,d)pyran-8-yl)-N-methyl-N-ethylsulfonylurea,
(1-difluoromethoxy-6-allyl-6H-dibenzo(b,d)pyran-8-yl)aniline,
(1-difluoromethoxy-6-allyl-6H-dibenzo(b,d)pyran-8-yl)-N-ethylaniline,
(1-difluoromethoxy-6-allyl-6H-dibenzo(b,d)pyran-8-yl)-N-methylaniline,
(1-difluoromethoxy-6-allyl-6H-dibenzo(b,d)pyran-8-yl)-N-(cyclopropylmethyl)aniline,
(1-difluoromethoxy-6-allyl-6H-dibenzo(b,d)pyran-8-yl)-N-benzylaniline,
(1-difluoromethoxy-6-allyl-6H-dibenzo(b,d)pyran-8-yl)benzenesulfonamide,
(1-difluoromethoxy-6-allyl-6H-dibenzo(b,d)pyran-8-yl)ethanesulfonamide,
(1-difluoromethoxy-6-allyl-6H-dibenzo(b,d)pyran-8-yl)isopropanesulfonamide,
(1-difluoromethoxy-6-allyl-6H-dibenzo(b,d)pyran-8-yl)-(2-fluorobenzene)sulfonamide,
(1-difluoromethoxy-6-allyl-6H-dibenzo(b,d)pyran-8-yl)-thiophene-2-sulfonamide,
(1-difluoromethoxy-6-phenyl-6H-dibenzo(b,d)pyran-8-yl)acetamide,
(1-difluoromethoxy-6-phenyl-6H-dibenzo(b,d)pyran-8-yl)propionamide,
(1-difluoromethoxy-6-phenyl-6H-dibenzo(b,d)pyran-8-yl)-(2-methyl)propionamide,
(1-difluoromethoxy-6-phenyl-6H-dibenzo(b,d)pyran-8-yl)benzamide,
(1-difluoromethoxy-6-phenyl-6H-dibenzo(b,d)pyran-8-yl)cyclopropanamide,
(1-difluoromethoxy-6-phenyl-6H-dibenzo(b,d)pyran-8-yl)-(2-methoxy)acetamide,
(1-difluoromethoxy-6-phenyl-6H-dibenzo(b,d)pyran-8-yl)trifluoroacetamide,
(1-difluoromethoxy-6-phenyl-6H-dibenzo(b,d)pyran-8-yl)-N,N-dimethylurea,
(1-difluoromethoxy-6-phenyl-6H-dibenzo(b,d)pyran-8-yl)-N,N-dimethylthiourea,
(1-difluoromethoxy-6-phenyl-6H-dibenzo(b,d)pyran-8-yl)-N,N-dimethylsulfonylurea,
(1-difluoromethoxy-6-phenyl-6H-dibenzo(b,d)pyran-8-yl)-N,N-diethylsulfonylurea,
(1-difluoromethoxy-6-phenyl-6H-dibenzo(b,d)pyran-8-yl)-N-methyl-N-ethylsulfonylurea,
(1-difluoromethoxy-6-phenyl-6H-dibenzo(b,d)pyran-8-yl)aniline,
(1-difluoromethoxy-6-phenyl-6H-dibenzo(b,d)pyran-8-yl)-N-ethylaniline,
(1-difluoromethoxy-6-phenyl-6H-dibenzo(b,d)pyran-8-yl)-N-methylaniline,
(1-difluoromethoxy-6-phenyl-6H-dibenzo(b,d)pyran-8-yl)-N-(cyclopropylmethyl)aniline,
(1-difluoromethoxy-6-phenyl-6H-dibenzo(b,d)pyran-8-yl)-N-benzylaniline,
(1-difluoromethoxy-6-phenyl-6H-dibenzo(b,d)pyran-8-yl)benzenesulfonamide,
(1-difluoromethoxy-6-phenyl-6H-dibenzo(b,d)pyran-8-yl)ethanesulfonamide,
(1-difluoromethoxy-6-phenyl-6H-dibenzo(b,d)pyran-8-yl)isopropanesulfonamide,
(1-difluoromethoxy-6-phenyl-6H-dibenzo(b,d)pyran-8-yl)-(2-fluorobenzene)sulfonamide,
(1-difluoromethoxy-6-phenyl-6H-dibenzo(b,d)pyran-8-yl)-thiophene-2-sulfonamide,
(1-difluoromethoxy-6-(3-chlorophenyl)-6H-dibenzo(b,d)pyran-8-yl)acetamide,
(1-difluoromethoxy-6-(3-chlorophenyl)-6H-dibenzo(b,d)pyran-8-yl)propionamide,
(1-difluoromethoxy-6-(3-chlorophenyl)-6H-dibenzo(b,d)pyran-8-yl)-(2-methyl)propionamide,
(1-difluoromethoxy-6-(3-chlorophenyl)-6H-dibenzo(b,d)pyran-8-yl)benzamide,
(1-difluoromethoxy-6-(3-chlorophenyl)-6H-dibenzo(b,d)pyran-8-yl)cyclopropanamide,
(1-difluoromethoxy-6-(3-chlorophenyl)-6H-dibenzo(b,d)pyran-8-yl)-(2-methoxy)acetamide,
(1-difluoromethoxy-6-(3-chlorophenyl)-6H-dibenzo(b,d)pyran-8-yl)trifluoroacetamide,
(1-difluoromethoxy-6-(3-chlorophenyl)-6H-dibenzo(b,d)pyran-8-yl)-N,N-dimethylurea,
(1-difluoromethoxy-6-(3-chlorophenyl)-6H-dibenzo(b,d)pyran-8-yl)-N,N-dimethylthiourea,
(1-difluoromethoxy-6-(3-chlorophenyl)-6H-dibenzo(b,d)pyran-8-yl)-N,N-dimethylsulfonylurea,
(1-difluoromethoxy-6-(3-chlorophenyl)-6H-dibenzo(b,d)pyran-8-yl)-N,N-diethylsulfonylurea,
(1-difluoromethoxy-6-(3-chlorophenyl)-6H-dibenzo(b,d)pyran-8-yl)-N-methyl-N-ethylsulfonylurea,
(1-difluoromethoxy-6-(3-chlorophenyl)-6 H-dibenzo(b,d)pyran-8-yl)aniline,
(1-difluoromethoxy-6-(3-chlorophenyl)-6H-dibenzo(b,d)pyran-8-yl)-N-ethylaniline,
(1-difluoromethoxy-6-(3-chlorophenyl)-6H-dibenzo(b,d)pyran-8-yl)-N-methylaniline, (1-difluoromethoxy-6-(3-chlorophenyl)-6H-dibenzo(b,d)pyran-8-yl)-N-(cyclopropylmethyl)aniline,
(1-difluoromethoxy-6-(3-chlorophenyl)-6H-dibenzo(b,d)pyran-8-yl)-N-benzylaniline,
(1-difluoromethoxy-6-(3-chlorophenyl)-6H-dibenzo(b,d)pyran-8-yl)benzenesulfonamide,
(1-difluoromethoxy-6-(3-chlorophenyl)-6H-dibenzo(b,d)pyran-8-yl)ethanesulfonamide,
(1-difluoromethoxy-6-(3-chlorophenyl)-6H-dibenzo(b,d)pyran-8-yl)isopropanesulfonamide,
(1-difluoromethoxy-6-(3-chlorophenyl)-6H-dibenzo(b,d)pyran-8-yl)-(2-fluorobenzene)sulfonamide,
(1-difluoromethoxy-6-(3-chlorophenyl)-6H-dibenzo(b,d)pyran-8-yl)-thiophene-2-sulfonamide,
(1-difluoromethoxy-6-(3-fluorophenyl)-6H-dibenzo(bed)pyran-8-yl)acetamide,
(1-difluoromethoxy-6-(3-fluorophenyl)-6H-dibenzo(b,d)pyran-8-yl)propionamide,
(1-difluoromethoxy-6-(3-fluorophenyl)-6H-dibenzo(b,d)pyran-8-yl)-(2-methyl)propionamide,
(1-difluoromethoxy-6-(3-fluorophenyl)-6H-dibenzo(b,d)pyran-8-yl)benzamide,
(1-difluoromethoxy-6-(3-fluorophenyl)-6H-dibenzo(b,d)pyran-8-yl)cyclopropanamide,
(1-difluoromethoxy-6-(3-fluorophenyl)-6H-dibenzo(b,d)pyran-8-yl)-(2-methoxy)acetamide,
(1-difluoromethoxy-6-(3-fluorophenyl)-6H-dibenzo(b,d)pyran-8-yl)trifluoroacetamide,
(1-difluoromethoxy-6-(3-fluorophenyl)-6H-dibenzo(b,d)pyran-8-yl)-N,N-dimethylurea,
(1-difluoromethoxy-6-(3-fluorophenyl)-6H-dibenzo(b,d)pyran-8-yl)-N,N-dimethylthiourea,
(1-difluoromethoxy-6-(3-fluorophenyl)-6H-dibenzo(b,d)pyran-8-yl)-N,N-dimethylsulfonylurea,
(1-difluoromethoxy-6-(3-fluorophenyl)-6H-dibenzo(b,d)pyran-8-yl)-N,N-diethylsulfonylurea,
(1-difluoromethoxy-6-(3-fluorophenyl)-6H-dibenzo(b,d)pyran-8-yl)-N-methyl-N-ethylsulfonylurea,
(1-difluoromethoxy-6-(3-fluorophenyl)-6H-dibenzo(b,d)pyran-8-yl)aniline,
(1-difluoromethoxy-6-(3-fluorophenyl)-6H-dibenzo(b,d)pyran-8-yl)-N-ethylaniline,
(1-difluoromethoxy-6-(3-fluorophenyl)-6H-dibenzo(b,d)pyran-8-yl)-N-methylaniline,
(1-difluoromethoxy-6-(3-fluorophenyl)-6H-dibenzo(b,d)pyran-8-yl)-N-(cyclopropylmethyl)aniline,
(1-difluoromethoxy-6-(3-fluorophenyl)-6H-dibenzo(b,d)pyran-8-yl)-N-benzylaniline,
(1-difluoromethoxy-6-(3-fluorophenyl)-6H-dibenzo(b,d)pyran-8-yl)benzenesulfonamide,
(1-difluoromethoxy-6-(3-fluorophenyl)-6H-dibenzo(b,d)pyran-8-yl)ethanesulfonamide,
(1-difluoromethoxy-6-(3-fluorophenyl)-6H-dibenzo(b,d)pyran-8-yl)isopropanesulfonamide,
(1-difluoromethoxy-6-(3-fluorophenyl)-6H-dibenzo(b,d)pyran-8-yl)-(2-fluorobenzene)sulfonamide,
(1-difluoromethoxy-6-(3-fluorophenyl)-6H-dibenzo(b,d)pyran-8-yl)-thiophene-2-sulfonamide,
(1-difluoromethoxy-6-(3-methoxyphenyl)-6H-dibenzo(b,d)pyran-8-yl)acetamide,
(1-difluoromethoxy-6-(3-methoxyphenyl)-6H-dibenzo(b,d)pyran-8-yl)propionamide,
(1-difluoromethoxy-6-(3-methoxyphenyl)-6H-dibenzo(b,d)pyran-8-yl)-(2-methyl)propionamide,
(1-difluoromethoxy-6-(3-methoxyphenyl)-6H-dibenzo(b,d)pyran-8-yl)benzamide,
(1-difluoromethoxy-6-(3-methoxyphenyl)-6H-dibenzo(b,d)pyran-8-yl)cyclopropanamide,
(1-difluoromethoxy-6-(3-methoxyphenyl)-6H-dibenzo(b,d)pyran-8-yl)-(2-methoxy)acetamide,
(1-difluoromethoxy-6-(3-methoxyphenyl)-6H-dibenzo(b,d)pyran-8-yl)trifluoroacetamide,
(1-difluoromethoxy-6-(3-methoxyphenyl)-6H-dibenzo(b,d)pyran-8-yl)-N,N-dimethylurea,
(1-difluoromethoxy-6-(3-methoxyphenyl)-6H-dibenzo(b,d)pyran-8-yl)-N,N-dimethylthiourea,
(1-difluoromethoxy-6-(3-methoxyphenyl)-6H-dibenzo(b,d)pyran-8-yl)-N,N-dimethylsulfonylurea,
(1-difluoromethoxy-6-(3-methoxyphenyl)-6H-dibenzo(b,d)pyran-8-yl)-N,N-diethylsulfonylurea,
(1-difluoromethoxy-6-(3-methoxyphenyl)-6H-dibenzo(b,d)pyran-8-yl)-N-methyl-N-ethylsulfonylurea,
(1-difluoromethoxy-6-(3-methoxyphenyl)-6H-dibenzo(b,d)pyran-8-yl)aniline,
(1-difluoromethoxy-6-(3-methoxyphenyl)-6H-dibenzo(b,d)pyran-8-yl)-N-ethylaniline,
(1-difluoromethoxy-6-(3-methoxyphenyl)-6H-dibenzo(b,d)pyran-8-yl)-N-methylaniline,
(1-difluoromethoxy-6-(3-methoxyphenyl)-6H-dibenzo(b,d)pyran-8-yl)-N-(cyclopropylmethyl)aniline,
(1-difluoromethoxy-6-(3-methoxyphenyl)-6H-dibenzo(b,d)pyran-8-yl)-N-benzylaniline,
(1-difluoromethoxy-6-(3-methoxyphenyl)-6H-dibenzo(b,d)pyran-8-yl)benzenesulfonamide,
(1-difluoromethoxy-6-(3-methoxyphenyl)-6H-dibenzo(b,d)pyran-8-yl)ethanesulfonamide,
(1-difluoromethoxy-6-(3-methoxyphenyl)-6H-dibenzo(b,d)pyran-8-yl)isopropanesulfonamide,
(1-difluoromethoxy-6-(3-methoxyphenyl)-6H-dibenzo(b,d)pyran-8-yl)-(2-fluorobenzene)sulfonamide,
(1-difluoromethoxy-6-(3-methoxyphenyl)-6H-dibenzo(b,d)pyran-8-yl)-thiophene-2-sulfonamide,
(1-difluoromethoxy-6-(3,4-dimethoxy)phenyl-6H-dibenzo(b,d)pyran-8-yl)acetamide,
(1-difluoromethoxy-6-(3,4-dimethoxy)phenyl-6H-dibenzo(b,d)pyran-8-yl)propionamide,
(1-difluoromethoxy-6-(3,4-dimethoxy)phenyl-6H-dibenzo(b,d)pyran-8-yl)-(2-methyl)propionamide,
(1-difluoromethoxy-6-(3,4-dimethoxy)phenyl-6H-dibenzo(b,d)pyran-8-yl)benzamide,
(1-difluoromethoxy-6-(3,4-dimethoxy)phenyl-6H-dibenzo(b,d)pyran-8-yl)cyclopropanamide,
(1-difluoromethoxy-6-(3,4-dimethoxy)phenyl-6H-dibenzo(b,d)pyran-8-yl)-(2-methoxy)acetamide,
(1-difluoromethoxy-6-(3,4-dimethoxy)phenyl-6H-dibenzo(b,d)pyran-8-yl)trifluoroacetamide,
(1-difluoromethoxy-6-(3,4-dimethoxy)phenyl-6H-dibenzo(b,d)pyran-8-yl)-N,N-dimethylurea,
(1-difluoromethoxy-6-(3,4-dimethoxy)phenyl-6H-dibenzo(b,d)pyran-8-yl)-N,N-dimethylthiourea,
(1-difluoromethoxy-6-(3,4-dimethoxy)phenyl-6H-dibenzo(b,d)pyran-8-yl)-N,N-dimethylsulfonylurea,
(1-difluoromethoxy-6-(3,4-dimethoxy)phenyl-6H-dibenzo(b,d)pyran-8-yl)-N,N-diethylsulfonylurea, (1-difluoromethoxy-6-(3,4-dimethoxy)phenyl-6H-dibenzo(b,d)pyran-8-yl)-N-methyl-N-ethylsulfonylurea, (1-difluoromethoxy-6-(3,4-dimethoxy)phenyl-6H-dibenzo(b,d)pyran-8-yl)aniline, (1-difluoromethoxy-6-(3,4-dimethoxy)phenyl-6H-dibenzo(b,d)pyran-8-yl)-N-ethylaniline, (1-difluoromethoxy-6-(3,4-dimethoxy)phenyl-6H-dibenzo(b,d)pyran-8-yl)-N-methylaniline, (1-difluoromethoxy-6-(3,4-dimethoxy)phenyl-6H-dibenzo(b,d)pyran-8-yl)-N-(cyclopropylmethyl)aniline, (1-difluoromethoxy-6-(3,4-dimethoxy)phenyl-6H-dibenzo(b,d)pyran-8-yl)-N-benzylaniline, (1-difluoromethoxy-6-(3,4-dimethoxy)phenyl-6H-dibenzo(b,d)pyran-8-yl)benzenesulfonamide, (1-difluoromethoxy-6-(3,4-dimethoxy)phenyl-6H-dibenzo(b,d)pyran-8-yl)ethanesulfonamide, (1-difluoromethoxy-6-(3,4-dimethoxy)phenyl-6H-dibenzo(b,d)pyran-8-yl)isopropanesulfonamide, (1-difluoromethoxy-6-(3,4-dimethoxy)phenyl-6H-dibenzo(b,d)pyran-8-yl)-(2-fluorobenzene)sulfonamide, (1-difluoromethoxy-6-(3,4-dimethoxy)phenyl-6H-dibenzo(b,d)pyran-8-yl)-thiophene-2-sulfonamide, (1-difluoromethoxy-6-(5-bromothien-2-yl)-6H-dibenzo(b,d)pyran-8-yl)acetamide, (1-difluoromethoxy-6-(5-bromothien-2-yl)-6H-dibenzo(b,d)pyran-8-yl)propionamide, (1-difluoromethoxy-6-(5-bromothien-2-yl)-6H-dibenzo(b,d)pyran-8-yl)-(2-methyl)propionamide, (1-difluoromethoxy-6-(5-bromothien-2-yl)-6H-dibenzo(b,d)pyran-8-yl)benzamide, (1-difluoromethoxy-6-(5-bromothien-2-yl)-6H-dibenzo(b,d)pyran-8-yl)cyclopropanamide, (1-difluoromethoxy-6-(5-bromothien-2-yl)-6H-dibenzo(b,d)pyran-8-yl)-(2-methoxy)acetamide, (1-difluoromethoxy-6-(5-bromothien-2-yl)-6H-dibenzo(b,d)pyran-8-yl)trifluoroacetamide, (1-difluoromethoxy-6-(5-bromothien-2-yl)-6H-dibenzo(b,d)pyran-8-yl)-N,N-dimethylurea, (1-difluoromethoxy-6-(5-bromothien-2-yl)-6H-dibenzo(b,d)pyran-8-yl)-N,N-dimethylthiourea, (1-difluoromethoxy-6-(5-bromothien-2-yl)-6H-dibenzo(b,d)pyran-8-yl)-N,N-dimethylsulfonylurea, (1-difluoromethoxy-6-(5-bromothien-2-yl)-6H-dibenzo(b,d)pyran-8-yl)-N,N-diethylsulfonylurea, (1-difluoromethoxy-6-(5-bromothien-2-yl)-6H-dibenzo(b,d)pyran-8-yl)-N-methyl-N-ethylsulfonylurea, (1-difluoromethoxy-6-(5-bromothien-2-yl)-6H-dibenzo(b,d)pyran-8-yl)aniline, (1-difluoromethoxy-6-(5-bromothien-2-yl)-6H-dibenzo(b,d)pyran-8-yl)-N-ethylaniline, (1-difluoromethoxy-6-(5-bromothien-2-yl)-6H-dibenzo(b,d)pyran-8-yl)-N-methylaniline, (1-difluoromethoxy-6-(5-bromothien-2-yl)-6H-dibenzo(b,d)pyran-8-yl)-N-(cyclopropylmethyl)aniline, (1-difluoromethoxy-6-(5-bromothien-2-yl)-6H-dibenzo(b,d)pyran-8-yl)-N-benzylaniline, (1-difluoromethoxy-6-(5-bromothien-2-yl)-6H-dibenzo(b,d)pyran-8-yl)benzenesulfonamide, (1-difluoromethoxy-6-(5-bromothien-2-yl)-6H-dibenzo(b,d)pyran-8-yl)ethanesulfonamide, (1-difluoromethoxy-6-(5-bromothien-2-yl)-6H-dibenzo(b,d)pyran-8-yl)isopropanesulfonamide, (1-difluoromethoxy-6-(5-bromothien-2-yl)-6H-dibenzo(b,d)pyran-8-yl)-(2-fluorobenzene)sulfonamide, and (1-difluoromethoxy-6-(5-bromothien-2-yl)-6H-dibenzo(b,d)pyran-8-yl)-thiophene-2-sulfonamide.

\* \* \* \* \*

UNITED STATES PATENT AND TRADEMARK OFFICE
CERTIFICATE OF CORRECTION

PATENT NO. : 6,593,480 B2
DATED : July 15, 2003
INVENTOR(S) : Philip R. Kym et al.

It is certified that error appears in the above-identified patent and that said Letters Patent is hereby corrected as shown below:

Column 114,
Line 7, replace "carboxy, carboxy, alkyl, cyano" with -- carboxy, carboxyalkyl, cyano --.

Column 117,
Line 5, insert -- (1-methoxy-6-phenyl-6H-dibenzo(b,d)pyran-8-yl)" (2-fluoro)benzenesulfonamide --.
Line 10, replace "benzylaniline." with -- benzylamine. --.

Column 118,
Line 35, replace "(5-chloropent-11-yl)" with -- (5-choropent-1-yl) --.

Column 123,
Line 20, replace "-6-(31-methoxypheny)" with -- -6-(3-methoxyphenyl) --.
Line 62, replace "-6-(31-chlorophenyl)" with ---6-(3-chorophenyl)--.

Column 124,
Line 63, replace "(bed)" with -- (b,d) --.
Line 66, replace "(1-methanesulfinyl-" with -- (1-ethanesulfinyl- --.

Column 125,
Line 57, replace "3(-dimethoxyphenyl)" with -- (5-bromothien-2y1) --.

Column 126,
Line 5, replace "(-bromothien-2-yl)" with -- (5-bromothien-2-yl) --.
Line 12, replace "(bud)" with -- (b,d) --.
Line 42, replace "(1-(2-thinyl)" with -- (1-(2-thienyl) --.

Column 127,
Line 60, replace "-6-(-bromothien-2-yl)" with -- -6-(5-bromothien-2-yl) --.

Column 128,
Line 5, replace "(3,4-dimethoxyphenyl)" with -- (3,4-dimethoxy)phenyl --.
Line 7, insert -- (1-cyano-6-(5-bromothien-2-yl)-6H-dibenzo(b,d)pyran-8-yl) methanesulfonamide, --.

UNITED STATES PATENT AND TRADEMARK OFFICE
CERTIFICATE OF CORRECTION

PATENT NO.    : 6,593,480 B2
DATED         : July 15, 2003
INVENTOR(S)   : Philip R. Kym et al.

It is certified that error appears in the above-identified patent and that said Letters Patent is hereby corrected as shown below:

Column 129,
Line 30, replace "(1-1-ethyl-6-" with -- (1-ethyl)-6- --.

Column 130,
Line 12, replace "(bud)" with -- (b,d) --.

Column 131,
Line 7, replace "(1-methoxy-2-(2-(2-methoxyethoxy)ethoxy)-6-phenyl-6H-dibenzo(b,d)pyran-8-yl)methanesulfonamide," with -- (1-methoxy-2-(2-(2-methoxyethoxy)ethoxy)-6(3-chlorophenyl)-6H-dibenzo(b,d)pyran-8-yl)methanesulfonamide, --.

Column 132,
Line 3, replace "(bud)" with -- (b,d) --.

Column 134,
Line 5, replace "-ethynyl)" with -- -(3-chlorophenyl) --.
Line 16, replace "pyran-9-yl)" with -- pyran-8-yl) --.

Column 135,
Line 15, replace "(bud)" with -- (b,d) --.
Line 40, replace "pyran-9-yl)" with -- pyran-8-yl) --.
Line 61, insert after methoxy -- 3-mthyl --.

Column 136,
Line 15, replace "(bud)" with -- (b,d) --.
Line 36, replace "-6H1-" with -- -6H- --.

Column 138,
Line 7, replace "(6-oxyhexyl)" with -- 6-methoxyhexyl) --.
Line 26, replace "(bed)" with -- (b,d) --.

Column 139,
Line 45, replace "(bud)" with -- (b,d) --.

UNITED STATES PATENT AND TRADEMARK OFFICE
CERTIFICATE OF CORRECTION

PATENT NO. : 6,593,480 B2
DATED : July 15, 2003
INVENTOR(S) : Philip R. Kym et al.

It is certified that error appears in the above-identified patent and that said Letters Patent is hereby corrected as shown below:

Column 140,
Line 21, replace "-dimethylcarbonyl)" with -- -dimethylaminocarbonyl) --.

Column 141,
Line 16, replace "(chlorothien-2-yl)" with -- (5-chlorothien-2-yl) --.

Column 146,
Line 21, replace "(bld)" with -- (b,d) --.
Line 44, replace "pyran-9-yl)" with -- pyran-8-yl) --.

Column 149,
Line 64, replace "(-bromothien-2-yl)" with -- (5-bromothien-2-yl) --.

Column 151,
Line 26, insert -- (1-methoxy-6-phenyl-6H-dibenzo(b,d)pyran-yl)-N-cyclopropylmethyl)aniline, --.

Column 152,
Line 28, insert -- (1-methoxy-6-3-fluoropheny-6H-dibenzo(,d)pyran-8-yl) cyclopropanamide --.
Line 30, replace "(2methoxy)" with -- (2-methoxy) --.

Column 156,
Line 62, replace "-6 H-" with -- -6H- --.

Signed and Sealed this

Seventeenth Day of August, 2004

JON W. DUDAS
*Acting Director of the United States Patent and Trademark Office*